(12) United States Patent
Ibrahim et al.

(10) Patent No.: US 12,076,322 B2
(45) Date of Patent: *Sep. 3, 2024

(54) COMPOUNDS AND METHODS FOR KINASE MODULATION, AND INDICATIONS THEREFOR

(71) Applicant: Plexxikon Inc., South San Francisco, CA (US)

(72) Inventors: Prabha N. Ibrahim, Mountain View, CA (US); Chao Zhang, Moraga, CA (US); Wayne Spevak, Berkeley, CA (US); Jiazhong Zhang, Foster City, CA (US); Guoxian Wu, Foster City, CA (US); Jack Lin, Hercules, CA (US); Hanna Cho, Oakland, CA (US); Marika Nespi, Berkeley, CA (US); Songyuan Shi, Fremont, CA (US); Todd Ewing, Walnut Creek, CA (US); Ying Zhang, Fremont, CA (US)

(73) Assignee: Plexxikon Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/895,972

(22) Filed: Aug. 25, 2022

(65) Prior Publication Data
US 2023/0277534 A1    Sep. 7, 2023

Related U.S. Application Data

(60) Continuation of application No. 17/722,229, filed on Apr. 15, 2022, now abandoned, which is a continuation of application No. 15/435,569, filed on Feb. 17, 2017, now Pat. No. 11,337,976, which is a division of application No. 13/820,734, filed as application No. PCT/US2012/023543 on Feb. 1, 2012, now Pat. No. 9,624,213.

(60) Provisional application No. 61/440,339, filed on Feb. 7, 2011.

(51) Int. Cl.
| A61K 31/506 | (2006.01) |
| A61K 31/437 | (2006.01) |
| A61K 31/5377 | (2006.01) |
| C07D 471/04 | (2006.01) |

(52) U.S. Cl.
CPC .......... *A61K 31/506* (2013.01); *A61K 31/437* (2013.01); *A61K 31/5377* (2013.01); *C07D 471/04* (2013.01)

(58) Field of Classification Search
CPC ................ A61K 31/506; A61K 31/437; A61K 31/5377; C07D 471/04
See application file for complete search history.

(56) References Cited

U.S. PATENT DOCUMENTS

| | | |
|---|---|---|
| 2,234,705 A | 3/1941 | Normington et al. |
| 2,413,258 A | 12/1946 | Soday |
| 4,150,949 A | 4/1979 | Smith |
| 4,301,159 A | 11/1981 | Ogata et al. |
| 4,439,444 A | 3/1984 | Nisato et al. |
| 4,568,649 A | 2/1986 | Bertoglio-Matte |
| 4,626,513 A | 12/1986 | Burton et al. |
| 4,634,701 A | 1/1987 | De Vincentiis |
| 4,714,693 A | 12/1987 | Targos |
| 4,727,395 A | 2/1988 | Oda et al. |
| 4,863,945 A | 9/1989 | Friebe et al. |
| 5,120,782 A | 6/1992 | Hubsch et al. |
| 5,143,854 A | 9/1992 | Pirrung et al. |
| 5,338,849 A | 8/1994 | Festal et al. |
| 5,360,882 A | 11/1994 | Dougherty et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,486,525 A | 1/1996 | Summers, Jr. et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |

(Continued)

FOREIGN PATENT DOCUMENTS

| CA | 2550361 | 7/2005 |
| DE | 2413258 | 10/1975 |

(Continued)

OTHER PUBLICATIONS

U.S. Appl. No. 16/400,801, filed May 1, 2019, Ibrahim et al.

(Continued)

*Primary Examiner* — Savitha M Rao
*Assistant Examiner* — Andrew P Lee
(74) *Attorney, Agent, or Firm* — Sheppard Mullin Richter & Hampton LLP

(57) ABSTRACT

Compounds active on protein kinases are described, as well as methods of making and using such compounds to treat diseases and conditions associated with aberrant activity of protein kinases.

7 Claims, No Drawings

(56) References Cited

U.S. PATENT DOCUMENTS

| | | |
|---|---|---|
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,908,401 A | 6/1999 | Henley |
| 5,952,362 A | 9/1999 | Cournoyer et al. |
| 5,958,930 A | 9/1999 | Gangjee |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,202,266 B2 | 4/2007 | Arnold et al. |
| 7,259,165 B2 | 8/2007 | Bernotas et al. |
| 7,271,262 B2 | 9/2007 | La Greca et al. |
| 7,348,338 B2 | 3/2008 | Arnold et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West |
| 7,531,568 B2 | 5/2009 | Lin et al. |
| 7,572,806 B2 | 8/2009 | Arnold et al. |
| 7,582,637 B2 | 9/2009 | Arnold et al. |
| 7,585,859 B2 | 9/2009 | Ibrahim et al. |
| 7,601,839 B2 | 10/2009 | Arnold et al. |
| 7,605,168 B2 | 10/2009 | Ibrahim et al. |
| 7,626,021 B2 | 12/2009 | Arnold et al. |
| 7,723,374 B2 | 5/2010 | Artis et al. |
| 7,759,475 B2 | 7/2010 | West |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 7,994,185 B2 | 8/2011 | Rheault |
| 8,053,463 B2 | 11/2011 | Lin et al. |
| 8,067,434 B2 | 11/2011 | Ibrahim et al. |
| 8,067,638 B2 | 11/2011 | Kai et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Ibrahim et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,470,821 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 9,663,517 B2 | 5/2017 | Desai et al. |
| 9,695,169 B2 | 7/2017 | Ibrahim |
| 9,730,918 B2 | 8/2017 | Bollag et al. |
| 9,745,298 B2 | 8/2017 | Ibrahim et al. |
| 9,771,363 B2 | 9/2017 | Ibrahim et al. |
| 9,771,369 B2 | 9/2017 | Lin et al. |
| 9,776,998 B2 | 10/2017 | Ibrahim et al. |
| 9,802,932 B2 | 10/2017 | Ibrahim et al. |
| 9,814,714 B2 | 11/2017 | Ibrahim et al. |
| 9,822,109 B2 | 11/2017 | Zhang et al. |
| 9,844,539 B2 | 12/2017 | Wu et al. |
| 9,856,259 B2 | 1/2018 | Shi et al. |
| 9,873,700 B2 | 1/2018 | Zhang et al. |
| 9,938,273 B2 | 4/2018 | Wu et al. |
| 9,975,894 B2 | 5/2018 | Ibrahim et al. |
| 9,994,567 B2 | 6/2018 | Ibrahim et al. |
| 10,040,792 B2 | 8/2018 | Ibrahim et al. |
| 10,123,998 B2 | 11/2018 | Bollag et al. |
| 10,160,747 B2 | 12/2018 | Lin et al. |
| 10,160,755 B2 | 12/2018 | Lin et al. |
| 10,189,833 B2 | 1/2019 | Ibrahim et al. |
| 10,227,357 B2 | 3/2019 | Lin et al. |
| 10,301,280 B2 | 5/2019 | Wu et al. |
| 10,316,032 B2 | 6/2019 | Ibrahim et al. |
| 10,370,374 B2 | 8/2019 | Ibrahim et al. |
| 10,399,975 B2 | 9/2019 | Ibrahim et al. |
| 10,421,761 B2 | 9/2019 | Zhang et al. |
| 10,426,760 B2 | 10/2019 | Wu et al. |
| 10,428,067 B2 | 10/2019 | Zhang et al. |
| 10,435,404 B2 | 10/2019 | Ibrahim et al. |
| 10,508,085 B2 | 12/2019 | Zhang et al. |
| 10,584,122 B2 | 3/2020 | Ibrahim et al. |
| 10,647,716 B2 | 5/2020 | Ibrahim et al. |
| 10,703,757 B2 | 7/2020 | Wu et al. |
| 10,730,876 B2 | 8/2020 | Ibrahim et al. |
| 10,829,484 B2 | 11/2020 | Holladay et al. |
| 10,941,142 B2 | 3/2021 | Ibrahim et al. |
| 10,961,240 B2 | 3/2021 | Ibrahim et al. |
| 11,103,505 B2 | 8/2021 | Rezaei et al. |
| 11,149,011 B2 | 10/2021 | Zhang et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0219489 A1 | 11/2003 | Curatolo et al. |

(56) References Cited

U.S. PATENT DOCUMENTS

| | | |
|---|---|---|
| 2004/0002534 A1 | 1/2004 | Lipson et al. |
| 2004/0022534 A1 | 2/2004 | Amano et al. |
| 2004/0073274 A1 | 4/2004 | Cook et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2004/0171062 A1 | 9/2004 | Hirth et al. |
| 2005/0026792 A1 | 2/2005 | Cartwright |
| 2005/0031692 A1 | 2/2005 | Beyerinck et al. |
| 2005/0048573 A1 | 3/2005 | Artis et al. |
| 2005/0079548 A1 | 4/2005 | Artis et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058324 A1 | 3/2006 | Capraro et al. |
| 2006/0058339 A1 | 3/2006 | Ibrahim et al. |
| 2006/0058340 A1 | 3/2006 | Ibrahim et al. |
| 2006/0135540 A1 | 6/2006 | Lin et al. |
| 2006/0160135 A1 | 7/2006 | Wang et al. |
| 2006/0167403 A1 | 7/2006 | Henley et al. |
| 2007/0032519 A1 | 2/2007 | Zhang et al. |
| 2007/0049615 A1 | 3/2007 | Ibrahim et al. |
| 2007/0054963 A1 | 3/2007 | Lifshitz-Liron et al. |
| 2007/0066641 A1 | 3/2007 | Ibrahim et al. |
| 2007/0072862 A1 | 3/2007 | Dimauro et al. |
| 2007/0072904 A1 | 3/2007 | Lin et al. |
| 2007/0161666 A1 | 7/2007 | Blumenkopf et al. |
| 2007/0218138 A1 | 9/2007 | Bittorf et al. |
| 2007/0225306 A1 | 9/2007 | Choi et al. |
| 2007/0287711 A1 | 12/2007 | Arnold et al. |
| 2008/0079906 A1 | 4/2008 | Finn |
| 2008/0167338 A1 | 7/2008 | Spevak et al. |
| 2008/0188514 A1 | 8/2008 | Wu et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0286783 A1 | 11/2009 | Ibrahim et al. |
| 2009/0306056 A1 | 12/2009 | Arnold et al. |
| 2009/0306086 A1 | 12/2009 | Ibrahim et al. |
| 2009/0306087 A1 | 12/2009 | Ibrahim et al. |
| 2010/0190777 A1 | 7/2010 | Wu et al. |
| 2010/0249118 A1 | 9/2010 | Ibrahim et al. |
| 2010/0286142 A1 | 11/2010 | Ibrahim et al. |
| 2010/0286178 A1 | 11/2010 | Ibrahim et al. |
| 2010/0310659 A1 | 12/2010 | Desai et al. |
| 2011/0028511 A1 | 2/2011 | Hildbrand et al. |
| 2011/0092538 A1 | 4/2011 | Spevak et al. |
| 2011/0112127 A1 | 5/2011 | Zhang et al. |
| 2011/0112136 A1 | 5/2011 | Diodone et al. |
| 2011/0152258 A1 | 6/2011 | Ibrahim et al. |
| 2011/0166174 A1 | 7/2011 | Zhang et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0172375 A1 | 7/2013 | Albano et al. |
| 2013/0237531 A1 | 9/2013 | Wu et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0037617 A1 | 2/2014 | Bollag et al. |
| 2014/0038948 A1 | 2/2014 | Wu et al. |
| 2014/0045840 A1 | 2/2014 | Zhang et al. |
| 2014/0094611 A1 | 4/2014 | Ibrahim |
| 2014/0128390 A1 | 5/2014 | Lin et al. |
| 2014/0213554 A1 | 7/2014 | Wu et al. |
| 2014/0243365 A1 | 8/2014 | Zhang et al. |
| 2014/0288070 A1 | 9/2014 | Ibrahim et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0080372 A1 | 3/2015 | Ibrahim et al. |
| 2015/0133400 A1 | 5/2015 | Zhang et al. |
| 2015/0166547 A1 | 6/2015 | Ibrahim et al. |
| 2015/0183793 A1 | 7/2015 | Zhang et al. |
| 2015/0290205 A1 | 10/2015 | Ibrahim et al. |
| 2016/0168146 A1 | 6/2016 | Wu et al. |
| 2016/0176865 A1 | 6/2016 | Ibrahim et al. |
| 2016/0326162 A1 | 11/2016 | Lin et al. |
| 2016/0340357 A1 | 11/2016 | Ibrahim et al. |
| 2017/0029413 A1 | 2/2017 | Holladay et al. |
| 2017/0157120 A1 | 6/2017 | Ibrahim et al. |
| 2017/0247370 A1 | 8/2017 | Zhang et al. |
| 2017/0267660 A1 | 9/2017 | Lin et al. |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1 | 12/2017 | Wu et al. |
| 2018/0030051 A1 | 2/2018 | Ibrahim et al. |
| 2018/0055828 A1 | 3/2018 | Bollag et al. |
| 2018/0072722 A1 | 3/2018 | Zhang et al. |
| 2018/0099939 A1 | 4/2018 | Zhang et al. |
| 2018/0099975 A1 | 4/2018 | Zhang et al. |
| 2018/0111929 A1 | 4/2018 | Ibrahim et al. |
| 2018/0111930 A1 | 4/2018 | Desai et al. |
| 2018/0215763 A1 | 8/2018 | Wu et al. |
| 2018/0265508 A1 | 9/2018 | Lin et al. |
| 2018/0305358 A1 | 10/2018 | Ibrahim et al. |
| 2018/0327403 A1 | 11/2018 | Ibrahim et al. |
| 2018/0354946 A1 | 12/2018 | Zhang et al. |
| 2019/0031654 A1 | 1/2019 | Ibrahim et al. |
| 2019/0119273 A1 | 4/2019 | Ibrahim et al. |
| 2019/0125747 A1 | 5/2019 | Rezaei et al. |
| 2019/0161484 A1 | 5/2019 | Ibrahim et al. |
| 2019/0175567 A1 | 6/2019 | Wu et al. |
| 2019/0209536 A1 | 7/2019 | Wu et al. |
| 2019/0241557 A1 | 8/2019 | Desai et al. |
| 2019/0263800 A1 | 8/2019 | Zhang et al. |
| 2019/0300487 A1 | 10/2019 | Zhang et al. |
| 2019/0337943 A1 | 11/2019 | Ibrahim et al. |
| 2019/0337944 A1 | 11/2019 | Ibrahim et al. |
| 2019/0367507 A1 | 12/2019 | Ibrahim et al. |
| 2020/0010465 A1 | 1/2020 | Ibrahim et al. |
| 2020/0299293 A1 | 9/2020 | Ibrahim et al. |
| 2020/0339571 A1 | 10/2020 | Ibrahim et al. |
| 2021/0198239 A1 | 7/2021 | Vander Wal et al. |
| 2021/0315869 A1 | 10/2021 | Albers et al. |
| 2021/0315872 A1 | 10/2021 | Spevak et al. |
| 2021/0346358 A1 | 11/2021 | Wu et al. |
| 2021/0353602 A1 | 11/2021 | Wu et al. |
| 2022/0054507 A1 | 2/2022 | Powell et al. |
| 2022/0081436 A1 | 3/2022 | Ibrahim et al. |
| 2022/0144805 A1 | 5/2022 | Shi et al. |
| 2022/0153737 A1 | 5/2022 | Ibrahim et al. |
| 2022/0184079 A1 | 6/2022 | Rezaei et al. |
| 2023/0081426 A1 | 3/2023 | Zhang et al. |

FOREIGN PATENT DOCUMENTS

| | | |
|---|---|---|
| EP | 0148725 | 7/1985 |
| EP | 0154734 | 9/1985 |
| EP | 0344603 | 12/1989 |
| EP | 0465970 | 1/1992 |
| EP | 0580860 | 2/1994 |
| EP | 0596406 | 5/1994 |
| EP | 0870768 | 10/1998 |
| EP | 0901786 | 3/1999 |
| EP | 0988863 | 3/2000 |
| EP | 1057826 | 12/2000 |
| EP | 1267111 | 12/2002 |
| EP | 1368001 | 12/2003 |
| EP | 1388541 | 2/2004 |
| EP | 1749829 | 2/2007 |

(56) References Cited

FOREIGN PATENT DOCUMENTS

| | | |
|---|---|---|
| EP | 2036990 | 3/2009 |
| FR | 2264804 | 10/1975 |
| GB | 1198301 | 7/1970 |
| GB | 1451299 | 9/1976 |
| GB | 2292143 | 2/1996 |
| GB | 2292145 | 2/1996 |
| GB | 2298198 | 8/1996 |
| GB | 2299581 | 10/1996 |
| JP | 1087629 | 4/1998 |
| JP | 10130269 | 5/1998 |
| JP | 2000095708 | 4/2000 |
| JP | 2001278886 | 10/2001 |
| JP | 2003073357 | 3/2003 |
| JP | 6135946 | 5/2017 |
| WO | WO-9313099 | 7/1993 |
| WO | WO-9414808 | 7/1994 |
| WO | WO-9420459 | 9/1994 |
| WO | WO-9420497 | 9/1994 |
| WO | WO-9504742 | 2/1995 |
| WO | WO-9507910 | 3/1995 |
| WO | WO-9528387 | 10/1995 |
| WO | WO-9600226 | 1/1996 |
| WO | WO-9605200 | 2/1996 |
| WO | WO-9611929 | 4/1996 |
| WO | WO-9617958 | 6/1996 |
| WO | WO-9618738 | 6/1996 |
| WO | WO-9638131 | 12/1996 |
| WO | WO-9703967 | 2/1997 |
| WO | WO-9746313 | 12/1997 |
| WO | WO-9746558 | 12/1997 |
| WO | WO-9749703 | 12/1997 |
| WO | WO-9806433 | 2/1998 |
| WO | WO-9822457 | 5/1998 |
| WO | WO-9847899 | 10/1998 |
| WO | WO-9900386 | 1/1999 |
| WO | WO-9909217 | 2/1999 |
| WO | WO-9932106 | 7/1999 |
| WO | WO-9932433 | 7/1999 |
| WO | WO-9951232 | 10/1999 |
| WO | WO-9951233 | 10/1999 |
| WO | WO-9951234 | 10/1999 |
| WO | WO-9951595 | 10/1999 |
| WO | WO-9951596 | 10/1999 |
| WO | WO-9951773 | 10/1999 |
| WO | WO-0009162 | 2/2000 |
| WO | WO-0012074 | 3/2000 |
| WO | WO-0012514 | 3/2000 |
| WO | WO-0017202 | 3/2000 |
| WO | WO-0029411 | 5/2000 |
| WO | WO-0053582 | 9/2000 |
| WO | WO-0055153 | 9/2000 |
| WO | WO-0064898 | 11/2000 |
| WO | WO-0071506 | 11/2000 |
| WO | WO-0071537 | 11/2000 |
| WO | WO-0075139 | 12/2000 |
| WO | WO-0109121 | 2/2001 |
| WO | WO-0124236 | 4/2001 |
| WO | WO-0129036 | 4/2001 |
| WO | WO-0146196 | 6/2001 |
| WO | WO-0160822 | 8/2001 |
| WO | WO-0162255 | 8/2001 |
| WO | WO-0174786 | 11/2001 |
| WO | WO-0198299 | 12/2001 |
| WO | WO-0200657 | 1/2002 |
| WO | WO-0218346 | 3/2002 |
| WO | WO-02078780 | 10/2002 |
| WO | WO-02083175 | 10/2002 |
| WO | WO-02085896 | 10/2002 |
| WO | WO-02102783 | 12/2002 |
| WO | WO-03000258 | 1/2003 |
| WO | WO-03000267 | 1/2003 |
| WO | WO-03003004 | 1/2003 |
| WO | WO-03004472 | 1/2003 |
| WO | WO-03006459 | 1/2003 |
| WO | WO-03008422 | 1/2003 |
| WO | WO-03011868 | 2/2003 |
| WO | WO-03020698 | 3/2003 |
| WO | WO-03028724 | 4/2003 |
| WO | WO-03037862 | 5/2003 |
| WO | WO-03051838 | 6/2003 |
| WO | WO-03062236 | 7/2003 |
| WO | WO-03064413 | 8/2003 |
| WO | WO-03068221 | 8/2003 |
| WO | WO-03082289 | 10/2003 |
| WO | WO-03082868 | 10/2003 |
| WO | WO-03082869 | 10/2003 |
| WO | WO-03087087 | 10/2003 |
| WO | WO-03101990 | 12/2003 |
| WO | WO-2004005283 | 1/2004 |
| WO | WO-2004009600 | 1/2004 |
| WO | WO-2004009601 | 1/2004 |
| WO | WO-2004014369 | 2/2004 |
| WO | WO-2004016609 | 2/2004 |
| WO | WO-2004016610 | 2/2004 |
| WO | WO-2004024895 | 3/2004 |
| WO | WO-2004052880 | 6/2004 |
| WO | WO-2004054581 | 7/2004 |
| WO | WO-2004054974 | 7/2004 |
| WO | WO-2004056830 | 7/2004 |
| WO | WO-2004065393 | 8/2004 |
| WO | WO-2004065394 | 8/2004 |
| WO | WO-2004069138 | 8/2004 |
| WO | WO-2004074278 | 9/2004 |
| WO | WO-2004074286 | 9/2004 |
| WO | WO-2004078756 | 9/2004 |
| WO | WO-2004078923 | 9/2004 |
| WO | WO-2004101565 | 11/2004 |
| WO | WO-2005005426 | 1/2005 |
| WO | WO-2005028475 | 3/2005 |
| WO | WO-2005028624 | 3/2005 |
| WO | WO-2005030128 | 4/2005 |
| WO | WO-2005030709 | 4/2005 |
| WO | WO-2005034869 | 4/2005 |
| WO | WO-2005044181 | 5/2005 |
| WO | WO-2005058891 | 6/2005 |
| WO | WO-2005062795 | 7/2005 |
| WO | WO-2005063746 | 7/2005 |
| WO | WO-2005063747 | 7/2005 |
| WO | WO-2005066347 | 7/2005 |
| WO | WO-2005082367 | 9/2005 |
| WO | WO-2005085244 | 9/2005 |
| WO | WO-2005086904 | 9/2005 |
| WO | WO-2005092896 | 10/2005 |
| WO | WO-2005095400 | 10/2005 |
| WO | WO-2005103050 | 11/2005 |
| WO | WO-2005115363 | 12/2005 |
| WO | WO-2005115374 | 12/2005 |
| WO | WO-2005116035 | 12/2005 |
| WO | WO-2006004984 | 1/2006 |
| WO | WO-2006009755 | 1/2006 |
| WO | WO-2006009797 | 1/2006 |
| WO | WO-2006010637 | 2/2006 |
| WO | WO-2006015123 | 2/2006 |
| WO | WO-2006015124 | 2/2006 |
| WO | WO-2006063167 | 6/2006 |
| WO | WO-2006114180 | 11/2006 |
| WO | WO-2006114520 | 11/2006 |
| WO | WO-2006127587 | 11/2006 |
| WO | WO-2006137376 | 12/2006 |
| WO | WO-2006137789 | 12/2006 |
| WO | WO-2007002325 | 1/2007 |
| WO | WO-2007002433 | 1/2007 |
| WO | WO-2007009799 | 1/2007 |
| WO | WO-2007013896 | 2/2007 |
| WO | WO-2007022380 | 2/2007 |
| WO | WO-2007106236 | 9/2007 |
| WO | WO-2008058341 | 5/2008 |
| WO | WO-2008063888 | 5/2008 |
| WO | WO-2008064255 | 5/2008 |
| WO | WO-2008064265 | 5/2008 |
| WO | WO-2008065417 | 6/2008 |
| WO | WO-2008076779 | 6/2008 |
| WO | WO-2008079903 | 7/2008 |
| WO | WO-2008079906 | 7/2008 |

(56) References Cited

FOREIGN PATENT DOCUMENTS

| WO | WO-2008079909 | 7/2008 |
|---|---|---|
| WO | WO-2008138755 | 11/2008 |
| WO | WO-2009012283 | 1/2009 |
| WO | WO-2009111277 | 9/2009 |
| WO | WO-2009111278 | 9/2009 |
| WO | WO-2009111279 | 9/2009 |
| WO | WO-2009111280 | 9/2009 |
| WO | WO-2009115084 | 9/2009 |
| WO | WO-2010020905 | 2/2010 |
| WO | WO-2010059658 | 5/2010 |
| WO | WO-2010104945 | 9/2010 |
| WO | WO-2010104973 | 9/2010 |
| WO | WO-2010111527 | 9/2010 |
| WO | WO-2010114928 | 10/2010 |
| WO | WO-2010129467 | 11/2010 |
| WO | WO-2010129567 | 11/2010 |
| WO | WO-2010129570 | 11/2010 |
| WO | WO-2011015522 | 2/2011 |
| WO | WO-2011057974 | 5/2011 |
| WO | WO-2011060216 | 5/2011 |
| WO | WO-2011063159 | 5/2011 |
| WO | WO-2011079133 | 6/2011 |
| WO | WO-2011133637 | 10/2011 |
| WO | WO-2012010538 | 1/2012 |
| WO | WO-2012022724 | 2/2012 |
| WO | WO-2012032236 | 3/2012 |
| WO | WO-2012037060 | 3/2012 |
| WO | WO-2012109075 | 8/2012 |
| WO | WO-2012138809 | 10/2012 |
| WO | WO-2012158957 | 11/2012 |
| WO | WO-2012161776 | 11/2012 |

OTHER PUBLICATIONS

U.S. Appl. No. 16/563,656, filed Sep. 6, 2019, Zhang et al.
U.S. Appl. No. 16/684,198, filed Nov. 14, 2019, Desai et al.
U.S. Appl. No. 16/687,015, filed Nov. 18, 2019, Zhang et al.
U.S. Appl. No. 16/706,497, filed Dec. 6, 2019, Ibrahim et al.
U.S. Appl. No. 16/749,893, filed Jan. 22, 2020, Ibrahim et al.
U.S. Appl. No. 16/814,632, filed Mar. 10, 2020, Wu et al.
U.S. Appl. No. 16/854,646, filed Apr. 21, 2020, Zhang et al.
U.S. Appl. No. 16/909,315, filed Jun. 23, 2020, Zhang et al.
U.S. Appl. No. 16/916,796, filed Jun. 30, 2020, Desai et al.
U.S. Appl. No. 16/930,823, filed Jul. 16, 2020, Ibrahim et al.
U.S. Appl. No. 17/018,986, filed Sep. 11, 2020, Ibrahim et al.
U.S. Appl. No. 17/077,764, filed Oct. 22, 2020, Wu et al.
U.S. Appl. No. 17/121,484, filed Dec. 14, 2020, Ibrahim et al.
U.S. Appl. No. 17/161,257, filed Jan. 28, 2021, Zhang et al.
U.S. Appl. No. 17/166,890, filed Feb. 3, 2021, Desai et al.
U.S. Appl. No. 17/180,212, filed Feb. 19, 2021, Ibrahim et al.
U.S. Appl. No. 17/238,076, filed Apr. 22, 2021, Ibrahim et al.
U.S. Appl. No. 17/335,898, filed Jun. 1, 2021, Wu et al.
U.S. Appl. No. 17/379,837, filed Jul. 19, 2021, Rezaei et al.
U.S. Appl. No. 17/387,775, filed Jul. 28, 2021, Ibrahim et al.
U.S. Appl. No. 17/477,240, filed Sep. 16, 2021, Zhang et al.
U.S. Appl. No. 17/478,148, filed Sep. 17, 2021, Desai et al.
U.S. Appl. No. 17/745,678, filed May 16, 2022, Ibrahim et al.
U.S. Appl. No. 18/056,917, filed Nov. 18, 2022, Desai et al.
U.S. Appl. No. 18/056,980, filed Nov. 18, 2022, Zhang et al.
U.S. Appl. No. 18/190,503, filed Mar. 27, 2023, Wu et al.
Abou-Khalil, et al., "Delayed bone regeneration is linked to chronic inflammation in murine muscular dystrophy," J. Bone Miner. Res., DOI 10.1002/jbmr.2038 (2013).
Agaram et al., "Novel V600E BRAF Mutations in Imatinib-Naive and Imatinib-Resistant Gastrointestinal Stromal Tumors", Genes Chromosomes Cancer, 2008, 47(10):853-859.
Ahmad, K., "BRAF mutation common to 70% of thyroid carcinomas," The Lancet, Oncology, (2003), 4:330.
Al-Obeidi, et al., Peptide and Peptidomimetic Libraries, Mol Biotechnol., (1998), 9:205-223.

Alfthan, K., "Surface Plasmon Resonance Biosensors as a Tool in Antibody Engineering" Biosensors & Bioelectronics (1998), 13:653-663.
Allegretti et al., "Palladium-Catalysed Functionalisation at 4- and 6-Position of the 7-Azaindole System," Synlett (2001), 5:609-612.
Alvarez et al., Synthesis of 3-Aryl- and 3-Heteroaryl-7-azaindoles. Synthesis 1999, 4: 615-620.
Amersdorfer et al., Phage Libraries for Generation of Anti-Botulinum scFv Antibodies. Methods in Molecular Biology 2000, 145: 219-240.
Amiel et al., Hirschsprung disease, associated syndromes and genetics: a review. J Med Genet. 2008, 45:1-14.
Anderson et al., Cooperative Catalyst Effects in Palladium-Mediated Cyanation Reactions of Aryl Halides and Triflates. J. Org. Chem. 1998, 63:8224-8228.
Antonini, et al., "Synthesis of 4-Amino-1-β-D-Ribofuranosyl-1H-pyrrolo[2,3-b]pyridine (1-Deazatubercidin) as a Potential Antitumor Agent," J. Med. Chem., (1982), 25:1258-1261.
Arbiser, The Journal of Clinical Investigation, 2007, 117(10), pp. 2762-2765.
Arthan et al., Leukemia inhibitory factor can mediate Ras/Raf/MEK/ERK-induced growth inhibitory signaling in medullary thyroid cancer cells. Cancer Letters 2010, 297: 31-41.
Ashman, et al., "The biology of stem cell factor and its receptor C-kit," The International Journal of Biochemistry & Cell Biology, (1999), 31:1037-1051.
Baghestanian, et al., "A Case of Malignant Mastocytosis with Circulating Mast Cell Precursors: Biologic and Phenotypic Characterization of the Malignant Clone," Leuk., (1996), 10:159-166.
Bagshaw et al., "Measurement of Ligand Binding to Proteins," Spectrophotometry and Spectrofluorimetry: a Practical Approach, (1987), 4:91-113.
Bagshawe, K., "Antibody-Directed Enzyme Prodrug Therapy: a Review," Drug Dev. Res., (1995), 34:220-230.
Balak, et al., "Novel D761Y and Common Secondary T790M Mutations in Epidermal Growth Factor Receptor 13 Mutant Lung Adenocarcinomas with Acquired Resistance to Kinase Inhibitors," Clin Cancer Res., (2006), 12:6494-501.
Bancalari et al., Blood markers of early and late airway responses to allergen in asthmatic subjects. Relationship with functional findings. Allergy (1997), 52:32-40.
Banker, G.S. et al., "Modern Pharmaceutics, 3ed.", Marcel Dekker, New York, 1996, p. 596.
Bartlett, et al., "CAVEAT: A Program to Facilitate the Structure-Derived Design of Biologically Active Molecules," Royal Society of Chemistry, (1989), 78:180-196.
Barton, et al., "The chemistry of pentavalent organobismuth reagents. Part X. Studies on the phenylation and oxidation of phenols," Tetrahedron, (1987), 43(2):323-332.
Bashford, et al., "Measurement of Ligand Binding to Proteins," Spectrophotometry and Spectrofluorimetry: a Practical Approach, (1987), 4:91-113.
Basta et al., High-dose intravenous immunoglobulin exerts its beneficial effect in patients with dermatomyositis by blocking endomysial deposition of activated complement fragments. J Clin Invest. 1994, 94:1729-1735.
Basto et al., Mutation analysis of B-RAF gene in human gliomas. Acta Neuropathol (2005), 109:207-210.
Bayindir et al., "Cellular mesoblastic nephroma (infantile renal fibrosarcoma): institutional review of clinical, diagnostic imaging, and pathologic features of a distinctive neoplasm of infancy," Pediatr. Radiol., 2009, 39(10):1066-74.
Beaucage et al., "Advances in Synthesis of Oligonucleotides by the Phosphoramidite Approach, " Tetrahedron (1992) 48:2223-2311.
Bedi et al., Bcr-Abl-mediated inhibition of apoptosis with delay of G2/M transition after DNA damage. A mechanism of resistance to multiple anticancer agents. Blood 1995; 86: 1148-1158.
Bell, J.E., "Fluorescence: Solution Studies" Spectroscopy in Biochemistry I, (1981), (4):155-194.
Bellone et al., Growth stimulation of colorectal carcinoma cells via the c-kit receptor is inhibited by TGF-β1. J Cell Physiol (1997), 172:1-11.

(56) References Cited

OTHER PUBLICATIONS

Berdel, et al., "Recombinant Human Stem Cell Factor Stimulates Growth of a Human Glioblastoma Cell Line Expressing c kit Protooncogene," Canc. Res., (1992), 52:3498-3502.
Bertolini et al., A New Rational Hypothesis for the Pharmacophore of the Active Metabolite of Leflunomide, a Potent Immunosuppressive Drug. J. Med. Chem. 1997, 40:2011-2016.
Björntorp, "Neuroendocrine Pertuirbations as a Cause of Insulin Resistance," Diabetes Metab. Res. Rev., (1999), 15:427-441.
Bloom, et al., "The Preparation of 2-Alkylaminobenzimidazoles," J. Org. Chem., (1939), 14-19.
Blundell et al., Knowledge-based protein modelling and design. Eur. J. Biochem. (1988), 172:513-520.
Bode, et al., "Mutations in the tyrosine kinase domain of the EGFR gene are rare in synovial sarcoma," Modern Pathology, (2006), 19:541-547.
Bohm, H.-J., "On the Use of LUDI to Search the Fine Chemicals Directory for Ligands of Proteins of Known Three-Dimensional Structure," J. Comp. Aided Molec. Design, (1994), 8:623-632.
Bokemeyer, et al., "Expression of Stem-Cell Factor and Its Receptor c-kit Protein in Normal Testicular Tissue and Malignant Germ-Cell Tumours," J. Cancer Res. Clin. Oncol., (1996), 122:301-306.
Bolger et al., "Computer Modeling of Combining Site Structure of Anti-Hapten Monoclonal Antibodies," Methods Enz., (1991), 203:21-45.
Bollag et al., "Clinical efficacy of a RAF inhibitor needs broad target blockade in BRAF-mutant melanoma", Nature, 2010, 467 (7315), 596-599.
Bongarzone et al., High frequency of activation of tyrosine kinase oncogenes in human papillary thyroid carcinoma. Oncogene 1989, 4(12):1457-1462.
Bothwell, M., "Keeping Track of Neurotrophin Receptors," Cell (1991), 65:915-918.
Bouzakri et al., "MAP4K4 Gene silencing in Human Skeletal Muscle Prevents Tumor Necrosis Factor-a-induced Insulin Resistance," J. Biol. Chem. (2007), 282:7783-7789.
Bouzas-Rodriguez et al., "Neurotrophin-3 production promotes human neuroblastoma cell survival by inhibiting TrkC-induced apoptosis," J. Clin. Invest., 120(3):850-8 (2010).
Bowtell, D., Options available from start to finish for obtaining expression data by microarray. Nature Genetics Supp. (1999), 21:25-32.
Breindl, "No Melanocyte is an Island: in Melanoma, Interfeon, Roles Need Rethinking," BioWorld Today, (2011), 22(17): 1:5.
Brenner et al., Encoded combinatorial chemistry. Proc. Natl. Acad. Sci. USA 1992, 89:5381-5383.
Brose et al., "BRAF and RAS Mutations in Human Lung Cancer and Melanoma1", Cancer Research, 2002, 62, pp. 6997-7000.
Broudy, V., "Stem Cell Factor and Hematopoiesis," Blood, (1997), 90:1345-1364.
Brunger, A. T., "Free R Value: a Novel Statistical Quantity for Assessing the Accuracy of Crystal Structures," Nature, (1992), 355:472-475.
Buchschacher et al., Human immunodeficiency virus vectors for inducible expression of foreign genes. J Virol. 1992, 66:2731-2739.
Bundgaard, Design of Prodrugs, p. 1 (1985).
Burns et al., "c-FMS Inhibitars: a Patent Review," Expert Opinion Ther. Patents (2011), 21(2), pp. 147-165.
Calabresi, et al., "Section IX: Chemotherapy of neoplastic diseases," Goodman & Gilman's The Pharmacological Basis of Therapeutics, Tenth Edition, McGraw-Hill Medical Publishing Division (2001), pp. 1381, 1383-1385 and 1388.
Capon et al., Designing CD4 immunoadhesins for AIDS therapy. Nature 1989, 337:525-531.
Carell, et al., "New Promise in Combinatorial Chemistry: Synthesis, Characterization, and Screening of Small-Molecule Libraries in Solution," Chem. Biol., (1995), 2:171-183.
Carpino et al., p62dok: A Constitutively Tyrosine-Phosphorylated, GAP-Associated Protein in Chronic Myelogenous Leukemia Progenitor Cells. Cell 1997, 88:197-204.

Castellone et al., A novel de novo germ-line V292M mutation in the extracellular region of RET in a patient with phaeochromocytoma and medullary thyroid carcinoma: functional characterization. Clinical Endocrinology 2010, 73:529-534.
Castells, et al., "The Presence of Membrane-Bound Stem Cell Factor on Highly Immature Nonmetachromatic Mast Cells in the Peripheral Blood of a Patient with Aggressive Systemic Mastocytosis," J. Aller. Clin. Immunol., (1996), 98:831-840.
Castro et al., "Utilizacion de dispersiones solidas como estrategia para aumentar la velocidad de disolucion de farmacos," Nuestra Farmcia (2008), 25:24-29 (No English Translation Available).
Chabala, J., "Solid-Phase Combinatorial Chemistry and Novel Tagging Methods for Identifying Leads," Curr Opin Biotechnol., (1995), 6:632-639.
Chapman et al., "Initial genome sequencing and analysis of multiple myeloma", Nature, 2011, vol. 471, pp. 467-472.
Chappell et al., Oncotarget, vol. 2, No. 3, 135-164 (2011).
Chayer et al., "Synthesis of Carboranylpyrroles," Tetrahedron Lett. (2001), 42(44):7759-7761.
Checovich, et al., "Fluorescence Polarization—a New Tool for Cell and Molecular Biology," Nature, (1995), 375:254-256.
Chou et al., "Chemotherapeutic Synergism, Potentiation and Antagonism," Encyclopedia of Human Biology, Academic Press, (1991), 2:371-379.
Chou et al., Computerized quantitation of synergism and antagonism of taxol, topotecan, and cisplatin against human teratocarcinoma cell growth: a rational approach to clinical protocol design. J Natl Cancer Inst. 1994, 86:1517-1524.
Chou et al., Quantitative analysis of dose-effect relationships: the combined effects of multiple drugs or enzyme inhibitors. Adv Enzyme Regul 1984, 22:27-55.
Chou et al., Synergism and antagonism in chemotherapy. Academic Press 1991, Chapter 2, 61-102.
Clark, et al., "PRO_LIGAND: an Approach to De Novo Molecular Design. 1. Application to the Design of Organic Molecules," J. Comp. Aided Molec. Design, (1995), 9:13-32.
Clohisy, et al., "Review of Cellular Mechanisms of Tumor Osteolysis," Clin. Orthop., (2000), 373:104-114.
Coe et al., "Solution-Phase Combinatorial Chemistry," Mol Divers., (1999), 4:31-38.
Coelho et al., "Studies of RET gene expression and acetylcholinesterase activity in a series of sporadic Hirschsprung's disease," Pediatr Surg Int, (2008), 24:1017-1021.
Cohen et al., Expression of stem cell factor and c-kit in human neuroblastoma. Blood 1994, 84:3465-3472.
Collins et al., A small interfereing RNA screen for modulators of tumor cell motility identifies MAP4K4 as a prommigratory kinase, Proc. Natl. Acad. Sci. USA (2006), 103:3775-3780.
Collioud et al., Oriented and covalent immobilization of target molecules to solid supports: Synthesis and application of a light-activatable and thiol-reactive cross-linking reagent. Bioconjugate Chem. 1993, 4:528-536.
Colman, P.M., "Structure-Based Drug Design," Current Opinion in Struc. Biol., (1994), 4:868-874.
Colombino et al., "BRAF and PIK3CA genes are somatically mutated in hepatocellular carcinoma among patients from Italy", Cell Death and Disease, 2012, 3, e259. (4 pages).
Columbo et al., The human recombinant c-kit receptor ligand, rhSCF, induces mediator release from human cutaneous mast cells and enhances IgE-dependent mediator release from both skin mast cells and peripheral blood basophils. J Immunol. 1992, 149:599-608.
Communication Pursuant to Article 94(3) EPC for European Application No. 04814626.0 dated Jun. 6, 2011.
Communication Pursuant to Article 94(3) EPC for European Application No. 04814626.0 dated Dec. 15, 2009.
Communication Pursuant to Article 94(3) EPC for European Application No. 05789913.0 dated Feb. 15, 2010.
Communication Pursuant to Article 94(3) EPC for European Application No. 06773861.7 dated Apr. 22, 2010.
Communication Pursuant to Article 94(3) EPC for European Application No. 06773861.7 dated Jul. 9, 2009.

(56) References Cited

OTHER PUBLICATIONS

Communication Pursuant to Article 94(3) EPC for European Application No. 06773861.7 dated Dec. 21, 2009.
Communication Pursuant to Article 94(3) EPC for European Application No. 06813186.1 dated Sep. 15, 2009.
Communication Pursuant to Article 94(3) EPC for European Application No. 07864681.7 dated Dec. 2, 2009.
Communication Pursuant to Article 94(3) EPC for European Application No. 10722860.3, dated Mar. 27, 2013.
Communication Pursuant to Article 94(3) EPC for European Appln. No. 07864681.7 dated Oct. 8, 2012.
Communication Pursuant to Article 94(3) EPC for European Appln. No. 11173701.1 dated Jan. 4, 2013.
Coniglio, et al., "Microglial stimulation of glioblastoma invasion involves epidermal growth factor receptor (EGFR) and colony stimulating factor 1 receptor (CSF-1R) signaling," *Mol. Med.*, (2012), 18: 519-527.
Costa et al., The Cells of the Allergic Response. JAMA 1997, 278:1815-1822.
Coste et al., Coupling N-Methylated Amino Acids Using PyBroP1 and PyCloP Halogenophosphonium Salts: Mechanism and Fields of Application, Journal of Organic Chemistry (1994), 59:2437-2446.
Coulie et al., Recombinant Human Neurotropic Factors Accelerate Colonic Transit and Relieve Constipation in Humans, Gastroenterology (2000), 119:41-50.
Creighton, T., "An Empirical Approach to Protein Conformation Stability and Flexibility," Biopolymers, (1983), 22(1):49-58.
Crouch et al., The use of ATP bioluminescence as a measure of cell proliferation and cytotoxicity. Journal of Immunological Methods 1993, 160: 81-88.
Crump, M., "Inhibition of Raf Kinase in the Treatment of Acute Myeloid Leukemia," Curr. Pharm. Design, (2002), 8(25):2243-2248.
Curtin, et al., "Discovery and Evaluation of a Series of 3-Acylindole Imidazopyridine Platelet-Activating Factor Antagonists," J. Med. Chem., (1998), 41:74-95.
Curtin, et al., "Somatic activation of KIT in distinct subtypes of melanoma," J. of Clinical Oncology, (2006), 24(26): 4340-4345.
Cwirla, et al., "Peptides on Phage: a Vast Library of Peptides for Identifying Ligands," Biochemistry, (1990), 87:6378-6382.
Dai et al., Targeted disruption of the mouse colony-stimulating factor 1 receptor gene results in osteopetrosis, mononuclear phagocyte deficiency, increased primitive progenitor cell frequencies, and reproductive defects. Blood 2002, 99:111-120.
Damasio, "Alzheimer's Disease and Related Dementias," Cecil Textbook of Medicine, 20th Edition, vol. 2, pp. 1992-1996 (1996).
Dandliker et al., Equilibrium and kinetic inhibition assays based upon fluorescence polarization. Methods in Enzymology 1981, 74:3-28.
Danziger et al., Automated Site-directed Drug Design: a General Algorithm for Knowledge Acquisition about Hydrogen-Bonding Regions at Protein Surfaces, Mar. 22, 1989, the Royal Society, Proceedings of the Royal Society of London.Series B, Biological Sciences, vol. 236, No. 1283, p. 101-113.s.
Das-Gupta et al., "Acridine Derivatives, Part VI," J. Indian Chem. Society, (1941), 18:25-28.
Dastych et al., Stem cell factor induces mast cell adhesion to fibronectin. J. Immunol. 1994, 152:213-219.
Davies et al., Mutations of the BRAF gene in human cancer. Nature 2002, 417:949-954.
Demetri, G.D., "Targeting c-kit mutations in solid tumors: Scientific rationale and novel therapeutic options," Seminars in Oncology, (2001), 28(5), Supp. 17, 19-26.
Denardo, et al., "Leukocyte complexity predicts breast cancer survival and functionally regulates response to chemotherapy," Cancer Discovery, (2011), 54-67.
Dewar et al., "Inhibition of c-fms by imatinib: expanding the spectrum of treatment." Cell Cycle, 2005, 4:851-853.
Dobeli et al., Recombinant Fusion Proteins for the Industrial Production of Disulfide Bridge containing Peptides: Purification, Oxidation without Cancatamer Formation, and Selective Cleavage. Protein Expr. Purif. (1998), 12:404-414.
Dolle, et al., "Comprehensive Survey of Combinatorial Library Synthesis: 1998," J Comb Chem., (1999), 1:235-282.
Dong et al., BRAF oncogenic mutations correlate with progression rather than initiation of human melanoma. Cancer Research 2003, 63:3883-3885.
Donis-Keller, et al., "Mutations in the RET Proto-Oncogene are Associated with MEN 2A and FMTC," Hum Mol Genet., (1993), 2(7):851-856.
Dorwald, "Side Reactions in Organic Synthesis: a Guide to Successful Synthesis Design." Wiley-VCH, Preface p. IX, 2005.
Douma et al., "Suppression of anoikis and induction of metastasis by the neurotrophic receptor TrkB." Nature. 2004; 430:1034-1039.
Doyle, eta al., "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," J. Org. Chem., (1979), 44:1572.
Dube et al., "Reductive N-Alkylation of Amides, Carbamates and Ureas," Tetrahedron Lett. (1999), 40:2295-2298.
Dumas, "Protein kinase inhibitors: emerging pharmacophores 1997-2000." Exp. Opin. Ther. Patents, 11 (3): 405-429, 2001.
Durbec et al., GDNF signalling through the Ret receptor tyrosine kinase. Nature (1996), 381:789-793.
Dutcher et al., "Studies of the C11H8N2OS Degradation Product of Gliotoxin," J. Am. Chem. Soc., (1951), 73:4139-4141.
Dyson et al., The Human Papilloma Virus 13 16 E7 Oncoprotein is Able to Bind to the Retinoblastoma Gene Product. Science (1989), 243:934-937.
Eklund et al., "Treatment of rheumatoid arthritis with imatinib mesylate: clinical improvements in three refractory cases," Annals of Medicine (2003), 35:362-367.
Eliseev et al., "Dynamic Combinatorial Chemistry: Evolutionary Formation and Screening of Molecular Libraries," Current Topics in Microbiology & Immunology, (1999), 243:159-172.
Engelman et al., "Effective use of PI3K and MEK inhibitors to treat mutant Kras G12D and PIK3CA H1047R murine lung cancers," Nature Medicine 14(12): 1351-1356 (2008).
Enjalbal et al., "Mass spectrometry in combinatorial chemistry." 2000, pp. 139-161.
Ertl et al., "Fast calculation of molecular polar surface area as a sum of fragment-based contributions and its application to the prediction of drug transport properties," J Med Chem, (2000), 43:3714-3717.
Escribano et al., "Expression of the c-kit (CD117) molecule in normal and malignant hematopoiesis." Leuk Lymphoma 1998, 30(5-6):459-66.
Exam Report in Australia Application No. 2012200933 dated Jul. 3, 2013.
Examination Report dated Jun. 27, 2008 for GCC Patent Application No. GCC/P/2005/4795.
Examination Report dated Mar. 13, 2012 in Australian Patent Application Serial No. 2007323644.
Examination Report dated Mar. 14, 2012 in New Zealand Patent Application Serial No. 577011.
Examination Report for European Patent Application No. 12745360.3 dated Sep. 1, 2017.
Examination Report for India Patent Application No. 6297/CHENP/2013 dated Sep. 8, 2017. (7 pages).
Examination Report in New Zealand Application No. 613786 dated May 5, 2014.
Extended European Search Report for EP Application 10832209.0 dated Apr. 17, 2013.
Extended European Search Report for EP Application 10840075.5 dated May 13, 2013.
Felder, E.R., The challenge of preparing and testing combinatorial compound libraries in the fast lane, at the front end of drug development. Chimia (1994), 48:531-541.
Feng et al., "Stable in Vivo Gene Transduction via a Novel Adenoviral/Retroviral Chimeric Vector," Nature Biotechnology, (1997), 15:866-870.

(56) References Cited

OTHER PUBLICATIONS

Feng et al., Tyrosines 559 and 807 in the Cytoplasmic Tail of the Macrophage Colony-Stimulating Factor Receptor Play Distinct Roles in Osteoclast Differentiation and Function. Endocrinology 2002, 143:4868-4874.
Final Office Action dated Jul. 25, 2011 for U.S. Appl. No. 12/773,798.
Final Office Action dated Jun. 24, 2011 in U.S. Appl. No. 12/467,194.
Finotto et al., "Glucocorticoids Disease Tissue Mast Cell Number by Reducing the Production of the c-kit Ligand, Stem Cell Factor, by Resident Cells," J. Clin. Invest., (1997), 99:1721-1728.
Fischer et al., "Targeting receptor tyrosine kinase signalling in small cell lung cancer (SCLC): What have we learned so far?", Cancer Treatment Reviews (2007) 33, pp. 391-406.
Fivash et al., BIAcore for macromolecular interaction. Current Opinion in Biotechnology 1998, 9:97-101.
Flanagan et al., "Macrophages and the various isoforms of macrophage colony-stimulating factor;" Curr Opin Hematol. 1998, 5:181-185.
Franz et al., "Surfuranes. X. Reagent for the facile cleavage of secondary amides." J. Am. Chem. Soc., 1973, 95 (6), pp. 2017-2019.
Friesen et al., "Hydroxypropyl Methylcellulose Acetate Succinate-Based Spray-Dried Dispersions: an Overview," Molecular Pharmaceutics, 5(6):1003-1019 (2008).
Furitsu et al., Identification of mutations in the coding sequence of the proto-oncogene c-kit in a human mast cell leukemia cell line causing ligand-independent activation of the c-kit product. J Clin Invest 1993, 92:1736-1744.
Furuta et al., Stem Cell Factor Influences Mast Cell Mediator Release in Response to Eosinophil-Derived Granule Major Basic Protein. Blood 1998, 92:1055-1061.
Gallego et al., "Increased opioid dependence in a mouse model of panic disorder," Front Behav. Neurosci., 3:60 (2010).
Gallop et al., Applications of combinatorial technologies to drug discovery. 1. Background and peptide combinatorial libraries. J Med Chem. 1994, 37:1233-1251.
Galofré et al., "Evaluation and treatment of thyroid nodules: a clinical guide." Mount Sinai Journal of Medicine, 2008, 75(3):299-311.
Garzya et al., "Indium(III)-catalysed aryl sulfonylation reactions," Tetrahedron Letters 45:1499-1501 (2004).
Gassman, et al., "Specific Ortho Substitution of Aromatic Heterocyclic Amines," J Am Chem Society, (1973), 95(13):4453-4455.
Ghebre-Sellassie et al., "Pharmaceuticast Extrusion Technology." Mercer Dekker, Inc., New York. Basel. CRC Press, 2003 p. 238.
Gimbel et al., Braf mutations are associated with increased mortality in colorectal cancer, Journal of the American College of Surgeons (2004), 199:S91-S92.
Girgis, et.al., "The Synthesis of 5-Azaindoles by Substitution-Rearrangement of 7-Azaindoles upon Treatment with Certain Primary Amines," J. Heterocyclic. Chem., (1989), 26:317-325.
Golkar et al., Mastocytosis. Lancet (1997), 349: 1379-1385.
Golub, et al., "Molecular Classification of Cancer: Class Discovery and Class Prediction by Gene Expression Monitoring," Science, (1999), 286:531-537.
Goodford, P.J., A computational procedure for determining energetically favorable binding sites on biologically important macromolecules. J. Med. Chem. 1985, 28:849-857.
Goodsell et al., Automated Docking of Substrates to Proteins by Simulated Annealing. Proteins: Structure, Function and Genetics (1990), 8:195-202.
Gordon et al., "Detection of Peroxides and Their Removal," The Chemist's Companion: a Handbook of Practical Data, Techniques, and References, (1972), p. 437.
Gordon et al., Applications of Combinatorial Technologies to Drug Discovery. 2. Combinatorial Organic Synthesis, Library Screening Strategies, and Future Directions. J. Med. Chem. 1994, 37:1385-1401.

Gram, H., "Phage Display in Proteolysis and Signal Transduction," Combinatorial Chemistry & High Throughput Screening (1999), 2:19-28.
Gravert, et al., "Synthesis on Soluble Polymers: New Reactions and the Construction of Small Molecules," Curr Opin Chem Biol., (1997), 1:107-113.
Greer, J., Model Structure for the Inflammatory Protein C5a. Science (1985), 228:1055-1060.
Grieco et al., PTC is a novel rearranged form of the ret proto-oncogene and is frequently detected in vivo in human thyroid papillary carcinomas. Cell 1990, 60(4):557-563.
Guida, W., "Software for Structure-Based Drug Design," Current Opinion in Struc. Biol., (1994), 4:777-781.
Gura, "Systems for identifying New Drugs Are Often Faulty," Cancer Models, Science, vol. 278, No. 5340, pp. 1041-1042, Nov. 1997.
Hafner et al., Isothermal amplification and multimerization of DNA by Bst DNA polymerase. Biotechniques 2001, 30(4):852-867.
Hallek et al., "Interaction of the receptor tyrosine kinase p145c-kit with the p210bcr/abl kinase in myeloid cells." British Journal of Haematology, 1996, 94, pp. 5-16.
Halvorson, et al., "A Blocking Antibody to Nerve Growth Factor Attenuates Skeletal Pain Induced by Prostate Tumor Cells Growing in Bone," Cancer Res., (2005), 65:9426-9435.
Hamel et al., "The Road Less Traveled: c-kit and Stem Cell Factor," J. Neuro-Onc., (1997), 35:327-333.
Hancock et al., "Characteristics and Significance of the Amorphous State in Pharmaceutical Systems," Journal of Pharmaceutical Sciences 86(1):1-12 (1997).
Hands et al. "A Convenient Method for the Preparation of 5-, 6- and 7-Azaindoles and Their Derivatives," Synthesis (1996), 877-882.
Hanselman et al., A cDNA-Dependant Scintillation Proximity Assay for Quantifying Apolipoprotein A1. J. Lipid Res. (1997), 38:2365-2373.
Hasegawa et al., "Visualizing Mechanosensory Endings of TrkC-Expressing Neurons in HS3ST-2-hPLAP Mice," J Comp. Neurol., 511(4):543-556 (2008).
Hassan, et al., "Expression of Protooncogene c-kit and Its Ligand Stem Cell Factor (SCF) in Gastric Carcinoma Cell Lines," Digest. Dis. Science, (1998), 43:8-14.
Hayashi, et al., "Dichloro[1,1 19-bis(diphenylophosphino)ferrocene]palladium-(II), an Effective Catalyst for Cross-Coupling of Secondary and Primary Alkyl Grignard and Alkylzinc Reagents with Organic Halides," J. Am. Chem. Soc., (1984), 106:158-163.
Haydock et al., "Analogues of clofibrate and clobuzarit containing fluorine in the side chains," Eur. J. Med. Chem., (1984), 19(3):205-214.
He et al. "c-Fms Signaling Mediates Neurofibromatosis Type-1 Osteoclast Gain-in-Functions," PLoS ONE, (2012), 7(11): 1-9.
He, et al., "Gamma-secretase activating protein, a therapeutic target for Alzheimer's disease," Nature (2010) 467(7311):95-98.
Heacock et al., "Orientation and Relative Reaction Rate Factors in Aromatic Substitution by the Benzenesulfonimido Radical." J. Am. Chem. Soc., 1960, 82 (13), pp. 3460-3463.
Heim et al., Engineering green fluorescent protein for improved brightness, longer wavelengths and fluorescence resonance energy transfer. Curr Biol. 1996, 6:178-182.
Heinrich et al., PDGFRA activating mutations in gastrointestinal stromal tumors. Science 2003, 299:708-710.
Heinrich, M. C. et al., "Inhibition of KIT Tyrosine Kinase Activity: a Novel Molecular Approach to the Treatment of KIT-Positive Malignancies," J. Clin. Oncol., vol. 20, No. 6, pp. 1692-1703, Mar. 15, 2002.
Hentschel et al., 2012, www.ncbi.nlm.nih.gov/pubmed/2163917.
Herbst et al., "Differential Effects of W Mutations on p145c-kit tyrosine Kinase Activity and Substrate Interaction." The Journal of Biological Chemistry, 1992, pp. 13210-13216.
Hibi et al., Coexpression of the stem cell factor and the c-kit genes in small-cell lung cancer. Oncogene (1991), 6:2291-2296.
Hirota et al., Gain-of-function mutations of c-kit in human gastrointestinal stromal tumors. Science 1998, 279:577-580.
Hoffmann, "m-Trifluoromethylbenzenesulfonyl Chloride," Organic Syntheses, (1981), 60:121-126.

(56) References Cited

OTHER PUBLICATIONS

Hogaboam et al., Novel role of transmembrane SCF for mast cell activation and eotaxin production in mast cell-fibroblast interactions. J Immunol. 1998, 160:6166-6171.
Holmes et al., "Long-term effects of Aβ42 immunization in Alzheimer's disease: follow-up of a randomised, placebo-controlled phase I trail," Lancet (2008), 372:216-233.
Hood et al., "Tumor Regression by Targeted Gene Delivery to the Neovasculature," Science, (2002), 296: 2404-2407.
Houghten et al., "Generation and use of synthetic peptide combinatorial libraries for basic research and drug discovery." Nature 1991, 354, pp. 84-86.
Houghten, R., "Parallel Array and Mixture-Based Synthetic Combinatorial Chemistry: Tools for the Next Millennium," Annu Rev Pharmacol Toxicol., (2000), 40:273-282.
Houghten, R., "Peptide Libraries: Criteria and Trends" Trends Genet. (1993), 9:235-239.
Hudson, et al., "A Simple Method for the Determination of Serum Acid Phosphatase," J. Urology, (1947), 58:89-92.
Hughes-Jones et al., Synthesis of Rh Fv phage-antibodies using VH and VL germline genes. British Journal of Haematology, 1999, 105: 811-816.
Ibrahim et al., Caplus an 2007:11300.
Iemura, et al., "The c-kit Ligand, Stem Cell Factor, Promotes Mast Cell Survival by Suppressing Apoptosis," Amer. J. Pathol., (1994), 144:321-328.
Inoue, et al., "Coexpression of the c-kit Receptor and the Stem Cell Factor in Gynecological Tumors," Cancer Res., (1994), 54:3049-3053.
International Preliminary Report on Patentability and Written Opinion dated Nov. 9, 2011 in application PCT/US2010/033576.
International Preliminary Report on Patentability in International Application No. PCT/US2012/023543 dated Aug. 13, 2013.
International Search Report & Written Opinion dated Sep. 23, 2011 in PCT Application No. PCT/US2010/061601.
International Search Report and Written Opinion dated Sep. 2, 2009 for PCT International Application No. PCT/US2009/046598.
International Search Report and Written Opinion dated Feb. 18, 2010 for PCT Patent Application No. PCT/US2009/044151.
International Search Report and Written Opinion dated Jan. 14, 2011 in application PCT/US2010/055519.
International Search Report and Written Opinion dated Jun. 11, 2010 in application PCT/US2010/026816.
International Search Report and Written Opinion dated Jan. 25, 2011 in application PCT/US2010/057293.
International Search Report and Written Opinion dated Jun. 11, 2010 in application PCT/US2010/026856.
International Search Report and Written Opinion for PCT/US2013/032835 dated May 7, 2013.
International Search Report and Written Opinion for PCT/US2013/043400 dated Jul. 22, 2013.
International Search Report and Written Opinion of International Application No. PCT/US2004/042470, dated Nov. 22, 2005.
International Search Report and Written Opinion of International Application No. PCT/US2005/021231 dated Apr. 20, 2006.
International Search Report and Written Opinion of International Application No. PCT/US2006/018726 dated Apr. 4, 2007.
International Search Report and Written Opinion of International Application No. PCT/US2006/024361 dated Oct. 24, 2006.
International Search Report and Written Opinion of International Application No. PCT/US2006/024524 dated Oct. 24, 2006.
International Search Report and Written Opinion of International Application No. PCT/US2007/083910 dated Jun. 5, 2008.
International Search Report and Written Opinion of International Application No. PCT/US2007/085289 dated Jun. 5, 2008.
International Search Report and Written Opinion of International Application No. PCT/US2007/085299 dated Jul. 28, 2008.
International Search Report and Written Opinion of International Application No. PCT/US2007/088231 dated Jun. 4, 2008.
International Search Report and Written Opinion of International Application No. PCT/US2007/088237 dated Jun. 4, 2008.
International Search Report and Written Opinion of International Application No. PCT/US2007/088243 dated Jun. 5, 2008.
International Search Report and Written Opinion of International Application No. PCT/US2007/088412 dated Nov. 17, 2008.
International Search Report and Written Opinion of International Application No. PCT/US2007/088443 dated Jul. 25, 2008.
International Search Report and Written Opinion of International Application No. PCT/US2010/029489 dated Oct. 5, 2010.
International Search Report and Written Opinion of International Application No. PCT/US2012/023543, dated May 31, 2012.
International Search Report and Written Opinion of International Application No. PCT/US2012/025965 dated May 31, 2012.
International Search Report dated Dec. 19, 2011 in International PCT Application No. PCT/US2011/033192.
International Search Report dated Sep. 13, 2010 in application PCT/US2010/033571.
International Search Report for PCT/US2012/038417 dated Aug. 10, 2012 (4 pages).
Isbel, et al., "Local macrophage proliferation correlates with increased renal M-CSF expression in human glomerulonephritis," Nephrol Dial Transplant, (2001), 16:1638-1647.
Ishizaka, et al., "Human ret Proto-Oncogene Mapped to Chromosome 10q11.2," Oncogene, (1989), 4(12):1519-1521.
Isozaki et al., "Deficiency of c-kit cells in patients with a myopathic form of chronic idiopathic intestinal pseudo-obstruction," Amer. J. of Gast. 1997, 9:332-334.
Ivanisevic et al., "Uses of X-Ray Powder Diffraction in the Pharmaceutical Industry," Pharm Sci Encyc:DDDM, (2010), 1-42.
Iwane et al., "Myosin Subfragment-1 is Fully Equipped with Factors Essential for Motor Function," Biochem. and Biophys. Res. Comm., (1997), 230:76-80.
Izquierdo, et al., "Differential Expression of the c kit Proto-Oncogene in Germ Cel Tumours," J. Pathol., (1995), 177:253-258.
Jaiswal et al., "Combined Targeting of BRAF and CRAF or BRAF and PI3K Effector Pathways is Required for Efficacy in NRAS Mutant Tumors," PLoS One, 4(5):e5717 (2009).
Jarugula et al., Nonlinear Pharmacokinetics of 5-Fluorouracil in Rats. J Pharm Sci 1997, 86(6):756-757.
Jensen et al., "Pharmacological targeting of the KIT growth factor receptor: a therapeutic consideration for mast cell disorders." Br J Pharmacol. 2008, 154, 1572-1582.
Jing, et al., "GDNF-Induced Activation of the Ret Protein Tyrosine Kinase is Mediated by GDNFR-a, a Novel Receptor for GDNF," Cell, (1996), 85:1113-1124.
Johann, et al., "GLVR1, a Receptor for gibbon Ape Leukemia Virus, Is Homologous to a Phosphate Permease of Neurospora crassa and is Expressed at High Levels in the Brain and Thymus," J. Virol., (1992), 66:1635-1640.
Johnson et al., "Relationships between drug activity in NCI preclinical in vitro and in vivo models and early clinical trials," British Journal of Cancer (2001) 64(1 0): 1424-1431.
Johnston, M., Gene chips: array of hope for understanding gene regulation. Curr Biol 1998, 8:R171-R174.
Jones et al., "Antiestrogens. 2. Structure-activity studies in a series of 3-aroyl-2-arylbenzo[b]thiophene derivatives leading to [6-hydroxy-2-(4-hydroxyphenyl)benzo[b]thien-3-yl]-[4-[2-(1-piperidinyl)ethoxy]phenyl]methanone hydrochloride (LY 156758) . . . " J. Med. Chem., 1984, 27(8), pp. 1057-1066.
Jones, R., "Biology and Treatment of Chronic Myeloid Leukemia," Curr. Opin. Onc., (1997), 9:3-7.
Jones, T., Interactive computer graphics: FRODO. Methods in Enzymology 1985, 115:157-171.
Jongh et al. Anesth Analg (2003), vol. 96, pp. 1096-1103.
Jose et al., "Blockade or Macrophage colony-Stimulating Factor Reduces Macrophage Proliferation and Accumulation in Renal Allograft Rejection," Am J Transplant 2003, 3(3):294-300.
Joseph-McCarthy, D., Computational approaches to structure-based ligand design. Pharmacology & Therapeutics., 1999, 84:179-191.
Kahl et al., A Multiple-Approach Scintillation Proximity Assay to Measure the Association Between Ras and Raf, Anal. Biochem. (1996), 243:282-283.

(56) References Cited

OTHER PUBLICATIONS

Kassel, et al., "Local increase in the number of mast cells and expression of nerve growth factor in the bronchus of asthmatic patients after repeated inhalation of allergen at low-dose," Clin. Exp. Allergy, (2001), 31:1432-1440.
Katritzky et al., Regiospecific C-acylation of pyrroles and indoles using N-acylbenzotriazoles. J Org Chem 2003, 68:5720-5723.
Kay, et al., "Eosinophils and Eosinophil-Associated Cytokines in Allergic Inflammation," Int. Arch. Aller. Immunol., (1997), 113:196-199.
Kern et al., Direct Hybridization of Large-Insert Genomic Clones on High-Density Gridded cDNA Filter Arrays. BioTechniques 1997, 23:120-124.
Khazak et al., 2012, www.ncbu.nlm.nih.gov/pms/articles/PMC2720036.
Kim et al., "A Merger of Rational Drug Design and Combinatorial Chemistry: Development and Application of Peptide Secondary Structure Mimetics," Combinatorial Chemistry & High Throughput Screening (2000), 3:167-183.
Kim et al., Database CAS on STN (Columbus, Oh, USA) No. 138:55974, Preparation of 2-anilino-4-indolyl pyrimidines as tyrosine kinase inhibitors, abstract, 2002) see whole article.
Kinashi et al., "Steel Factor and c-kit Cell-Matrix Adhesion," Blood, (1994), 83:1033-1038.
Kirkpatrick et al., "Structure-Based Drug Design: Combinatorial Chemistry and Molecular Modeling," Combinatorial Chemistry & High Throughput Screening (1999), 2:211-221.
Kitamura et al., Synthesis of Quinolines and 2H-Dihydropyrroles by Nucleophilic Substitution at the Nitrogen Atom of Oxime Derivatives. Synthesis 2003, 15:2415-2426.
Kline, et al., "Studies by 1H Nuclear Magnetic Resonance and Distance Geometry of the Solution Conformation of the x-Amylase Inhibitor Tendamistat," J. Mol. Biol., (1986), 189:377-382.
Knighton, et al., "Structural Basis of the Intrasteric Regulation of Myosin Light Chain Kinases," Science, (1992), 258:130-135.
Kodama et al., Congenital osteoclast deficiency in osteopetrotic (op/op) mice is cured by injections of macrophage colony-stimulating factor. J Exp Med. 1991, 173:269-272.
Kolaskar et al., A semi-empirical method for prediction of antigenic determinants on protein antigens. FEBS Lett. (1990), 276:172-174.
Komoyira et al., "Design, synthesis and biological activity of amidinobicyclic compounds (derivatives of DX-9065a) as a factor Xa inhibitors: SAR study of S1 and aryl binding sites," Bioorg. Med. Chem. 2004, 12:2099-2114.
Kondoh et al., Establishment and further characterization of a line of transgenic mice showing testicular tumorigenesis at 100% incidence. J Urol 1994, 152:2151-2154.
Kondoh et al., Very high incidence of germ cell tumorigenesis (seminomagenesis) in human papillomavirus type 16 transgenic mice. J Virol 1991, 65:3335-3339.
Kondoh, et al., "An in vivo model for receptor tyrosine kinase autocrine/paracrine activation: auto-stimulated Kit receptor acts as a tumor promoting factor in papillomavirus-induced tumorigenesis," Oncogene, (1995), 10:341-347.
Konishi, et al., "Overexpression of leucocyte common antigen (LAR) P-subunit in thyroid carcinomas," Brit J Cancer, (2003), 88:1223-1228.
Konno et al., "Influence of Different Polymers on the Crystallization Tendency of Molecularly Dispersed Amorphous Felodipine," Journal of Pharmaceutical Sciences 95(12):2692-2705 (2006).
Kroll et al., "A Malfunctional Prokaryotic Protein Expression System: Overproduction, Affinity Purification, and Selective Detection," DNA Cell. Biol., (1993), 12:441-453.
Kubo et al., "Resequencing Analysis of the Human Tyrosine Kinase Gene Family in Pancreatic Cancer," Pancreas, 38(7):e200-e206, (2009).
Kubo et al., "Resequencing and copy number analysis of the human tyrosine kinase gene family in poorly differentiated gastric cancer," Carcinogenesis, 30(11): 1857-64 (2009).

Kundu, et al., "Combinatorial Chemistry: Polymer Supported Synthesis of Peptide and Non-Peptide Libraries" Progress in Drug Research 53:89-156 (1999).
Kunisada et al., "Murine Cutaneous Mastocytosis and Epidermal Melanocytosis Induced by Keratinocyte Expression of Transgenic Stem Cell Factor." J Exp Med. 1998, 187(10):1565-1573.
Kunkel, T., "Rapid and Efficient Site-Specific Mutagenesis Without Phenotypic Selection," Proc. Natl. Acad. Sci. USA, (1985), 82:488-492.
Kunnimalaiyaan, et al., "The Raf-1 pathway: a molecular target for treatment of select neuroendocrine tumors?" Anticancer Drugs, (2006), 17(2):139-42.
Kuntz et al., A geometric approach to macromolecule-ligand interactions. J Mol Biol. 1982, 25;161(2):269-288.
Kuntz et al., Structure-Based Molecular Design. Acc. Chem. Res. 1994, 27:117-123.
Lahm et al., Interleukin 4 down-regulates expression of c-kit and autocrine stem cell factor in human colorectal carcinoma cells. Cell Growth & Differ 1995, 6:1111-1118.
Lala et al., Role of nitric oxide in tumor progression: lessons from experimental tumors. Cancer and Metastasis Reviews 1998, 17:91-106.
Lam et al., A new type of synthetic peptide library for identifying ligand-binding activity. Nature (1991), 354:82-84.
Lambros et al., "Genomic profile of a secretory breast cancer with an ETV6-NTRK3 duplication," J. Clin. Pathol., 62(7):604-12 (2009).
Langham et al., "Metalation and Halogen-Metal Interconversion Reactions of Some Halogenated Phenyl Ethers," J. of the Am. Chem. Society, (1941), 63:545-549.
Lawicki et al., "The pretreatment plasma level and diagnostic utility of M-CSF in benign breast tumor and breast cancer patients." Clin Chim Acta. 2006;371:112-116.
Layzer, "Degenerative Diseases of the Nervous System," Cecil Textbook of Medicine, 20th Edition, vol. 2, pp. 2050-2057 (1996).
Le Meur, et al., "Macrophage accumulation at a site of renal inflammation is dependent on the M-CSF/c-fms pathway," J Leukocyte Biology, (2002), 72:530-537.
Lebl et al., "One-bead-one-structure combinatorial libraries." Biopolymers 1995, 37, pp. 177-198.
Lee et al., "FMS-like tyrosine kinase 3 inhibitors: a patent review," Expert Opinion Ther. Patents (2011), 21 (4), pp. 483-503.
Lee et al., "HLA-DR-Triggered Inhibition of Hemopoiesis Involves Fas/Fas Ligand Interactions and is Prevented by c-kit Ligand," J. Immunol., (1997), 159:3211-3219.
Lee et al., Mast cells: a cellular link between autoantibodies and inflammatory arthritis. Science 2002, 297:1689-1692.
Leuner, et al., "Improving drug solubility for oral delivery using solid dispersions," European Journal of Pharma. and Biopharma., (2000), 50(1):47-60.
Levin et al., "Neoplasms of the Central Nervous System," Cancer Principles & Practice of Oncology (1997), 2:2022-2082.
Levis et al., "A FLT3 tyrosine kinase inhibitor is selectively cytotoxic to acute myeloid leukemia blasts harboring FL T3 internal tandem duplication mutations," Blood, 98:885-887 (2001).
Li, et al., "Abrogation of c-kit/Steel Factor-Dependent Tumorigenesis by Kinase Defective Mutants of the c-kit Receptor: c-kit Kinase Defective Mutants as Candidate Tools for Cancer Gene Therapy," Canc. Res., (1996), 56:4343-4346.
Libby, P., Inflammation in atherosclerosis. Nature (2002), 420:868-874.
Liparoto et al., "Biosensor Analysis of the Interleukin-2 Receptor Complex," Journal of Molecular Recognition, (1999), 12:316-321.
Lipinski et al., Experimental and computational approaches to estimate solubility and permeability in drug discovery and development settings. Advanced Drug Delivery Reviews 1997, 23:3-25.
Lipschultz et al., Experimental design for analysis of complex kinetics using surface plasmon resonance. Methods 2000, 20(3):310-318.
Liu et al., "Sorafenib blocks the RAF/MEK/ERK pathway, inhibits tumor angiogenesis, and induces tumor cell apoptosis in hepatocellular carcinoma model PLC/PRF/5," Cancer Res. (2006), 66:11852-11858.

(56) References Cited

OTHER PUBLICATIONS

Liu, et al., "CD68 Expression is Markedly Different in Crohn's Disease and the Colitis Associated with Chronic Granulomatous Disease," Inflamm. Bowel Dis., (2009), 15(8): 1213-1217.
London et al., "Expression of Stem Cell Factor Receptor (c-kit) by the Malignant Mast Cells from Spontaneous Canine Mast Cell Tumors," J. Compar. Pathol. 1996, 115:399-414.
Longley et al., "Altered metabolism of mast-cell growth factor (c-kit ligand) in cutaneous mastocytosis." N Engl J Med. 1993, 328:1302-1307.
Longley et al., Chymase cleavage of stem cell factor yields a bioactive, soluble product. Proc Natl Acad Sci 1997, 94:9017-9021.
Longley, et al., "Somatic c-KIT Activating Mutation in Urticaria Pigmentosa and Aggressive Mastocytosis: Establishment of Clonality in a Human Mast Cell Neoplasm," Nat. Gen., (1996), 12:312-314.
Louvet et al., "Tyrosine kinase inhibitors reverse type 1 diabetes in nonobese diabetic mice," Proc. Nat. Acad. Sci., (2008), 105(48): 18895-18900.
Loveland et al., Stem Cell Factor and c-kit in the Mammalian Testis: Lessons Originating from Mother Nature 19s Gene Knockouts. J. Endocrinol (1997), 153:337-344.
Lu et al., "Oriented Immobilization of Fab' Fragments on Silica Surfaces." Anal. Chem., 1995, 67(1), pp. 83-87.
Lukacs et al., Stem cell factor (c-kit ligand) influences eosinophil recruitment and histamine levels in allergic airway inflammation. J Immunol. 1996, 156:3945-3951.
Luo et al., Close linkage with the RET proto-oncogene and boundaries of deletion mutations in autosomal dominant Hirschsprung disease. Hum Mol Genet 1993, 2(11):1803-1808.
Lyman et al., c-kit Ligand and Flt3 Ligand: Stem/Progenitor Cell Factors With Overlapping Yet Distinct Activities. Blood (1998), 91: 1101-1134.
Ma et al., Indolinone derivatives inhibit constitutively activated KIT mutants and kill neoplastic mast cells. J Invest Dermatol 2000, 114:392-394.
Ma et al., The c-KIT Mutation Causing Human Mastocytosis is Resistant to ST1571 and Other Kit Kinase Inhibitors; Kinases with Enzymatic Site Mutations Show Different Inhibitor Sensitivity Profiles Than Wild-type Kinases and Those With Regulatory-Type Mutations. Blood (2002), 99:1741-1744.
Machens et al., Modification of multiple endocrine neoplasia 2A phenotype by cell membrane proximity of RET mutations in exon 10. Endocrine-Related Cancer 2009, 16:171-177.
Machida et al., Mitogen-activated protein kinase kinase kinase kinase 4 as a putative effector of Rap2 to activate the c-Jun N-terminal kinase. J. Biol. Chem. (2004), 279:15711-15714.
Mack et al., Functional identification of kinases essential for T-cell activation through a genetic suppression screen. Immunol Lett. 2005, 96:129-145.
Madden et al., "Synthetic Combinatorial Libraries: Views on Techniques and Their Application" Perspectives in Drug Discovery and Design (1994), 2:269-285.
Madhusdan et al., Clinical Biochemistry, 2004, 37, 618-635.
Malaysian Examination Report dated Aug. 15, 2012 in Malaysian Application Serial No. PI20092547.
Malaysian Substantive Examination Report dated Aug. 15, 2012 in Malaysian Application Serial No. PI20092040.
Malmborg et al., BIAcore as a tool in antibody engineering. Journal of Immunological Methods 1995, 183:7-13.
Malmqvist et al., Biomolecular interaction analysis: affinity biosensor technologies for functional analysis of proteins. Current Opinion in Chemical Biology 1997, 1:378-383.
Malmqvist, M., "BIACORE: an Affinity Biosensor System for Characterization of Biomolecular Interactions," Biochemical Society Transactions (1999), 27:335-340.
Marchetti et al., "Frequent Mutations in the Neurotrophic Tyrosine Receptor Kinase Gene Family in Large Cell Neuroendocrine Carcinoma of the Lung," Hum. Mutat., 29(5):609-16(2008).

Markiewicz, et al., "Synthetic Oligonucleotide Combinatorial Libraries and Their Applications," II Farmaco, (2000), 55:174-177.
Marshall, et al., "Blockade of colony stimulating Factor-1 (CSF-1) Leads to inhibition of DSS-induced colitis," Inflamm. Bowel Dis., (2007), 13(2): 219-224.
Martin, Y., "Computer-Assisted Rational Drug Design," Methods Enz. (1991), 203:587-613.
Matayoshi et al., "Actions of brain-derived neurotrophic factor on spinal nociceptive transmission during inflammation in the rat." J Physiol. 2005, 569, pp. 685-695.
Matsumoto et al., Physical properties of solid molecular dispersions of indomethacin with poly(vinylpyrrolindone) and poly(vinylpyrrolidone-co-vinyl-acetate) in relation to indomethacin crystallization. Pharmaceutical Research 1999, 16(11):1722-1728.
Mazeas, et al., "Synthesis of new melatoninergic ligands including azaindole moiety," Heterocycles, (1999), 50:1065-1080.
McCall, et al., "Characterization of Anti-Mouse FcγRII Single-Chain Fv Fragments Derived from Human Phage Display Libraries," Immunotechnology, (1998), 4:71-87.
McDermott et al.,"Identification of genotype-correlated sensitivity to selective kinase inhibitors by using high throughput tumor cell line profiling." PNAS, 104(50): 19936-19941 (2007).
McPherson, A., "Current Approaches to Macromolecule Crystallization," Eur. J. Biochem., (1990), 189:1-23.
Mekori et al., "The Role of c-Kit and Its Ligand, Stem Cell Factor, in Mast Cell Apoptosis," Int. Arch. Allergy Immunol. (1995), 107:136-138.
Mekori, et al., "Transforming Growth Factor-β Prevents Stem Cell Factor-Mediated Rescue of Mast Cells from Apoptosis After IL-3 Deprivation," J. Immunol., (1994), 153:2194-2203.
Meltzer, E.O., "The pharmacological basis for the treatment of perennial allergic rhinitis and non-allergic rhinitis with topical corticosteroids," Aller., (1997), 52:33-40.
Meng, E.C., Automated Docking with Grid-Based Energy Evaluation, J. Comp Chem., (1992), 13:505-524.
Menke et al., "Sunlight triggers cutaneous lupus through a CSF-1-dependent mechanism in MRL-Fas1pr mice," Journal of Immunology , (2008), 181: 7367-7379.
Merour, et al., "Synthesis and Reactivity of 7-Azaindoles (1H-Pyrrolo[2,3-b]pyridine)," Curr. Org. Chem., (2001), 5:471-506.
Merritt, A., Solution phase combinatorial chemistry. Comb. Chem. High Throughput Screening, (1998), 1, 57-72.
Metcalf, D., Lineage commitment in the progeny of murine hematopoietic preprogenitor cells: Influence of thrombopoietin and interleukin 5. Proc. Natl. Acad. Sci. 1998, 95:6408-6412.
Metcalfe et al., Mast cells. Physiol Rev. 1997, 77:1033-1079.
Metcalfe, D. "Classification and Diagnosis of Mastocytosis: Current Status," J. Invest. Derm., (1991), 93:2S-4S.
Mettey et al., "Aloisines, a New family of CDK.GSK-3 Inhibitors. SAR Study, Crystal Structure in Complex with CDK2, Enzyme Selectivity, and Cellular Effects," J. Med. Chem., 46:222-236 (2003).
Meula Pomeda, et al., "Efecto De Codisolventes Y Dispersiones Solida De Polivinilpirrolidona K-30 En La Solubilidad Tel Tiabendazol," Departamento de Farmacia y Tecnologia Farmaceutica. Facultad de Farmacia. Universidad de Alcala, pp. 85-87 (2002) (No English Translation Available).
Miller et al., "FLOG, a System to Select Quasi-Flexible Ligands Complementary to a Receptor of Known Three-Dimensional Structure." J. Comp. Aided Molec. Design, 1994, 8:153-174.
Minakata et al., "Functionalization of 1H-Pyrrolo[2,3-b]pyridine." Bulletin of the Chemical Society of Japan (1992), 65(11): 2992-2997.
Minakata, et al., "Regioselective Functionalization of 1H-Pyrrolo[2,3-b]pyridine via its N-Oxide," Synthesis, (1992), 661-663.
Miranker, at al., "Functionality Maps of Binding Sites: a Multiple Copy Simultaneous Search Method," Proteins: Structure, Function, and Genetics, (1991), 11:29-34.
Mitra et al., Fluorescence resonance energy transfer between blue-emitting and red-shifted excitation derivatives of the green fluorescent protein. Gene 1996, 173:13-17.
Miyaura et al., Palladium-Catalyzed Cross-Coupling Reactions of Organoboron Compounds. Chem. Rev. 1995, 95:2457-2483.

(56) References Cited

OTHER PUBLICATIONS

Mokhtari et al., Potential utility of small tyrosine kinase inhibitors in the treatment of diabetes. Clinical Science 2010; 118(4):241-247.
Mol et al., Structural basis for the autoinhibition and STI-571 inhibition of c-Kit tyrosine kinase. J Biol Chem 2004, 279:31655-31663.
Mol et al., Structure of a c-kit product complex reveals the basis for kinase transactivation. J Biol Chem 2003, 278:31461-31464.
Morgan, et al., "Isolation and Characterization of a Cloned Growth Factor Dependent Macrophage Cell Line, BAC1.2F5," J. of Cell. Physiology, (1987), 130:420-427.
Motoyoshi, K., Biological activities and clinical application of M-CSF. Int J Hematol. 1998, 67:109-122.
Murphy, et al., "Expression of macrophage colony-stimulating factor receptor is increased in the A?PPV717F transgenic mouse model of Alzheimer's disease," Am. J. of Pathology, (2000), 157:(3) 895-904.
Murty, et al., "A Genetic Perspective of Male Germ Cell Tumors," Sem. Oncol., (1998), 25:133-144.
Naclerio et al., Rhinitis and Inhalant Allergens. JAMA. 1997, 278:1842-1848.
Nagafuji et al., "A General Synthesis of Pyrroles and Fused Pyrrole Systems from Ketones and Amino Acids," J. Org. Chem., (1996), 61:4999-5003.
Nagata et al., Elevated expression of the proto-oncogene c-kit in patients with mastocytosis. Leukemia (1998), 12:175-181.
Nahm et al., N-methoxy-N-methylamides as effective acylating agents. Tetrahedron Lett. 1981, 22(39):3815-3818.
Nakagawara et al., Expression and Function of TRK-B an BDNF in Human Neuroblastomas. Mol. Cell Biol. (1994), 14:759-767.
Nakai et al., "New Potent Antagonists of Leukotrienes C4 and D4. 01. Synthesis and Structure-Activity Relationships," J. Med. Chem., (1988), 31:(1):84-91.
Nassentein et al., The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma. J. Exp. Med. (2003), 198:455-467.
Natali, et al., "Breast cancer is associated with loss of the c-kit oncogene product," Int. J. Cancer (1992) 52:713-717.
Navaza, J., AMoRe: an automated package for molecular replacement. Acta Cryst. (1994), A50:157-163.
Neidle et al., "Molecular Modeling to Study DNA Intercalation by Anti-Tumor Drugs" Methods Enz. (1991), 203:433-458.
Ng et al., Engineering protein-lipid interactions: targeting of histidine-tagged proteins to metal-chelating lipid monolayers. Langmuir (1995), 11:4048-4055.
Nicholls et al., Protein folding and association: insights from the interfacial and thermodynamic properties of hydrocarbons. Proteins 1991, 11:281-296.
Nichols et al., "Development of a Scintillation Proximity Assay for Peroxisome Proliferator-Activated Receptor y Ligand Binding Domain," Anal. Biochem., (1998), 257:112-119.
Niihori, et al., "Germline KRAS and BRAF mutations in cardio-facio-cutaneous syndrome," Nature Genet., (2006), 38(3):294-296.
Non-Final Office Action dated Feb. 3, 2011 in U.S. Appl. No. 12/467,194.
Non-Final Office Action dated Jan. 20, 2011 for U.S. Appl. No. 12/733,798.
Non-Final Office Action dated May 13, 2011 in U.S. Appl. No. 12/721,500.
Notice of Allowance and Fees Due dated Dec. 6, 2011 in U.S. Appl. No. 12/467,194.
Notice of Allowance and Fees Due dated Nov. 3, 2011 in U.S. Appl. No. 12/721,500.
Notice of Allowance for U.S. Appl. No. 12/082,665 dated Jul. 26, 2011.
Notification on the Result of Substantive Examination (wEnglish Translation) dated Oct. 17, 2014 for Vietnamese Application No. 1-2010-02238.
Notification Prior to Examination (English translation) dated May 4, 2010 for IL Application No. 199194.
O'Shannessy et al., Interpretation of deviations from pseudo-first-order kinetic behavior in the characterization of ligand binding by biosensor technology. Analytical Biochemistry (1996), 236:275-283.
O'Shannessy, D., Determination of kinetic rate and equilibrium binding constants for macromolecular interactions: a critique of the surface plasmon resonance literature. Current Opinions in Biotechnology 1994, 5:65-71.
Ochs et al., A phase I/II trial of recombinant methionyl human brain derived neurotrophic factor administered by intrathecal infusion to patients with amyotrophic lateral sclerosis. Amyotroph Lateral Scler Other Motor Neuron Disord. 2000, 1:201-206.
Odegaard et al. "Macrophage-specific PPARg controls alternative activation and improves insulin resistance," Nature, (2007), 447: 1116-1121.
Office Action dated Mar. 23, 2014 for Australian Application No. 2012214762.
Office Action dated Jul. 8, 2014 for Chinese Application No. 2012800170177.
Office Action dated Jul. 26, 2011 in Russian application No. 2009117475/04.
Office Action for European Patent Application No. 12745360.3 dated Sep. 7, 2017. (4 pages).
Office Action for Japanese Patent Application No. 2017-080199 dated Nov. 14, 2017. (4 pages).
Office Action for Mexican Patent Application No. MX/a/2013/009068 dated Oct. 9, 2017. (6 pages).
Office Action for Thai Application No. 1301004352 dated Sep. 29, 2014.
Office Action for Ukraine Application No. A200800780 dated Jul. 12, 2010.
Office Action in Australian Application No. 2006261993 dated Aug. 15, 2011.
Office Action in Canadian Application No. 2,738,573 dated Jan. 10, 2012.
Office Action in Chilean Application No. 3326-2007 dated Sep. 28, 2011.
Office Action in Chinese Application No. 200780050245.3 dated Jul. 20, 2011.
Office Action in Colombian Application No. 08-005.567 dated Sep. 9, 2011.
Office Action in Dominican Republic Application No. P2011-0291 dated Apr. 23, 2012 (English Translation).
Office Action in Israeli Application No. 198624 dated Apr. 18, 2012 (English Translation).
Office Action in Japanese Application No. 2006-545481 dated Oct. 27, 2011.
Office Action in Japanese Application No. 2008-518402 dated Nov. 29, 2011 (English Translation).
Office Action in Japanese Application No. 2009-538496 dated Jan. 29, 2013.
Office Action in Japanese Application No. 2009-538496 dated Aug. 20, 2013.
Office Action in Japanese Application No. 2013-552610 dated Nov. 4, 2014.
Office Action in Malaysian Application No. PI2011004969 dated Apr. 30, 2014.
Office Action in Mexican Application No. MX/a/2009/006162 dated Sep. 8, 2011.
Office Action in New Zealand Application No. 577612 dated Mar. 21, 2012.
Office Action in Norwegian Application No. 20076659 dated Aug. 15, 2012 (With English Translation).
Office Action in Peruvian Application No. 1602-2007 dated Sep. 2, 2011.
Office Action in Peruvian Application No. 1796-2007 dated Sep. 15, 2011.
Office Action in Philippine Application No. 1-2009-501241 dated Jul. 27, 2012.
Office Action in Philippine Application No. 12009501009 dated Jul. 27, 2012.

(56) References Cited

OTHER PUBLICATIONS

Office Action in Philippine Application No. 12009501009 dated Nov. 24, 2011.
Office Action in Taiwan Application No. 095122373 dated Dec. 9, 2011 (English Translation).
Office Action in Taiwan Application No. 099110011 dated Jun. 26, 2012 (With English Translation).
Office Action in Taiwan Application No. 102123382 dated Nov. 16, 2013.
Ohno, et al. "A c-fms tyrosine kinase inhibitor, KI202227, suppresses osteoclast differentiation and osteolytic bone destruction in a bone metastasis model," Mol. Cancer Ther., (2006), 5(11):2634-2643. 2634-43, 5, 2006.
Ohno, et al., "The orally-active and selective c_FMS tyrosine kinase inhibitor Ki20227 inhibits disease progression in a collagen-induced arthritis mouse model," Eur. J Immunol., (2008), 38: 1-9.
Okada et al., "Gene therapy against an experimental glioma using adeno-associated virus vectors." Gene Ther. 1996, 3:957-964.
Okayama et al., Activation of Eosinophils with Cytokines Produced by Lung Mast Cells. Int Arch Allergy Immunol 1997, 114(suppl 1):75-77.
Okayama, et al., "Human Lung Mast Cells are Enriched in the Capacity to Produce Granulocyte-Macrophage Colony-Stimulating Factor in Response to IgE-Dependent Stimulation," Eur. J. Immunol., (1998), 28:708-715.
Olah et al., "Synthetic Methods and Reactions: Part 209. Improved Preparation of Aldehydes and Ketones from N,N-Dimethylamides and Grignard Reagents," Synthesis (1984), 228-230.
Ottoni et al., Efficient and simple methods for the introduction of the sulfonyl, acyl and alkyl protecting groups on the nitrogen of indole and its derivatives. Tetrahedron 1998, 54:13915-13928.
Otwinowski, Z., Maximum likelihood refinement of heavy atom parameters. Dept. of Molecular Biophysics and Biochemistry 1991, 80-86.
Owicki et al., "Application of Fluorescence Polarization Assays in High-Throughput Screening," Genetic Engineering News (1997), 17:27.
Panitumumab, clinicaltrials.gov/ct2/show/NCT0132054, 2012.
Parker et al., Development of high throughput screening assays using fluorescence polarization: nuclear receptor-ligand-binding and kinase/phosphatase assays. J Biomol Screen. 2000, 5:77-88.
Patani et al., Bioisosterism: a Rational Approach in Drug Design. Chem Rev. 1996, 96:3147-3176.
Pearce et al., Failure modes in anticancer drug discovery and development, Cancer Drug Design and Discovery Edited by Stephen Neidle, Chapter 18, pp. 424-435 (2008).
Perrin, D., Nucleic Acids for Recognition and Catalysis Landmarks, Limitations, and Looking to the Future. Combinatorial Chemistry & High Throughput Screening 2000, 3:243-269.
Petty et al., The effect of systemically administered recombinant human nerve growth factor in healthy human subjects. Ann Neurol. 1994, 36:244-246.
Pflugrath et al., Crystal Structure Determination, Refinement and the Molecular Model of the x-Amylase Inhibitor Hoe-467A, J. Mol. Biol. (1986), 189:383-386.
Pierce et al., "Local anesthetics. I. beta-Monoaklylaminoethyl Esters of Alkoxybenzoic Acids," J. Am. Chem. Soc., (1942), 64:1691-1694.
Pignon, J.M., C-kit mutations and mast cell disorders a model of activating mutations of growth factor receptors. Hermatol Cell Ther (1997), 39:114-116.
Plunkett et al., "A silicon-based linker for traceless solid-phase synthesis," J. Org. Chem. (1995), 60:6006-6007.
Poul et al., "Selection of Tumor-Specific Internalizing Human Antibodies from Phage Libraries," J. Mol. Biol., (2000), 301:1149-1161.
Poulikakos et al., "RAF inhibitors transactivate RAF dimers and ERK signalling in cells with wild-type BRAF," Nature, 2010, 464, pp. 427-430.
Prada et al., "Neurofibroma-associated Macrophages Play Roles in Tumor Growth and Response to Pharmacological Inhibition," Acta Neuropathol, (2013), 125: 159-168.
Pratilas et al., Hcaplus 2008:670875 "Marker genes showing changes in levels of expression in response to antineoplastic drug therapy and their use in selection of chemotherapy", 2008.
Price et al., Summary report on the ISOBM TD-4 Workshop: analysis of 56 monoclonal antibodies against the MUC1 mucin. Tumour Biol, 1996, 19:1-20.
Prien, "Target-family-oriented focused libraries for kinases—Conceptual design aspects and commercial availability," ChemBioChem, 6:500-505, 2005.
Qiao, et al., "Role of Macrophage Colony-Stimulating Factor in Atherosclerosis," Am. J. Path., (1997), 150:1687-1699.
Rajavashisth et al., Heterozygous osteopetrotic (op) mutation reduces atherosclerosis in LDL receptor- deficient mice. J Clin Invest. 1998, 101:2702-2710.
Rajpert-De Meyts et al., Expression of the c-kit protein product in carcinoma-in-situ and invasive testicular germ cell tumours. Int J Androl. 1994, 17:85-92.
Rapp et al., "Raf kinases in lung tumor development," Advan. Enzyme Regul. (2003) 43:183-195.
Remington: The Science and Practice of Pharmacy, vol. II, pp. 1454-1460 (1995).
Ricotti et al., c-kit is expressed in soft tissue sarcoma of neuroectodermic origin and its ligand prevents apoptosis of neoplastic cells. Blood 1998, 91:2397-2405.
Ridge, et al., "FMS mutations in myelodysplastic, leukemic, and normal subjects," Proc. Nat. Acad. Sci., (1990), 87:1377-1380.
Ritz, et al., "Elevated blood levels of inflammatory monocytes (CD14+CD16+) in patients with complex regional pain syndrome," Clin. Exper. Immunology, (2011), 1-10.
Roberts et al., Targeting the Raf-MEK-ERK mitogen-activated protein kinase cascade for the treatment of cancer. Oncogene (2007), 26: 3291-3310.
Roberts et al., Generation of an antibody with enhanced affinity and specificity for its antigen by protein engineering. Nature. 1987, 328:731-734.
Robinson et al., Activated BRAF induces gliomas in mice when combined with Ink4a/Arf loss or Akt activation, Oncogene, 29(3), 335-344, 2010.
Robinson et al., Stimulation of Bone Marrow Colony Growth In Vitro by Human Urine. Blood 1969, 33:396-399.
Robison, et al., "7-Azaindole. I. Synthesis and Conversion to 7-Azatryptophan and Other Derivatives," J. Am. Chem. Soc., (1955), 77:457-460.
Rodan et al., Therapeutic approaches to bone diseases. Science 2000, 289:1508-1514.
Rodriguez-Viciana et al., Germline mutations in genes within the MAPK pathway cause cardio-facio-cutaneous syndrome. Science 2006, 311:1287-1290.
Rosenfeld, M.A., Human artificial chromosomes get real. Nat Genet (1997), 15:333-335.
Rosnet et al., "Isolation and Chromosomal Localization of a Novel FMS-like Tyrosine Kinase Gene," Genomics, 9: 380-385 (1991).
Ryan, et al., "Role for the Stem Cell Factor/KIT Complex in Schwann Cell Neoplasia and Mast Cell Proliferation Associated with Neurofibromatosis," J. Neuro. Res. (1994), 37:415-432.
Saify et al., Database CAS on STN (Columbus, OH, USA) No. 124:170379, Synthesis of some 2-azaindole derivatives: their cyctotoxicity and antibacterial activity, abstract, (1996), See RN 271-63-6.
Saify et al., Synthesis of some 7-azaindole derivatives: Their cytotoxicity and antibacterial activity, Pakistan Journal of Scientific and Industrial Research 1994, 37(10): 439-441.
Saiki, R.K. Amplification of genomic DNA. PCR Protocols: a Guide to Methods and Applications. 1990, 13-20.
Sambrook et al., Introduction of Recombinant Vectors into Mammalian Cells. Molecular Cloning: a Laboratory Manual (1989), 2:16.30-16.37.
Sandlow et al., Expression of c-kit and its ligand, stem cell factor, in normal and subfertile human testicular tissue. J. Androl. 1996, 17:403-408.

(56) References Cited

OTHER PUBLICATIONS

Santoro et al., The ret proto-oncogene is consistently expressed in human pheochromocytomas and thyroid medullary carcinomas. Oncogene. 1990, 5(10):1595-1598.
Sathornsumetee et al., AAL881, a novel small molecule inhibitor of RAF and vascular endothelial growth factor receptor activities, blocks the growth of malignant glioma. Cancer Res. 2006, 66:8722-8730.
Sawada et al., Role of cytokines in leukemic type growth of myelodysplastic CD34+ cells. Blood 1996, 88:319-327.
Sawada, et al., "4-(Benzoylindolizinyl)butyric acids; Novel nonsteroidal inhibitors of steroid 5;1-reductase. III," Chemical and Pharmaceutical Bulletin, (2001), 49(7):799-813.
Sawai et al., Aberrant growth of granulocyte-macrophage progenitors in juvenile chronic myelogenous leukemia in serum-free culture. Exp. Hem. 1996, 2:116-122.
Scheffner et al., "The E6 Oncoprotein Encoded by Human Papillomavirus Types 16 and 18 Promotes the Degredation of p53," Cell, (1990), 63:1129-1136.
Schiemann et al., "p-Fluorobenzoic Acid," Org. Syn. Coll., (1943), 2:299-301.
Schneider, et al., "Functional Purification of a Bacterial ATP-Binding Cassette Transporter Protein (MaIK) from the Cytoplasmic Fraction of an Overproducing Strain," Protein Expr. Purif., (1995), 6:10-14.
Schneller, et al., "Synthesis of 4-Amino-1 H-pyrrolo[2,3-b]pyridine {1,7-Dideazaadenine} and 1H-Pyrrolo[2,3-b]pyridine-4-ol (1,7-Dideazahypoxanthine)," J. Org. Chem., (1980), 45:4045-4048.
Schuhmann, et al., "Immobilization of Enzymes on Langmuir-Blodgett Films via a Membrane-Bound Receptor. Possible Applications for Amperometric Biosensors" Adv. Mater. (1991), 3:388-391.
Schummer et al., Inexpensive handheld device for the construction of high-density nucleic acid arrays. Biotechniques 1997, 23:1087-1092.
Schweizer et al., Combinatorial synthesis of carbohydrates. Curr. Opin. Chem. Biol. 1999, 3(3):291-298.
Sclabas et al., Overexpression of Tropomysin-Related Kinase Bin Metastatic Human Pancreatic Cancer Cells, Clin. Cancer. Res, VII :440-449 (2005).
Search Report for European Application No. 04814626.0, dated Aug. 4, 2009.
Search Report for European Application No. 11173701.1 dated Mar. 6, 2012.
Search Report for European Application No. 11173701.1, dated Oct. 26, 2011.
Search Report for European Application No. 12745360.3 dated Jul. 23, 2014.
Search Report for Taiwan Patent Application No. 094120055 dated Aug. 25, 2011.
Secor et al., "Mast cells are essential for early onset and severe disease in a murine model of multiple sclerosis," J. Exp. Med., (2000), 5:813-821.
Selvin, P., "Fluorescence Resonance Energy Transfer," Meth. Enzymol., (1995), 246:300-345.
Shah et al., "Development of Novel Microprecipitated Bulk Power(MBP) Technology for Manufacturing Stable Amorphous Formulations of Poorly Soluble Drugs", International Journal of Pharmaceutics, vol. 438, 2012, pp. 53-60.
Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process", Journal of Pharmaceutical Sciences, 2012, pp. 1-15.
Shan et al., Prodrug strategies based on intramolecular cyclization reactions. Journal of Pharmaceutical Sciences 1997, 86(7):765-767.
Sheets et al., "Efficient construction of a large nonimmune phage antibody library: the production of high-affinity human single-chain antibodies to protein antigens." Proc Natl Acad Sci USA, 1998, 95, pp. 6157-6162.

Shibata et al., "Alveolar macrophage deficiency in osteopetrotic mice deficient in macrophage colony-stimulating factor is spontaneously corrected with age and associated with matrix metalloproteinase expression and emphysema." Blood 2001, 98, pp. 2845-2852.
Siegel et al., "Mass Spectral Analysis of a Protein Complex Using Single-Chain Antibodies Selected on a Peptide Target: Applications to Functional Genomics," Journal of Molecular Biology, (2000), 302:285-293.
Sigal et al., A self-assembled monolayer for the binding and study of histidine-tagged proteins by surface plasmon resonance. Anal Chem. 1996, 68:490-497.
Silverman, "Prodrugs and Drug Delivery Systems, the Organic Chemistry of Drug Design and Drug Action," pp. 352-399, 1992.
Simone, Oncology, Textbook of Medicine, 1997, pp. 1003-1010 (Year: 1997).
Simone, Oncology: Introduction, Cecil Textbook of Medicine, 20th Edition, 1996, vol. 1, pp. 1004-1010.
Singer et al., "Mutations in BRAF and KRAS Characterize the Development of Low-Grade Ovarian Serous Carcinoma", Journal of the National Cancer Institute, 2003, vol. 95, No. 6, pp. 484-486.
Small et al., "STK-I, the human homolog ofFlk-2/Flt-3, is selectively expressed in CD34+ human bone marrow cells and is involved in the proliferation of early progenitor/stem cells," Proc. Nat. Acad. Sci., 91: 459-463 (1994).
Smalley et al., c-KIT signaling as the driving oncogenic event in sub-groups of melanomas. Histol Histopathol (2009) 24:643-650.
Smith, et al., "The Role of kinase inhibitors in the treatment of patients with acute myeloid leukemia," (2013), Am Soc Clin Oncol Educ Book, (2013), 313-318.
Solinas-Toldo et al., Matrix-based comparative genomic hybridization: biochips to screen for genomic imbalances. Genes Chromosomes & Cancer. 1997, 20:399-407.
Song, et al., "Isomerism of Bis(7-azaindolyl)methane," Organic Letters (2002), 4(23):4049-4052, Table of content p. 1-16 and Supporting information p. 1-15.
Sorafenib, 2012, www.cancer.gov/cancertopics/druginfo/sorafenibtosylate.
Specchia et al., "Constitutive expression ofiL-I?, M-CSF and c-fms during the myeloid blastic phase of chronic myelogenous leukaemia," Br J Haematol., Mar. 80(3):310-6 (1992).
Sperling et al., "Expression of the Stem Cell Factor Receptor c-Kit (CD117) in Acute Leukemias," Haemat (1997), 82:617-621.
Stanulla, et al., "Coexpression of Stem Cell Factor and Its Receptor c-Kit in Human Malignant Glioma Cell Lines," Act Neuropath., (1995), 89:158-165.
Steinman, L., "Multiple Sclerosis: a Coordinated Immunological Attack against Myelin in the Central Nervous System." Cell, 1996, 85, pp. 299-302.
Strohmeyer, et al., "Expression of the C-kit Proto-Oncogene and its Ligand Stem Cell Factor (SCF) in Normal and Malignant Human Testicular Tissue," J. Urol., (2005), 153:511-515.
Strohmeyer, et al., "Expression of the hst-1 and c-kit Protooncogenes in Human Testicular Germ Cell Tumors," Canc. Res., (1991), 51:1811-1816.
Su, et al., "Synthesis of bromo-substituted Idoxyl Esters for Cytochemical Demonstration of Enzyme Activity," J. Am. Chem. Soc., (1960), 82:1187-1189.
Sun et al., "Design, Synthesis, and Evaluations of Substituted 3-[(3- or 4-Carboxyethylpyrrol-2-yl) Methylidenyllindolin-2-Ones as Inhibitors of VEGF, PGF, and PDGF Receptor Tyrosine Kinases," J. Med. Chem., (1999), 42:5120-5130.
Sun, C., "Recent Advances in Liquid-Phase Combinatorial Chemistry," Comb. Chem. & High Throughput Screening, (1999), 2:299-318.
Supplementary Search Report dated Aug. 4, 2009 for European Application No. 04814626.0.
Tada, et al., "Analysis of Cytokine Receptor Messenger RNA Expression in Human Glioblastoma Cells and Normal Astrocytes by Reverse-Transcription Polymerase Chain Reaction," J. Neuro., (1994), 80:1063-1073.
Takahashi et al., Activation of a novel human transforming gene, ret, by DNA rearrangement. Cell. 1985, 42(2):581-588.

(56) References Cited

OTHER PUBLICATIONS

Takahashi et al., Cloning and expression of the ret proto-oncogene encoding a tyrosine kinase with two potential transmembrane domains. Oncogene. 1988, 3(5):571-578.
Takahashi, et al., "ret Transforming Gene Encodes a Fusion Protein Homologous to Tyrosine Kinases," Mol Cell Biol., (1987), 7:1378-1385.
Tang et al., "An RNA interference-based screen identifies MAP4K4/ NIK as a negative regulator of PPARγ, adipogenesis, and insulin-responsive hexose transport," Proc. Natl. Acad. Sci., (2006), 103:2087-2092.
Tanno et al., "Evaluation of Hypromellose Acetate Succinate (HPMCAS) as a Carrier in Solid Dispersions," Drug Development and Industrial Pharmacy 30(1):9-17 (2004).
Taylor et al. "The Rapid Generation of Oligonucleotide-directed Mutations at High Frequency Using Phosphorothloate-Modified DNA," Nucl. Acids Res. (1985), 13:8764-8785.
Technical Report for Peru Patent Application No. 001837-2013/ DIN dated Dec. 29, 2017. (9 pages).
Technical Report for Peru Patent Application No. 001837-2013/ DIN dated Jul. 5, 2017. (11 pages).
Teitelbaum, S.L., Bone resorption by osteoclasts. Science 2000, 289:1504-1508.
Thibault et al., Concise and efficient synthesis of 4-fluoro-1H-pyrrolo[2,3-b]pyridine. Org Lett. 2003, 5:5023-5025.
Thomas et al., Light-Emitting Carbazole Derivatives: Potential Electroluminescent Materials. J. Am. Chem. Soc. 2001, 123: 9404-9411.
Thomas, et al., "The Eosinophil and its Role in Asthma," Gen. Pharmac., (1996), 27:593-597.
Toste et al., a Versatile Procedure for the Preparation of Aryl Thiocyanates Using N-Thiocyanatosuccinimide (NTS), Synth. Comm. (1995), 25(8):1277-1286.
Toy et al., "Enhanced ovarian cancer tumorigenesis and metastasis by the mecrophage colony-stimulating factor," Neoplasia, (2009), 11:(2) 136-144.
Toyota et al., "Expression of c-kit and kit Ligand in Human Colon Carcinoma Cells," Turn Biol., (1993), 14:295-302.
Trupp et al., Functional receptor for GDNF encoded by the c-ret proto-oncogene. Nature (1996), 381:785-789.
Tsai et al., "Discovery of a selective inhibitor of oncogenic B-Raf kinase with potent antimelanoma activity", Proceedings of the National Academy of Sciences of the United States of America, 2008, 105(8), pp. 3041-3046.
Tsuda, et al., "Microglia and Intractable Chronic Pain," (2012), GLIA, 1-7.
Tsujimura et al., Ligand-Independent Activation of c-kit Receptor Tyrosine Kinase in a Murine Mastocytoma Cell Line P-815 Generated by a Point Mutation, Blood (1994), 9:2619-2626.
Tsujimura, et al., "Substitution of an Aspartic Acid Results in Constitutive Activation of c-kit Receptor Tyrosine Kinase in a Rat Tumor Mast Cell Line RBL-2H3," Int. Arch. Aller. Immunol., (1995), 106:377-385.
Tsujimura, T., Role of c-kit receptor tyrosine kinase in the development, survival and neoplastic transformation of mast cells. Pathol Int (1996), 46:933-938.
Turner et al., "Nonhematopoeietic Tumor Cell Lines Express Stem Cell Factor and Display c-kit Receptors," Blood, (1992), 80:374-381.
Tutuka, "PLX8394, a new generation BRAF inhibitor, selectively inhibits BRAF in colonic adenocarcinoma cells and prevents paradoxical MAPK pathway activation," Molecular Cancer, (2017), 16, 112.
U.S. Notice of Allowance and Fees Due dated Feb. 9, 2012 for U.S. Appl. No. 12/773,798.
U.S. Notice of Allowance of U.S. Appl. No. 11/154,988, dated Jun. 6, 2008.
Udenfriend et al., Scintillation proximity assay: a sensitive and continuous isotopic method for monitoring ligand/receptor and antigen/antibody interactions. Anal Biochem 1987, 161:494-500.
Uemura et al., "The Selective M-CSF Receptor Tyrosine Kinase Inhibitor Ki20227 Suppresses Experimental Autoimmune Encephalomyelitis," J. Neuroimmunology, (2008), 195: 73-80.
Uritskaya, et al., STN Accession No. 1974-27133; Document No. 08:27133; Abstract of Khimiya Geterotsiklicheskikh Soedinenii (1973), 10:1370-1373.
US Notice of Allowance of U.S. Appl. No. 11/016,350 dated Dec. 26, 2007.
US Notice of Allowance of U.S. Appl. No. 11/154,988 dated Jul. 23, 2008.
US Notice of Allowance of U.S. Appl. No. 11/154,988 dated Sep. 8, 2008.
US Notice of Allowance of U.S. Appl. No. 11/435,381 dated May 27, 2010.
US Notice of Allowance of U.S. Appl. No. 11/435,381 dated Jul. 27, 2010.
US Notice of Allowance of U.S. Appl. No. 11/473,347 dated Jun. 18, 2010.
US Notice of Allowance of U.S. Appl. No. 11/473,347 dated Sep. 8, 2010.
US Notice of Allowance of U.S. Appl. No. 11/960,590 dated Aug. 11, 2010.
US Notice of Allowance of U.S. Appl. No. 11/961,901 dated May 17, 2012.
US Notice of Allowance of U.S. Appl. No. 11/962,044 dated Aug. 13, 2010.
US Notice of Allowance of U.S. Appl. No. 11/986,667 dated Aug. 6, 2010.
US Notice of Allowance of U.S. Appl. No. 12/244,730 dated Jan. 6, 2011.
US Notice of Allowance of U.S. Appl. No. 12/616,079 dated Oct. 25, 2012.
US Notice of Allowance of U.S. Appl. No. 13/216,200 dated Dec. 8, 2011.
US Notice of Allowance of U.S. Appl. No. 13/546,923 dated Nov. 19, 2012.
US Office Action dated Aug. 2, 2007 U.S. Appl. No. 11/016,350.
US Office Action in U.S. Appl. No. 11/016,350 dated Jun. 6, 2007.
US Office Action in U.S. Appl. No. 11/016,350 dated Aug. 2, 2007.
US Office Action in U.S. Appl. No. 11/016,350 dated Oct. 26, 2007.
US Office Action in U.S. Appl. No. 11/154,988 dated Jan. 4, 2008.
US Office Action in U.S. Appl. No. 11/154,988 dated Oct. 19, 2007.
US Office Action in U.S. Appl. No. 11/435,381 dated Feb. 19, 2010.
US Office Action in U.S. Appl. No. 11/435,381 dated Mar. 4, 2009.
US Office Action in U.S. Appl. No. 11/435,381 dated Jun. 1, 2009.
US Office Action in U.S. Appl. No. 11/473,347 dated Dec. 18, 2009.
US Office Action in U.S. Appl. No. 11/487,134 dated May 15, 2008.
US Office Action in U.S. Appl. No. 11/487,134 dated Aug. 22, 2007.
US Office Action in U.S. Appl. No. 11/961,901 dated Jan. 23, 2012.
US Office Action in U.S. Appl. No. 11/961,901 dated Aug. 4, 2011.
US Office Action in U.S. Appl. No. 11/962,044 dated Feb. 17, 2010.
US Office Action in U.S. Appl. No. 11/962,044 dated Sep. 23, 2009.
US Office Action in U.S. Appl. No. 11/986,667 dated Feb. 26, 2010.
US Office Action in U.S. Appl. No. 11/986,667 dated Sep. 22, 2009.
US Office Action in U.S. Appl. No. 12/082,665 dated Nov. 8, 2010.
US Office Action in U.S. Appl. No. 12/244,730 dated Jul. 22, 2010.
US Office Action in U.S. Appl. No. 12/616,079 dated Feb. 9, 2012.
US Office Action in U.S. Appl. No. 12/616,079 dated Jun. 29, 2012.
US Office Action in U.S. Appl. No. 12/669,450 dated Dec. 27, 2012.
US Office Action in U.S. Appl. No. 12/752,035 dated Jun. 18, 2013.
US Office Action in U.S. Appl. No. 12/752,035 dated Oct. 3, 2012.
US Office Action in U.S. Appl. No. 12/906,980 dated Feb. 29, 2012.
US Office Action in U.S. Appl. No. 12/906,980 dated Oct. 17, 2012.
US Office Action in U.S. Appl. No. 12/958,376 dated Apr. 18, 2012.
US Office Action in U.S. Appl. No. 12/958,379 dated Jul. 17, 2012.
US Office Action in U.S. Appl. No. 12/958,379 dated Nov. 14, 2012.
US Office Action in U.S. Appl. No. 12/981,427 dated Mar. 5, 2013.
US Office Action in U.S. Appl. No. 13/243,748 dated Jun. 27, 2013.
US Office Action in U.S. Appl. No. 13/546,923 dated Sep. 18, 2012.
US Office Action in U.S. Appl. No. 13/786,219 dated Jul. 21, 2014.
US Office Action in U.S. Appl. No. 13/786,219 dated Nov. 8, 2013.
US Office Action in U.S. Appl. No. 13/866,469 dated Oct. 31, 2013.

(56) References Cited

OTHER PUBLICATIONS

Vachon et al., The influence of microencapsulation using Eudragit RS100 on the hydrolysis kinetics of acetylsalicylic acid. J. Microencapsulation 1997, 14(3):281-301.
Valent, P., "Biology, Classification and Treatment of Human Mastocytosis" Wein/Klin Wochenschr (1996), 108:385-397.
Van Heyningen, V. One gene—four syndromes. Nature (1994), 367:319-320.
Van Regenmortel, M.H.V., "Use of biosensors to characterize recombinant proteins," Developments in Biological Standardization, (1994), 83:143-151.
Vandelli et al., "Analysis of release data in the evaluation of the physical state of progesterone in matrix systems," J. Microencapsulation, (1993), 10(1):55-65.
Vely et al., "BIAcore Analysis to Test Phosphopeptide-SH2 Domain Interactions," Methods in Molecular Biology, (2000), 121:313-321.
Verfaillie, C.M., Chronic myelogenous leukemia: too much or too little growth, or both?. Leukemia (1998), 12:136-138.
Viskochil, D., It takes two to tango: mast cell and Schwann cell interactions in neurofibromas. J Clin Invest. 2003, 112:1791-1793.
Vliagoftis, et al., "The protooncogene c-kit and c-kit ligand in human disease," Journ. Clin. Immunol, (1997), 100:435-440.
Wakefield, Basil "Fluorinated Pharmaceuticals" Innovations in Pharmaceutical Technology 2003, 74, 76-78. Online web.archive/org/web/20030905122408; www.iptonline.com/articles/public/IPTFOUR74NP.pdf. (accessed via Wayback machine Nov. 20, 2009 showing web availability as of Sep. 2003).
Waldo et al., "Heterogeneity of human macrophages in culture and in atherosclerotic plaques," Am. J. of Pathology, 172(4): 1112-1126 (2008).
Weber, P., Physical principles of protein crystallization. Adv Protein Chem. 1991, 41:1-36.
Wells et al., Targeting the RET pathway in thyroid cancer. Clin Cancer Res. 2009, 15(23):7119-7123.
Wendt et al., "Identification of novel binding interactions in the development of potent, selective 2-naphthamidine inhibitors of urokinase. Synthesis, structural analysis, and SAR of N-phenyl amide 6-substitution." J Med Chem. 2004, 47, pp. 303-324.
Wentworth et al., "Pro-Inflammatory CD11C+CD206+ Adipose Tissue Macrophages Are Associated With Insulin Resistance in Human Obesity," Diabetes, (2010), 59:1648-1656.
Werness et al., Association of human papillomavirus types 16 and 18 E6 proteins with p53. Science 1990, 248:76-79.
Wessjohann. L., Synthesis of natural-product-based compound libraries. Curr Opin Chem Biol (2000), 4: 303-309.
Wharam et al., "Specific detection of DNA and RNA targets using a novel isothermal nucleic acid amplification assay based on the formation of a three-way junction structure." Nucleic Acids Res. 2001, 29, pp. 1-8.
Wild et al., Antibodies to nerve growth factor reverse established tactile allodynia in rodent models of neuropathic pain without tolerance. J Pharmacol Exp Ther. 2007, 322:282-287.
Williams et al., "Dissection of the extracellular human interferon y receptor a-chain into two immunoglobulin-like domains. Production in an *Escherichia coli* thioredoxin gene fusion expression system and recognition by neutralizing antibodies," Biochemistry (1995), 34:1787-1797.
Willmore-Payne, C., et al. Human Pathology vol. 36, pp. 486-493. Published May 2005.
Wolff, Manfred E. "Burger's Medicinal Chemistry, 5ed, Part 1", John Wiley & Sons, 1995, pp. 975-977.
Woon et al., Construction and characterization of a 10-fold genome equivalent rat P1-derived artificial chromosome library. Genomics 1998, 50:306-316.
Wright et al., The STE20 Kinase KGK Is Broadly Expressed in Human tumor Cells and Can Modulate Cellular Transformation, Invasion, and Adhesion. Mol. Cell. Biol. (2003), 23:2068-2082.
Wuthrich, K., "Chapter 10: Three-Dimensional Protein Structures by NMR," NMR of Proteins and Nucleic Acids, (1986), 10:176-199.
Wyckoff, et al., "Direct visualization of macrophage-assisted tumor cell intravasation in mammary tumors," Cancer Research, (2007), 67(6):2649-2656.
Xing et al., BRAF mutation predicts a poorer clinical prognosis for papillary thyroid cancer. J Clin Endocrinol Metab 2005, 90(12):6373-6379.
Xing, M., BRAF mutation in thyroid cancer. Endocrine-Related Cancer 2005, 12:245-262.
Xu et al., "CSF1R signaling blockade stanches tumor-infiltrating myeloid cells and improves the efficacy of radiotherapy in prostate cancer," Cancer Res., (2013), 73(9): 2782-94.
Xu et al., "High Prevalence of BRAF Gene Mutation in Papillary Thyroid Carcinomas and Thyroid Tumor Cell Lines[1]", Cancer Research, 2003, 63, pp. 4561-4567.
Xu, et al., "Modulation of Endothelial Cell function by Normal Polyspecific Human Intraveneous immunoglobulins," Am. J. Path., (1998), 153:1257-1266.
Yakhontov et al., Derivatives of 7-azaindole. XV. Electrophilic substitution of 4-methyl-7-azaindole and its derivatives. Zhurnal Obshchei Khimii (1965), 1(11): 2032-2040. (English abstract only).
Yamaguchi et al., "Calcium Restriction Allows cAMP Activation of the B-Raf/ERK Pathway, Switching Cells to a cAMP-dependent Growth-stimulated Phenotype." Journal of Biological Chemistry 2004, 279, pp. 40419-40430.
Yamaguchi, et al., "Cyclic AMP activates B-Raf and ERK in cyst epithelial cells from autosomal-dominant polycystic kidneys," Kidney International, (2003), 63:1983-1994.
Yang et al., "Synthesis of some 5-substituted indoles," Heterocycles 1992, 34:1169-1175.
Yang et al., Identification of Brain-Derived Neurotrophic Factor as a Novel Functional Protein in Hepatocellular Carcinoma. Cancer Res 2005, 65:219-225.
Yang et al., Neurofibromin-deficient Schwann cells secrete a potent migratory stimulus for Nf1+/− mast cells. J. Clin. Invest. (2003), 112:1851-1861.
Yang, et al., "Nf1-Dependent tumors require a microenvironment containing Nf1+/−-and c-kit-Dependent bone marrow," Cell, (2008), 135:437-448.
Yao et al., A novel human STE20-related protein kinase, HGK, that specifically activates the c-Jun N-terminal kinase signaling pathway. J Biol Chem 1999, 274:2118-2125.
Yee et al., Role of kit-ligand in proliferation and suppression of apoptosis in mast cells: Basis for radiosensitivity of white spotting and steel mutant mice. J Exp Med 1994, 179:1777-1787.
Yeung et al., Friedel-Crafts acylation of indoles in acidic imidazolium chloroaluminate ionic liquid at room temperature. Tetrahedron Letters 2002, 43(33):5793-5795.
Yoshida et al., "Studies on anti-helicobacter pylori agents, Part 1: Benzyloxyisoquinoline derivatives," Bioorganic & Medicinal Chemistry, Elsevier Science Ltd, 7(11):2647-2666 (1999).
Yuan et al., Human peripheral blood eosinophils express a functional c-kit receptor for stem cell factor that stimulates very late antigen 4 (VLA-4)-mediated cell adhesion to fibronectin and vascular cell adhesion molecule 1 (VCAM-1). J Exp Med 1997, 186:313-323.
Zaidi et al., "Interferon -? links ultraviolet radiation to melanomagenesis in mice." Nature, (2011), 469: 548-553.
Zanon et al., Copper-Catalyzed Domino Halide Exchange-Cyanation of Aryl Bromides. J. Am. Chem. Soc. 2003, 125:2890-2891.
Zhang et al., "RAF inhibitors that evade paradoxical MAPK pathway activation," Nature, 2015, 526, pp. 583-586.
Zhang, et al., "An Effective Procedure for the Acylation of Azaindoles at C-3", Journal of Organic Chemistry 2002, 67(17), 6226-6227.
Zhang, et al., "Design and pharmacology of a highly specific dual FMS and KIT kinase inhibitor," Proc. Natl. Acad. Sci., (2013), 110:(14) 5689-5694.

COMPOUNDS AND METHODS FOR KINASE MODULATION, AND INDICATIONS THEREFOR

This application is a continuation of U.S. patent application Ser. No. 17/722,229, filed Apr. 15, 2022, which is a continuation of U.S. patent application Ser. No. 15/435,569, filed Feb. 17, 2017, now U.S. Pat. No. 11,337,976, which is a divisional of U.S. patent application Ser. No. 13/820,734, filed Oct. 22, 2013, now U.S. Pat. No. 9,624,213, which is a U.S. National Stage Application under 35 U.S.C. § 371 of International Application No. PCT/US2012/023543, filed Feb. 1, 2012, which claims the benefit of U.S. Provisional Patent Application No. 61/440,339, filed Feb. 7, 2011, the complete disclosures of which are hereby incorporated by reference in their entireties.

FIELD OF THE INVENTION

The present invention relates to kinases and compounds which selectively modulate kinases, and uses therefor. Particular embodiments contemplate disease indications which are amenable to treatment by modulation of kinase activity by the compounds of the present invention.

BACKGROUND OF THE INVENTION

Receptor protein kinases regulate key signal transduction cascades that control or are involved in the control of a plethora of physiological functions including cellular growth and proliferation, cell differentiation, cellular development, cell division, cell adhesion, stress response, short-range contact-mediated axonal guidance, transcription regulation, aberrant mitogenesis, angiogenesis, abnormal endothelial cell-cell or cell-matrix interactions during vascular development, inflammation, lymphohematopoietic stem cell activity, protective immunity against specific bacteria, allergic asthma, aberrant tissue-specific responses to the activation of the JNK signal transduction pathway, cell transformation, memory, apoptosis, competitive activity-dependent synapse modification at the neuromuscular synapse, immunological mediation of disease, and calcium regulation.

Specific disease states associated with aberrant regulation of protein kinases include, for example without limitation, acrocephalo-syndactyly type I, acute myeloid leukemia, AIDS-induced non-Hodgkin's lymphoma, Alzheimer's disease, amyotrophic lateral sclerosis, arthritis, asthma, atherosclerosis, atopic dermatitis, autoimmune diseases, bacterial infection, bladder cancer, cancer of the breast, cancer of the central nervous system, cancer of the colon, cancer of the endometrium, cancer of the fallopian tube, cancer of the gastrointestinal tract, cancer of the ovary, heart failure, chronic myeloid leukemia, colon carcinoma, colorectal cancer, chronic obstructive pulmonary disease (COPD), Crouzon Syndrome, diabetes, diabetic nephropathy, emphysema, endometriosis, epidermoid cancer, fibrotic disorders, gastrointestinal stromal tumor (GIST), glomerulonephritis, Graves' disease, head injury, hepatocellular carcinoma, Hirschsprung's disease, human gliomas, immunodeficiency diseases, inflammatory disorders, ischemic stroke, Jackson-Weiss syndrome, leiomyosarcoma, leukemias, lupus nephritis, malignant melanoma, malignant nephrosclerosis, mastocytosis, mast cell tumors, melanoma of the colon, MEN2 syndromes, metabolic disorders, migraine, multiple sclerosis, myeloproliferative disorders, nephritis, neurodegenerative diseases, neurotraumatic diseases, non small cell lung cancer, organ transplant rejection, osteoporosis, pain, Parkinson's disease, Pfeiffer Syndrome, polycystic kidney disease, primary lymphedema, prostate cancer, psoriasis, vascular restenosis, rheumatoid arthritis, dermal and tissue scarring, selective T-cell defect (STD), severe combined immunodeficiency (SCID), small cell lung cancer, spinal cord injury, squamous cell carcinoma, systemic lupus erythematosis, testicular cancer, thrombotic microangiopathy syndromes, Wegener's granulomatosis, X-linked agammaglobulinemia, viral infection, diabetic retinopathy, alopecia, erectile dysfunction, macular degeneration, chronic lymphocytic leukemia (CLL), myelodysplastic syndrome (MDS), neurofibromatosis, and tuberous sclerosis. Accordingly, there is a need in the art for compounds and methods of use thereof for the modulation of receptor protein kinases. The present invention meets this and other needs.

SUMMARY OF THE INVENTION

In one aspect, the present invention provides a compound of formula I:

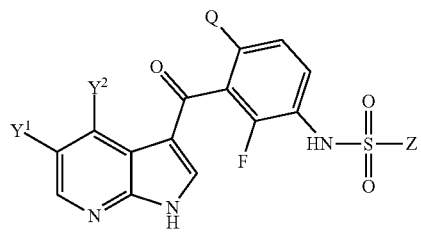

and pharmaceutically acceptable salts, hydrates, solvates, tautomers and isomers thereof, wherein:

$Y^1$ is selected from the group consisting of CN, halogen, —OH, optionally substituted $C_{1-6}$ alkyl, optionally substituted $C_{1-6}$ alkoxy, optionally substituted $C_{3-6}$ cycloalkyl, optionally substituted $C_{1-6}$ haloalkyl, optionally substituted $C_{1-6}$ haloalkoxy, optionally substituted aryl and optionally substituted heteroaryl; optionally wherein two adjacent substituents on a substituted aryl or a substituted heteroaryl ring together with the atoms to which they are attached form an optionally substituted 5- or 6-membered ring having from 0 to 3 additional heteroatoms selected from N, O or S;

$Y^2$ is H, halogen, CN, $C_{1-6}$ alkyl, $C_{1-6}$ alkoxy, $C_{1-6}$ haloalkyl, $C_{1-6}$ haloalkoxy, aryl, arylalkyl, heteroaryl, heteroarylalkyl, $C_{3-8}$ cycloalkyl-$C_{0-4}$ alkyl or $(R^2)(R^3)$N—, wherein $R^2$ and $R^3$ are each independently selected from the group consisting of H, $C_{1-6}$ alkyl, $C_{1-6}$ alkoxy, aryl, arylalkyl, heteroaryl, heteroarylalkyl, $C_{3-8}$ cycloalkyl-$C_{0-4}$ alkyl, heterocycloalkyl and heterocycloalkyl-$C_{1-4}$ alkyl; or $R^2$ and $R^3$ taken together with the nitrogen atom to which they are attached form a three to eight-membered ring having from 0-2 additional heteroatoms as ring members selected from N, O or S; wherein $Y^2$ is optionally substituted with from one to three groups independently selected from $R^e$;

Q is selected from H, F, Cl or $CH_3$;

Z is —$N(R^4)(R^5)$ or —$C(R^6)(R^7)(R^8)$, wherein
$R^4$ and $R^5$ are each independently selected from the group consisting of H, optionally substituted $C_{1-6}$ alkyl, optionally substituted $C_{3-8}$ cycloalkyl, optionally substituted $C_{3-8}$ cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl; or $R^4$ and $R^5$ taken together with the nitrogen atom to which they are attached form a four to eight-membered ring having from 0-2 additional heteroatoms as ring members selected from N, O or S, wherein the four to eight-membered ring is optionally substituted;

$R^6$, $R^7$ and $R^8$ are each independently H, optionally substituted $C_{1-6}$ alkyl, optionally substituted, $C_{1-6}$ haloalkyl, optionally substituted $C_{1-6}$ haloalkoxy, optionally substituted $C_{3-8}$ cycloalkyl, optionally substituted $C_{3-8}$ cycloalkylalkyl, optionally substituted aryl, optionally substituted arylalkyl, optionally substituted heterocycloalkyl, optionally substituted heterocycloalkylalkyl, optionally substituted heteroaryl, optionally substituted heteroarylalkyl or —$X^2R^9$, wherein $X^2$ is —$NR^{10}$, O or S; $R^{10}$ is H, $C_{1-6}$ alkyl or aryl; and $R^9$ is H, $C_{1-6}$ alkyl, $C_{1-6}$ haloalkyl, $C_{1-6}$ haloalkoxy, $C_{3-8}$ cycloalkyl, $C_{3-8}$ cycloalkylalkyl, aryl, arylalkyl, heteroaryl or heteroarylalkyl, wherein $R^9$ is optionally substituted with from 1 to 3 $R^e$ substituents; or any two of the $R^6$, $R^7$ and $R^8$ groups taken together with the carbon atom to which they are attached form a 3 to 8-membered optionally substituted non-aromatic ring having from 0 to 2 heteroatoms selected from N, O or S; provided at each occurrence, at least two of the $R^6$, $R^7$ and $R^8$ groups are not simultaneously hydrogen; and with the proviso when (i) $Y^1$ is halogen, —$CH_3$, —CN, —OMe or 2-methoxypyrimidin-5-yl, Z is other than dimethylamino, diethylamino, 1-pyrrolidine, 1-piperidinyl, 4-morpholinyl, isopropyl, —$CH(CH_3)(CH_2CH_3)$, —$CH(CH_3)(CH_2CH_2CH_3)$, cyclobutyl, cyclopentyl or cyclohexyl; and (ii) when $Y^1$ is 1-methyl-4-pyrazolyl, 3-methylsulfonylphenyl or 3-methylsulfonylaminophenyl, Z is other than cyclopropyl, cyclobutyl, cyclopentyl or cyclohexyl.

In some embodiments, $Y^1$ is CN, halogen, —OH, $C_{1-6}$ alkyl, $C_{1-6}$ alkoxy, optionally substituted $C_{3-6}$cycloalkyl, $C_{1-6}$ haloalkyl, $C_{1-6}$ haloalkoxy, aryl and heteroaryl, wherein the aliphatic or aromatic portion of $Y^1$ is each independently optionally substituted with from 1-5 $R^1$ substituents;

each $R^1$ is independently selected from $C_{1-6}$ alkyl, $C_{1-6}$ alkoxy, $C_{1-6}$ haloalkyl, $C_{1-6}$ haloalkoxy, $C_{3-8}$ cycloalkyl, $C_{3-8}$ cycloalkyl-$C_{1-4}$-alkyl, aryl, arylalkyl, heteroaryl, heteroarylalkyl, heterocycloalkyl, heterocycloalkyl-$C_{1-4}$ alkyl or —$R^a$, wherein $R^a$ is selected from halogen, —CH=$CH_2$, —CN, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^b$, —$SR^b$, —OC(O)$R^b$, —OC(S)$R^b$, —C(O)$R^b$, —C(S)$R^b$, —C(O)$OR^b$, —C(S)$OR^b$, —S(O)$R^b$, —S(O)$_2R^b$, —C(O)$NHR^b$, —C(S)$NHR^b$, —C(O)$NR^bR^b$, —C(S)$NR^bR^b$, —S(O)$_2NHR^b$, —S(O)$_2NR^bR^b$, —C(NH)$NHR^b$, —C(NH)$NR^bR^b$, —NHC(O)$R^b$, —NHC(S)$R^b$, —$NR^bC(O)R^b$, —$NR^bC(S)R^b$, —NHS(O)$_2R^b$, —$NR^bS(O)_2R^b$, —NHC(O)$NH_2$, —NHC(S)$NH_2$, —$NR^bC(O)NH_2$, —$NR^bC(S)NH_2$, —$NR^bC(O)NHR^b$, —$NR^bC(S)NHR^b$, —NHC(O)$NR^bR^b$, —NHC(S)$NR^bR^b$, —$NR^bC(O)NR^bR^b$, —$NR^bC(S)$ $NR^bR^b$, —NHS(O)$_2NHR^b$, —NRS(O)$_2NH_2$, —NRS(O)$_2NHR^b$, —NHS(O)$_2NR^bR^b$, —NRS(O)$_2NR^bR^b$, —$NH^bR^b$ or —$NR^bR^b$, each $R^b$ is independently selected from the group consisting of $C_{1-6}$ alkyl, halogen, —CN, $C_{1-6}$ alkoxy, $C_{3-8}$ cycloalkyl, $C_{3-8}$ cycloalkyl-$C_{1-4}$-alkyl, —OH, $C_{1-6}$ haloalkyl, $C_{1-6}$ haloalkoxy, aryl, aryl-$C_{1-4}$ alkyl, heteroaryl and heteroarylalkyl; or two $R^b$ substituents when attached to the same nitrogen atom taken together with the nitrogen atom form a three to eight-membered ring having from 0-2 additional heteroatoms as ring members selected from N, O or S; wherein the aliphatic or aromatic portion of $R^1$ is further optionally substituted with from 1-3 groups selected from $C_{1-6}$ alkyl, $C_{1-6}$ alkoxy, $C_{1-6}$ haloalkyl, $C_{1-6}$haloalkoxy, aryl, arylalkyl, heteroaryl, heteroarylalkyl, heterocycloalkyl, heterocycloalkyl-$C_{1-4}$alkyl or —$R^c$, each $R^c$ is independently selected from halogen, —CN, —OH, —CH=$CH_2$, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^d$, —$SR^d$, —OC(O)$R^d$, —OC(S)$R^d$, —C(O)$R^d$, —C(S)$R^d$, —C(O)$OR^d$, —C(S)$OR^d$, —S(O)$R^d$, —S(O)$_2R^d$, —C(O)$NHR^d$, —C(S)$NHR^d$, —C(O)$NR^dR^d$, —C(S)$NR^dR^d$, —S(O)$_2NHR^d$, —S(O)$_2NR^dR^d$, —C(NH)$NHR^d$, —C(NH)$NR^dR^d$, —NHC(O)$R^d$, —NHC(S)$R^d$, —$NR^dC(O)R^d$, —$NR^dC(S)R^d$, —NHS(O)$_2R^d$, —NRS(O)$_2R^d$, —NHC(O)$NHR^d$, —NHC(S)$NHR^d$, —$NR^dC(O)NH_2$, —$NR^dC(S)NH_2$, —$NR^dC(O)NHR^d$, —$NR^dC(S)NHR^d$, —NHC(O)$NR^dR^d$, —NHC(S)$NR^dR^d$, —$NR^dC(O)NR^dR^d$, —$NR^dC(S)NR^dR^d$, —NHS(O)$_2NHR^d$, —NRS(O)$_2NH_2$, —NRS(O)$_2NHR^d$, —NHS(O)$_2NR^dR^d$, —NR'S(O)$_2NR^dR^d$, —$NHR^d$, $R^f$ or —$NR^dR^d$, each $R^d$ is independently selected from $C_{1-6}$alkyl, arylalkyl, aryl, heteroaryl, heteroarylalkyl, cycloalkyl, cycloalkylalkyl, heterocycloalkyl or heterocycloalkylalkyl; and wherein the aromatic portion of $R^1$ is optionally substituted with from 1-3 substituents independently selected from $R^e$, $R^e$ is selected from the group consisting of halogen, —CN, —CH=$CH_2$, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^f$, —$SR^f$, —OC(O)$R^f$, —OC(S)$R^f$, —C(O)$R^f$, —C(S)$R^f$, —C(O)$OR^f$, —C(S)$OR^f$, —S(O)$R^f$, —S(O)$_2R^f$, —C(O)$NHR^f$, —C(S)$NHR^f$, —C(O)$NR^fR^f$, —C(S)$NR^fR^f$, —S(O)$_2NHR^f$, —S(O)$_2NR^fR^f$, —C(NH)$NHR^f$, —C(NH)$NR^fR^f$, —NHC(O)$R^f$, —NHC(S)$R^f$, —$NR^fC(O)R^f$, —$NR^fC(S)R^f$, —NHS(O)$_2R^f$, —NRS(O)$_2R^f$, —NHC(O)$NHR^f$, —NHC(S)$NHR^b$, —$NR^fC(O)NH_2$, —$NR^fC(S)NH_2$, —$NR^fC(O)NHR^f$, —$NR^fC(S)NHR^f$, —NHC(O)$NR^fR^f$, —NHC(S)$NR^fR^f$, —$NR^fC(O)NR^fR^f$, —$NR^fC(S)NR^fR^f$, —NHS(O)$_2NHR^f$, —$NR^fS(O)_2NH_2$, —$NR^fS(O)_2NHR^f$, —NHS(O)$_2NR^fR^f$, —NRS(O)$_2NR^fR^f$, —$NHR^f$, —$NR^fR^f$ and $R^f$, $R^f$ is $C_{1-6}$alkyl or aryl; or two adjacent $R^1$ groups on the aryl or heteroaryl ring together with the atoms to which they are attached form a 5- or 6-membered ring having from 0 to 2 additional heteroatoms selected from N, O or S, optionally substituted with from 1 to 3 $R^d$ substituents;

$R^4$ and $R^5$ are each independently selected from the group consisting of H, $C_{1-6}$ alkyl, $C_{3-8}$ cycloalkyl, $C_{3-8}$ cycloalkylalkyl, heterocycloalkyl, heterocycloalkylalkyl, aryl, arylalkyl, heteroaryl and heteroarylalkyl, wherein $R^4$ or $R^5$ is optionally substituted with from 1 to 3 members independently selected from $C_{1-6}$ alkoxy, $C_{1-6}$ haloalkyl, $C_{1-6}$ haloalkoxy, $C_{1-6}$ alkyl, $C_{3-8}$ cycloalkyl, $C_{3-8}$ cycloalkylalkyl, heterocycloalkyl, heterocycloalkylalkyl, aryl, arylalkyl, heteroaryl, heteroarylalkyl or R; or $R^4$ and $R^5$ taken together with the nitrogen atom to which they are attached form a four to eight membered ring having from 0-2 additional heteroatoms as ring members selected from N, O or S, wherein said four to eight membered ring is optionally substituted with from one to three groups independently selected from $C_{1-6}$ haloalkyl, $C_{1-6}$ haloalkoxy, $C_{1-6}$ alkyl, $C_{3-8}$ cycloalkyl, $C_{3-8}$ cycloalkylalkyl, aryl, arylalkyl or $R^e$; and $R^6$, $R^7$ and $R^8$ are each independently H, $C_{1-6}$ alkyl, $C_{1-6}$ haloalkyl, $C_{1-6}$ haloalkoxy, $C_{3-8}$ cycloalkyl, $C_{3-8}$ cycloalkylalkyl, aryl, arylalkyl, heterocycloalkyl, heterocycloalkylalkyl, heteroaryl, heteroarylalkyl or —$X^2R^9$; wherein the aliphatic or aromatic portion of $R^6$, $R^7$ and $R^8$ are each optionally substituted with from 1 to 3 members independently selected from the group consisting of $C_{3-8}$ cycloalkyl, $C_{3-8}$ cycloalkylalkyl, aryl, arylalkyl, heterocycloalkyl, heterocycloalkylalkyl, heteroaryl, heteroarylalkyl and $R^e$; or any two of the $R^6$, $R^7$ and $R^8$ groups taken together with the carbon atom to which they are attached form a 3 to 8-membered carbocyclic ring or a 4 to 8-membered heterocyclic ring having from 1 to 2 heteroatoms as ring members selected from N, O or S, wherein the 3 to 8-membered carbocyclic ring or the 4 to 8-membered heterocyclic ring is optionally substituted with from one to three groups independently selected from $C_{1-6}$ haloalkyl, $C_{1-6}$ haloalkoxy, $C_{1-6}$ alkyl optionally substituted with $R^e$, $C_{3-8}$ cycloalkyl, $C_{3-8}$ cycloalkylalkyl, aryl, arylalkyl, heteroaryl or heteroarylalkyl or $R^e$.

In another aspect, the invention provides a composition. The composition includes a compound of any of formulas I to In, a compound as recited in any of the claims and described herein or a pharmaceutically acceptable salt or solvate thereof, and a pharmaceutically acceptable excipient or carrier. The invention also provides a composition, which includes a compound as recited in the claims and described herein, a pharmaceutically acceptable excipient or carrier, and another therapeutic agent.

In yet another aspect, the invention provides a kit, which includes a compound of any of formulas I to In, a compound as recited in any of the claims and described herein, or a pharmaceutically acceptable salt or solvate thereof. The invention also provides a kit, which includes a composition comprising a compound of formulas I to In, a compound as recited in any of the claims and described herein, or a pharmaceutically acceptable salt or solvate thereof.

In another aspect, the invention provides a method for preparing a compound of formula (I) and any of the subgeneric formulas.

In still another aspect, the invention provides a method for treating a subject suffering from or at risk of a protein kinase mediated diseases or conditions. The method includes administering to the subject an effective amount of a compound of any of formulas I to In, a compound as recited in any of the claims and described herein, or a pharmaceutically acceptable salt or solvate thereof, or a composition comprising a compound of any of formulas I to In, a compound as recited in any of the claims and described herein, or a pharmaceutically acceptable salt or solvate thereof.

DETAILED DESCRIPTION OF THE INVENTION

I. Definitions

As used herein the following definitions apply unless clearly indicated otherwise:

It is noted here that as used in this specification and the appended claims, the singular forms "a," "an," and "the" include plural reference unless the context clearly dictates otherwise.

"Halogen" or "halo" refers to all halogens, that is, chloro (Cl), fluoro (F), bromo (Br), or iodo (I).

"Hydroxyl" or "hydroxy" refers to the group —OH.

"Thiol" refers to the group —SH.

The term "alkyl", by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl, arylalkyl, cycloalkylalkyl, heterocycloalkylalkyl, heteroarylalkyl), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-8}$ alkyl refers to a straight or branched hydrocarbon having 1, 2, 3, 4, 5 or 6 carbon atoms and includes, but are not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. "Fluoro substituted alkyl" denotes a alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

The term "alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$—, —$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms being preferred in the present invention. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

The term "alkenylene" refers to a linear bivalent hydrocarbon moiety or a branched monovalent hydrocarbon moiety having the number of carbon atoms indicated in the prefix and containing at least one double bond. For example, i.e., $C_{2-6}$ means two to six carbons; $C_{2-6}$ alkenylene is meant to include, but are not limited to, —CH=CH—, —CH$_2$—CH=CH—, —CH$_2$—CH=C(CH$_3$)—, —CH=CH—CH=CH—, and the like). Similarly, the term "alkynylene" refers to a linear bivalent hydrocarbon moiety or a branched monovalent hydrocarbon moiety containing at least one triple bond and having the number of carbon atoms indicated in the prefix. For example, (i.e., $C_{2-6}$ means two to six carbons; $C_{2-6}$ alkynylene is meant to include, but are not limited to, —C≡C—, —C≡CCH$_2$—, —CH$_2$—C≡CCH$_2$—, —C≡CCH(CH$_3$)—, and the like. When a prefix is not included to indicate the number of carbon atoms in an alkenylene or alkynylene portion, the alkenylene moiety or portion thereof will have 12 or fewer main chain carbon atoms or 8 or fewer main chain carbon atoms or 6 or fewer main chain carbon atoms, or 4 or fewer main chain carbon atoms.

"Cycloalkyl" by itself or as part of another substituent, refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, 1-cyclohexenyl, adamantyl, and the like. Cycloalkyl refers to hydrocarbon rings having the indicated number of ring atoms (e.g., $C_{3-8}$ cycloalkyl means three to eight ring carbon atoms)

"Cycloalkylalkyl" refers to an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms. $C_{3-8}$cycloalkylalkyl is meant to have 3 to 8 ring carbon atoms. Exemplary cycloalkylalkyl include, e.g., cyclopropylmethylene, cyclobutylethylene, cyclobutylmethylene, and the like.

"Haloalkyl," is meant to include alkyl substituted by one to seven halogen atoms. Haloalkyl includes monohaloalkyl and polyhaloalkyl. For example, the term "$C_{1-6}$ haloalkyl" is meant to include trifluoromethyl, difluoromethyl, 2,2,2-trifluoroethyl, 4-chlorobutyl, 3-bromopropyl, and the like.

"Haloalkoxy" refers to a —O-haloalkyl group, where haloalkyl is as defined herein, e. g., trifluoromethoxy, 2,2,2-trifluoroethoxy, difluoromethoxy, and the like.

"Alkoxy" refers to a —O-alkyl group, where alkyl is as defined herein. "Cycloalkoxy" refers to a —O-cycloalkyl group, where cycloalkyl is as defined herein. "Fluoro substituted alkoxy" denotes alkoxy in which the alkyl is substituted with one or more fluoro atoms, where preferably the alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —NH$_2$.

"Alkylamino" refers to a —NH-alkyl group, where alkyl is as defined herein. Exemplary alkylamino groups include CH$_3$NH—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like.

"Cycloalkylamino" denotes the group —NR$^{dd}$R$^{ee}$, where R$^{dd}$ and R$^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Alkylthio" refers to —S-alkyl, where alkyl is as defined herein. Exemplary alkylthio groups include CH$_3$S—, ethylthio, and the like.

"Aryl" by itself or as part of another substituent refers to a monocyclic, bicyclic or polycyclic polyunsaturated aromatic hydrocarbon moiety containing 6 to 14 ring carbon atoms. Non-limiting examples of unsubstituted aryl groups include phenyl, 1-naphthyl, 2-naphthyl and 4-biphenyl. Exemplary aryl group, such as phenyl or naphthyl, which may be optionally fused with a cycloalkyl of preferably 5-7, more preferably 5-6, ring members.

"Arylalkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, and the like.

"Heteroaryl" by itself or as part of another substituent refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any heteroatoms are N.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. Examples of heteroarylalkyl include 2-pyridylmethyl, 2-thiazolylethyl, and the like.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, preferably 4 to 10 ring atoms, more preferably 5 to 8 ring atoms in which one to five ring atoms are heteroatoms selected from —N=, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, and the like. A heterocycloalkyl group can be attached to the remainder of the molecule through a ring carbon or a heteroatom.

"Heterocycloalkylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Examples of heterocycloalkylalkyl include 2-pyridylmethyl, 2-thiazolylethyl, and the like.

The substituents for alkyl, alkoxy, haloalkyl, haloalkoxy, cycloalkyl, cycloalkylalkyl, alkylene, alkenylene, alkynylene include, but are not limited to, R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S)R', —C(O)OR', —C(S)OR', —S(O)R, —S(O)$_2$R, —C(O)NHR, —C(S)NHR', —C(O)NR'R", —C(S)NR'R", —S(O)$_2$NHR', —S(O)$_2$NR'R", —C(NH)NHR', —C(NH)NR'R", —NHC(O)R', —NHC(S)R', —NR"C(O)R', —NR'C(S)R", —NHS(O)$_2$R', —NR'S(O)$_2$R", —NHC(O)NHR', —NHC(S)NHR', —NR'C(O)NH$_2$, —NR'C(S)NH$_2$, —NR'C(O)NHR", —NR'C(S)NHR", —NHC(O)NR'R", —NHC(S)NR'R", —NR C(O)NR"R'", —NR'"C(S)NR'R", —NHS(O)$_2$NHR', —NR'S(O)$_2$NH$_2$, —NR'S(O)$_2$NHR", —NHS(O)$_2$NR'R", —NR S(O)$_2$NR"R'", —NHR', and —NR'R" in a number ranging from zero to (2 m'+1), where m' is the total number of carbon atoms in such group. R', R" and R'" each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. R', R" and R'" can be further substituted with R$^{a1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{a1}$, —SR$^{a1}$, —OC(O)R$^{a1}$, —OC(S)R$^{a1}$, —C(O)R$^{a1}$, —C(S)R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —N$^{a1}$S(O)$_2$R$^{a2}$, —NHC(O)NHR$^{a1}$, —NHC(S)NHR$^{a1}$, —NR$^{a1}$C(O)NH$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, and —NR$^{a1}$R$^{a2}$ in a number ranging from zero to (2n'+1), where n' is the total number of carbon atoms in such group. R$^{a1}$, R$^{a2}$ and R$^{a3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. R$^{a1}$, R$^{a2}$ and R$^{a3}$ can be further substituted with R$^1$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{b1}$, —SR$^{b1}$, —OC(O)R$^{b1}$, —OC(S)R$^{b1}$, —C(O)R$^{b1}$, —C(S)R$^{b1}$, —C(O)OR$^{b1}$, —C(S)OR$^{b1}$, —S(O)R$^{b1}$, —S(O)$_2$R$^{b1}$, —C(O)NHR$^{b1}$, —C(S)NHR$^{b1}$, —C(O)NR$^{b1}$R$^{b2}$, —C(S)NR$^{b1}$R$^{b2}$, —S(O)$_2$NHR$^{b1}$, —S(O)$_2$NR$^{b1}$R$^{b2}$, —C(NH)NHR$^{b1}$, —C(NH)NR$^{b1}$R$^{b2}$, —NHC(O)R$^{b1}$, —NHC(S)R$^{b1}$, —NR$^{b2}$C(O)R$^{b1}$, —NRlC(S)R$^{b2}$, —NHS(O)$_2$R$^{b1}$, —NR$^{b1}$S(O)$_2$R$^{b2}$, —NHC(O)NHR$^{b1}$, —NHC(S)NHR$^{b1}$, —NR$^{b1}$C(O)NH$_2$, —NR$^{b1}$C(S)NH$_2$, —NR$^{b1}$C(O)NHR$^{b2}$, —NR$^{b1}$C(S)NHR$^{b2}$, —NHC(O)NR$^{b1}$R$^{b2}$, —NHC(S)NR$^{b1}$R$^{b2}$, —NR$^{b1}$C(O)NR$^{b2}$R$^{b3}$, —NR$^{b3}$C(S)NR$^{b1}$R$^{b2}$, —NHS(O)$_2$NHR$^{b1}$, —NR$^{b1}$S(O)$_2$NH$_2$, —NR$^{b1}$S(O)$_2$NHR$^{b2}$, —NHS(O)$_2$NR$^{b1}$R$^{b2}$, —NR$^{b1}$S(O)$_2$NR$^{b2}$R$^{b3}$, —NHR$^{b1}$, and —NR$^{b1}$R$^{b2}$ in a number ranging from zero to (2p'+1), where p' is the total number of carbon atoms in such group. R$^{b1}$, R$^{b2}$ and R$^{b3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups.

Substituents for the aryl and heteroaryl groups are varied and are generally selected from: R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR, —SR', —OC(O)R', —OC(S)R', —C(O)R', —C(S)R', —C(O)OR', —C(S)OR', —S(O)R', —S(O)$_2$R', —C(O)NHR', —C(S)NHR', —C(O)NR'R", —C(S)NR'R", —S(O)$_2$NHR', —S(O)$_2$NR'R", —C(NH)NHR', —C(NH)NR'R", —NHC(O)R', —NHC(S)R', —NR"C(O)R', —NR'C(S)R", —NHS(O)$_2$R', —NR'S(O)$_2$R", —NHC(O)NHR', —NHC(S)NHR', —NR'C(O)NH$_2$, —NR'C(S)NH$_2$, —NR'C(O)NHR", —NR'C(S)NHR", —NHC(O)NR'R", —NHC(S)NR'R", —NR'C(O)NR"R'", —NR'"C(S)NR'R", —NHS(O)$_2$NHR', —NR'S(O)$_2$NH$_2$, —NR'S(O)$_2$NHR", —NHS(O)$_2$NR'R", —NR'S(O)$_2$NR"R'", —NHR', —NR'R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, and aryloxy-C$_{1-4}$ alkyl. Other suitable substituents include each of the above aryl substituents attached to a ring atom by an alkylene tether of from 1-4 carbon atoms. R', R" and R'" can be further substituted with R$^{a1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{a1}$, —SR$^{a1}$, —OC(O)R$^{a1}$, —OC(S)R$^{a1}$, —C(O)R$^{a1}$, —C(S)R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O)NHR$^{a1}$, —NHC(S)NHR$^{a1}$, —NR$^{a1}$C(O)NH$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, —NR$^{a1}$R$^{a2}$, —N$_3$, perfluoro(C$_1$-C$_4$)alkoxy, and perfluoro(C$_1$-C$_4$)alkyl, in a number ranging from zero to the total number of open valences on the aromatic ring system; and where R$^{a1}$, R$^{a2}$ and R$^{a3}$ are each independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, or aryloxy-C$_{1-4}$ alkyl. Other suitable substituents include each of the above aryl substituents attached to a ring atom by an alkylene tether of from 1-4 carbon atoms.

When two substituents are present on adjacent atoms of a substituted aryl or a substituted heteroaryl ring, such substituents may optionally be replaced with a substituent of the formula -T-C(O)—(CH$_2$)$_q$-U—, wherein T and U are independently —NH—, —O—, —CH$_2$— or a single bond, and q is an integer of from 0 to 2. Alternatively, when two substituents are present on adjacent atoms of a substituted aryl or a substituted heteroaryl ring, such substituents may optionally be replaced with a substituent of the formula -A-(CH$_2$)$_r$B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, when two substituents are present on adjacent atoms of a substituted aryl or a substituted heteroaryl ring, such substituents may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically-acceptable salt" refers to a salt which is acceptable for administration to a patient, such as a mammal (e.g., salts having acceptable mammalian safety for a given dosage regime). Such salts can be derived from pharmaceutically-acceptable inorganic or organic bases and from pharmaceutically-acceptable inorganic or organic acids, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary, tertiary and quaternary amines, including substituted amines, cyclic amines, naturally-occurring amines and the like, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Salts derived from pharmaceutically-acceptable acids include acetic, ascorbic, benzenesulfonic, benzoic, camphorsulfonic, citric, ethanesulfonic, fumaric, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, tartaric, p-toluenesulfonic and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less, 1 □M or less, 100 nM or less, 10 nM or less, or 1 nM or less.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials. Further, by "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present invention.

"Isomers" mean compounds having identical molecular formulae but differ in the nature or sequence of bonding of their atoms or in the arrangement of their atoms in space. Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are nonsuperimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

Certain compounds of the present invention can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not hinted to, any mammal, such as a human, other primates, sports animals, animals of commercial interest such as cattle, farm animals such as horses, or pets such as dogs and cats.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^4$C, $^{15}$N, $^{18}$F, $^{31}$P, $^{32}$P, $^{35}$S, $^{36}$Cl, and $^{125}$I. Unless otherwise stated, when a position is designated specifically as "H" or "hydrogen", the position is understood to have hydrogen at its natural abundance isotopic composition or its isotopes, such as deuterium (D) or tritium ($^3$H). Certain isotopically-labeled compounds of the present invention (e.g., those labeled with .sup.3H and .sup.14C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes and in the Examples herein below, by substituting an isotopically labeled reagent for a non-isotopically labeled reagent.

II. General

The present invention concerns compounds of Formula I and all sub-generic formulae, compounds as recited in the claims, and compounds described herein that are modulators of protein kinases, for example without limitation, the compounds are modulators of at least one of the kinases selected from the group consisting of ABL1, ABL2, ACK, ADRBK1, AKT1, AMPK_A2, A-RAF, ARK5, Aurora_A-C, BMX, CDC42_BPA, CAMK2A, CDK5_p35, CSF1R, DYRK1B, EPHA5, EPHA8, EPHB4, FES, FLT3, FYN, GSK3β, JAK1, KDR, KIT, MAP4K2, MAPK3, MARK2, MARK4, MATK, MET, MINK1, NEK1, NEK2, PAK3, PAK6, PDGFRb, PHKG1, PKC_beta_I, PKC_beta_II, PKC_delta, PKC_gamma, PKC_zeta, SRC, STK24, STK4, ACVR1B_(ALK4), ADRBK2_(GRK3), AKT2_(PKBb), AKT3_(PKBg), ALK, AMPK_A1/B1/G1, ARK5, ASK1, AXL, BRSK1_(SAD1), BrSK2, BTK, CAMK1, CAMK1D, CAMK2A, CAMK2B, CAMK2D, CaMKIdelta, CaMKIIbeta, CaMKIIdelta, CaMKIIgamma, CDC42_BPB, CDK1/CyclinB, CDK2/CyclinA, CDK2/cyclinE, CDK3/cyclinE, CDK5_p25, CDK6/cyclinD3, CDK7/CyclinH/MNAT1, CDK9/CyclinT1, CHEK1, CHEK2, CK1 delta, CK1 gamma1, CK1 gamma2, CK1 gamma3, CK2 alpha2, CLK1, CLK2, CLK3, CSNK1A1, CSNK1D, CSNK1E, CSNK1G1, CSNK1G2, CSNK1G3, CSNK2A1, CSNK2A2, DAPK1, DAPK2, DAPK3_(ZIPK), DCAMKL2_(DCK2), DDR2, DMPK, DRAK1, DYRK1A, DYRK2, DYRK3, DYRK4, EEF2K, EGFR, EPHA1, EPHA2, EPHA3 EPHA4, EphA7, EPHB1, EPHB2, EPHB3, ERBB2, ERBB4, FER, FGFR1, FGFR2, FGFR3, FGFR4, FLT1, FLT4, FRAP1, GCK, GRK4, GRK5, GRK6, GRK7, GSK3A, GSK3B, Haspin, HCK, Hck activated, HIPK, HIPK2, HIPK3, HIPK4, IGF1R, IGF-1R-activated, IKBKB, IKBKE, IKKalpha, IKKbeta, INSR, INSRR, IR-activated, IRAK1, IRAK4, ITK, JAK2, JAK2_JH1_JH2, JAK3, JNK1 alpha1, JNK2 alpha2, Lck-activated, LIMK1, LKB1, LOK, LTK, MAP2K1, MAP2K2, MAP2K6, MAP3K8, MAP3K9, MAP4K4, MAPK1, MAPK10, MAPK11, MAPK12, MAPK13, MAPK14, MAPK2, MAPK8, MAPK9, MAPKAPK2, MAPKAPK3, MAPKAPK5, MARK1, MARK3, MELK, MERTK, MKK7 beta, MLCK, MRCKalpha, MRCKbeta, MST1R, MST4, mTOR/FKBP12, MUSK, NEK3, NEK4, NEK6, NEK7, NEK9, NLK, NTRK1, NTRK2, NTRK3, PAK2, PAK4, PAK7_(KIAA1264), PAR-1 Balpha, PASK, PDGFRalpha, PDGFRbeta, PDK1, PHKG2, PhKgamma2, PIK3CA/PIK3R1, PIK3CG) PIM1, PIM2, Pim-3, PKBalpha, PKBbeta, PKBgamma, PKCalpha, PKCbetaI, PKCbetaII, PKCdelta, PKCepsilon, PKCeta, PKCgamma, PKCiota, PKCmu, PKCtheta, PKCzeta, PKG1 alpha, PKG1 beta, PKN1, PLK2, PLK3, PRK2, PRKACA, PRKCA, PRKCE, PRKCH, PRKCI, PRKCN, PRKCQ, PRKD1, PRKD2, PRKG1, PRKG2, PRKX, PTK2, PTK2B, RET, RIPK2, ROCK1, ROCK2, ROS1, RPS6KA1, RPS6KA2, RPS6KA3, RPS6KA4, RPS6KA5, RPS6KA6, RPS6KB1, SGK, SGK2, SGKL, SIK, SNF1LK2, Snk, SRPK1, SRPK2, STK22B, STK22D, STK23, STK25, STK3, STK33, SYK, TAK1, TAO3, TAOK2, TBK1, Tec activated, TEK, TLK2, Txk, TYK2, TYRO3, ULK2, ULK3, VRK2, WNK2, WNK3, and ZAP70 and the use of such compounds in the treatment of diseases or conditions. In some embodiments, the kinases have less than 20% Inhibition at 1 µM. In other embodiments, the kinases have less than 10% Inhibition at 1 µM.

III. Compounds

In one aspect, the present invention provides compounds of formula (I):

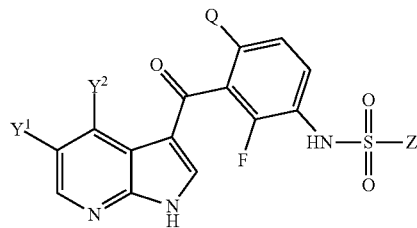

I and pharmaceutically acceptable salts, hydrates, solvates, tautomers and isomers thereof, wherein the substituents are as defined in the Summary of the Invention.

In some embodiments of compounds of formula (I), $Y^1$ is as defined in the summary of the invention. The All the other substituents of formula (I) are as defined in any of the embodiments described herein. In some preferred embodiments, the compounds have molecular weights less than 600, more preferably, the compounds have molecular weights less than 550. In other preferred embodiments, the compounds have molecular weights less than 500.

In some embodiments of compounds of formula (I), $Y^1$ is CN, halogen, —OH, $C_{1-6}$ alkyl, $C_{1-6}$ alkoxy, $C_{3-6}$cycloalkyl, $C_{1-6}$ haloalkyl, $C_{1-6}$ haloalkoxy, aryl or heteroaryl, wherein the aliphatic or aromatic portion of $Y^1$ is each independently optionally substituted with from 1-5 $R^1$ substituents; each $R^1$ is independently selected from $C_{1-6}$ alkyl, $C_{1-6}$ alkoxy, $C_{1-6}$ haloalkyl, $C_{1-6}$ haloalkoxy, $C_{3-8}$ cycloalkyl, $C_{3-8}$ cycloalkyl-$C_{1-4}$-alkyl, aryl, arylalkyl, heteroaryl, heteroarylalkyl, heterocycloalkyl, heterocycloalkyl-$C_{1-4}$ alkyl or —$R^a$, wherein $R^a$ is selected from halogen, —CH=CH$_2$, —CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^b$, —SR$^b$, —OC(O)R$^b$, —OC(S)R$^b$, —C(O)R$^b$, —C(S)R$^b$, —C(O)OR$^b$, —C(S)OR$^b$, —S(O)R$^b$, —S(O)$_2$R$^b$, —C(O)NHR$^b$, —C(S)NHR$^b$, —C(O)NR$^b$R$^b$, —C(S)NR$^b$R$^b$, —S(O)$_2$NHR$^b$, —S(O)$_2$NR$^b$R$^b$, —C(NH)NHR$^b$, —C(NH)NR$^b$R$^b$, —NHC(O)R$^b$, —NHC(S)R$^b$, —NR$^b$C(O)R$^b$, —NR$^b$C(S)R$^b$, —NHS(O)$_2$R$^b$, —NR$^b$S(O)$_2$R$^b$, —NHC(O)NHR$^b$, —NHC(S)NHR$^b$, —NR$^b$C(O)NH$_2$, —NR$^b$C(S)NH$_2$, —NR$^b$C(O)NHR$^b$, —NR$^b$C(S)NHR$^b$, —NHC(O)NR$^b$R$^b$, —NHC(S)NR$^b$R$^b$, —NR$^b$C(O)NR$^b$R$^b$, —NR$^b$C(S)NR$^b$R$^b$, —NHS(O)$_2$NHR$^b$, —NR$^b$S(O)$_2$NH$_2$, —NR$^b$S(O)$_2$NHR$^b$, —NHS(O)$_2$NR$^b$R$^b$, —NRS(O)$_2$NR$^b$R$^b$, —NHR$^b$ or —NR$^b$R$^b$, wherein each R$^b$ is independently selected from the group consisting of $C_{1-6}$alkyl, halogen, —CN, $C_{1-6}$alkoxy, $C_{3-8}$cycloalkyl, $C_{3-8}$cycloalkyl-$C_{1-4}$-alkyl, —OH, $C_{1-6}$ haloalkyl, $C_{1-6}$haloalkoxy, aryl, aryl-$C_{1-4}$alkyl, heteroaryl and heteroarylalkyl; or two R$^b$ substituents when attached to the same nitrogen atom taken together with the nitrogen atom form a three to eight-membered ring having from 0-2 additional heteroatoms as ring members selected from N, O or S; wherein the aliphatic or aromatic portion of $R^1$ is further optionally substituted with from 1-3 groups selected from $C_{1-6}$ alkyl, $C_{1-6}$ alkoxy, $C_{1-6}$ haloalkyl, $C_{1-6}$ haloalkoxy, aryl, arylalkyl, heteroaryl, heteroarylalkyl, heterocycloalkyl, heterocycloalkyl-$C_{1-4}$alkyl or —R$^c$, wherein each R$^c$ is independently selected from halogen, —CH=CH$_2$, —CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^d$, —SR$^d$, —OC(O)R$^d$, —OC(S)R$^d$, —C(O)R$^d$, —C(S)R$^d$, —C(O)OR$^d$, —C(S)OR$^d$, —S(O)R$^d$, —S(O)$_2$R$^d$, —C(O)NHR$^d$, —C(S)NHR$^d$, —C(O)NR$^d$R$^d$, —C(S)NR$^d$R$^d$, —S(O)$_2$NHR$^d$, —S(O)$_2$NR$^d$R$^d$, —C(NH)NHR$^d$, —C(NH)NR$^d$R$^d$, —NHC(O)R$^d$, —NHC(S)R$^d$, —NR$^d$C(O)R$^d$, —NR$^d$C(S)R$^d$, —NHS(O)$_2$R$^d$, —NRS(O)$_2$R$^d$, —NHC(O)NHR$^d$, —NHC(S)NHR$^d$, —NR$^d$C(O)NH$_2$, —NR$^d$C(S)NH$_2$, —NR$^d$C(O)NHR$^d$, —NR$^d$C(S)NHR$^d$, —NHC(O)NR$^d$R$^d$, —NHC(S)NR$^d$R$^d$, —NR$^d$C(O)NR$^d$R$^d$, —NR$^d$C(S)NR$^d$R$^d$, —NHS(O)$_2$NHR$^d$, —NRS(O)$_2$NH$_2$, —NRS(O)$_2$NHR$^d$, —NHS(O)$_2$NR$^d$R$^d$, —NR$^d$S(O)$_2$NR$^d$R$^d$, —NHR$^d$, R$^f$ or —NR$^d$R$^d$, wherein each $R^d$ is independently selected from $C_{1-6}$ alkyl, arylalkyl, aryl, heteroaryl, heteroarylalkyl, cycloalkyl, cycloalkylalkyl, heterocycloalkyl or heterocycloalkylalkyl; and wherein the aromatic portion of $R^1$ is optionally substituted with from 1-3 substituents independently selected from R$^e$, wherein R$^e$ is selected from the group consisting of halogen, —CH=CH$_2$, —CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^f$, —SR$^f$, —OC(O)R$^f$, —OC(S)R$^f$, —C(O)R$^f$, —C(S)R$^f$, —C(O)OR$^f$, —C(S)OR$^f$, —S(O)R$^f$, —S(O)$_2$R$^f$, —C(O)NHR$^f$, —C(S)NHR$^f$, —C(O)NR$^f$R$^f$, —C(S)NR$^f$R$^f$, —S(O)$_2$NHR$^f$, —S(O)$_2$NR$^f$R$^f$, —C(NH)NHR$^f$, —C(NH)NR$^f$R$^f$, —NHC(O)R$^f$, —NHC(S)R$^f$, —NR$^f$C(O)R$^f$, —NR$^f$C(S)R$^f$, —NHS(O)$_2$R, —NRS(O)$_2$R$^f$, —NHC(O)NHR$^f$, —NHC(S)NHR$^f$, —NR$^f$C(O)NH$_2$, —NR$^f$C(S)NH$_2$, —NR$^f$C(O)NHR$^f$, —NR$^f$C(S)NHR$^f$, —NHC(O)NR$^f$R$^f$, —NHC(S)NR$^f$R$^f$, —NR$^f$C(O)NR$^f$R$^f$, —NR$^f$C(S)NR$^f$R$^f$, —NHS(O)$_2$NHR$^f$, —NR$^f$S(O)$_2$NH$_2$, —NR$^f$S(O)$_2$NHR$^f$, —NHS(O)$_2$NR$^f$R$^f$, —NRS(O)$_2$NR$^f$R$^f$, —NHR$^f$, —NR$^f$R$^f$ and R$^f$, wherein R$^f$ is $C_{1-6}$alkyl or aryl; or two adjacent $R^1$ groups on the aryl or heteroaryl ring together with the atoms to which they are attached form a 5- or 6-membered ring having from 0 to 2 additional heteroatoms selected from N, O or S, optionally substituted with from 1 to 3 R$^d$ or R$^e$ substituents. In some instances, R$^f$ is $C_{1-6}$alkyl. In other instances, R$^f$ is aryl, such as phenyl. All the other variables $Y^2$, Q, Z of formula (I) and $R^4$, R, $R^6$, $R^7$ and $R^8$ are as defined in any of the embodiments described herein.

In some embodiments of compounds of formula (I), $Y^1$ is aryl or heteroaryl groups, wherein the heteroaryl group has from 1 to 4 heteroatoms as ring members selected from N, O or S; and wherein the aryl or heteroaryl groups are optionally substituted with from 1 to 3 $R^1$ substituents; or two adjacent $R^1$ groups on the phenyl or naphthyl ring together with the atoms to which they are attached form a 5- or 6-membered ring having from 0 to 2 additional heteroatoms selected from N, O or S, optionally substituted with from 1 to 3 R$^d$ substituents. In some embodiments, $Y^1$ is CN, halogen, —OH, $C_{1-6}$ alkyl, $C_{1-6}$ alkoxy, $C_{1-6}$ haloalkyl or $C_{1-6}$haloalkoxy. In some instances, $Y^1$ is phenyl, 1-naphthyl or 2-naphthyl, each of which is optionally substituted with from one to three $R^1$. In other instances, $Y^1$ is phenyl, 1-naphthyl or 2-naphthyl, each of which is optionally substituted with from one to three R$^a$. In other instances, $Y^1$ is phenyl, 1-naphthyl or 2-naphthyl, each of which is optionally substituted with from one to three R$^b$. In other instances, $Y^1$ is phenyl, 1-naphthyl or 2-naphthyl, each of which is optionally substituted with from one to three R$^c$. In other instances, $Y^1$ is phenyl, 1-naphthyl or 2-naphthyl, each of which is optionally substituted with from one to three R$^d$. In other instances, $Y^1$ is phenyl, 1-naphthyl or 2-naphthyl, each of which is optionally substituted with from one to three R$^e$. In yet other instances, $Y^1$ is phenyl, 1-naphthyl or 2-naphthyl, each of which is optionally substituted with from one to three R$^a$. In some instances, $Y^1$ is phenyl, 1-naphthyl or 2-naphthyl, is F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino or 1-hydroxy-1-methylethyl or methylcarbamoyl. All the other variables $Y^2$, Q, Z of formula (I) and $R^4$, $R^5$, $R^6$, $R^7$ and R are as defined in any of the embodiments described herein.

In some embodiments of compounds of formula (I), $Y^1$ is 1H-4-benzotriazolyl, 1H-5-benzotriazolyl, 1H-4-benzimidazolyl, 1H-5-benzimidazolyl, 1H-4-indazolyl, 1H-5-indazolyl, 1H-6-indazolyl, 1H-7-indazolyl, 1H-4-indolyl, 1H-5-indolyl, 1H-6-indolyl, 1H-7-indolyl, 2-oxo-6-indolinyl, 2-oxo-4-indolinyl, 2-oxo-5-indolinyl, 2-oxo-7-indolinyl, 1,2-benzoxazol-4-yl, 1,2-benzoxazol-5-yl, 1,2-benzoxazol-6-yl, 1,2-benzoxazol-7-yl, 1,3-benzoxazol-4-yl, 1,3-benzoxazol-5-yl, 1,3-benzoxazol-6-yl, 1,3-benzoxazol-7-yl, 1,2-benzothiazol-4-yl, 1,2-benzothiazol-5-yl, 1,2-benzothiazol-6-yl, 1,2-benzothiazol-7-yl, 5-quinolinyl, 6-quinolinyl, 7-quinolinyl, 8-quinolinyl, 5-isoquinolinyl, 6-isoquinolinyl, 7-isoquinolinyl, 8-isoquinolinyl, 5-cinnolinyl, 6-cinnolinyl, 7-cinnolinyl, 8-cinnolinyl, 5-quinazolinyl, 6-quinazolinyl, 7-quinazolinyl, 8-quinazolinyl, 5-quinoxalinyl, 6-quinoxalinyl, 7-quinoxalinyl, 8-quinoxalinyl, 4-indanyl, 5-indanyl, 5-tetralinyl, 6-tetralinyl, 1,3-dihydroisobenzofuran-4-yl, 1,3-dihydroisobenzofuran-5-yl, 2,3-dihydrobenzofuran-4-yl, 2,3-dihydrobenzofuran-5-yl, 2,3-dihydrobenzofuran-6-yl, 2,3-dihydrobenzofuran-7-yl, 1,3-dihydroisobenzothiophen-4-yl, 1,3-dihydroisobenzothiophen-5-yl, 2,3-dihydrobenzothiophen-4-yl, 2,3-dihydrobenzothiophen-5-yl, 2,3-dihydrobenzothiophen-6-yl, 2,3-dihydrobenzothiophen-7-yl, 4-indolinyl, 5-indolinyl, 6-indolinyl, 7-indolinyl, 5-isochromanyl, 6-isochromanyl, 7-isochromanyl, 8-isochromanyl, 5-chromanyl, 6-chromanyl, 7-chromanyl, 8-chromanyl, 2,3-dihydro-1,3-benzothiazo-4-yl, 2,3-dihydro-1,3-benzothiazo-5-yl, 2,3-dihydro-1,3-benzothiazo-6-yl, 2,3-dihydro-1,3-benzothiazo-7-yl, 2,3-dihydro-1,2-benzothiazo-4-yl, 2,3-dihydro-1,2-benzothiazo-5-yl, 2,3-dihydro-1,2-benzothiazo-6-yl, 2,3-dihydro-1,2-benzothiazo-7-yl, 2,3-dihydro-1,3-benzoxazol-4-yl, 2,3-dihydro-1,3-benzoxazol-5-yl, 2,3-dihydro-1,3-benzoxazol-6-yl, 2,3-dihydro-1,3-benzoxazol-7-yl, 2,3-dihydro-1,2-benzoxazol-4-yl, 2,3-dihydro-1,2-benzoxazol-5-yl, 2,3-dihydro-1,2-benzoxazol-6-yl, 2,3-dihydro-1,2-benzoxazol-7-yl, 4-benzofuranyl, 5-benzofuranyl, 6-benzofuranyl, 7-benzofuranyl, 4-benzothiophenyl, 5-benzothiophenyl, 6-benzothiophenyl or 7-benzothiophenyl, each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino or 1-hydroxy-1-methylethyl or methylcarbamoyl. All the other variables $Y^2$, Q, Z of formula (I) and $R^4$, $R^5$, $R^6$, $R^7$ and $R^8$ are as defined in any of the embodiments described herein.

In some embodiments, $Y^1$ is 5 or 6-membered heteroaryl, each of which is optionally independently substituted with from 1-3 $R^1$ groups, wherein the aromatic portion of $R^1$ is optionally substituted with from 1-3 substituents independently selected from $R^e$; or two adjacent $R^1$ groups on the phenyl or naphthyl ring together with the atoms to which they are attached form a 5- or 6-membered ring having from 0 to 2 additional heteroatoms selected from N, O or S, optionally substituted with from 1 to 3 $R^d$ substituents. All the other variables $Y^2$, Q, Z of formula (I) and $R^4$, $R^5$, $R^6$, $R^7$ and $R^8$ are as defined in any of the embodiments described herein.

In some embodiments of compounds of formula (I), $Y^1$ is 5-pyrimidinyl, 2-pyrimidinyl, 4-pyrimidinyl, 2-pyridyl, 3-pyridyl, 4-pyridyl, 2-pyrazinyl, 2-pyridazinyl, 3-pyridazinyl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiopentyl or 3-thiophenyl, each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl. All the other variables $Y^2$, Q, Z of formula (I) and $R^4$, $R^5$, $R^6$, $R^7$ and $R^8$ are as defined in any of the embodiments described herein.

In certain embodiments of compounds of formula (I), $Y^1$ is selected from the group consisting of 4-pyrimidinyl, 5-pyrimidinyl, 2-pyrazinyl, 2-thiazolyl, 4-thiazolyl, 5-thiazolyl, 2-thiophenyl, 3-thiophenyl, 2-amino-quinazolin-5-yl, 2-amino-quinazolin-6-yl, 2-amino-quinazolin-6-yl, 2-amino-quinazolin-7-yl, 2-amino-quinazolin-8-yl, 2-oxo-6-indolinyl, 2-oxo-4-indolinyl, 2-oxo-5-indolinyl, 2-oxo-7-indolinyl, 2-pyridyl, 3-pyridyl, 4-pyridyl, 1H-indazol-4-yl, 1H-indazol-5-yl, 1H-indazol-6-yl and 1H-indazol-7-yl, each of which is substituted with from 1 to 2 substituents independently selected from F, Cl, Br, I, —CN, —OH, —CF$_3$, NH$_2$, CF$_3$O—, CH$_3$—, CH$_3$O, C$_2$HsO—, —NO$_2$, cyclopropyl, cyclopropylmethyl, cyclopropylamino, cyclopropylmethylamino, 1-cyanocyclopropyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 5-methylamino-1,3,4-thiadiazol-2-yl, methylamino methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. All the other variables $Y^2$, Q, Z of formula (I) and $R^4$, $R^5$, $R^6$, $R^7$ and $R^8$ are as defined in any of the embodiments described herein In other embodiments of compounds of formula (I), $Y^1$ is 1-benzotriazolyl, 1-benzimidazolyl, 1H-2-benzimidazolyl, 1-indazolyl, 1H-3-indazolyl, 1-indolyl, 1H-2-indolyl, 1H-3-indolyl, 1,2-benzoxazol-3-yl, 1,3-benzoxazol-2-yl, 1,2-benzothiazol-3-yl, 1,3-benzothiazol-2-yl, 2-quinolinyl, 3-quinolinyl, 4-quinolinyl, 1-isoquinolinyl, 3-isoquinolinyl, 4-isoquinolinyl, 3-cinnolinyl, 4-cinnolinyl, 2-quinazolinyl, 4-quinazolinyl, 2-quinoxalinyl, 2-benzofuranyl, 3-benzofuranyl, 2-benzothiophenyl or 3-benzothiophenyl, each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl. All the other variables $Y^2$, Q, Z of formula (I) and $R^4$, $R^5$, $R^6$, $R^7$ and $R^8$ are as defined in any of the embodiments described herein.

In some embodiments of compounds of formula (I), $Y^1$ is selected from:

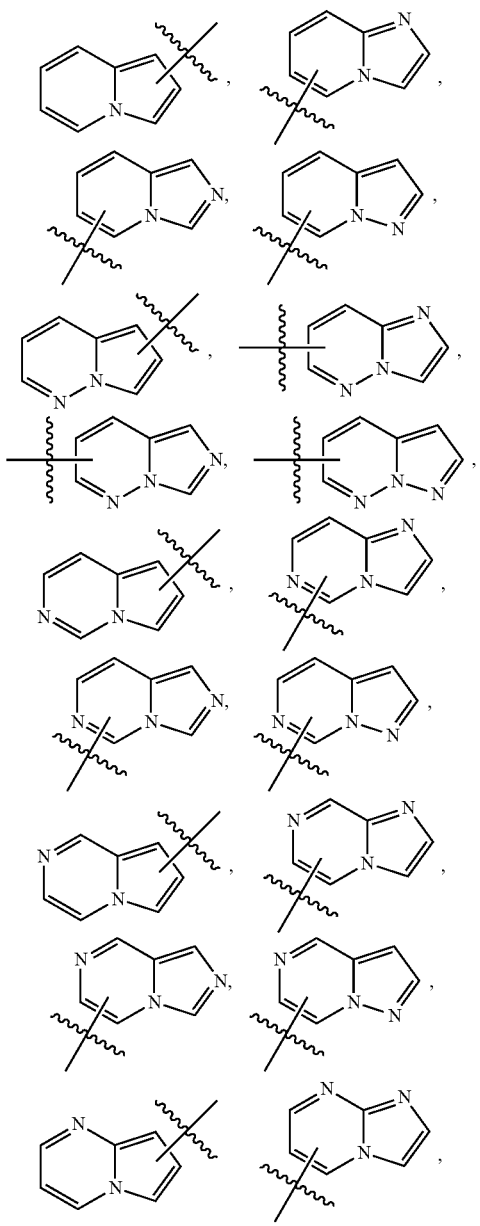

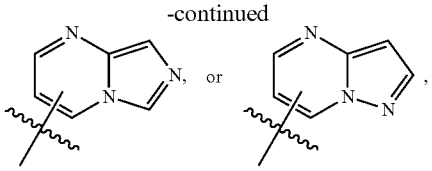

or each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl, where the wavy line indicate the point of attachment to the rest of the molecule. The notation

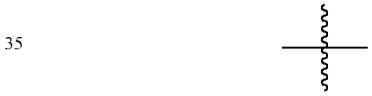

means $Y^1$ can be attached to the rest of the molecule at any of the available positions of the $Y^1$ group set forth above. For example

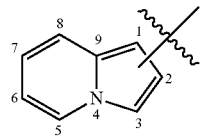

is meant to include 1-indolizinyl, 2-indolizinyl, 3-indolizinyl, 4-indolizinyl, 5-indolizinyl, 6-indolizinyl, 7-indolizinyl, and 8-indolizinyl (i.e., substitutions can be at 1, 2, 3, 5, 6, 7 or 8 positions of the indolizine ring).

In some embodiments of compounds of formula (I), $Y^1$ is selected from:

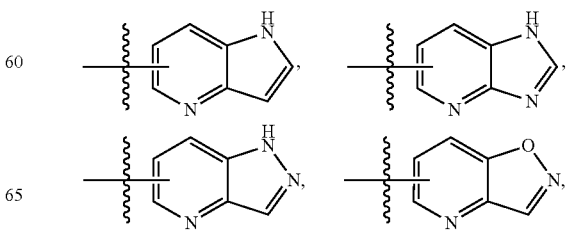

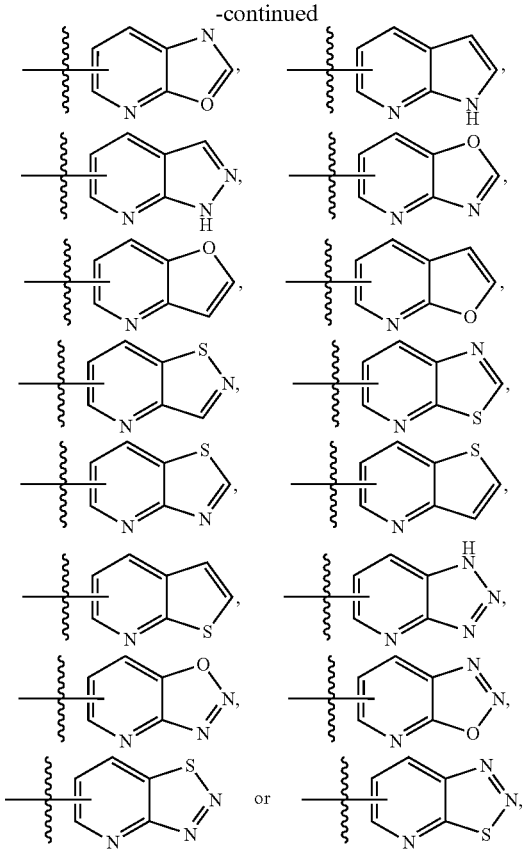

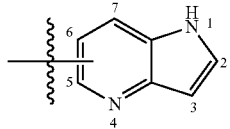

is meant to include 1H-pyrrolo[3,2-b]pyridin-1-yl, 1H-pyrrolo[3,2-b]pyridin-2-yl, 1H-pyrrolo[3,2-b]pyridin-3-yl, 1H-pyrrolo[3,2-b]pyridin-5-yl, 1H-pyrrolo[3,2-b]pyridin-6-yl and 1H-pyrrolo[3,2-b]pyridin-7-yl (i.e., substitutions can be at 1, 2, 3, 5, 6, or 7 positions of the pyrrolo[3,2-b]pyridine ring). All the other variables $Y^2$, Q, Z of formula (I) and $R^4$, $R^5$, $R^6$, $R^7$ and $R^8$ are as defined in any of the embodiments described herein.

In some embodiments of compounds of formula (I), $Y^1$ is selected from:

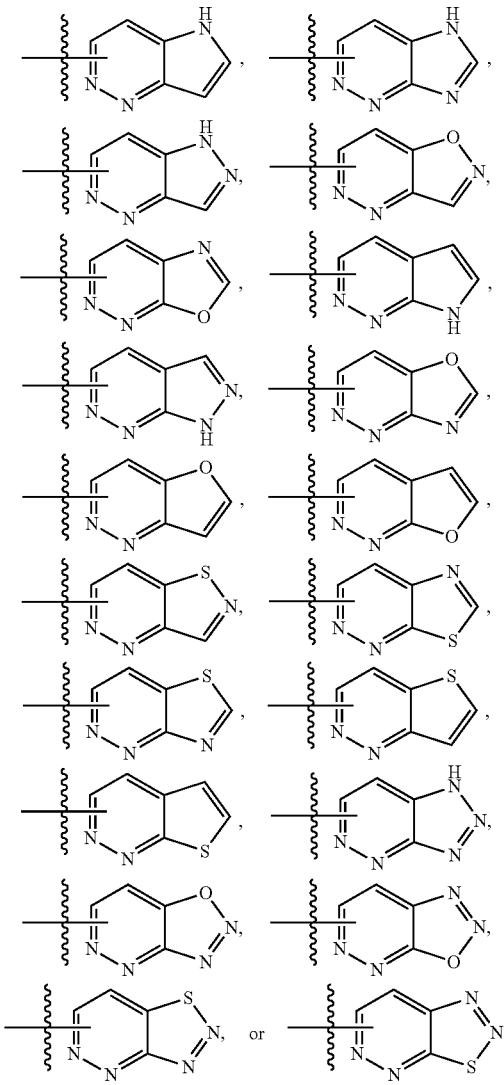

each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl, where the wavy line indicates the point of attachment to the rest of the molecule. The notation

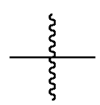

means $Y^1$ can be attached to the rest of the molecule at any of the available positions of the $Y^1$ group set forth above. For example, each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl, where the wavy line indicates the point of attachment to the rest of the molecule. The notation

means $Y^1$ can be attached to the rest of the molecule at any of the available positions of the $Y^1$ group set forth above. For example,

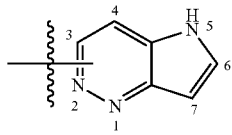

is meant to include 5H-pyrrolo[3,2-c]pyridazin-3-yl, 5H-pyrrolo[3,2-c]pyridazin-4-yl, 5H-pyrrolo[3,2-c]pyridazin-5-yl, 5H-pyrrolo[3,2-c]pyridazin-6-yl, 5H-pyrrolo[3,2-c]pyridazin-7-yl (i.e., substitutions can be at 3, 4, 5, 6, or 7 positions of the 5H-pyrrolo[3,2-c]pyridazine ring). All the other variables $Y^2$, Q, Z of formula (I) and $R^4$, $R^5$, $R^6$, $R^7$ and $R^8$ are as defined in any of the embodiments described herein.

In some embodiments of compounds of formula (I), $Y^1$ is selected from:

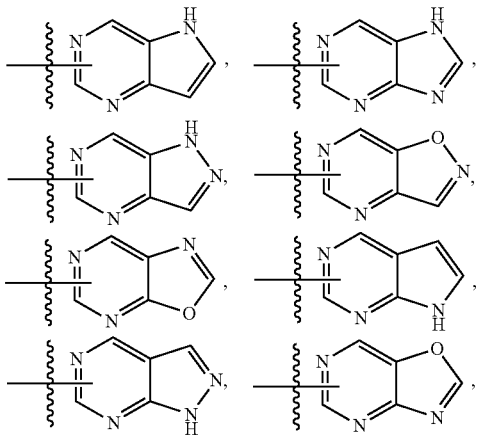

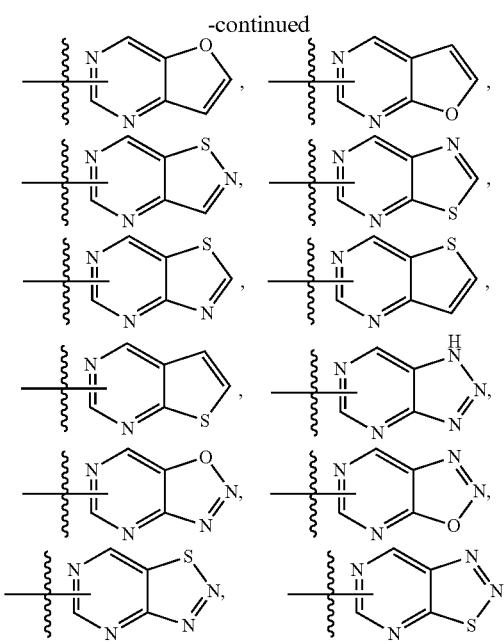

each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl, where the wavy line indicates the point of attachment to the rest of the molecule. The notation

means $Y^1$ can be attached to the rest of the molecule at any of the available positions of the $Y^1$ group set forth above. For example,

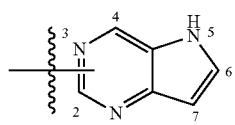

is meant to include 5H-pyrrolo[3,2-c]pyrimidin-2-yl, 5H-pyrrolo[3,2-c]pyrimidin-4-yl, 5H-pyrrolo[3,2-c]pyrimidin-5-yl, 5H-pyrrolo[3,2-c]pyrimidin-6-yl and 5H-pyrrolo[3,2-c]pyrimidin-7-yl (i.e., substitutions can be at 2, 4, 5, 6, or 7 positions of the 5H-pyrrolo[3,2-c]pyrimidine ring). All the other variables $Y^2$, Q, Z of formula (I) and $R^4$, $R^5$, $R^6$, $R^7$ and $R^8$ are as defined in any of the embodiments described herein.

In some embodiments of compounds of formula (I), $Y^1$ is selected from:

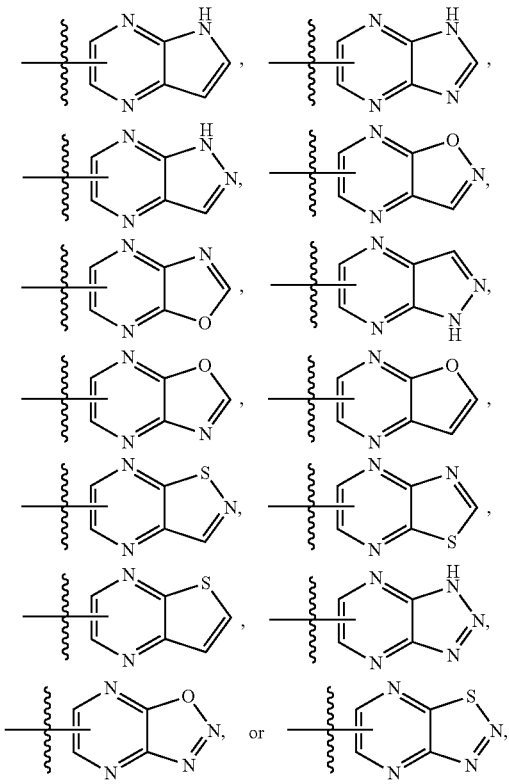

each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl, where the wavy line indicates the point of attachment to the rest of the molecule. The notation

means $Y^1$ can be attached to the rest of the molecule at any of the available positions of the $Y^1$ group set forth above. For example,

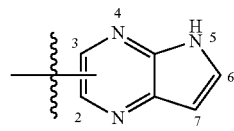

is meant to include 5H-pyrrolo[2,3-b]pyrazin-2-yl, 5H-pyrrolo[2,3-b]pyrazin-3-yl, 5H-pyrrolo[2,3-b]pyrazin-5-yl, 5H-pyrrolo[2,3-b]pyrazin-6-yl, 5H-pyrrolo[2,3-b]pyrazin-7-yl, (i.e., substitutions can be at 2, 3, 5, 6, or 7 positions of the 5H-pyrrolo[2,3-b]pyrazine ring). All the other variables $Y^2$, Q, Z of formula (I) and $R^4$, R, $R^6$, $R^7$ and $R^8$ are as defined in any of the embodiments described herein.

In some embodiments of compounds of formula (I), $Y^1$ is CN, halogen, —OH, optionally substituted $C_{1-6}$ alkyl, optionally substituted $C_{1-6}$ alkoxy, optionally substituted $C_{1-6}$ haloalkyl, or optionally substituted $C_{1-6}$haloalkoxy. In other embodiments, $Y^1$ is CN, halogen, —OH, $C_{1-6}$ alkyl, $C_{1-6}$ alkoxy, $C_{1-6}$ haloalkyl or $C_{1-6}$haloalkoxy, each of which is optionally substituted with from 1 to 3 $R^1$ substituents; or 1 to 3 $R^a$ substituents; or 1 to 3 $R^b$ substituents; or 1 to 3 $R^c$ substituents; or 1 to 3 $R^d$ substituents; or 1 to 3 $R^e$ substituents; 1 to 3 $R^f$ substituents; or 1 to 3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl, In other embodiments, $Y^1$ is CN, halogen, —OH, CH$_3$, CH$_3$O—, CF$_3$, CF$_3$O, cyclopropyl or cyclopropylmethyl. All the other variables $Y^2$, Q, Z of formula (I)

and $R^4$, R, $R^6$, $R^7$ and $R^8$ are as defined in any of the embodiments described herein.

In any of embodiments of compounds of formula (I) above and described herein, where appropriate, each $R^1$ is independently selected from halogen, —CN, —OH, —CF$_3$, CF$_3$O—, $C_{1-6}$alkyl, $C_{1-6}$alkoxy, $C_{3-6}$cycloalkoxy, —NO$_2$, benzyl, phenyl, cyclopropyl, cyclopropylmethyl, 1-cyanocyclopropyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, $C_{1-6}$alkyl-1,2,4-oxadiazol-3-yl, 5-$C_{1-6}$alkyl-1,3,4-oxadiazol-2yl, 5-di($C_{1-6}$alkyl)amino-1,3,4-oxadiazol-2yl, 5-$C_{1-6}$alkylamino-1,3,4-thiadiazol-2-yl, cyclobutyl, cyclobutylmethyl, cyclopentyl, cyclopentylmethyl, cyclohexyl, cyclohexymethyl, —OC(O)R$^b$, —C(O)R$^b$, —C(O)OR$^b$, —NHC(O)R$^b$, —C(O)NHR$^b$, —NHR$^b$ or —NR$^b$R$^b$. In certain instances, $R^1$ is F, Cl, Br, I, —CN, —OH, —CF$_3$, NH$_2$, CF$_3$O—, CH$_3$—, CH$_3$O, C$_2$H$_5$O—, —NO$_2$, cyclopropyl, cyclopropylmethyl, cyclopropylamino, cyclopropylmethylamino, 1-cyanocyclopropyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 1,3,4-thiadiazol-2-yl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl.

In some embodiments of compounds of formula (I), $Y^1$ is selected from the group consisting of 5-pyrimidinyl, 2-pyrimidinyl, 4-pyrimidinyl, 2-methoxy-5-pyrimidinyl, 2-methoxy-3-pyrimidinyl, 2-methoxy-4-pyrimidinyl, 4-methoxy-2-pyrimidinyl, 4-methoxy-4-pyrimidinyl, 4-methoxy-5-pyrimidinyl, 5-methoxy-2-pyrimidinyl, 5-methoxy-4-pyrimidinyl, 2-cyclopropyl-5-pyrimidinyl, 2-cyclopropyl-3-pyrimidinyl, 2-cyclopropyl-4-pyrimidinyl, 4-cyclopropyl-2-pyrimidinyl, 4-cyclopropyl-4-pyrimidinyl, 4-cyclopropyl-5-pyrimidinyl, 5-cyclopropyl-2-pyrimidinyl, 5-cyclopropyl-4-pyrimidinyl, 2-cyclopropylmethyl-5-pyrimidinyl, 2-cyclopropylmethyl-3-pyrimidinyl, 2-cyclopropylmethyl-4-pyrimidinyl, 4-cyclopropylmethyl-2-pyrimidinyl, 4-cyclopropylmethyl-4-pyrimidinyl, 4-cyclopropylmethyl-5-pyrimidinyl, 5-cyclopropylmethyl-2-pyrimidinyl, 5-cyclopropylmethyl-4-pyrimidinyl, 2-methyl-5-pyrimidinyl, 2-methyl-3-pyrimidinyl, 2-methyl-4-pyrimidinyl, 4-methyl-2-pyrimidinyl, 4-methyl-4-pyrimidinyl, 4-methyl-5-pyrimidinyl, 5-methyl-2-pyrimidinyl, 5-methyl-4-pyrimidinyl, 2-halo-5-pyrimidinyl, 2-halo-3-pyrimidinyl, 2-halo-4-pyrimidinyl, 4-halo-2-pyrimidinyl, 4-halo-4-pyrimidinyl, 4-halo-5-pyrimidinyl, 5-halo-2-pyrimidinyl, 5-halo-4-pyrimidinyl, 2-(1-cyanocyclopropyl)-5-pyrimidinyl, 2-(1-cyanocyclopropyl)-3-pyrimidinyl, 2-(1-cyanocyclopropyl)-4-pyrimidinyl, 4-(1-cyanocyclopropyl)-2-pyrimidinyl, 4-(1-cyanocyclopropyl)-4-pyrimidinyl, 4-(1-cyanocyclopropyl)-5-pyrimidinyl, 5-(1-cyanocyclopropyl)-2-pyrimidinyl, 5-(1-cyanocyclopropyl)-4-pyrimidinyl, 2-cyclopropylamino-5-pyrimidinyl, 2-cyclopropylamino-3-pyrimidinyl, 2-cyclopropylamino-4-pyrimidinyl, 4-cyclopropylamino-2-pyrimidinyl, 4-cyclopropylamino-4-pyrimidinyl, 4-cyclopropylamino-5-pyrimidinyl, 5-cyclopropylamino-2-pyrimidinyl, 5-cyclopropylamino-4-pyrimidinyl, 2-dimethylamino-5-pyrimidinyl, 2-dimethylamino-3-pyrimidinyl, 2-dimethylamino-4-pyrimidinyl, 4-dimethylamino-2-pyrimidinyl, 4-dimethylamino-4-pyrimidinyl, 4-dimethylamino-5-pyrimidinyl, 5-dimethylamino-2-pyrimidinyl, 5-dimethylamino-4-pyrimidinyl, 2-cyano-5-pyrimidinyl, 2-cyano-3-pyrimidinyl, 2-cyano-4-pyrimidinyl, 4-cyano-2-pyrimidinyl, 4-cyano-4-pyrimidinyl, 4-cyano-5-pyrimidinyl, 5-cyano-2-pyrimidinyl, 5-cyano-4-pyrimidinyl, 2-trifluoromethyl-5-pyrimidinyl, 2-trifluoromethyl-3-pyrimidinyl, 2-trifluoromethyl-4-pyrimidinyl, 4-trifluoromethyl-2-pyrimidinyl, 4-trifluoromethyl-4-pyrimidinyl, 4-trifluoromethyl-5-pyrimidinyl, 5-trifluoromethyl-2-pyrimidinyl, 5-trifluoromethyl-4-pyrimidinyl, 2-trifluoromethoxy-5-pyrimidinyl, 2-trifluoromethoxy-3-pyrimidinyl, 2-trifluoromethoxy-4-pyrimidinyl, 4-trifluoromethoxy-2-pyrimidinyl, 4-trifluoromethoxy-4-pyrimidinyl, 4-trifluoromethoxy-5-pyrimidinyl, 5-trifluoromethoxy-2-pyrimidinyl, 5-trifluoromethoxy-4-pyrimidinyl, 2-hydroxy-5-pyrimidinyl, 2-hydroxy-3-pyrimidinyl, 2-hydroxy-4-pyrimidinyl, 4-hydroxy-2-pyrimidinyl, 4-hydroxy-4-pyrimidinyl, 4-hydroxy-5-pyrimidinyl, 5-hydroxy-2-pyrimidinyl, 5-hydroxy-4-pyrimidinyl, 2-amino-5-pyrimidinyl, 2-amino-3-pyrimidinyl, 2-amino-4-pyrimidinyl, 4-amino-2-pyrimidinyl, 4-amino-4-pyrimidinyl, 4-amino-5-pyrimidinyl, 5-amino-2-pyrimidinyl, 5-amino-4-pyrimidinyl, 2-methylamino-5-pyrimidinyl, 2-methylamino-3-pyrimidinyl, 2-methylamino-4-pyrimidinyl, 4-methylamino-2-pyrimidinyl, 4-methylamino-4-pyrimidinyl, 4-methylamino-5-pyrimidinyl, 5-methylamino-2-pyrimidinyl, 5-methylamino-4-pyrimidinyl, 2-dimethylamino-5-pyrimidinyl, 2-dimethylamino-3-pyrimidinyl, 2-dimethylamino-4-pyrimidinyl, 4-dimethylamino-2-pyrimidinyl, 4-dimethylamino-4-pyrimidinyl, 4-dimethylamino-5-pyrimidinyl, 5-dimethylamino-2-pyrimidinyl, 5-dimethylamino-4-pyrimidinyl, 2-acetamido-5-pyrimidinyl, 2-acetamido-3-pyrimidinyl, 2-acetamido-4-pyrimidinyl, 4-acetamido-2-pyrimidinyl, 4-acetamido-4-pyrimidinyl, 4-acetamido-5-pyrimidinyl, 5-acetamido-2-pyrimidinyl, 5-acetamido-4-pyrimidinyl, 2-methylthio-5-pyrimidinyl, 2-methylthio-3-pyrimidinyl, 2-methylthio-4-pyrimidinyl, 4-methylthio-2-pyrimidinyl, 4-methylthio-4-pyrimidinyl, 4-methylthio-5-pyrimidinyl, 5-methylthio-2-pyrimidinyl, 5-methylthio-4-pyrimidinyl, 2-acetoxy-5-pyrimidinyl, 2-acetoxy-3-pyrimidinyl, 2-acetoxy-4-pyrimidinyl, 4-acetoxy-2-pyrimidinyl, 4-acetoxy-4-pyrimidinyl, 4-acetoxy-5-pyrimidinyl, 5-acetoxy-2-pyrimidinyl, 5-acetoxy-4-pyrimidinyl, 2-acetyl-5-pyrimidinyl, 2-acetyl-3-pyrimidinyl, 2-acetyl-4-pyrimidinyl, 4-acetyl-2-pyrimidinyl, 4-acetyl-4-pyrimidinyl, 4-acetyl-5-pyrimidinyl, 5-acetyl-2-pyrimidinyl, 5-acetyl-4-pyrimidinyl, 2-methoxycarbonyl-5-pyrimidinyl, 2-methoxycarbonyl-3-pyrimidinyl, 2-methoxycarbonyl-4-pyrimidinyl, 4-methoxycarbonyl-2-pyrimidinyl, 4-methoxycarbonyl-4-pyrimidinyl, 4-methoxycarbonyl-5-pyrimidinyl, 5-methoxycarbonyl-2-pyrimidinyl, 5-methoxycarbonyl-4-pyrimidinyl, 2-methylcarbamoyl-5-pyrimidinyl, 2-methylcarbamoyl-3-pyrimidinyl, 2-methylcarbamoyl-4-pyrimidinyl, 4-methylcarbamoyl-2-pyrimidinyl, 4-methylcarbamoyl-4-pyrimidinyl, 4-methylcarbamoyl-5-pyrimidinyl, 5-methylcarbamoyl-2-pyrimidinyl, 5-methylcarbamoyl-4-pyrimidinyl, 2-pyridyl, 3-pyridyl, 4-pyridyl, 5-pyridyl, 3-methoxy-2-pyridyl, 4-methoxy-2-pyridyl, 5-methoxy-2-pyridyl, 6-methoxy-2-pyridyl, 2-methoxy-3-pyridyl, 4-methoxy-3-pyridyl, 5-methoxy-3-pyridyl, 6-methoxy-3-pyridyl, 2-methoxy-4-pyridyl, 3-methoxy-4-pyridyl, 3-halo-2-pyridyl, 4-halo-2-pyridyl, 5-halo-2- pyridyl, 6-halo-2-pyridyl, 2-halo-3-pyridyl, 4-halo-3-pyridyl, 5-halo-3-pyridyl, 6-halo-3-pyridyl, 2-halo-4-pyridyl, 3-halo-4-pyridyl, 3-cyano-2-pyridyl, 4-cyano-2-pyridyl, 5-cyano-2-pyridyl, 6-cyano-2-pyridyl, 2-cyano-3-pyridyl, 4-cyano-3-pyridyl, 5-cyano-3-pyridyl, 6-cyano-3-pyridyl, 2-cyano-4-pyridyl, 3-cyano-4-pyridyl, 3-hydroxy-2-pyridyl, 4-hydroxy-2-pyridyl, 5-hydroxy-2-pyridyl, 6-hydroxy-2-pyridyl, 2-hydroxy-3-pyridyl, 4-hydroxy-3-pyridyl, 5-hydroxy-3-pyridyl, 6-hydroxy-3-pyridyl, 2-hydroxy-4-pyridyl, 3-hydroxy-4-pyridyl, 3-trifluoromethyl-2-pyridyl, 4-trifluoromethyl-2-pyridyl, 5-trifluoromethyl-2-pyridyl, 6-trifluoromethyl-2-pyridyl, 2-trifluoromethyl-3-pyridyl, 4-trifluoromethyl-3-pyridyl, 5-trifluoromethyl-3-pyridyl, 6-trifluoromethyl-3-pyridyl, 2-trifluoromethyl-4-pyridyl, 3-trifluoromethyl-4-pyridyl, 3-amino-2-pyridyl, 4-amino-2-pyridyl, 5-amino-2-pyridyl, 6-amino-2-pyridyl, 2-amino-3-pyridyl, 4-amino-3-pyridyl, 5-amino-3-pyridyl, 6-amino-3-pyridyl, 2-amino-4-pyridyl, 3-amino-4-pyridyl, 3-trifluoromethoxy-2-pyridyl, 4-trifluoromethoxy-2-pyridyl, 5-trifluoromethoxy-2-pyridyl, 6-trifluoromethoxy-2-pyridyl, 2-trifluoromethoxy-3-pyridyl, 4-trifluoromethoxy-3-pyridyl, 5-trifluoromethoxy-3-pyridyl, 6-trifluoromethoxy-3-pyridyl, 2-trifluoromethoxy-4-pyridyl, 3-trifluoromethoxy-4-pyridyl, 3-methyl-2-pyridyl, 4-methyl-2-pyridyl, 5-methyl-2-pyridyl, 6-methyl-2-pyridyl, 2-methyl-3-pyridyl, 4-methyl-3-pyridyl, 5-methyl-3-pyridyl, 6-methyl-3-pyridyl, 2-methyl-4-pyridyl, 3-methyl-4-pyridyl, 3-methoxy-2-pyridyl, 4-methoxy-2-pyridyl, 5-methoxy-2-pyridyl, 6-methoxy-2-pyridyl, 2-methoxy-3-pyridyl, 4-methoxy-3-pyridyl, 5-methoxy-3-pyridyl, 6-methoxy-3-pyridyl, 2-methoxy-4-pyridyl, 3-methoxy-4-pyridyl, 3-cyclopropyl-2-pyridyl, 4-cyclopropyl-2-pyridyl, 5-cyclopropyl-2-pyridyl, 6-cyclopropyl-2-pyridyl, 2-cyclopropyl-3-pyridyl, 4-cyclopropyl-3-pyridyl, 5-cyclopropyl-3-pyridyl, 6-cyclopropyl-3-pyridyl, 2-cyclopropyl-4-pyridyl, 3-cyclopropyl-4-pyridyl, 3-cyclopropylmethyl-2-pyridyl, 4-cyclopropylmethyl-2-pyridyl, 5-cyclopropylmethyl-2-pyridyl, 6-cyclopropylmethyl-2-pyridyl, 2-cyclopropylmethyl-3-pyridyl, 4-cyclopropylmethyl-3-pyridyl, 5-cyclopropylmethyl-3-pyridyl, 6-cyclopropylmethyl-3-pyridyl, 2-cyclopropylmethyl-4-pyridyl, 3-cyclopropylmethyl-4-pyridyl, 3-cyclopropylamino-2-pyridyl, 4-cyclopropylamino-2-pyridyl, 5-cyclopropylamino2-pyridyl, 6-cyclopropylamino-2-pyridyl, 2-cyclopropylamino-3-pyridyl, 4-cyclopropylamino-3-pyridyl, 5-cyclopropylamino-3-pyridyl, 6-cyclopropylamino-3-pyridyl, 2-cyclopropylamino-4-pyridyl, 3-cyclopropylamino-4-pyridyl, 3-cyclopropylmethylamino-2-pyridyl, 4-cyclopropylmethylamino-2-pyridyl, 5-cyclopropylmethylamino-2-pyridyl, 6-cyclopropylmethylamino-2-pyridyl, 2-cyclopropylmethylamino-3-pyridyl, 4-cyclopropylmethylamino-3-pyridyl, 5-cyclopropylmethylamino-3-pyridyl, 6-cyclopropylmethylamino-3-pyridyl, 2-cyclopropylmethylamino-4-pyridyl, 3-cyclopropylmethylamino-4-pyridyl, 3-methylamino-2-pyridyl, 4-methylamino-2-pyridyl, 5-methylamino-2-pyridyl, 6-methylamino-2-pyridyl, 2-methylamino-3-pyridyl, 4-methylamino-3-pyridyl, 5-methylamino-3-pyridyl, 6-methylamino-3-pyridyl, 2-methylamino-4-pyridyl, 3-methylamino-4-pyridyl, 3-dimethylamino-2-pyridyl, 4-dimethylamino-2-pyridyl, 5-dimethylamino-2-pyridyl, 6-dimethylamino-2-pyridyl, 2-dimethylamino-3-pyridyl, 4-dimethylamino-3-pyridyl, 5-dimethylamino-3-pyridyl, 6-dimethylamino-3-pyridyl, 2-dimethylamino-4-pyridyl, 3-dimethylamino-4-pyridyl, 3-methylthio-2-pyridyl, 4-methylthio-2-pyridyl, 5-methylthio-2-pyridyl, 6-methylthio-2-pyridyl, 2-methylthio-3-pyridyl, 4-methylthio-3-pyridyl, 5-methylthio-3-pyridyl, 6-methylthio-3-pyridyl, 2-methylthio-4-pyridyl, 3-methylthio-4-pyridyl, 3-acetoxy-2-pyridyl, 4-acetoxy-2-pyridyl, 5-acetoxy-2-pyridyl, 6-acetoxy-2-pyridyl, 2-acetoxy-pyridyl, 4-acetoxy-3-pyridyl, 5-acetoxy-3-pyridyl, 6-acetoxy-3-pyridyl, 2-acetoxy-4-pyridyl, 3-acetoxy-4-pyridyl, 3-acetyl-2-pyridyl, 4-acetyl-2-pyridyl, 5-acetyl-2-pyridyl, 6-acetyl-2-pyridyl, 2-acetyl-pyridyl, 4-acetyl-3-pyridyl, 5-acetyl-3-pyridyl, 6-acetyl-3-pyridyl, 2-acetyl-4-pyridyl, 3-acetyl-4-pyridyl, 3-methoxycarbonyl-2-pyridyl, 4-methoxycarbonyl-2-pyridyl, 5-methoxycarbonyl-2-pyridyl, 6-methoxycarbonyl-2-pyridyl, 2-methoxycarbonyl-3-pyridyl, 4-methoxycarbonyl-3-pyridyl, 5-methoxycarbonyl-3-pyridyl, 6-methoxycarbonyl-3-pyridyl, 2-methoxycarbonyl-4-pyridyl, 3-methoxycarbonyl-4-pyridyl, 3-methylcarbamoyl-2-pyridyl, 4-methylcarbamoyl-2-pyridyl, 5-methylcarbamoyl-2-pyridyl, 6-methylcarbamoyl-2-pyridyl, 2-methylcarbamoyl-3-pyridyl, 4-methylcarbamoyl-3-pyridyl, 5-methylcarbamoyl-3-pyridyl, 6-methylcarbamoyl-3-pyridyl, 2-methylcarbamoyl-4-pyridyl, 3-methylcarbamoyl-4-pyridyl, 3-acetamido-2-pyridyl, 4-acetamido-2-pyridyl, 5-acetamido-2-pyridyl, 6-acetamido-2-pyridyl, 2-acetamido-3-pyridyl, 4-acetamido-3-pyridyl, 5-acetamido-3-pyridyl, 6-acetamido-3-pyridyl, 2-acetamido-4-pyridyl and 3-acetamido-4-pyridyl, 3-(1-cyanocyclopropyl)-2-pyridyl, 4-(1-cyanocyclopropyl)-2-pyridyl, 5-(1-cyanocyclopropyl)-2-pyridyl, 6-(1-cyanocyclopropyl)-2-pyridyl, 2-(1-cyanocyclopropyl)-3-pyridyl, 4-(1-cyanocyclopropyl)-3-pyridyl, 5-(1-cyanocyclopropyl)-3-pyridyl, 6-(1-cyanocyclopropyl)-3-pyridyl, 2-(1-cyanocyclopropyl)-4-pyridyl, 3-(1-cyanocyclopropyl)-4-pyridyl, each of which is optionally substituted with from 1, 2, or 3 substituents independently selected from F, Cl, Br, I, —CN, —OH, —CF$_3$, NH$_2$, CF$_3$O—, CH$_3$—, CH$_3$O, —NO$_2$, cyclopropyl, 1-cyanocyclopropyl, cyclopropylmethyl, cyclopropylamino, cyclopropylmethylamino, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. In some instances, the 1, 2, 3 substituents are on the aromatic portion of $Y^1$. In other instances, the 1, 2, 3 substituents are on the aliphatic portion of $Y^1$. All the other variables $Y^2$, Q, Z of formula (I) and $R^4$, $R^5$, $R^6$, $R^7$ and $R^8$ are as defined in any of the embodiments described herein.

In certain embodiments of compounds of formula (I), $Y^1$ is phenyl substituted with from 1 to 2 substituents independently selected from F, Cl, Br, I, —CN, —OH, —CF$_3$, NH$_2$, CF$_3$O—, CH$_3$—, CH$_3$O, C$_2$H$_5$O—, —NO$_2$, cyclopropyl, cyclopropylmethyl, cyclopropylamino, cyclopropylmethylamino, 1-cyanocyclopropyl, 1-carboxycyclopropyl, 1-carbamoylcyclopropyl, 1-methoxycarbonylcyclopropyl, 1-cyanisopropyl, 1-hydroxycyclopropyl, 1-hydroxyisopropyl, cyclobutoxy, cyclopentoxy, cycloheyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 5-methylamino-1,3,4-thiadiazol-2-yl, methylamino methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl.

In other embodiments of compounds of formula (I), $Y^1$ is selected from the group consisting of phenyl, 2-halophenyl, 3-halophenyl, 4-halophenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-trifluoromethylphenyl, 3-trifluoromethylphenyl, 4-trifluoromethylphenyl, 2-aminophenyl, 3-aminophenyl, 4-aminophenyl, 2-trifluoromethylphenyl, 3-trifluoromethylphenyl, 4-trifluoromethylphenyl, 2-methylphenyl, 3-methylphenyl, 4-methylphenyl, 2-methoxyphenyl, 3-methoxyphenyl, 4-methoxyphenyl, 2-cyclopropylphenyl, 3-cyclopropylphenyl, 4-cyclopropylphenyl, 2-cyclopropylmethylphenyl, 3-cyclopropylmethylphenyl, 4-cyclopropylmethylphenyl, 2-cyclopropylmethylaminophenyl, 3-cyclopropylmethylaminophenyl, 4-cyclopropylmethylaminophenyl, 2-cyclopropylaminophenyl, 3-cyclopropylaminophenyl, 4-cyclopropylaminophenyl, 2-methylaminophenyl, 3-methylaminophenyl, 4-methylaminophenyl, 2-dimethylaminophenyl, 3-dimethylaminophenyl, 4-dimethylaminophenyl, 2-methylthiophenyl, 3-methylthiophenyl, 4-methylthiophenyl, 2-acetoxyphenyl, 3-acetoxyphenyl, 4-acetoxyphenyl, 2-acetylphenyl, 3-acetylphenyl, 4-acetylphenyl, 2-methoxycarbonylphenyl, 3-methoxycarbonylphenyl, 4-methoxycarbonylphenyl, 2-acetamidophenyl, 3-acetamidophenyl, 4-acetamidophenyl, 2-methylcarbomoylphenyl, 3-methylcarbomoylphenyl, 4-methylcarbomoylphenyl, 2-(1-cyanocyclopropyl)phenyl, 3-(1-cyanocyclopropyl)phenyl and 4-(1-cyanocyclopropyl)phenyl, each of which is optionally substituted with from 1, 2 or substituents independently selected from F, Cl, Br, I, —CN, —OH, —CF$_3$, NH$_2$, CF$_3$O—, CH$_3$—, CH$_3$O, —NO$_2$, cyclopropyl, 1-cyanocyclopropyl, cyclopropylmethyl, cyclopropylamino, cyclopropylmethylamino, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino or 1-hydroxy-1-methylethyl or methylcarbamoyl. In some instances, the 1, 2, 3 substituents are on the aromatic portion of $Y^1$. In other instances, the 1, 2, 3 substituents are on the aliphatic portion of $Y^1$. All the other variables $Y^2$, Q, Z of formula (I) and $R^4$, R, $R^6$, $R^7$ and $R^8$ are as defined in any of the embodiments described herein.

In some embodiments of compounds of formula (I), $Y^2$ is as defined in the summary of the invention and the other variables $Y^1$, Q and Z of formula (I) and $R^4$, $R^5$, $R^6$, $R^7$ and $R^8$ are as defined in any of the above embodiments and any of the embodiments described herein.

In some embodiments of compounds of formula (I), $Y^2$ is H, halogen, CN, $C_{1-6}$alkyl, $C_{1-6}$alkoxy, $C_{3-6}$cycloalkylamino, $C_{3-6}$cycloalkyl-$C_{1-3}$alkylamino, aryl, heteroaryl, arylalkyl or heteroarylalkyl, wherein the aliphatic or aromatic portion of $Y^2$ is optionally substituted with 1, 2 or 3 substituents independently selected from H, F, Cl, I, CN, CH$_3$, CH$_3$O—, phenyl, CF$_3$ or CF$_3$O. In certain instances, $Y^2$ is H, halogen, CN, $C_{1-6}$alkyl, $C_{1-6}$alkoxy, $C_{3-6}$cycloalkylamino or $C_{3-6}$cycloalkyl-$C_{1-3}$alkylamino, wherein the aliphatic portion of $Y^2$ is optionally substituted with 1, 2 or 3 substituents independently selected from H, F, Cl, I, CN, CH$_3$, CH$_3$O—, phenyl, CF$_3$ or CF$_3$O. All other variables $Y^1$, Q and Z of formula (I) and $R^4$, $R^5$, $R^6$, $R^7$ and $R^8$ are as defined in any of the embodiments described herein.

In some embodiments of compounds of formula (I), $Y^2$ is H, F, Cl, I, CN, CH$_3$, CH$_3$O—, cyclopropylamino or cyclopropylmethylamino. All the other variables $Y^1$, Q and Z of formula (I) and $R^4$, $R^5$, $R^6$, $R^7$ and $R^8$ are as defined in any of the embodiments described herein.

In some preferred embodiments of compounds of formula (I), $Y^2$ is H and all the other variables $Y^1$, Q and Z of formula (I) and $R^4$, $R^5$, $R^6$, $R^7$ and $R^8$ are as defined in any of the embodiments described herein.

In some embodiments of compounds of formula (I), Q is selected from H, F, Cl or CH$_3$. In one embodiment, Q is H. In another embodiment, Q is F. In yet another embodiment, Q is CH$_3$. In still other embodiment, Q is Cl. In another embodiment, Q is H or F. All the other variables $Y^1$, $Y^2$, Z of formula (I) and $R^4$, $R^5$, $R^6$, $R^7$ and R are as defined in any of the embodiments described herein.

In some embodiments of compounds of formula (I), Z is as defined in the summary of invention. All the other variables of formula (I) and $R^4$, $R^5$, $R^6$, $R^7$ and R are as defined in any of the embodiments described herein.

In some embodiments of compounds of formula (I), Z is —N($R^4$)($R^5$) or —C($R^6$)($R^7$)($R^8$), wherein $R^4$ and $R^5$ are each independently selected from the group consisting of H, optionally substituted $C_{1-6}$alkyl, optionally substituted $C_{3-8}$cycloalkyl, optionally substituted $C_{3-8}$cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl; or $R^4$ and $R^5$ taken together with the nitrogen atom to which they are attached form a four to eight-membered ring having from 0-2 additional heteroatoms as ring members selected from N, O or S, wherein the four to eight-membered ring is optionally substituted with from one to three groups independently selected from $C_{1-6}$ haloalkyl, $C_{1-6}$ haloalkoxy, $C_{1-6}$ alkyl, $C_{3-8}$ cycloalkyl, $C_{3-8}$ cycloalkylalkyl, aryl, arylalkyl or $R^e$. $R^6$, $R^7$ and $R^8$ are each independently H, $C_{1-6}$ alkyl, $C_{1-6}$ haloalkyl, $C_{1-6}$ haloalkoxy, $C_{3-8}$ cycloalkyl, $C_{3-8}$ cycloalkylalkyl, aryl, arylalkyl, heterocycloalkyl, heterocycloalkylalkyl, heteroaryl, heteroarylalkyl or —$X^2R^9$; wherein the aliphatic or aromatic portion of $R^6$, $R^7$ and $R^8$ are each optionally substituted with from 1 to 3 members independently selected from the group consisting of $C_{3-8}$cycloalkyl, $C_{3-8}$cycloalkylalkyl, aryl, arylalkyl, heterocycloalkyl, heterocycloalkylalkyl, heteroaryl, heteroarylalkyl and $R^e$; or any two of the $R^6$, $R^7$ and $R^8$ groups taken together with the carbon atom to which they are attached form a 3 to 8-membered carbocyclic ring or a 4 to 8-membered heterocyclic ring having from 1 to 2 heteroatoms as ring members selected from N, O or S, wherein the 3 to 8-membered carbocyclic ring or the 4 to 8-membered heterocyclic ring is optionally substituted with from one to three groups independently selected from $C_{1-6}$ haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl or heteroarylalkyl or $R^e$, provided at each occurrence, at least two of the $R^6$, $R^7$ and $R^8$ groups are not simultaneously hydrogen. All the other variables $Y^1$, $Y^2$ and Q of formula (I) are as defined in any of the embodiments described herein.

In some embodiments of compounds of formula (I), Z is —N($R^4$)($R^5$), wherein $R^4$ and $R^5$ are each independently selected from $C_{1-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from (i) 1-3 substituents independently selected from $C_{1-6}$alkoxy, $C_{1-6}$ haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl, heteroarylalkyl or $R^e$; or (ii) 1, 2 or 3 $R^a$ substituents; or (iii) 1, 2 or 3 $R^b$ substituents; or (iv) 1, 2 or 3 $R^c$ substituents; or (v) 1, 2 or 3 $R^d$ substituents; or (vi) 1, 2 or 3 $R^f$ groups. All the other variables $Y^1$, $Y^2$ and Q of formula (I) are as defined in any of the embodiments described herein.

In some embodiments of compounds of formula (I), $R^4$ is —CH$_3$ and $R^5$ is $C_{2-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from (i) 1-3 substituents independently selected from $C_{1-6}$alkoxy, $C_{1-6}$haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl, heteroarylalkyl or $R^e$; or (ii) 1, 2 or 3 $R^a$ substituents; or (iii) 1, 2 or 3 $R^b$ substituents; or (iv) 1, 2 or 3 $R^c$ substituents; or (v) 1, 2 or 3 $R^d$ substituents; or (vi) 1, 2 or 3 $R^f$ groups. In certain instances, $R^4$ is —CH$_3$ and $R^5$ is $C_{2-6}$alkyl. All the other variables $Y^1$, $Y^2$ and Q of formula (I) are as defined in any of the embodiments described herein.

In some embodiments of compounds of formula (I), $R^4$ and $R^5$ are each independently selected from $C_{1-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from 1, 2 or 3 $R^X$ members selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In certain instances, $R^X$ is F, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. All the other variables $Y^1$, $Y^2$ and Q of formula (I) are as defined in any of the embodiments described herein.

In some embodiments of compounds of formula (I), $R^4$ is —CH$_3$ and $R^5$ is $C_{2-6}$alkyl, $C_{3-8}$cycloalkyl, $C_{3-8}$cycloalkylalkyl, aryl, aryl-$C_{1-4}$alkyl, heteroaryl or heteroaryl-$C_{1-4}$alkyl, each of which is optionally substituted with from 1, 2 or 3 $R^x$ members selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In certain instances, R is F, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. All the other variables $Y^1$, $Y^2$ and Q of formula (I) are as defined in any of the embodiments described herein.

In some embodiments of compounds of formula (I), $R^4$ is —CH$_3$ and $R^5$ is selected from ethyl, propyl, butyl, pentyl, cyclopropyl, cyclopropylmethyl, cyclobutyl, cyclobutylmethyl, cyclopentyl, cyclopentylmethyl, cyclohexyl, cyclohexylmethyl, phenyl or benzyl, each of which is optionally substituted with from 1-3 substituents independently selected from F, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. All the other variables $Y^1$, $Y^2$ and Q of formula (I) are as defined in any of the embodiments described herein.

In some embodiments of compounds of formula (I), Z is —N(R$^4$)(R$^5$), wherein —N(R$^4$)(R$^5$) is selected from 1-azetidinyl, 1-pyrrolidinyl, 1-piperidinyl, 4-morpholinyl, 4-thiomorpholinyl, 3-oxazolidinyl, 3-thiazolidinyl, 2-isoxazolidinyl, 2-isothiazolidinyl, 1-pyrazolidinyl, 1-piperazinyl, 1-hexahydropyrimidinyl or 1-hexahydropyridazinyl, each of which is (i) optionally substituted with from 1 to 3 $R^{26}$ substituents independently selected from the group consisting of halogen, $C_{1-6}$alkyl, $C_{1-6}$alkoxy, $C_{1-6}$ haloalkyl, $C_{1-6}$haloalkoxy, $C_{1-6}$alkyl, $C_{3-8}$cycloalkyl, $C_{3-8}$cycloalkylalkyl, heterocycloalkyl, heterocycloalkylalkyl, aryl, arylalkyl, heteroaryl, heteroarylalkyl and $R^c$; or (ii) two adjacent $R^{26}$ substituents together with the atom to which they are attached form a 5 or 6-membered aromatic ring having from 0 to 2 additional atoms as ring members selected from O, N or S or (iii) optionally substituted with from 1 to 8 deuteriums with at least 52.5%, 60%, 70%, 75%, 80%, 90%, 95%, 99%, 99.5% or 99.9% deuterium incorporation for each deuterium. In certain instances, $R^{26}$ is F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In other instances, $R^{26}$ is F, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In other instances, $R^{26}$ is F, CH$_3$, methoxycarbonyl, ethoxycarbonyl, —CH₃, CH₃(CO)NH—, vinyl, propen-3-yl or CH₃(CO)(CH₃)N—. In some embodiments, each hydrogen atom in Z is optionally replaced by a deuterium atom with at least 52.5%, 60%, 70%, 75%, 80%, 90%, 95%, 99%, 99.5% or 99.9% deuterium incorporation for each deuterium. All the other variables $Y^1$, $Y^2$ and Q of formula (I) are as defined in any of the embodiments described herein.

In some embodiments of compounds of formula (I), Z is —C($R^6$)($R^7$)($R^8$), where $R^6$ is H and $R^7$ and $R^8$ are each independently $C_{1-6}$alkyl, optionally substituted with from 1 to 3 $R^d$ or $R^e$. In some embodiments, $R^6$, $R^7$ and $R^8$ are each independently $C_{1-6}$alkyl, optionally substituted with from 1 to 3 $R^d$ or $R^e$. In some embodiments, —C($R^6$)($R^7$)($R^8$) is cyclopropyl, cyclobutyl, cyclohexyl, cyclopentyl, cycloheptyl, cyclooctyl, each of which is optionally substituted with from 1-3 $R^{28}$ substituents independently selected from F, Cl, Br, I, —CN, —OH, —CF₃, NH₂, CF₃O—, CH₃—, CH₃O, —CH₂CH=CH₂, —NO₂, cyclopropyl, cyclopropylmethyl, cyclopropylamino, cyclopropylmethylamino, 1-cyanocyclopropyl, vinyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In some instances, $R^{28}$ is F, —CN, —OH, —CF₃, NH₂, CF₃O—, CH₃—, CH₃O, —NO₂, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In some embodiments, —C($R^6$)($R^7$)($R^8$) is 2-azetidinyl, 3-azetidinyl, 3-pyrrolidinyl, 2-pyrrolidinyl, 2-piperidinyl, 3-piperidinyl, 4-piperidinyl, 2-morpholinyl, 3-morpholinyl, 2-thiomorpholinyl, 3-thiomorpholinyl, 2-oxazolidinyl, 4-oxazolidinyl, 5-oxazolidinyl, 2-thiazolidinyl, 4-thiazolidinyl, 5-thiazolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 2-piperazinyl, 2-hexahydropyrimidinyl, 4-hexahydropyrimidinyl, 5-hexahydropyrimidinyl, 3-hexahydropyridazinyl or 4-hexahydropyridazinyl, each of which is optionally substituted with 1 to 3 $R^{28}$ substituents. In some embodiments, each hydrogen atom in Z is optionally replaced by a deuterium atom with at least 52.5%, 60%, 70%, 75%, 80%, 90%, 95%, 99%, 99.5% or 99.9% deuterium incorporation for each deuterium. All the other variables $Y^1$, $Y^2$ and Q of formula (I) are as defined in any of the embodiments described herein.

In some embodiments of compounds of formula (I), Z is selected from the group consisting of cyclopropyl, cyclobutyl, cyclohexyl, cyclopentyl, cycloheptyl, cyclooctyl, 1-azetidinyl, 1-pyrrolidinyl, 1-piperidinyl, 4-morpholinyl, 4-thiomorpholinyl, 3-oxazolidinyl, 3-thiazolidinyl, 2-isoxazolidinyl, 2-isothiazolidinyl, 1-pyrazolidinyl, 1-piperazinyl, 1-hexahydropyrimidinyl, 1-hexahydropyridazinyl, (CH₃)(CF₃CH₂)N—, cyclopropylmethylamino, sec-butyl, pentan-2-yl and pentan-3-yl, each of which is (i) optionally substituted with from one to three $R^{27}$ substituents independently selected from the group consisting of halogen, $C_{1-6}$alkyl, $C_{1-6}$alkoxy, $C_{1-6}$ haloalkyl, $C_{1-6}$haloalkoxy, $C_{1-6}$alkyl, $C_{3-8}$ cycloalkyl, $C_{3-8}$ cycloalkylalkyl, heterocycloalkyl, heterocycloalkylalkyl, aryl, arylalkyl, heteroaryl, heteroarylalkyl and $R^c$; or (ii) two adjacent $R^{27}$ substituents together with the atom to which they are attached form a 5 or 6-membered aromatic ring having from 0 to 2 additional atoms as ring members selected from O, N or S; or (iii) optionally substituted with from 1 to 11 deuteriums having at least 52.5%, 60%, 70%, 75%, 80%, 90%, 95%, 99%, 99.5% or 99.9% deuterium incorporation for each deuterium. In one embodiment, Z is cyclopropyl optionally substituted with 1 to 2 $R^{27}$ groups. In another embodiment, Z is cyclopentyl optionally substituted with 1 to 2 $R^{27}$ groups. In yet another embodiment Z is 1-pyrrolidinyl optionally substituted with 1 to 2 $R^{27}$ groups. In other embodiment, Z is 1-piperidinyl optionally substituted with 1 to 2 $R^{27}$ groups. In another embodiment, Z is 1-pyrrolidinyl, 3-fluoro-1-pyrrolidinyl, (3S)-3-fluoro-1-pyrrolidinyl, (3R)-3-fluoro-1-pyrrolidinyl, 3,3-difluoro-1-pyrrolidinyl, 3-$C_{1-6}$alkyl-C(O)—$C_{1-6}$alkyl-N-1-pyrrolidinyl, 3-$C_{1-6}$alkyl-C(O)NH-1-pyrrolidinyl, $C_{1-6}$alkoxycarbonyl-1-pyrrolidinyl or 3,3-dimethyl-1-pyrrolidinyl. In certain instances, $R^{27}$ is F, Cl, Br, I, —CN, —OH, —CF₃, NH₂, CF₃O—, CH₃—, CH₃O, —NO₂, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In one instance, $R^{27}$ is —F, methoxycarbonyl, ethoxycarbonyl, —CH₃, CH₃(CO)NH—, vinyl, propen-3-yl or CH₃(CO)(CH₃)N—. In another instance, $R^{27}$ is —F, methoxycarbonyl, ethoxycarbonyl, —CH₃, CH₃(CO)NH— or CH₃(CO)(CH₃)N—. In yet another instance, $R^{27}$ is vinyl or propen-3-yl. All the other variables $Y^1$, $Y^2$ and Q of formula (I) are as defined in any of the embodiments described herein.

Subformulae of Formula I

In one embodiment of the invention, compounds of formula (I) have subformula (Ia):

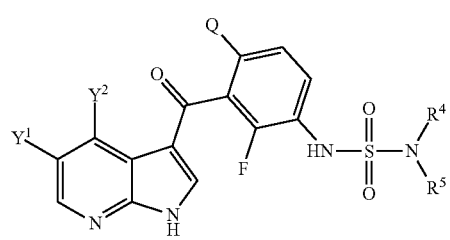

Ia where the substituents $Y^1$, $Y^2$, Q, $R^4$ and $R^5$ are as defined in any of the embodiments disclosed herein. In some embodiments, $R^4$ is CH₃ and $R^5$ is $C_{2-6}$alkyl optionally substituted with from 1-3 substituents independently selected from F, Cl, Br, I, —CN, —OH, —CF₃, NH₂, CF₃O—, CH₃—, CH₃O, —NO₂, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl.

In a second embodiment of the invention, compounds of formula (I) have subformula (IBN):

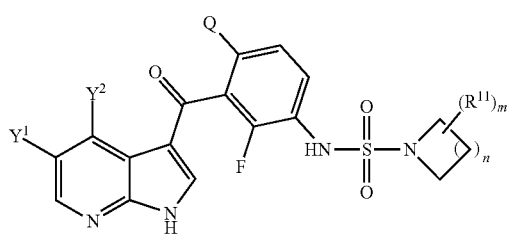

where $R^{11}$ is $C_{1-6}$alkyl, $C_{1-6}$alkoxy, $C_{1-6}$ haloalkyl, $C_{1-6}$haloalkoxy, $C_{3-8}$cycloalkyl, $C_{3-8}$cycloalkylalkyl, aryl, arylalkyl, heteroaryl, heteroarylalkyl, heterocycloalkyl, heterocycloalkylalkyl or $R^e$, each of which is optionally substituted with from (i) 1-3 substituents independently selected from $C_{1-6}$alkoxy, $C_{1-6}$ haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl, heteroarylalkyl, $R^d$ or $R^e$; or (ii) 1, 2 or 3 $R^a$ substituents; or (iii) 1, 2 or 3 $R^b$ substituents; or (iv) 1, 2 or 3 $R^c$ substituents; or (v) 1, 2 or 3 $R^d$ substituents; or (vi) 1, 2 or 3 $R^f$ groups; the subscript n is 1, 2, 3, 4 or 5 and the subscript m is 0, 1, 2 or 3. In some embodiments, $R^{11}$ is $C_{1-6}$alkyl, F, Cl, Br, I, —CN, —OH, —CF$_3$, NH$_2$, CF$_3$O—, CH$_3$—, ethyl, propyl, butyl, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In some embodiments, m is 0. In other embodiments, the subscript n is 1, 2, 3 or 4. In some embodiments, n is 1, 2 or 3 and m is 1 or 2. All the other variables $Y^1$, $Y^2$ and Q are as defined in any of the embodiments described herein.

In a third embodiment of the invention, compounds of formula (I) have subformula (Ic):

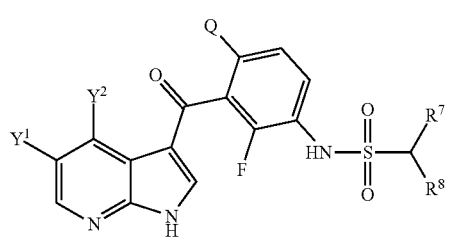

wherein $R^7$ and $R^8$ are each independently $C_{1-6}$alkyl, $C_{1-6}$haloalkyl, $C_{1-6}$haloalkoxy, $C_{3-8}$cycloalkyl, $C_{3-8}$cycloalkylalkyl, aryl, arylalkyl, heteroaryl, heteroarylalkyl or —$X^2R^9$, wherein the aliphatic or aromatic portion of $R^7$ and $R^8$ are each optionally substituted with from 1 to 3 members independently selected from the group consisting of $C_{3-8}$cycloalkyl, $C_{3-8}$cycloalkylalkyl, aryl, arylalkyl, heteroaryl, heteroarylalkyl and $R^e$; and wherein $X^2$ is —$NR^{10}$, O or S; $R^{10}$ is H, $C_{1-6}$alkyl or aryl; and $R^9$ is H, $C_{1-6}$alkyl, $C_{1-6}$haloalkyl, $C_{1-6}$haloalkoxy, $C_{3-8}$cycloalkyl, $C_{3-8}$cycloalkylalkyl, aryl, arylalkyl, heteroaryl or heteroarylalkyl, wherein $R^9$ is optionally substituted with from 1 to 3 $R^e$ substituents. In some embodiments, $R^7$ and $R^8$ groups taken together with the carbon atom to which they are attached form a 3 to 8-membered carbocyclic ring or a 4 to 8-membered heterocyclic ring having from 1 to 2 heteroatoms as ring members selected from N, O or S, wherein the 3 to 8-membered carbocyclic ring or the 4 to 8-membered heterocyclic ring is optionally substituted with from one to three groups independently selected from $C_{1-6}$ haloalkyl, $C_{1-6}$haloalkoxy, $C_{1-6}$alkyl, $C_{3-8}$cycloalkyl, $C_{3-8}$cycloalkylalkyl, aryl, arylalkyl, heteroaryl or heteroarylalkyl or $R^e$. All the other variables $Y^1$, $Y^2$ and Q are as defined in any of the embodiments described herein.

In a fourth embodiment of the invention, compounds of formula (I) have subformula (Id):

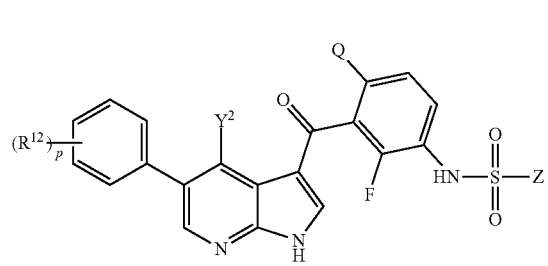

wherein $R^{12}$ is H or $R^1$; or two adjacent $R^{12}$ together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the subscript p is an integer of 1 to 5. In one embodiment, p is 1. In another embodiment, p is 2. In yet another embodiment, p is 5 and two adjacent $R^{12}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and each $R^{12}$ is independently H, $R^d$ or $R^e$. In some embodiments, the two adjacent $R^{12}$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{12}$ together with the atoms to which they are attached form an optionally substituted fused heterocyclic ring, including, but not limiting to, pyrrole, furan, thiophen, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. All the other variables $Y^2$, Q and Z are as defined in any of the embodiments described herein.

In a fifth embodiment of the invention, compounds of formula (I) have subformula (Id-1):

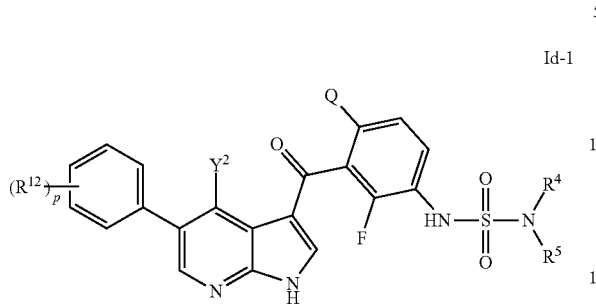

Id-1 wherein $R^{12}$ is H or $R^1$; or two adjacent $R^{12}$ together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the subscript p is an integer of 1 to 5. In one embodiment, p is 1. In another embodiment, p is 2. In yet another embodiment, p is 5 and two adjacent $R^{12}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the other three $R^{12}$ is each independently H, $R^d$ or $R^e$. In some embodiments, the two adjacent $R^{12}$ together with the atoms to which they are attached form an optionally substituted fused carbocyclic ring, including, but not limiting to, benzene, cyclopentane, cyclohexane and benzene rings. The substituents on the carbocyclic ring can be from 1-2 $R^d$ or $R^e$ groups. In other embodiments, two adjacent $R^{12}$ together with the atoms to which they are attached form an optionally substituted fused heterocyclic ring, including, but not limiting to, pyrrole, furan, thiophen, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. All the other variables $Y^2$, Q, $R^4$ and $R^5$ are as defined in any of the embodiments described herein.

In a sixth embodiment of the invention, compounds of formula (I) have subformula (Id-2):

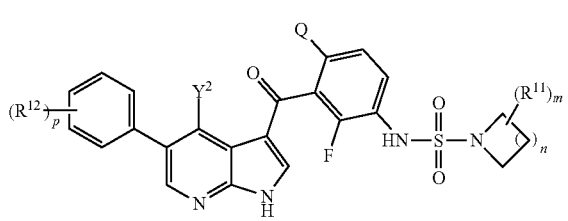

Id-2

All the variables $R^{12}$, p, m, n, $Y^2$, Q, and $R^{11}$ are as defined in any of the embodiments described herein. In some embodiments, $R^{11}$ is $C_{1-6}$alkyl, $C_{3-8}$cycloalkyl, $C_{3-8}$cycloalkylalkyl, aryl, arylalkyl, heteroaryl, heteroarylalkyl, heterocycloalkyl, heterocycloalkylalkyl or $R^e$, the subscript m is an integer from 0 to 3, and the subscript n is an integer from 1 to 5.

In a seventh embodiment of the invention, compounds of formula (I) have subformula (Id-3):

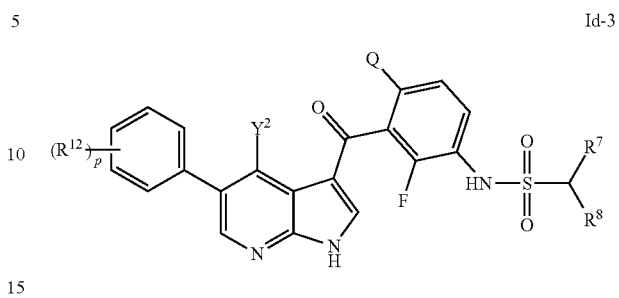

Id-3

All the variables $R^{12}$, p, $Y^2$, Q, $R^7$ and $R^8$ are as defined in any of the embodiments described herein. In some embodiments, $R^7$ and $R^8$ are each independently $C_{1-6}$alkyl, $C_{1-6}$ haloalkyl, $C_{1-6}$haloalkoxy, $C_{3-8}$cycloalkyl, $C_{3-8}$cycloalkylalkyl, aryl, arylalkyl, heteroaryl, heteroarylalkyl or —$X^2R^9$, wherein the aliphatic or aromatic portion of $R^7$ and $R^8$ are each optionally substituted with from 1 to 3 members independently selected from the group consisting of $C_{3-8}$cycloalkyl, $C_{3-8}$cycloalkylalkyl, aryl, arylalkyl, heteroaryl, heteroarylalkyl and $R^e$, provided at each occurrence, at least two of the $R^6$, $R^7$ and $R^8$ groups are not simultaneously hydrogen; and wherein $X^2$ is —$NR^{10}$, O or S; $R^{10}$ is H, $C_{1-6}$alkyl or aryl; and $R^9$ is H, $C_{1-6}$alkyl, $C_{1-6}$ haloalkyl, $C_{1-6}$haloalkoxy, $C_{3-8}$cycloalkyl, $C_{3-8}$cycloalkylalkyl, aryl, arylalkyl, heteroaryl or heteroarylalkyl, wherein $R^9$ is optionally substituted with from 1 to 3 $R^e$ substituents.

In an eighth embodiment of the invention, compounds of formula (I) have subformula (Ie):

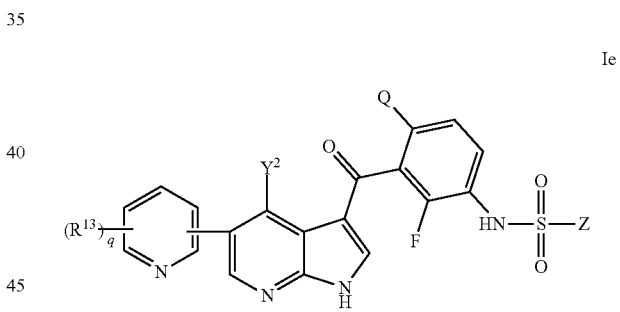

Ie wherein $R^{13}$ is H or $R^1$; or two adjacent $R^{13}$ together with the atoms to which they are attached form a 5 to 6-membered ring having 0-2 heteroatoms as ring members selected from O, N or S; and the subscript q is an integer of 1 to 4, where the 5 to 6-membered-ring is optionally substituted with from 1-3 $R^d$ or $R^e$substituents. In one embodiment, q is 1. In another embodiment, q is 2. In yet another embodiment, q is 4 and two adjacent $R^{13}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the other two $R^{13}$ groups are each independently H, $R^d$ or $R^e$. In some embodiments, the two adjacent $R^{13}$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{13}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. All the other variables $Y^2$, Q and Z are as defined in any of the embodiments described herein.

In a ninth embodiment of the invention, compounds of formula (I) have subformula (If):

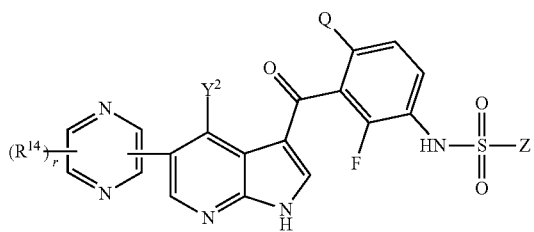

If $R^{14}$ is H or $R^1$; or two adjacent $R^{14}$ together with the atoms to which they are attached form a 5 to 6-membered ring having 0-2 heteroatoms as ring members selected from O, N or S; and the subscript r is an integer of 1 to 3, where the 5 to 6-membered-ring is optionally substituted with from 1-3 $R^d$ or $R^e$ substituents. In one embodiment, r is 1. In another embodiment, r is 2. In yet another embodiment, r is 3 and two adjacent $R^{14}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the other $R^{14}$ is H, $R^d$ or $R^e$. In some embodiments, the two adjacent $R^{14}$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{14}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. All the other variables $Y^2$, Q and Z are as defined in any of the embodiments described herein.

In a tenth embodiment of the invention, compounds of formula (I) have subformula (Ig):

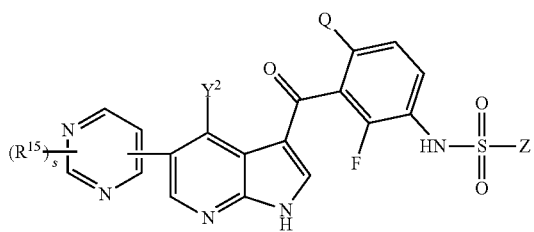

Ig $R^{15}$ is H or $R^1$; or two adjacent $R^5$ together with the atoms to which they are attached form a 5 to 6-membered ring having 0-2 heteroatoms as ring members selected from O, N or S; and the subscript s is an integer of 1 to 3, where the 5 to 6-membered-ring is optionally substituted with from 1-3 $R^d$ or R substituents. In one embodiment, s is 1. In another embodiment, s is 2. In yet another embodiment, s is 3 and two adjacent $R^{15}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the other $R^5$ is H, $R^d$ or $R^e$. In some embodiments, the two adjacent $R^5$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{15}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In other embodiments, $R^{15}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)$R^b$, —C(O)$R^b$, —C(O)O$R^b$, —NHC(O)$R^b$, —C(O)NH$R^b$, —NH$R^b$ or —N$R^b R^b$. In some embodiments, $R^5$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido or methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. All the other variables $Y^2$, Q and Z are as defined in any of the embodiments described herein.

In an eleventh embodiment of the invention, compounds of formula (I) have subformula (Ig-1):

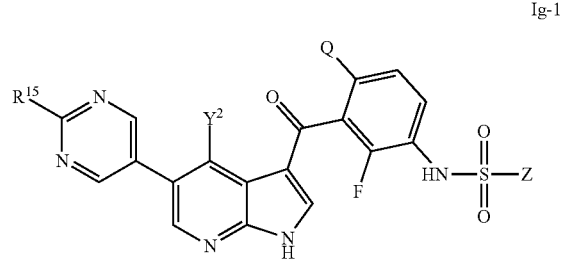

Ig-1

All the other variables $R^5$, $Y^2$, Q and Z are as defined in any of the embodiments described herein. In a preferred embodiment, $Y^2$ is H. In some embodiments, $R^5$ is H or $R^1$. In some embodiments, $R^5$ is $R^a$, $R^b$, $R^c$, $R^d$ or $R^e$. In other embodiments, $R^5$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)R, —C(O)R, —C(O)OR, —NHC(O)R, —C(O)

NHR$^b$, —NHR$^b$ or —NR$^b$R$^b$. In some embodiments, R$^5$ is F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido or methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. In some embodiments, Z is —N(R$^4$)(R$^5$) or —N(CH$_3$)(R$^5$). All the other variables are as defined in any of the embodiments described herein.

In a twelfth embodiment of the invention, compounds of formula (I) have subformula (Ig-2):

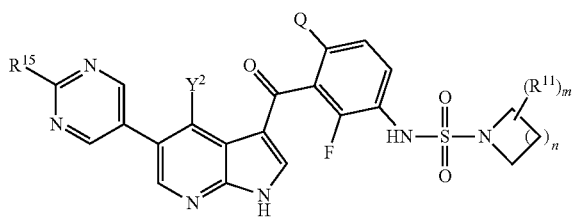

Ig-2

All the variables R$^1$, Y$^2$, Q, R$^{11}$, m and are as defined in any of the embodiments described herein. In a preferred embodiment, Y$^2$ is H. In some embodiments, R$^5$ is H or R$^1$. In some embodiments, R$^5$ is R$^a$, R$^b$, R, R$^d$ or R$^e$. In one embodiment, R$^{15}$ is C$_{1-6}$alkyl. In another embodiment, R$^5$ is C$_{3-6}$cycloalkyl. In yet another embodiment, R$^5$ is heterocycloalkyl. The subscript m is an integer from 0 to 3. The subscript n is an integer from 1 to 5. In some embodiments, m is 0. In other embodiments, the subscript n is 1, 2, 3 or 4. In some embodiments, n is 1, 2 or 3 and m is 1 or 2. In some embodiments, R$^1$ is C$_{1-6}$alkyl, C$_{3-8}$cycloalkyl, C$_{3-8}$cycloalkylalkyl, aryl, arylalkyl, heteroaryl, heteroarylalkyl or R$^e$. In some embodiments, R$^{11}$ is C$_{1-6}$alkyl, C$_{1-6}$alkoxy, C$_{1-6}$haloalkyl, C$_{1-6}$haloalkoxy, C$_{3-8}$cycloalkyl, C$_{3-8}$cycloalkylalkyl, aryl, arylalkyl, heteroaryl, heteroarylalkyl, heterocycloalkyl, heterocycloalkylalkyl or R$^e$, each of which is optionally substituted with from (i) 1-3 substituents independently selected from C$_{1-6}$alkoxy, C$_{1-6}$haloalkyl, C$_{1-6}$haloalkoxy, C$_{1-6}$alkyl, C$_{3-8}$cycloalkyl, C$_{3-8}$cycloalkylalkyl, aryl, arylalkyl, heteroaryl, heteroarylalkyl, R$^d$ or R$^e$; or (ii) 1, 2 or 3 R$^a$ substituents; or (iii) 1, 2 or 3 R$^b$ substituents; or (iv) 1, 2 or 3 R$^c$ substituents; or (v) 1, 2 or 3 R$^d$ substituents; or (vi) 1, 2 or 3 R$^f$ groups; the subscript n is 1, 2, 3, 4 or 5 and the subscript m is 0, 1, 2 or 3. In other embodiments, R$^{11}$ is C$_{1-6}$alkyl, C$_{3-8}$cycloalkyl, C$_{3-8}$cycloalkylalkyl, aryl, arylalkyl, heteroaryl, heteroarylalkyl or R$^e$. In some embodiments, R$^{11}$ is halogen, C$_{1-6}$alkyloxycarbonyl, C$_{1-6}$alkyl, C$_{1-6}$alkyl-(CO)NH— or C$_{1-6}$alkyl-(CO)(C$_{1-6}$alkyl)N—. In certain embodiments, R$^{11}$ is methoxycarbonyl, ethoxycarbonyl, —CH$_3$, CH$_3$(CO)NH—, vinyl, propen-3-yl or CH$_3$(CO)(CH$_3$)N—. In one embodiment of compounds of formula Ig-2, the subscript n is 1, m is 0 or 1. In another embodiment of compounds of formula Ig-2, the subscript n is 2, m is 0, 1 or 2. In yet another embodiment, of compounds of formula Ig-2, the subscript n is 3, m is 0, 1 or 2. All the other variables are as defined in any of the embodiments described herein.

In a thirteenth embodiment of the invention, compounds of formula (I) have subformula (Ig-3):

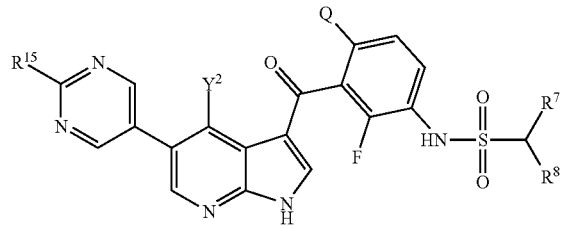

Ig-3

All the variables R$^{15}$, Y$^2$, Q, R$^7$ and R$^8$ are as defined in any of the embodiments described herein. In a preferred embodiment, Y$^2$ is H. In some embodiments, R$^5$ is H or R$^1$. In some embodiments, R$^{15}$ is R$^a$R$^b$, R, R$^d$ or R$^e$. In one embodiment, R$^{15}$ is C$_{1-6}$alkyl. In another embodiment, R$^5$ is C$_{3-6}$cycloalkyl. In yet another embodiment, R$^5$ is heterocycloalkyl. In some embodiments, R$^7$ and R$^8$ are each independently C$_{1-6}$alkyl, C$_{1-6}$haloalkyl, C$_{1-6}$haloalkoxy, C$_{3-8}$cycloalkyl, C$_{3-8}$cycloalkylalkyl, aryl, arylalkyl, heteroaryl, heteroarylalkyl or —X$^2$R$^9$, wherein the aliphatic or aromatic portion of R$^7$ and R$^8$ are each optionally substituted with from 1 to 3 members independently selected from the group consisting of C$_{3-8}$cycloalkyl, C$_{3-8}$cycloalkylalkyl, aryl, arylalkyl, heteroaryl, heteroarylalkyl and R$^e$, provided at each occurrence, at least two of the R$^6$, R$^7$ and R$^8$ groups are not simultaneously hydrogen; and wherein X$^2$ is —NR$^{10}$, O or S; R$^{10}$ is H, C$_{1-6}$alkyl or aryl; and R$^9$ is H, C$_{1-6}$alkyl, C$_{1-6}$haloalkyl, C$_{1-6}$haloalkoxy, C$_{3-8}$cycloalkyl, C$_{3-8}$cycloalkylalkyl, aryl, arylalkyl, heteroaryl or heteroarylalkyl, wherein R$^9$ is optionally substituted with from 1 to 3 R$^e$ substituents. In certain instances, —C(R$^7$)(R$^8$) is a branched C$_{3-6}$alkyl. In one embodiment, —C(R$^7$)(R$^8$) is isopropyl. In another embodiment, —C(R$^7$)(R$^8$) is sec-butyl. In yet another embodiment, —C(R$^7$)(R$^8$) is pentan-2-yl. In still another embodiment, —C(R$^7$)(R$^8$) is pentan-3-yl. All the other variables are as defined in any of the embodiments described herein.

In a fourteenth embodiment of the invention, compounds of formula (I) have subformula (Ih):

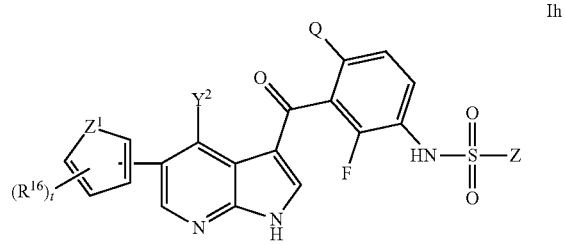

Ih wherein Z$^1$ is O or S; R$^{16}$ is H or R$^1$; or two adjacent R$^{16}$ together with the atoms to which they are attached form a 5 to 6-membered ring having 0-2 heteroatoms as ring members selected from O, N or S; where the 5 to 6-membered-ring is optionally substituted with from 1 to 3 R$^d$ or R$^e$ substituents; and the subscript t is an integer of 1 to 3. In one embodiment, Z$^1$ is O. In another embodiment, Z$^1$ is S. In one embodiment, t is 1. In another embodiment, t is 2. In yet another embodiment, t is 3 and two adjacent R$^{16}$ substituents together with the atoms to which they are attached form a 5 to 6-membered ring having 0-2 heteroatoms as ring members selected from O, N or S; wherein the 5 to 6-memberedring is optionally substituted with from 1-3 $R^d$ or $R^e$ substituents, and the other $R^{16}$ is H, $R^d$ or $R^e$. In some embodiments, the two adjacent $R^{16}$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{16}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In other embodiments, $R^{16}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)$R^b$, —C(O)$R^b$, —C(O)O$R^b$, —NHC(O)$R^b$, —C(O)NH$R^b$, —NH$R^b$ or —N$R^b R^b$. In some embodiments, $R^{16}$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. All the other variables $Y^2$, Q and Z are as defined in any of the embodiments described herein.

In a fifteenth embodiment of the invention, compounds of formula (I) have subformula (Ii):

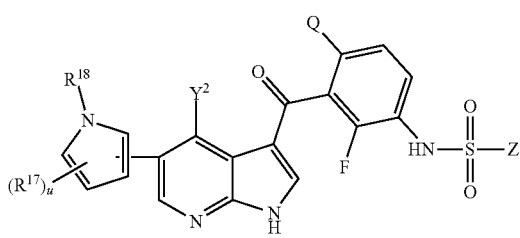

Ii wherein $R^{18}$ is H, $C_{1-6}$alkyl, $C_{1-6}$ haloalkyl, $C_{3-6}$cycloalkyl or $C_{3-6}$cycloalkyl. $R^{17}$ is H or $R^1$; or two adjacent $R^{17}$ together with the atoms to which they are attached form a 5 to 6-membered ring having 0-2 heteroatoms as ring members selected from O, N or S; or $R^{17}$ and $R^{18}$ taken together with the atoms to which they are attached form a 5 to 6-membered ring having 0-2 heteroatoms as ring members selected from O, N or S, where the 5 to 6-membered-ring is optionally substituted with from 1 to 3 $R^d$ or R substituents; $R^{18}$ is H, $C_{1-6}$alkyl or $C_{1-6}$ haloalkyl; and the subscript u is an integer of 1 to 3. In one embodiment, u is 1. In another embodiment, u is 2. In yet another embodiment, u is 3 and two adjacent $R^{17}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the other $R^{17}$ is H, $R^d$ or $R^e$. In other embodiments, $R^{17}$ and $R^{18}$ taken together with the atoms to which they are attached form a 5 to 6-membered ring having 0-2 heteroatoms as ring members selected from O, N or S, where the 5 to 6-membered-ring is optionally substituted with from 1 to 3 $R^d$ or $R^e$ substituents. In some embodiments, (i) the two adjacent $R^{17}$ together with the atoms to which they are attached or (ii) $R^{17}$ and $R^{18}$ taken together with the atoms to which they are attached, form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, (i) two adjacent $R^{17}$ groups together with the atoms to which they are attached or (ii) $R^{17}$ and $R^{18}$ taken together with the atoms to which they are attached, form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In some embodiments, $R^{17}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)$R^b$, —C(O)$R^b$, —C(O)O$R^b$, —NHC(O)$R^b$, —C(O)NH$R^b$, —NH$R^b$ or —N$R^b R^b$. In some embodiments, $R^{17}$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. In certain instances, $R^8$ is H, $C_{1-6}$alkyl or $C_{1-6}$ haloalkyl. In some embodiments, $R^{18}$ is H, $C_{1-6}$alkyl or cyclopropyl, cyclopropylmethyl, cyclobutyl, cyclobutylmethyl, cyclopentyl, cyclopentylmethyl, cyclohexyl, or cyclohexylmethyl. In some embodiments, $R^{18}$ is H or $CH_3$. All the other variables $Y^2$, Q and Z are as defined in any of the embodiments described herein.

In a sixteenth embodiment of the invention, compounds of formula (I) have subformula (Ij):

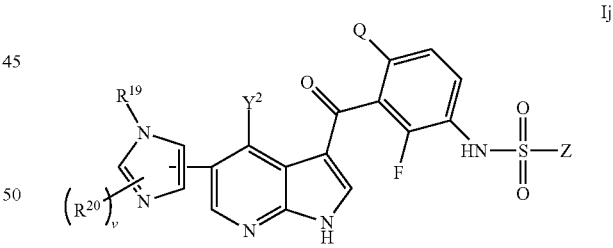

Ij $R^{19}$ is H, $C_{1-6}$alkyl, $C_{1-6}$ haloalkyl, $C_{3-6}$cycloalkyl or $C_{3-6}$cycloalkyl. $R^{20}$ is H or $R^1$; or two adjacent $R^{20}$ together with the atoms to which they are attached form a 5 to 6-membered ring having 0-2 heteroatoms as ring members selected from O, N or S; or $R^{20}$ and $R^{19}$ taken together with the atoms to which they are attached form a 5 to 6-membered ring having 0-2 heteroatoms as ring members selected from O, N or S; $R^{19}$ is H, $C_{1-6}$alkyl or $C_{1-6}$ haloalkyl; and the subscript v is an integer of 1 or 2, where the 5 to 6-membered-ring is optionally substituted with from 1 to 3 $R^d$ or $R^e$ substituents. In one embodiment, v is 1. In some embodiments, two adjacent $R^{20}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents. In other embodiments, v is 2, $R^{19}$ and $R^{20}$ taken together with the atoms to which they are attached form a 5 to 6-membered ring having from 0-2 heteroatoms as ring members selected from O, N or S, where the 5 to 6-membered-ring is optionally substituted with from 1 to 3 $R^d$ or $R^e$ substituents, and the other $R^{20}$ is H, $R^d$ or $R^e$. In some embodiments, (i) the two adjacent $R^{20}$ together with the atoms to which they are attached or (ii) $R^{19}$ and $R^{20}$ taken together with the atoms to which they are attached, form an optionally substituted fused carbocyclic ring, including, but not limiting to, cyclopentane, cyclohexane and benzene rings. The substituents on the carbocyclic ring can be from 1-2 $R^d$ or $R^e$ groups. In other embodiments, (i) two adjacent $R^{19}$ groups together with the atoms to which they are attached or (ii) $R^{19}$ and $R^{20}$ taken together with the atoms to which they are attached, form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In other embodiments, $R^{20}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)R, —C(O)R, —C(O)$OR^b$, —NHC(O)$R^b$, —C(O)$NHR^b$, —$NHR^b$ or —$NR^bR^b$. In some embodiments, $R^{20}$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. In certain instances, $R^{19}$ is H, $C_{1-6}$alkyl or $C_{1-6}$ haloalkyl. In some embodiments, $R^{19}$ is H, $C_{1-6}$alkyl or cyclopropyl, cyclopropylmethyl, cyclobutyl, cyclobutylmethyl, cyclopentyl, cyclopentylmethyl, cyclohexyl, or cyclohexylmethyl. In some embodiments, $R^{19}$ is H or $CH_3$. All the other variables $Y^2$, Q and Z are as defined in any of the embodiments described herein.

In a seventeenth embodiment of the invention, compounds of formula (I) have subformula (Ik):

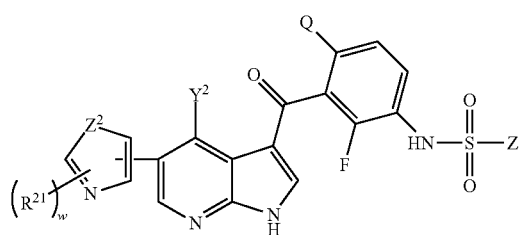

Ik $Z^2$ is O or S. The subscript w is 1 or 2. $R^{21}$ is H or $R^1$; or two adjacent $R^{21}$ together with the atoms to which they are attached form a 5 to 6-membered ring having 0-2 heteroatoms as ring members selected from O, N or S, where the 5 to 6-membered-ring is optionally substituted with from 1 to 3 $R^d$ or $R^e$ substituents. In one embodiment, w is 1. In another embodiment, w is 2. In some embodiments, two adjacent $R^{21}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents. In some embodiments, the two adjacent $R^{21}$ together with the atoms to which they are attached form an optionally substituted fused carbocyclic ring, including, but not limiting to, cyclopentane, cyclohexane and benzene rings. In certain instances, the substituents on the carbocyclic ring can be from 1-2 $R^d$ or $R^e$ groups. In other embodiments, two adjacent $R^{21}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In certain instances, the substituents on the heterocyclic ring can be from 1-2 $R^d$ or $R^e$ groups. In other embodiments, $R^{21}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)R, —C(O)$R^b$, —C(O)$OR^b$, —NHC(O)$R^b$, —C(O)$NHR^b$, —$NHR^b$ or —$NR^bR^b$. In some embodiments, $R^{21}$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. All the other variables $Y^2$, Q and Z are as defined in any of the embodiments described herein.

In an eighteenth embodiment of the invention, compounds of formula (I) have subformula (Il):

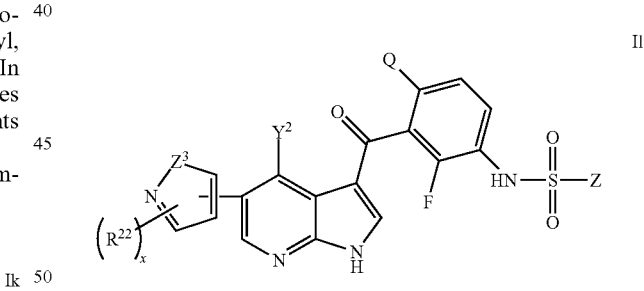

Il $Z^3$ is O, S or —N($R^{30}$), where $R^{30}$ is H, $C_{1-6}$alkyl, $C_{1-6}$ haloalkyl, $C_{3-6}$cycloalkyl or $C_{3-6}$cycloalkyl. The subscript x is 1 or 2. $R^{22}$ is H or $R^1$; or two adjacent $R^{22}$ together with the atoms to which they are attached form a 5 to 6-membered ring having 0-2 heteroatoms as ring members selected from O, N or S, where the 5 to 6-membered-ring is optionally substituted with from 1 to 3 $R^d$ or $R^e$ substituents. In one embodiment, x is 1. In another embodiment, x is 2. In some embodiments, two adjacent $R^{22}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents. In other embodiments, x is 2, $R^{22}$ and $R^{30}$ taken together with the atoms to which they are attached form a 5 to 6-membered ring having from 0-2 heteroatoms as ring members selected from O, N or S, where the 5 to 6-membered-ring is optionally substituted with from 1 to 3 $R^d$ or $R^e$ substituents. In some embodiments, (i) the two adjacent $R^{22}$ together with the atoms to which they are attached or (ii) $R^{22}$ and $R^{30}$ taken together with the atoms to which they are attached, form an optionally substituted fused carbocyclic ring, including, but not limiting to, cyclopentane, cyclohexane and benzene rings. In certain instances, the substituents on the carbocyclic ring can be from 1-2 $R^d$ or $R^e$ groups. In other embodiments, (i) two adjacent $R^{22}$ groups together with the atoms to which they are attached or (ii) $R^{22}$ and $R^{30}$ taken together with the atoms to which they are attached, form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In other embodiments, $R^{22}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)$R^b$, —C(O)$R^b$, —C(O)$OR^b$, —NHC(O)$R^b$, —C(O)$NHR^b$, —$NHR^b$ or —$NR^bR^b$. In some embodiments, $R^{22}$ is F, Cl, Br, I, —CN, —OH, —$CF_3$, $NH_2$, $CF_3O$—, $CH_3$—, $CH_3O$—, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. In certain instances, $R^{30}$ is H, $C_{1-6}$alkyl or $C_{1-6}$ haloalkyl. In some embodiments, $R^{30}$ is H, $C_{1-6}$alkyl or cyclopropyl, cyclopropylmethyl, cyclobutyl, cyclobutylmethyl, cyclopentyl, cyclopentylmethyl, cyclohexyl, or cyclohexylmethyl. In some embodiments, $R^{30}$ is H or $CH_3$. All the other variables $Y^2$, Q and Z are as defined in any of the embodiments described herein.

In a nineteenth embodiment of the invention, compounds of formula (I) have subformula (Im):

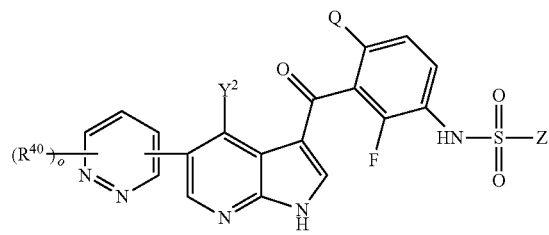

Im $R^{40}$ is H or R'; or two adjacent $R^{40}$ together with the atoms to which they are attached form a 5 to 6-membered ring having 0-2 heteroatoms as ring members selected from O, N or S; and the subscript o is an integer of 1 to 3, where the 5 to 6-membered-ring is optionally substituted with from 1-3 $R^d$ or $R^e$ substituents. In one embodiment, the subscript o is 1. In another embodiment, the subscript o is 2. In yet another embodiment, the subscript o is 3 and two adjacent $R^{40}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents, and the other $R^{40}$ is H, $R^d$, $R^e$ or $R^f$. In some embodiments, the two adjacent $R^{40}$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{40}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In other embodiments, $R^{40}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)R, —C(O)R, —C(O)$OR^b$, —NHC(O)$R^b$, —C(O)$NHR^b$, —$NHR^b$ or —$NR^bR^b$. In some embodiments, $R^{40}$ is F, Cl, Br, I, —CN, —OH, —$CF_3$, $NH_2$, $CF_3O$—, $CH_3$—, $CH_3O$—, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido or methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. All the other variables $Y^2$, Q and Z are as defined in any of the embodiments described herein.

In a twentieth embodiment of the invention, compounds of formula (I) have subformula (In):

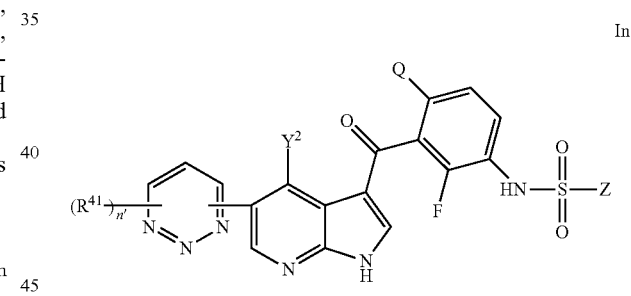

In $R^{41}$ is H or $R^1$; or two adjacent $R^{41}$ together with the atoms to which they are attached form a 5 to 6-membered ring having 0-2 heteroatoms as ring members selected from O, N or S; and the subscript n' is an integer of 1 or 2, where the 5 to 6-membered-ring is optionally substituted with from 1-3 $R^d$ or $R^e$ substituents. In one embodiment, the subscript n' is 1. In another embodiment, the subscript n' is 2. In some embodiments, the two adjacent $R^{41}$ substituents together with the atoms to which they are attached form a 5 to 6-membered ring having 0-2 heteroatoms as ring members selected from O, N or S; wherein the 5 to 6-membered-ring is optionally substituted with from 1-3 $R^d$ or $R^e$ substituents. In some embodiments, the two adjacent $R^{41}$ together with the atoms to which they are attached form an optionally substituted fused carbocyclic ring, including, but not limiting to, benzene, cyclopentane and cyclohexane rings. The substituents on the carbocyclic ring can be from 1-2 $R^d$ or $R^e$ groups. In other embodiments, two adjacent $R^{41}$ groups together with the atoms to which they are attached form an optionally substituted fused heterocyclic ring, including, but not limiting to, pyrrole, furan, thiophene, pyrazole, imidazole, oxazole, isoxazole, thiazole, isothiazole, pyridine, pyrazine, pyridazine, tetrahydrofuran, tetrahydropyran, tetrahydrothiophene, pyrazolidine, isoxazolidine, imidazolidine, oxazolidine, thiazolidine, isothiazolidine, piperidine, piperazine, and hexahydropyrimidine rings. In other embodiments, $R^{41}$ is halogen, —CN, —OH, —$CF_3$, $CF_3O$—, $C_{1-6}$alkyl, $C_{1-6}$alkoxy, —$NO_2$, benzyl, phenyl, cyclopropyl, cyclopropylmethyl, cyclobutyl, cyclobutylmethyl, cyclopentyl, cyclopentylmethyl, cyclohexyl, cyclohexymethyl, —OC(O)R, —C(O)R, —C(O)OR, —NHC(O)R, —C(O)NHR, —NHR or —NRR. In some embodiments, $R^{41}$ is F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido or methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. All the other variables $Y^2$, Q and Z are as defined in any of the embodiments described herein.

In some embodiments, the invention provides a compound selected from the group consisting of:

N-[3-[5-(4-chlorophenyl)-1H-pyrrolo[2,3-b]pyridine-3-carbonyl]-2-fluoro-phenyl]pyrrolidine-1-sulfonamide (P-0012);

5-chloro-3-[3-[[ethyl(methyl)sulfamoyl]amino]-2,6-difluoro-benzoyl]-1H-pyrrolo[2,3-b]pyridine (P-0013);

5-(4-chlorophenyl)-3-[3-[[ethyl(methyl)sulfamoyl]amino]-2,6-difluoro-benzoyl]-1H-pyrrolo[2,3-b]pyridine (P-0014);

3-[3-[[ethyl(methyl)sulfamoyl]amino]-2,6-difluoro-benzoyl]-5-(2-methoxypyrimidin-5-yl)-1H-pyrrolo[2,3-b]pyridine (P-0015);

N-[2,4-difluoro-3-(5-fluoro-4-iodo-1H-pyrrolo[2,3-b]pyridine-3-carbonyl)phenyl]pyrrolidine-1-sulfonamide (P-0016);

N-[3-[4-(cyclopropylmethylamino)-5-fluoro-1H-pyrrolo[2,3-b]pyridine-3-carbonyl]-2,4-difluoro-phenyl]pyrrolidine-1-sulfonamide (P-0017);

5-cyano-3-[3-[[ethyl(methyl)sulfamoyl]amino]-2,6-difluoro-benzoyl]-1H-pyrrolo[2,3-b]pyridine (P-0018);

5-chloro-3-[3-[[ethyl(methyl)sulfamoyl]amino]-2-fluoro-benzoyl]-1H-pyrrolo[2,3-b]pyridine (P-0019);

5-(4-chlorophenyl)-3-[3-[[ethyl(methyl)sulfamoyl]amino]-2-fluoro-benzoyl]-1H-pyrrolo[2,3-b]pyridine (P-0020);

3-[3-[1[ethyl(methyl)sulfamoyl]amino]-2-fluoro-benzoyl]-5-(2-methoxypyrimidin-5-yl)-1H-pyrrolo[2,3-b]pyridine (P-0021);

N-[3-[5-(4-chlorophenyl)-1H-pyrrolo[2,3-b]pyridine-3-carbonyl]-2,4-difluoro-phenyl]pyrrolidine-1-sulfonamide (P-0022);

N-[3-[5-[2-(dimethylamino)pyrimidin-5-yl]-1H-pyrrolo[2,3-b]pyridine-3-carbonyl]-2,4-difluoro-phenyl]pyrrolidine-1-sulfonamide (P-0023);

N-[2-fluoro-3-(5-methyl-1H-pyrrolo[2,3-b]pyridine-3-carbonyl)phenyl]pyrrolidine-1-sulfonamide (P-0024);

N-[2,4-difluoro-3-(5-iodo-1H-pyrrolo[2,3-b]pyridine-3-carbonyl)phenyl]pyrrolidine-1-sulfonamide (P-0025);

3-[3-[[cyclopropyl(methyl)sulfamoyl]amino]-2-fluoro-benzoyl]-5-(2-methoxypyrimidin-5-yl)-1H-pyrrolo[2,3-b]pyridine (P-0026);

[2-fluoro-3-(methylsulfamoylamino)phenyl]-[5-(2-methoxypyrimidin-5-yl)-1H-pyrrolo[2,3-b]pyridin-3-yl]methanone (P-0027);

5-(4-cyanophenyl)-3-[3-(dimethylsulfamoylamino)-2-fluoro-benzoyl]-1H-pyrrolo[2,3-b]pyridine (P-0028);

3-[3-(dimethylsulfamoylamino)-2-fluoro-benzoyl]-5-(3-pyridyl)-1H-pyrrolo[2,3-b]pyridine (P-0029);

3-[3-(dimethylsulfamoylamino)-2-fluoro-benzoyl]-5-(6-methyl-3-pyridyl)-1H-pyrrolo[2,3-b]pyridine (P-0030);

5-[6-(dimethylamino)-3-pyridyl]-3-[3-(dimethylsulfamoylamino)-2-fluoro-benzoyl]-1H-pyrrolo[2,3-b]pyridine (P-0031);

5-(4-cyanophenyl)-3-[3-[[ethyl(methyl)sulfamoyl]amino]-2-fluoro-benzoyl]-1H-pyrrolo[2,3-b]pyridine (P-0032);

3-[3-[[ethyl(methyl)sulfamoyl]amino]-2-fluoro-benzoyl]-5-(3-pyridyl)-1H-pyrrolo[2,3-b]pyridine (P-0033);

3-[3-[[ethyl(methyl)sulfamoyl]amino]-2-fluoro-benzoyl]-5-(6-methyl-3-pyridyl)-1H-pyrrolo[2,3-b]pyridine (P-0034);

3-[3-[[ethyl(methyl)sulfamoyl]amino]-2-fluoro-benzoyl]-5-(4-fluorophenyl)-1H-pyrrolo[2,3-b]pyridine (P-0035);

3-[3-(dimethylsulfamoylamino)-2-fluoro-benzoyl]-5-(4-fluorophenyl)-1H-pyrrolo[2,3-b]pyridine;

3-[3-[[ethyl(methyl)sulfamoyl]amino]-2-fluoro-benzoyl]-5-phenyl-1H-pyrrolo[2,3-b]pyridine (P-0036);

3-[3-(dimethylsulfamoylamino)-2-fluoro-benzoyl]-5-phenyl-1H-pyrrolo[2,3-b]pyridine (P-0037);

5-bromo-3-[3-[[ethyl(methyl)sulfamoyl]amino]-2-fluoro-benzoyl]-1H-pyrrolo[2,3-b]pyridine (P-0038);

5-cyano-3-[3-[[ethyl(methyl)sulfamoyl]amino]-2-fluoro-benzoyl]-1H-pyrrolo[2,3-b]pyridine (P-0039);

3-[2-fluoro-3-[[methyl(propyl)sulfamoyl]amino]benzoyl]-5-(2-methoxypyrimidin-5-yl)-1H-pyrrolo[2,3-b]pyridine (P-0040);

3-benzyloxy-N-[2-fluoro-3-[5-(2-methoxypyrimidin-5-yl)-1H-pyrrolo[2,3-b]pyridine-3-carbonyl]phenyl]pyrrolidine-1-sulfonamide (P-0041);

1-cyclopropyl-N-[2-fluoro-3-[5-(1-methylpyrazol-4-yl)-1H-pyrrolo[2,3-b]pyridine-3-carbonyl]phenyl]methanesulfonamide (P-0042);

N-[2-fluoro-3-[5-(3-pyridyl)-1H-pyrrolo[2,3-b]pyridine-3-carbonyl]phenyl]pyrrolidine-1-sulfonamide (P-0043);

N-[3-[5-(2,4-dimethoxypyrimidin-5-yl)-1H-pyrrolo[2,3-b]pyridine-3-carbonyl]-2-fluoro-phenyl]pyrrolidine-1-sulfonamide (P-0044);

N-[2-fluoro-3-[5-(6-methyl-3-pyridyl)-1H-pyrrolo[2,3-b]pyridine-3-carbonyl]phenyl]pyrrolidine-1-sulfonamide (P-0045);

N-[3-[5-[6-(dimethylamino)-3-pyridyl]-1H-pyrrolo[2,3-b]pyridine-3-carbonyl]-2-fluoro-phenyl]pyrrolidine-1-sulfonamide (P-0046);

N-[2-fluoro-3-[5-(2-isopropylpyrimidin-5-yl)-1H-pyrrolo[2,3-b]pyridine-3-carbonyl]phenyl]pyrrolidine-1-sulfonamide (P-0047);

N-[3-[5-(2-cyclopropylpyrimidin-5-yl)-1H-pyrrolo[2,3-b]pyridine-3-carbonyl]-2-fluoro-phenyl]pyrrolidine-1-sulfonamide (P-0048);

N-[3-[5-(4-cyano-3-methoxy-phenyl)-1H-pyrrolo[2,3-b]pyridine-3-carbonyl]-2-fluoro-phenyl]pyrrolidine-1-sulfonamide (P-0049);

N-[3-[5-[4-(1-cyanocyclopropyl)phenyl]-1H-pyrrolo[2,3-b]pyridine-3-carbonyl]-2-fluoro-phenyl]pyrrolidine-1-sulfonamide (P-0050);

3-[3-(dimethylsulfamoylamino)-2-fluoro-benzoyl]-5-(2-isopropylpyrimidin-5-yl)-1H-pyrrolo[2,3-b]pyridine (P-0051);

5-(2-cyclopropylpyrimidin-5-yl)-3-[3-(dimethylsulfamoylamino)-2-fluoro-benzoyl]-1H-pyrrolo[2,3-b]pyridine (P-0052);

3-[3-(dimethylsulfamoylamino)-2-fluoro-benzoyl]-5-[6-(trifluoromethyl)-3-pyridyl]-1H-pyrrolo[2,3-b]pyridine (P-0053);

5-(4-cyano-3-methoxy-phenyl)-3-[3-(dimethylsulfamoylamino)-2-fluoro-benzoyl]-1H-pyrrolo[2,3-b]pyridine (P-0054);

5-[4-(1-cyanocyclopropyl)phenyl]-3-[3-(dimethylsulfamoylamino)-2-fluoro-benzoyl]-1H-pyrrolo[2,3-b]pyridine (P-0055);

3-[3-[[ethyl(methyl)sulfamoyl]amino]-2-fluoro-benzoyl]-5-(2-methylpyrimidin-5-yl)-1H-pyrrolo[2,3-b]pyridine (P-0056);

3-[3-[[ethyl(methyl)sulfamoyl]amino]-2-fluoro-benzoyl]-5-(2-isopropylpyrimidin-5-yl)-1H-pyrrolo[2,3-b]pyridine (P-0057);

5-(2-cyclopropylpyrimidin-5-yl)-3-[3-[[ethyl(methyl)sulfamoyl]amino]-2-fluoro-benzoyl]-1H-pyrrolo[2,3-b]pyridine (P-0058);

3-[3-[[ethyl(methyl)sulfamoyl]amino]-2-fluoro-benzoyl]-5-[6-(trifluoromethyl)-3-pyridyl]-1H-pyrrolo[2,3-b]pyridine (P-0059);

5-(4-cyano-3-methoxy-phenyl)-3-[3-[[ethyl(methyl)sulfamoyl]amino]-2-fluoro-benzoyl]-1H-pyrrolo[2,3-b]pyridine (P-0060);

5-[4-(1-cyanocyclopropyl)phenyl]-3-[3-[[ethyl(methyl)sulfamoyl]amino]-2-fluoro-benzoyl]-1H-pyrrolo[2,3-b]pyridine (P-0061);

N-[2-fluoro-3-[5-(4-fluorophenyl)-1H-pyrrolo[2,3-b]pyridine-3-carbonyl]phenyl]pyrrolidine-1-sulfonamide (P-0062);

N-[2-fluoro-3-(5-phenyl-1H-pyrrolo[2,3-b]pyridine-3-carbonyl)phenyl]pyrrolidine-1-sulfonamide (P-0063);

5-[2-(cyclopropylamino)pyrimidin-5-yl]-3-[3-(dimethylsulfamoylamino)-2-fluoro-benzoyl]-1H-pyrrolo[2,3-b]pyridine (P-0064);

N-[2-fluoro-3-[5-(2-methoxypyrimidin-5-yl)-1H-pyrrolo[2,3-b]pyridine-3-carbonyl]phenyl]-2-methoxy-ethanesulfonamide (P-0065);

methyl 3-[[2-fluoro-3-[5-(2-methoxypyrimidin-5-yl)-1H-pyrrolo[2,3-b]pyridine-3-carbonyl]phenyl]sulfamoyl]propanoate (P-0066);

N-[2-fluoro-3-[5-(2-methoxypyrimidin-5-yl)-1H-pyrrolo[2,3-b]pyridine-3-carbonyl]phenyl]cyclopropanesulfonamide (P-0067);

[3-(ethylsulfamoylamino)-2-fluoro-phenyl]-[5-(2-methoxypyrimidin-5-yl)-1H-pyrrolo[2,3-b]pyridin-3-yl]methanone (P-0068);

[3-(ethylsulfamoylamino)-2-fluoro-phenyl]-(5-iodo-1H-pyrrolo[2,3-b]pyridin-3-yl)methanone (P-0069);

3-[2-fluoro-3-[[isobutyl(methyl)sulfamoyl]amino]benzoyl]-5-iodo-1H-pyrrolo[2,3-b]pyridine (P-0070);

[2-fluoro-3-(isopropylsulfonylamino)phenyl]-(5-iodo-1H-pyrrolo[2,3-b]pyridin-3-yl)methanone (P-0071);

3-[2-fluoro-3-[[isobutyl(methyl)sulfamoyl]amino]benzoyl]-5-(2-methoxypyrimidin-5-yl)-1H-pyrrolo[2,3-b]pyridine (P-0072);

3-[2-fluoro-3-[[2-methoxyethyl(methyl)sulfamoyl]amino]benzoyl]-5-(2-methoxypyrimidin-5-yl)-1H-pyrrolo[2,3-b]pyridine (P-0073);

N-[2-fluoro-3-[5-(2-methoxypyrimidin-5-yl)-1H-pyrrolo[2,3-b]pyridine-3-carbonyl]phenyl]-2-methyl-pyrrolidine-1-sulfonamide (P-0074);

3-[2-fluoro-3-[[isopropyl(methyl)sulfamoyl]amino]benzoyl]-5-(2-methoxypyrimidin-5-yl)-1H-pyrrolo[2,3-b]pyridine (P-0075);

5-[6-(dimethylamino)-3-pyridyl]-3-[3-[[ethyl(methyl)sulfamoyl]amino]-2-fluoro-benzoyl]-1H-pyrrolo[2,3-b]pyridine (P-0076);

5-[2-(cyclopropylamino)pyrimidin-5-yl]-3-[3-[[ethyl(methyl)sulfamoyl]amino]-2-fluoro-benzoyl]-1H-pyrrolo[2,3-b]pyridine (P-0077);

5-(2-cyclopropylpyrimidin-5-yl)-3-[2,6-difluoro-3-[[methyl(propyl)sulfamoyl]amino]benzoyl]-1H-pyrrolo[2,3-b]pyridine (P-0078);

5-[4-(1-cyanocyclopropyl)phenyl]-3-[2,6-difluoro-3-[[methyl(propyl)sulfamoyl]amino]benzoyl]-1H-pyrrolo[2,3-b]pyridine (P-0079);

5-[4-(1-cyanocyclopropyl)phenyl]-3-[2-fluoro-3-[[2-methoxyethyl(methyl)sulfamoyl]amino]benzoyl]-1H-pyrrolo[2,3-b]pyridine (P-0080);

5-[2-(cyclopropylamino)pyrimidin-5-yl]-3-[2-fluoro-3-[[2-methoxyethyl(methyl)sulfamoyl]amino]benzoyl]-1H-pyrrolo[2,3-b]pyridine (P-0081);

5-[2-(cyclopropylamino)pyrimidin-5-yl]-3-[2-fluoro-3-[[methyl(propyl)sulfamoyl]amino]benzoyl]-1H-pyrrolo[2,3-b]pyridine (P-0082);

3-[3-[[cyclopropylmethyl(methyl)sulfamoyl]amino]-2-fluoro-benzoyl]-5-(2-methoxypyrimidin-5-yl)-1H-pyrrolo[2,3-b]pyridine (P-0083);

3-[3-[[cyclopropylmethyl(methyl)sulfamoyl]amino]-2-fluoro-benzoyl]-5-(2-cyclopropylpyrimidin-5-yl)-1H-pyrrolo[2,3-b]pyridine (P-0084);

5-(2-cyclopropylpyrimidin-5-yl)-3-[2-fluoro-3-[[2-methoxyethyl(methyl)sulfamoyl]amino]benzoyl]-1H-pyrrolo[2,3-b]pyridine (P-0085);

5-(2-cyclopropylpyrimidin-5-yl)-3-[2-fluoro-3-[[methyl(propyl)sulfamoyl]amino]benzoyl]-1H-pyrrolo[2,3-b]pyridine (P-0086);

5-(6-cyclopropyl-3-pyridyl)-3-[3-[[ethyl(methyl)sulfamoyl]amino]-2-fluoro-benzoyl]-1H-pyrrolo[2,3-b]pyridine (P-0087);

3,3-difluoro-N-[2-fluoro-3-[5-(2-methoxypyrimidin-5-yl)-1H-pyrrolo[2,3-b]pyridine-3-carbonyl]phenyl]azetidine-1-sulfonamide (P-0088);

4-[[(1S)-1-cyclopropylethyl]amino]-5-[3-[[ethyl(methyl)sulfamoyl]amino]-2-fluoro-benzoyl]-7H-pyrrolo[2,3-d]pyrimidine (P-0089);

N-[3-[5-(4-cyanophenyl)-1H-pyrrolo[2,3-b]pyridine-3-carbonyl]-2-fluoro-phenyl]pyrrolidine-1-sulfonamide (P-0090);

N-[3-[5-(2-cyanopyrimidin-5-yl)-1H-pyrrolo[2,3-b]pyridine-3-carbonyl]-2-fluoro-phenyl]pyrrolidine-1-sulfonamide (P-0091);

N-[2-fluoro-3-[5-(2-methylpyrimidin-5-yl)-1H-pyrrolo[2,3-b]pyridine-3-carbonyl]phenyl]pyrrolidine-1-sulfonamide (P-0092);

N-[3-[5-(5-cyano-3-pyridyl)-1H-pyrrolo[2,3-b]pyridine-3-carbonyl]-2-fluoro-phenyl]pyrrolidine-1-sulfonamide (P-0093);

N-[2-fluoro-3-[5-[6-(trifluoromethyl)-3-pyridyl]-1H-pyrrolo[2,3-b]pyridine-3-carbonyl]phenyl]pyrrolidine-1-sulfonamide (P-0095);

5-(2-cyanopyrimidin-5-yl)-3-[3-(dimethylsulfamoylamino)-2-fluoro-benzoyl]-1H-pyrrolo[2,3-b]pyridine (P-0096);

3-[3-(dimethylsulfamoylamino)-2-fluoro-benzoyl]-5-(2-methylpyrimidin-5-yl)-1H-pyrrolo[2,3-b]pyridine (P-0097);

5-(5-cyano-3-pyridyl)-3-[3-(dimethylsulfamoylamino)-2-fluoro-benzoyl]-1H-pyrrolo[2,3-b]pyridine (P-0098);

5-(6-cyano-3-pyridyl)-3-[3-(dimethylsulfamoylamino)-2-fluoro-benzoyl]-1H-pyrrolo[2,3-b]pyridine (P-0099);

5-(2-cyanopyrimidin-5-yl)-3-[3-[[ethyl(methyl)sulfamoyl]amino]-2-fluoro-benzoyl]-1H-pyrrolo[2,3-b]pyridine (P-0100);

5-(5-cyano-3-pyridyl)-3-[3-[[ethyl(methyl)sulfamoyl]
amino]-2-fluoro-benzoyl]-1H-pyrrolo[2,3-b]pyridine
(P-0101);

5-(6-cyano-3-pyridyl)-3-[3-[[ethyl(methyl)sulfamoyl]
amino]-2-fluoro-benzoyl]-1H-pyrrolo[2,3-b]pyridine
(P-0102);

3-[3-(dimethylsulfamoylamino)-2-fluoro-benzoyl]-5-[4-(1-
hydroxy-1-methyl-ethyl)phenyl]-1H-pyrrolo[2,3-b]pyri-
dine (P-0103);

3-[3-[[ethyl(methyl)sulfamoyl]amino]-2-fluoro-benzoyl]-5-
[4-(1-hydroxy-1-methyl-ethyl)phenyl]-1H-pyrrolo[2,3-b]
pyridine (P-0104);

N-[2-fluoro-3-[5-[4-(1-hydroxy-1-methyl-ethyl)phenyl]-
1H-pyrrolo[2,3-b]pyridine-3-carbonyl]phenyl]pyrroli-
dine-1-sulfonamide (P-0105);

5-[2-(dimethylamino)pyrimidin-5-yl]-3-[3-(dimethylsulfa-
moylamino)-2-fluoro-benzoyl]-1H-pyrrolo[2,3-b]pyri-
dine (P-0106);

3-[3-(dimethylsulfamoylamino)-2-fluoro-benzoyl]-5-(2-
pyrrolidin-1-ylpyrimidin-5-yl)-1H-pyrrolo[2,3-b]pyri-
dine (P-0107);

3-[3-1[[ethyl(methyl)sulfamoyl]amino]-2-fluoro-benzoyl]-
5-(2-pyrrolidin-1-ylpyrimidin-5-yl)-1H-pyrrolo[2,3-b]
pyridine (P-0108);

N-[2-fluoro-3-[5-(2-pyrrolidin-1-ylpyrimidin-5-yl)-1H-pyr-
rolo[2,3-b]pyridine-3-carbonyl]phenyl]pyrrolidine-1-
sulfonamide (P-0109);

3-[3-(dimethylsulfamoylamino)-2-fluoro-benzoyl]-5-iodo-
1H-pyrrolo[2,3-b]pyridine (P-0110);

3-[2-fluoro-3-[[methyl(propyl)sulfamoyl]amino]benzoyl]-
5-(2-methylpyrimidin-5-yl)-1H-pyrrolo[2,3-b]pyridine
(P-0111);

3-[3-[[cyclopropylmethyl(methyl)sulfamoyl]amino]-2-
fluoro-benzoyl]-5-(2-methylpyrimidin-5-yl)-1H-pyrrolo
[2,3-b]pyridine (P-0112);

5-(6-cyclopropyl-3-pyridyl)-3-[3-(dimethylsulfamoy-
lamino)-2-fluoro-benzoyl]-1H-pyrrolo[2,3-b]pyridine
(P-0113);

5-(6-cyclopropyl-3-pyridyl)-3-[2-fluoro-3-[[methyl(propyl)
sulfamoyl]amino]benzoyl]-1H-pyrrolo[2,3-b]pyridine
(P-0114);

3-[3-[[cyclopropylmethyl(methyl)sulfamoyl]amino]-2-
fluoro-benzoyl]-5-(6-cyclopropyl-3-pyridyl)-1H-pyrrolo
[2,3-b]pyridine (P-0115);

3-[2,6-difluoro-3-[[methyl(propyl)sulfamoyl]amino]ben-
zoyl]-5-(2-methoxypyrimidin-5-yl)-1H-pyrrolo[2,3-b]
pyridine (P-0116);

[2-fluoro-3-(propylsulfamoylamino)phenyl]-(5-iodo-1H-
pyrrolo[2,3-b]pyridin-3-yl)methanone (P-0117);

[2-fluoro-3-(propylsulfamoylamino)phenyl]-(5-methyl-1H-
pyrrolo[2,3-b]pyridin-3-yl)methanone (P-0223);

N-[2-fluoro-3-[5-(2-methoxypyrimidin-5-yl)-1H-pyrrolo[2,
3-b]pyridine-3-carbonyl]phenyl]butane-2-sulfonamide
(P-0024);

N-[2-fluoro-3-[5-(2-pyrrolidin-1-ylpyrimidin-5-yl)-1H-pyr-
rolo[2,3-b]pyridine-3-carbonyl]phenyl]butane-2-sulfona-
mide (P-0225);

N-[3-[5-[2-(cyclopropylamino)pyrimidin-5-yl]-1H-pyrrolo
[2,3-b]pyridine-3-carbonyl]-2-fluoro-phenyl]butane-2-
sulfonamide (P-0226);

N-[3-[5-[4-(1-cyanocyclopropyl)phenyl]-1H-pyrrolo[2,3-b]
pyridine-3-carbonyl]-2-fluoro-phenyl]butane-2-sulfona-
mide (P-00227);

N-[3-[5-(2-cyclopropylpyrimidin-5-yl)-1H-pyrrolo[2,3-b]
pyridine-3-carbonyl]-2-fluoro-phenyl]butane-2-sulfona-
mide (P-0228);

N-[2-fluoro-3-[5-(2-isopropylpyrimidin-5-yl)-1H-pyrrolo
[2,3-b]pyridine-3-carbonyl]phenyl]butane-2-sulfonamide
(P-0229);

N-[3-[5-[6-(dimethylamino)-3-pyridyl]-1H-pyrrolo[2,3-b]
pyridine-3-carbonyl]-2-fluoro-phenyl]butane-2-sulfona-
mide (P-0230);

N-[2-fluoro-3-[5-(2-methylpyrimidin-5-yl)-1H-pyrrolo[2,3-
b]pyridine-3-carbonyl]phenyl]butane-2-sulfonamide
(P-0231);

N-[3-[5-[2-(cyclopropylamino)pyrimidin-5-yl]-1H-pyrrolo
[2,3-b]pyridine-3-carbonyl]-2-fluoro-phenyl]pyrrolidine-
1-sulfonamide (P-0232);

5-(2-cyclopropylpyrimidin-5-yl)-3-[2-fluoro-3-[[isopropyl
(methyl)sulfamoyl]amino]benzoyl]-1H-pyrrolo[2,3-b]
pyridine (P-0233);

N-[2-fluoro-3-[5-(2-morpholinopyrimidin-5-yl)-1H-pyrrolo
[2,3-b]pyridine-3-carbonyl]phenyl]pyrrolidine-1-sulfo-
namide; (P-0235);

N-[2-fluoro-3-[5-(2-morpholinopyrimidin-5-yl)-1H-pyrrolo
[2,3-b]pyridine-3-carbonyl]phenyl]butane-2-sulfonamide
(P-0236);

5-[4-(1-cyanocyclopropyl)phenyl]-3-[3-(dimethylsulfamoy-
lamino)-2,6-difluoro-benzoyl]-1H-pyrrolo[2,3-b]pyridine
(P-0237);

5-(2-cyclopropylpyrimidin-5-yl)-3-[3-(dimethylsulfamoy-
lamino)-2,6-difluoro-benzoyl]-1H-pyrrolo[2,3-b]pyridine
(P-0238);

5-[4-(1-cyanocyclopropyl)phenyl]-3-[3-[[ethyl(methyl)sul-
famoyl]amino]-2,6-difluoro-benzoyl]-1H-pyrrolo[2,3-b]
pyridine (P-0239);

5-(2-cyclopropylpyrimidin-5-yl)-3-[3-[[ethyl(methyl)sulfa-
moyl]amino]-2,6-difluoro-benzoyl]-1H-pyrrolo[2,3-b]
pyridine (P-0240);

N-[3-[5-(2-cyclopropylpyrimidin-5-yl)-1H-pyrrolo[2,3-b]
pyridine-3-carbonyl]-2,4-difluoro-phenyl]pyrrolidine-1-
sulfonamide (P-0241);

[2-fluoro-3-(propylsulfamoylamino)phenyl]-[5-(1-meth-
ylpyrazol-4-yl)-1H-pyrrolo[2,3-b]pyridin-3-yl]metha-
none (P-0242);

1-[4-[3-[2-fluoro-3-(pyrrolidin-1-ylsulfonylamino)ben-
zoyl]-1H-pyrrolo[2,3-b]pyridin-5-yl]phenyl]cyclopro-
panecarboxylic acid (P-0243);

3-[3-(dimethylsulfamoylamino)-2,6-difluoro-benzoyl]-5-
(5-ethoxypyrazin-2-yl)-1H-pyrrolo[2,3-b]pyridine
(P-0244);

5-[4-(1-cyano-1-methyl-ethyl)phenyl]-3-[3-(dimethylsulfa-
moylamino)-2-fluoro-benzoyl]-1H-pyrrolo[2,3-b]pyri-
dine (P-0245);

N-[3-[5-(2-cyclopropylpyrimidin-5-yl)-1H-pyrrolo[2,3-b]
pyridine-3-carbonyl]-2-fluoro-phenyl]-3,3-dimethyl-pyr-
rolidine-1-sulfonamide (P-0246);

N-[3-[5-(2-cyclopropylpyrimidin-5-yl)-1H-pyrrolo[2,3-b]
pyridine-3-carbonyl]-2-fluoro-phenyl]-3-methyl-pyrroli-
dine-1-sulfonamide (P-0247);

N-[3-[5-[4-(1-cyanocyclopropyl)phenyl]-1H-pyrrolo[2,3-b]
pyridine-3-carbonyl]-2,4-difluoro-phenyl]pyrrolidine-1-
sulfonamide (P-0248);

3-[3-[[cyclopropyl(methyl)sulfamoyl]amino]-2-fluoro-ben-
zoyl]-5-(2-cyclopropylpyrimidin-5-yl)-1H-pyrrolo[2,3-b]
pyridine (P-0249);

[5-(2-cyclopropylpyrimidin-5-yl)-1H-pyrrolo[2,3-b]pyri-
din-3-yl]-[2-fluoro-3-(propylsulfamoylamino)phenyl]
methanone (P-0251);

3-[3-[[cyclopropyl(methyl)sulfamoyl]amino]-2,6-difluoro-
benzoyl]-5-(2-cyclopropylpyrimidin-5-yl)-1H-pyrrolo[2,
3-b]pyridine (P-0252);

1-[4-[3-[2-fluoro-3-(pyrrolidin-1-ylsulfonylamino)benzoyl]-1H-pyrrolo[2,3-b]pyridin-5-yl]phenyl]cyclopropanecarboxamide (P-0253);

methyl 1-[4-[3-[2-fluoro-3-(pyrrolidin-1-ylsulfonylamino)benzoyl]-1H-pyrrolo[2,3-b]pyridin-5-yl]phenyl]cyclopropanecarboxylate (P-0254);

5-[4-(1-cyano-1-methyl-ethyl)phenyl]-3-[3-(dimethylsulfamoylamino)-2,6-difluoro-benzoyl]-1H-pyrrolo[2,3-b]pyridine (P-0255);

5-(2-ethoxypyrimidin-5-yl)-3-[3-[[ethyl(methyl)sulfamoyl]amino]-2,6-difluoro-benzoyl]-1H-pyrrolo[2,3-b]pyridine (P-0256);

ethyl 1-[[2-fluoro-3-[5-(2-methoxypyrimidin-5-yl)-1H-pyrrolo[2,3-b]pyridine-3-carbonyl]phenyl]sulfamoyl]pyrrolidine-2-carboxylate (P-0257);

4-[5-[3-[3-[[ethyl(methyl)sulfamoyl]amino]-2,6-difluoro-benzoyl]-1H-pyrrolo[2,3-b]pyridin-5-yl]pyrimidin-2-yl]morpholine (P-0258);

4-[3-[3-[3-[[ethyl(methyl)sulfamoyl]amino]-2,6-difluoro-benzoyl]-1H-pyrrolo[2,3-b]pyridin-5-yl]phenyl]morpholine (P-0259);

N-[2,4-difluoro-3-[5-[2-(4-methylpiperazin-1-yl)pyrimidin-5-yl]-1H-pyrrolo[2,3-b]pyridine-3-carbonyl]phenyl]pyrrolidine-1-sulfonamide (P-0260);

N-[2,4-difluoro-3-[5-(2-piperazin-1-ylpyrimidin-5-yl)-1H-pyrrolo[2,3-b]pyridine-3-carbonyl]phenyl]pyrrolidine-1-sulfonamide (P-0261);

N-[2,4-difluoro-3-[5-[2-(4-hydroxy-1-piperidyl)pyrimidin-5-yl]-1H-pyrrolo[2,3-b]pyridine-3-carbonyl]phenyl]pyrrolidine-1-sulfonamide (P-0262);

3-[3-[[ethyl(methyl)sulfamoyl]amino]-2,6-difluoro-benzoyl]-5-[2-(4-methylpiperazin-1-yl)pyrimidin-5-yl]-1H-pyrrolo[2,3-b]pyridine (P-0263);

tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxylate (P-0264);

N-[2,4-difluoro-3-[5-[2-(1-hydroxy-1-methyl-ethyl)thiazol-4-yl]-1H-pyrrolo[2,3-b]pyridine-3-carbonyl]phenyl]pyrrolidine-1-sulfonamide (P-0265);

N-[2,4-difluoro-3-[5-(2-morpholinopyrimidin-5-yl)-1H-pyrrolo[2,3-b]pyridine-3-carbonyl]phenyl]pyrrolidine-1-sulfonamide (P-0266);

N-[1-[[3-[5-(2-cyclopropylpyrimidin-5-yl)-1H-pyrrolo[2,3-b]pyridine-3-carbonyl]-2-fluoro-phenyl]sulfamoyl]pyrrolidin-3-yl]-N-methyl-acetamide (P-0267);

3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (P-0268);

N-[3-[5-[2-(azetidin-1-yl)pyrimidin-5-yl]-1H-pyrrolo[2,3-b]pyridine-3-carbonyl]-2,4-difluoro-phenyl]pyrrolidine-1-sulfonamide (P-0269);

N-[2,4-difluoro-3-[5-(2-methoxythiazol-5-yl)-1H-pyrrolo[2,3-b]pyridine-3-carbonyl]phenyl]pyrrolidine-1-sulfonamide (P-0270);

(3R)—N-[3-[5-(2-cyclopropylpyrimidin-5-yl)-1H-pyrrolo[2,3-b]pyridine-3-carbonyl]-2-fluoro-phenyl]-3-methyl-pyrrolidine-1-sulfonamide (P-0271);

N-[3-[5-(2-cyclopropylpyrimidin-5-yl)-1H-pyrrolo[2,3-b]pyridine-3-carbonyl]-2-fluoro-phenyl]-3-(methylamino)pyrrolidine-1-sulfonamide (P-0272);

N-[2,4-difluoro-3-[5-(4-pyridyl)-1H-pyrrolo[2,3-b]pyridine-3-carbonyl]phenyl]pyrrolidine-1-sulfonamide (P-0273);

N-[3-(5-cyclopropyl-1H-pyrrolo[2,3-b]pyridine-3-carbonyl)-2-fluoro-phenyl]pyrrolidine-1-sulfonamide (P-0274);

3-[3-[[ethyl(methyl)sulfamoyl]amino]-2,6-difluoro-benzoyl]-5-[2-(4-hydroxy-1-piperidyl)pyrimidin-5-yl]-1H-pyrrolo[2,3-b]pyridine (P-0275);

5-[3-(1-cyanocyclopropyl)phenyl]-3-[3-[[ethyl(methyl)sulfamoyl]amino]-2,6-difluoro-benzoyl]-1H-pyrrolo[2,3-b]pyridine (P-0276);

5-[2-(azetidin-1-yl)pyrimidin-5-yl]-3-[3-[[ethyl(methyl)sulfamoyl]amino]-2,6-difluoro-benzoyl]-1H-pyrrolo[2,3-b]pyridine (P-0277);

N-[3-[5-(2-aminopyrimidin-5-yl)-1H-pyrrolo[2,3-b]pyridine-3-carbonyl]-2,4-difluoro-phenyl]pyrrolidine-1-sulfonamide (P-0279);

N-[3-[5-(2-aminopyrimidin-4-yl)-1H-pyrrolo[2,3-b]pyridine-3-carbonyl]-2,4-difluoro-phenyl]pyrrolidine-1-sulfonamide (P-0280);

N-[2-fluoro-3-[5-(4-pyridyl)-1H-pyrrolo[2,3-b]pyridine-3-carbonyl]phenyl]pyrrolidine-1-sulfonamide (P-0281);

N-[2,4-difluoro-3-[5-(2-morpholinopyrimidin-4-yl)-1H-pyrrolo[2,3-b]pyridine-3-carbonyl]phenyl]pyrrolidine-1-sulfonamide (P-0282);

3-[3-[[ethyl(methyl)sulfamoyl]amino]-2,6-difluoro-benzoyl]-5-(2-fluoro-4-pyridyl)-1H-pyrrolo[2,3-b]pyridine (P-0283);

N-[2,4-difluoro-3-[5-(2-morpholino-4-pyridyl)-1H-pyrrolo[2,3-b]pyridine-3-carbonyl]phenyl]pyrrolidine-1-sulfonamide (P-0284);

N-[2,4-difluoro-3-[5-[2-(4-methylpiperazin-1-yl)-4-pyridyl]-1H-pyrrolo[2,3-b]pyridine-3-carbonyl]phenyl]pyrrolidine-1-sulfonamide (P-0285);

N-[3-[5-[2-(cyclobutoxy)-4-pyridyl]-1H-pyrrolo[2,3-b]pyridine-3-carbonyl]-2,4-difluoro-phenyl]pyrrolidine-1-sulfonamide (P-0286);

N-[2,4-difluoro-3-[5-(2-methoxy-4-pyridyl)-1H-pyrrolo[2,3-b]pyridine-3-carbonyl]phenyl]pyrrolidine-1-sulfonamide (P-0287);

N-[3-[5-(2-cyclopropylpyrimidin-5-yl)-1H-pyrrolo[2,3-b]pyridine-3-carbonyl]-2,4-difluoro-phenyl]-3,3-difluoro-pyrrolidine-1-sulfonamide (P-0288);

(3S)—N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0289);

methyl 2-[[3-[5-(2-cyclopropylpyrimidin-5-yl)-1H-pyrrolo[2,3-b]pyridine-3-carbonyl]-2-fluoro-phenyl]sulfamoyl]propanoate (P-0291);

5-[2-(dimethylamino)pyrimidin-5-yl]-3-[3-[[ethyl(methyl)sulfamoyl]amino]-2,6-difluoro-benzoyl]-1H-pyrrolo[2,3-b]pyridine (P-0292);

3-[3-[[ethyl(methyl)sulfamoyl]amino]-2,6-difluoro-benzoyl]-5-(2-pyrrolidin-1-ylpyrimidin-5-yl)-1H-pyrrolo[2,3-b]pyridine (P-0293);

N-[2,4-difluoro-3-[5-[6-(trifluoromethyl)pyrimidin-4-yl]-1H-pyrrolo[2,3-b]pyridine-3-carbonyl]phenyl]pyrrolidine-1-sulfonamide (P-0294);

N-[3-[5-(2-cyclopropyl-4-pyridyl)-1H-pyrrolo[2,3-b]pyridine-3-carbonyl]-2,4-difluoro-phenyl]pyrrolidine-1-sulfonamide (P-0295);

5-cyclobutyl-3-[3-[[ethyl(methyl)sulfamoyl]amino]-2-fluoro-benzoyl]-1H-pyrrolo[2,3-b]pyridine (P-0297);

5-cyclopropyl-3-[3-[[ethyl(methyl)sulfamoyl]amino]-2-fluoro-benzoyl]-1H-pyrrolo[2,3-b]pyridine (P-0298);

N-[3-[5-(6-aminopyrimidin-4-yl)-1H-pyrrolo[2,3-b]pyridine-3-carbonyl]-2-fluoro-phenyl]pyrrolidine-1-sulfonamide (P-0299);

5-(4-cyanophenyl)-3-[3-[[ethyl(methyl)sulfamoyl]amino]-2,6-difluoro-benzoyl]-1H-pyrrolo[2,3-b]pyridine (P-0300);

3-[3-[[ethyl(methyl)sulfamoyl]amino]-2,6-difluoro-benzoyl]-5-[4-(trifluoromethyl)phenyl]-1H-pyrrolo[2,3-b]pyridine (P-0301);

5-[3-(dimethylamino)phenyl]-3-[3-[[ethyl(methyl)sulfamoyl]amino]-2,6-difluoro-benzoyl]-1H-pyrrolo[2,3-b]pyridine (P-0302);

3-[3-[[ethyl(methyl)sulfamoyl]amino]-2,6-difluoro-benzoyl]-5-(4-pyrrolidin-1-ylphenyl)-1H-pyrrolo[2,3-b]pyridine (P-0303);

2-[4-[3-[3-[[ethyl(methyl)sulfamoyl]amino]-2,6-difluoro-benzoyl]-1H-pyrrolo[2,3-b]pyridin-5-yl]phenyl]-5-methyl-1,3,4-oxadiazole (P-0304);

2-[4-[3-[3-[[ethyl(methyl)sulfamoyl]amino]-2,6-difluoro-benzoyl]-1H-pyrrolo[2,3-b]pyridin-5-yl]phenyl]-5-(methylamino)-1,3,4-thiadiazole (P-0305);

3-[3-[[ethyl(methyl)sulfamoyl]amino]-2,6-difluoro-benzoyl]-5-[5-(1-hydroxy-1-methyl-ethyl)-3-pyridyl]-1H-pyrrolo[2,3-b]pyridine (P-0306);

3-[3-[[ethyl(methyl)sulfamoyl]amino]-2,6-difluoro-benzoyl]-5-[6-(1-hydroxy-1-methyl-ethyl)-3-pyridyl]-1H-pyrrolo[2,3-b]pyridine (P-0307);

5-[4-(diethylamino)phenyl]-3-[3-[[ethyl(methyl)sulfamoyl]amino]-2,6-difluoro-benzoyl]-1H-pyrrolo[2,3-b]pyridine (P-0308);

3-[3-[[ethyl(methyl)sulfamoyl]amino]-2,6-difluoro-benzoyl]-5-(2-oxoindolin-6-yl)-1H-pyrrolo[2,3-b]pyridine (P-0309);

3-[5-[3-[3-[[ethyl(methyl)sulfamoyl]amino]-2,6-difluoro-benzoyl]-1H-pyrrolo[2,3-b]pyridin-5-yl]-2-thienyl]-5-methyl-1,2,4-oxadiazole (P-0310);

2-amino-6-[3-[3-[[ethyl(methyl)sulfamoyl]amino]-2,6-difluoro-benzoyl]-1H-pyrrolo[2,3-b]pyridin-5-yl]quinazoline (P-0311);

N-cyclopropyl-5-[3-[3-[[ethyl(methyl)sulfamoyl]amino]-2,6-difluoro-benzoyl]-1H-pyrrolo[2,3-b]pyridin-5-yl]pyridine-2-carboxamide (P-0312);

2-(dimethylamino)-6-[3-[3-1[[ethyl(methyl)sulfamoyl]amino]-2,6-difluoro-benzoyl]-1H-pyrrolo[2,3-b]pyridin-5-yl]quinazoline (P-0313);

3-[3-1[[ethyl(methyl)sulfamoyl]amino]-2,6-difluoro-benzoyl]-5-[4-(1-hydroxycyclopropyl)phenyl]-1H-pyrrolo[2,3-b]pyridine (P-0314);

5-[3-[3-[[ethyl(methyl)sulfamoyl]amino]-2,6-difluoro-benzoyl]-1H-pyrrolo[2,3-b]pyridin-5-yl]thiazole (P-0315);

4-[3-[3-[[ethyl(methyl)sulfamoyl]amino]-2,6-difluoro-benzoyl]-1H-pyrrolo[2,3-b]pyridin-5-yl]-2-(1-hydroxy-1-methyl-ethyl)thiazole (P-0316);

3-[3-[[ethyl(methyl)sulfamoyl]amino]-2,6-difluoro-benzoyl]-5-(6-methoxypyridazin-3-yl)-1H-pyrrolo[2,3-b]pyridine (P-0317);

N-[2,4-difluoro-3-[5-(6-morpholinopyrimidin-4-yl)-1H-pyrrolo[2,3-b]pyridine-3-carbonyl]phenyl]pyrrolidine-1-sulfonamide (P-0318);

N-[2,4-difluoro-3-[5-[6-(4-methylpiperazin-1-yl)pyrimidin-4-yl]-1H-pyrrolo[2,3-b]pyridine-3-carbonyl]phenyl]pyrrolidine-1-sulfonamide (P-0319);

(3S)—N-[3-[5-(2-cyclopropylpyrimidin-5-yl)-1H-pyrrolo[2,3-b]pyridine-3-carbonyl]-2,4-difluoro-phenyl]-3-methyl-pyrrolidine-1-sulfonamide (P-0320);

N-[2-fluoro-3-[5-(6-morpholinopyrimidin-4-yl)-1H-pyrrolo[2,3-b]pyridine-3-carbonyl]phenyl]pyrrolidine-1-sulfonamide (P-0321);

N-[2-fluoro-3-[5-[6-(4-methylpiperazin-1-yl)pyrimidin-4-yl]-1H-pyrrolo[2,3-b]pyridine-3-carbonyl]phenyl]pyrrolidine-1-sulfonamide (P-0322);

N-[2-fluoro-3-[5-[6-(4-methylpiperazin-1-yl)-2-pyridyl]-1H-pyrrolo[2,3-b]pyridine-3-carbonyl]phenyl]pyrrolidine-1-sulfonamide (P-0324);

N-[2-fluoro-3-[5-(4-methoxypyrimidin-2-yl)-1H-pyrrolo[2,3-b]pyridine-3-carbonyl]phenyl]pyrrolidine-1-sulfonamide (P-0325);

N-[2-fluoro-3-[5-(4-methylpyrimidin-2-yl)-1H-pyrrolo[2,3-b]pyridine-3-carbonyl]phenyl]pyrrolidine-1-sulfonamide (P-0326);

(3R)—N-[3-[5-(2-cyclopropylpyrimidin-5-yl)-1H-pyrrolo[2,3-b]pyridine-3-carbonyl]-2-fluoro-phenyl]-3-fluoro-pyrrolidine-1-sulfonamide (P-0327);

[5-(2-cyclopropylpyrimidin-5-yl)-1H-pyrrolo[2,3-b]pyridin-3-yl]-[2,6-difluoro-3-(methylsulfamoylamino)phenyl]methanone (P-0334);

[5-(2-cyclopropylpyrimidin-5-yl)-1H-pyrrolo[2,3-b]pyridin-3-yl]-[3-(ethylsulfamoylamino)-2,6-difluoro-phenyl]methanone (P-0335);

5-(2-cyclopropylpyrimidin-5-yl)-3-[2,6-difluoro-3-(sulfamoylamino)benzoyl]-1H-pyrrolo[2,3-b]pyridine (P-0336);

N-[3-[5-(4-chlorophenyl)-1H-pyrrolo[2,3-b]pyridine-3-carbonyl]-2,4-difluoro-phenyl]butane-2-sulfonamide (P-0337);

(3R)—N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0338);

N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0339);

5-(2-cyclopropylpyrimidin-5-yl)-3-[2,6-difluoro-3-[[methyl(2,2,2-trifluoroethyl)sulfamoyl]amino]benzoyl]-1H-pyrrolo[2,3-b]pyridine (P-0340);

N-[3-[5-(2-cyclopropylpyrimidin-5-yl)-1H-pyrrolo[2,3-b]pyridine-3-carbonyl]-2,4-difluoro-phenyl]butane-2-sulfonamide (P-0342);

5-[3-[3-[[ethyl(methyl)sulfamoyl]amino]-2,6-difluoro-benzoyl]-1H-pyrrolo[2,3-b]pyridin-5-yl]-2-methoxy-thiazole (P-0343);

3-[3-[[ethyl(methyl)sulfamoyl]amino]-2,6-difluoro-benzoyl]-5-(1H-indazol-6-yl)-1H-pyrrolo[2,3-b]pyridine (P-0344);

N-[2,4-difluoro-3-[5-(2-pyrrolidin-1-ylpyrimidin-5-yl)-1H-pyrrolo[2,3-b]pyridine-3-carbonyl]phenyl]pyrrolidine-1-sulfonamide (P-0345);

N-[3-(5-cyclobutyl-1H-pyrrolo[2,3-b]pyridine-3-carbonyl)-2-fluoro-phenyl]pyrrolidine-1-sulfonamide (P-0346);

N-[2-fluoro-3-[5-(2-methoxypyrimidin-5-yl)-1H-pyrrolo[2,3-b]pyridine-3-carbonyl]phenyl]cyclopropanesulfonamide (P-0347);

1-allyl-N-[3-(5-cyano-1H-pyrrolo[2,3-b]pyridine-3-carbonyl)-2,4-difluoro-phenyl]cyclopropanesulfonamide (P-0348);

N-[2,4-difluoro-3-[5-(2-methoxypyrimidin-5-yl)-1H-pyrrolo[2,3-b]pyridine-3-carbonyl]phenyl]cyclopropanesulfonamide (P-0349);

N-[2,4-difluoro-3-[5-(5-methoxy-3-pyridyl)-1H-pyrrolo[2,3-b]pyridine-3-carbonyl]phenyl]cyclopropanesulfonamide (P-0350); and N-[3-(5-cyano-1H-pyrrolo[2,3-b]pyridine-3-carbonyl)-2,4-difluoro-phenyl]cyclopropanesulfonamide (P-0351);

or pharmaceutically acceptable salts, hydrates, solvates, tautomers or isomers thereof. In some embodiments, the invention provides the above selected compounds and pharmaceutically acceptable salts thereof. In other embodiments, the invention provides the above selected compounds and pharmaceutically acceptable salts and tautomers and isomers thereof.

In other embodiments, the invention provides a compound selected from any of P-0108 to P-0222 as set forth in Table 3 and pharmaceutically acceptable salts, hydrates, solvates, tautomers and isomers thereof. In some embodiments, the invention provides any of the above selected compounds and pharmaceutically acceptable salts thereof. In some embodiments, the invention provides any of the above selected compounds and pharmaceutically acceptable salts and tautomers and isomers thereof.

In some embodiments, when $Y^1$ is optionally substituted 2-pyridyl, 3-pyridyl or 4-pyridyl, Z is other than —N(CH$_3$)(CH$_3$) or —N(R$^4$)$_2$, wherein R$^4$ is C$_{1-6}$alkyl. In some embodiments, when Y$_1$ is phenyl, Z is other than —N(CH$_3$)(CH$_3$) or —N(R$^4$)$_2$, wherein R$^4$ is C$_{1-6}$alkyl. In other embodiments, when Y$_1$ is halogen, Z is other than —N(CH$_3$)(CH$_3$), —N(Et)$_2$, 1-pyrrolinyl, 1-piperidinyl, 4-morpholinyl or —N(R$^4$)$_2$, wherein R$^4$ is C$_{1-6}$alkyl. In some embodiments, when Y$_1$ is CH$_3$ or C$_{1-6}$alkyl, Z is other than —N(CH$_3$)(CH$_3$), —N(Et)$_2$, 1-pyrrolinyl, 1-piperidinyl, 4-morpholinyl or —N(R$^4$)$_2$, wherein R$^4$ is C$_{1-6}$alkyl. In some embodiments, when Y$^1$ is CH$_3$O— or C$_{1-6}$alkoxy, Z is other than —N(CH$_3$)(CH$_3$), —N(Et)$_2$, 1-pyrrolinyl, 1-piperidinyl, 4-morpholinyl or —N(R$^4$)$_2$, wherein R$^4$ is C$_{1-6}$alkyl. In some embodiments, when Y$^1$ is CN, Z is other than —N(CH$_3$)(CH$_3$), —N(Et)$_2$, 1-pyrrolinyl, 1-piperidinyl, 4-morpholinyl or —N(R$^4$)$_2$, wherein R$^4$ is C$_{1-6}$alkyl. In certain instances, when Y$^1$ is halogen, —CH$_3$, —CN, —OMe or 2-methoxypyrimidin-5-yl, Z is other than C$_{3-6}$cycloalkyl. In other instances, when Y$^1$ is 1-methyl-4-pyrazolyl, 3-methylsulfonylphenyl or 3-methylsulfonylaminophenyl, Z is other than C$_{3-6}$cycloalkyl. In other instances, when Y$^1$ is C$_{1-6}$alkyl or C$_{1-6}$alkoxy, Z is other than C$_{3-6}$cycloalkyl. In other instances, when Y$^1$ is 1-C$_{1-6}$alkyl-4-pyrazolyl, Z is other than cyclopropyl, cyclobutyl, cyclopentyl or cyclohexyl. In other instances, when Y$^1$ is 1-C$_{1-8}$alkyl-4-pyrazolyl, Z is other than C$_{3-6}$cycloalkyl. In other instances, when Y$^1$ is methylsulfonylphenyl or methylsulfonylaminophenyl, Z is other than cyclopropyl, cyclobutyl, cyclopentyl or cyclohexyl. In other instances, when Y$^1$ is methylsulfonylphenyl or methylsulfonylaminophenyl, Z is other than C$_{3-6}$cycloalkyl. In some instances, when Y$^1$ is 3-C$_{1-6}$alkylsulfonylphenyl or 3-C$_{1-6}$alkylsulfonylaminophenyl, Z is other than cyclopropyl, cyclobutyl, cyclopentyl or cyclohexyl. In other instances, when Y$^1$ is 3-C$_{1-6}$alkylsulfonylphenyl or 3-C$_{1-6}$alkylsulfonylaminophenyl, Z is other than C$_{3-6}$cycloalkyl.

The following compounds in Table 1 are excluded from the generic formulas I and Ia to In:

TABLE 1

3-[3-(dimethylsulfamoylamino)-2,6-difluoro-benzoyl]-5-(3-pyridyl)-1H-pyrrolo[2,3-b]pyridine;
5-bromo-3-[3-(dimethylsulfamoylamino)-2,6-difluoro-benzoyl]-1H-pyrrolo[2,3-b]pyridine;
3-[3-(dimethylsulfamoylamino)-2,6-difluoro-benzoyl]-5-phenyl-1H-pyrrolo[2,3-b]pyridine;
N-[3-(5-chloro-1H-pyrrolo[2,3-b]pyridine-3-carbonyl)-2,4-difluoro-phenyl]piperidine-1-sulfonamide;
5-(4-chlorophenyl)-3-[3-(dimethylsulfamoylamino)-2,6-difluoro-benzoyl]-1H-pyrrolo[2,3-b]pyridine;
5-chloro-3-[3-(dimethylsulfamoylamino)-2,6-difluoro-benzoyl]-1H-pyrrolo[2,3-b]pyridine;
(5-chloro-1H-pyrrolo[2,3-b]pyridin-3-yl)-[3-[dimethylsulfamoyl(methyl)amino]-2,6-difluoro-phenyl]methanone;
N-[2,4-difluoro-3-(5-methoxy-1H-pyrrolo[2,3-b]pyridine-3-carbonyl)phenyl]pyrrolidine-1-sulfonamide;
N-[3-(5-chloro-1H-pyrrolo[2,3-b]pyridine-3-carbonyl)-2,4-difluoro-phenyl]pyrrolidine-1-sulfonamide;
N-[2,4-difluoro-3-(5-methyl-1H-pyrrolo[2,3-b]pyridine-3-carbonyl)phenyl]pyrrolidine-1-sulfonamide;
N-[3-(5-cyano-1H-pyrrolo[2,3-b]pyridine-3-carbonyl)-2,4-difluoro-phenyl]pyrrolidine-1-sulfonamide;
5-cyano-3-[3-(dimethylsulfamoylamino)-2,6-difluoro-benzoyl]-1H-pyrrolo[2,3-b]pyridine;
3-[3-(dimethylsulfamoylamino)-2,6-difluoro-benzoyl]-5-methyl-1H-pyrrolo[2,3-b]pyridine;
5-chloro-3-[3-(diethylsulfamoylamino)-2,6-difluoro-benzoyl]-1H-pyrrolo[2,3-b]pyridine;
5-cyano-3-[3-(diethylsulfamoylamino)-2,6-difluoro-benzoyl]-1H-pyrrolo[2,3-b]pyridine;
3-[3-(diethylsulfamoylamino)-2,6-difluoro-benzoyl]-5-methyl-1H-pyrrolo[2,3-b]pyridine;
3-[3-(diethylsulfamoylamino)-2,6-difluoro-benzoyl]-5-methoxy-1H-pyrrolo[2,3-b]pyridine;
N-[3-(5-chloro-1H-pyrrolo[2,3-b]pyridine-3-carbonyl)-2,4-difluoro-phenyl]morpholine-4-sulfonamide;
N-[2,4-difluoro-3-(5-methoxy-1H-pyrrolo[2,3-b]pyridine-3-carbonyl)phenyl]morpholine-4-sulfonamide;
N-[2,4-difluoro-3-(5-methyl-1H-pyrrolo[2,3-b]pyridine-3-carbonyl)phenyl]morpholine-4-sulfonamide;
N-[3-(5-cyano-1H-pyrrolo[2,3-b]pyridine-3-carbonyl)-2,4-difluoro-phenyl]morpholine-4-sulfonamide;
3-[3-(dimethylsulfamoylamino)-2,6-difluoro-benzoyl]-5-(2-methoxypyrimidin-5-yl)-1H-pyrrolo[2,3-b]pyridine;
N-[2,4-difluoro-3-[5-(2-methoxypyrimidin-5-yl)-1H-pyrrolo[2,3-b]pyridine-3-carbonyl]phenyl]pyrrolidine-1-sulfonamide;
3-[3-(diethylsulfamoylamino)-2,6-difluoro-benzoyl]-5-(2-methoxypyrimidin-5-yl)-1H-pyrrolo[2,3-b]pyridine;
N-[2,4-difluoro-3-[5-(2-methoxypyrimidin-5-yl)-1H-pyrrolo[2,3-b]pyridine-3-carbonyl]phenyl]morpholine-4-sulfonamide;
5-cyano-3-[3-(dimethylsulfamoylamino)-2-fluoro-benzoyl]-1H-pyrrolo[2,3-b]pyridine;
N-[3-(5-cyano-1H-pyrrolo[2,3-b]pyridine-3-carbonyl)-2-fluoro-phenyl]pyrrolidine-1-sulfonamide;
N-[3-(5-cyano-1H-pyrrolo[2,3-b]pyridine-3-carbonyl)-2-fluoro-phenyl]morpholine-4-sulfonamide;
N-[2-fluoro-3-[5-(2-methoxypyrimidin-5-yl)-1H-pyrrolo[2,3-b]pyridine-3-carbonyl]phenyl]pyrrolidine-1-sulfonamide;
5-(4-chlorophenyl)-3-[3-(dimethylsulfamoylamino)-2-fluoro-benzoyl]-1H-pyrrolo[2,3-b]pyridine;
3-[3-(dimethylsulfamoylamino)-2-fluoro-benzoyl]-5-(2-methoxypyrimidin-5-yl)-1H-pyrrolo[2,3-b]pyridine;

TABLE 1-continued

Propane-2-sulfonic acid [2,4-difluoro-3-(5-methoxy-1H-pyrrolo[2,3-b]pyridine-3-carbonyl)-phenyl]-amide;
Pyrrolidine-1-sulfonic acid [2,4-difluoro-3-(5-methoxy-1H-pyrrolo[2,3-b]pyridine-3-carbonyl)-phenyl]-amide;
Propane-2-sulfonic acid [3-(5-chloro-1H-pyrrolo[2,3-b]pyridine-3-carbonyl)-2,4-difluoro-phenyl]-amide;
Propane-2-sulfonic acid [3-(5-cyano-1H-pyrrolo[2,3-b]pyridine-3-carbonyl)-2,4-difluoro-phenyl]-amide;
Propane-2-sulfonic acid {2,4-difluoro-3-[5-(2-methoxy-pyrimidin-5-yl)-1H-pyrrolo[2,3-b]pyridine-3-carbonyl]-phenyl}-amide;
Butane-2-sulfonic acid [2,4-difluoro-3-(5-methoxy-1H-pyrrolo[2,3-b]pyridine-3-carbonyl)-phenyl]-amide;
Pentane-2-sulfonic acid [2,4-difluoro-3-(5-methoxy-1H-pyrrolo[2,3-b]pyridine-3-carbonyl)-phenyl]-amide;
Butane-2-sulfonic acid [3-(5-chloro-1H-pyrrolo[2,3-b]pyridine-3-carbonyl)-2,4-difluoro-phenyl]-amide;
Pentane-2-sulfonic acid [3-(5-chloro-1H-pyrrolo[2,3-b]pyridine-3-carbonyl)-2,4-difluoro-phenyl]-amide;
Butane-2-sulfonic acid [2,4-difluoro-3-(5-methyl-1H-pyrrolo[2,3-b]pyridine-3-carbonyl)-phenyl]-amide;
Pentane-2-sulfonic acid [3-(5-cyano-1H-pyrrolo[2,3-b]pyridine-3-carbonyl)-2,4-difluoro-phenyl]-amide;
Pentane-2-sulfonic acid [2,4-difluoro-3-(5-methyl-1H-pyrrolo[2,3-b]pyridine-3-carbonyl)-phenyl]-amide;
Butane-2-sulfonic acid [3-(5-cyano-1H-pyrrolo[2,3-b]pyridine-3-carbonyl)-2,4-difluoro-phenyl]-amide;
Butane-2-sulfonic acid {2,4-difluoro-3-[5-(2-methoxy-pyrimidin-5-yl)-1H-pyrrolo[2,3-b]pyridine-3-carbonyl]-phenyl}-amide;
Cyclobutanesulfonic acid [3-(5-cyano-1H-pyrrolo[2,3-b]pyridine-3-carbonyl)-2,4-difluoro-phenyl]-amide;
Cyclobutanesulfonic acid [3-(5-chloro-1H-pyrrolo[2,3-b]pyridine-3-carbonyl)-2,4-difluoro-phenyl]-amide;
Cyclohexanesulfonic acid [2,4-difluoro-3-(5-methoxy-1H-pyrrolo[2,3-b]pyridine-3-carbonyl)-phenyl]-amide;
Cyclopentanesulfonic acid [2,4-difluoro-3-(5-methoxy-1H-pyrrolo[2,3-b]pyridine-3-carbonyl)-phenyl]-amide;
Cyclohexanesulfonic acid [3-(5-chloro-1H-pyrrolo[2,3-b]pyridine-3-carbonyl)-2,4-difluoro-phenyl]-amide;
Cyclopentanesulfonic acid [3-(5-chloro-1H-pyrrolo[2,3-b]pyridine-3-carbonyl)-2,4-difluoro-phenyl]-amide;
Cyclopentanesulfonic acid [3-(5-cyano-1H-pyrrolo[2,3-b]pyridine-3-carbonyl)-2,4-difluoro-phenyl]-amide;
Cyclohexanesulfonic acid [2,4-difluoro-3-(5-methyl-1H-pyrrolo[2,3-b]pyridine-3-carbonyl)-phenyl]-amide;
Cyclobutanesulfonic acid [2,4-difluoro-3-(5-methyl-1H-pyrrolo[2,3-b]pyridine-3-carbonyl)-phenyl]-amide;
Cyclopentanesulfonic acid [2,4-difluoro-3-(5-methyl-1H-pyrrolo[2,3-b]pyridine-3-carbonyl)-phenyl]-amide;
Cyclohexanesulfonic acid [3-(5-cyano-1H-pyrrolo[2,3-b]pyridine-3-carbonyl)-2,4-difluoro-phenyl]-amide;
Cyclohexanesulfonic acid {2,4-difluoro-3-[5-(2-methoxy-pyrimidin-5-yl)-1H-pyrrolo[2,3-b]pyridine-3-carbonyl]-phenyl}-amide;
Cyclopentanesulfonic acid {2,4-difluoro-3-[5-(2-methoxy-pyrimidin-5-yl)-1H-pyrrolo[2,3-b]pyridine-3-carbonyl]-phenyl}-amide;
Cyclobutanesulfonic acid {2,4-difluoro-3-[5-(2-methoxy-pyrimidin-5-yl)-1H-pyrrolo[2,3-b]pyridine-3-carbonyl]-phenyl}-amide;
Pyrrolidine-1-sulfonic acid [2,4-difluoro-3-(5-methoxy-1H-pyrrolo[2,3-b]pyridine-3-carbonyl)-phenyl]-amide;
Pyrrolidine-1-sulfonic acid [3-(5-chloro-1H-pyrrolo[2,3-b]pyridine-3-carbonyl)-2,4-difluoro-phenyl]-amide;
Pyrrolidine-1-sulfonic acid [2,4-difluoro-3-(5-methyl-1H-pyrrolo[2,3-b]pyridine-3-carbonyl)-phenyl]-amide;
Pyrrolidine-1-sulfonic acid [2,4-difluoro-3-(5-cyano-1H-pyrrolo[2,3-b]pyridine-3-carbonyl)-phenyl]-amide;
N,N-dimethylamino-sulfonic acid [2,4-difluoro-3-(5-cyano-1H-pyrrolo[2,3-b]pyridine-3-carbonyl)-phenyl]-amide;
N,N-dimethylamino-sulfonic acid [2,4-difluoro-3-(5-methyl-1H-pyrrolo[2,3-b]pyridine-3-carbonyl)-phenyl]-amide;
N,N-diethylamino-sulfonic acid [3-(5-chloro-1H-pyrrolo[2,3-b]pyridine-3-carbonyl)-2,4-difluoro-phenyl]-amide;
N,N-diethylamino-sulfonic acid [3-(5-cyano-1H-pyrrolo[2,3-b]pyridine-3-carbonyl)-2,4-difluoro-phenyl]-amide;
N,N-diethylamino-sulfonic acid [2,4-difluoro-3-(5-methyl-1H-pyrrolo[2,3-b]pyridine-3-carbonyl)-phenyl]-amide;
N,N-diethylamino-sulfonic acid [2,4-difluoro-3-(5-methoxy-1H-pyrrolo[2,3-b]pyridine-3-carbonyl)-phenyl]-amide;
Morpholine-4-sulfonic acid [3-(5-cyano-1H-pyrrolo[2,3-b]pyridine-3-carbonyl)-2,4-difluoro-phenyl]-amide;
Morpholine-4-sulfonic acid [3-(5-chloro-1H-pyrrolo[2,3-b]pyridine-3-carbonyl)-2,4-difluoro-phenyl]-amide;

TABLE 1-continued

Morpholine-4-sulfonic acid [2,4-difluoro-3-(5-methoxy-1H-pyrrolo[2,3-b]pyridine-3-carbonyl)-phenyl]-amide;
Morpholine-4-sulfonic acid [2,4-difluoro-3-(5-methyl-1H-pyrrolo[2,3-b]pyridine-3-carbonyl)-phenyl]-amide;
Propane-2-sulfonic acid [3-(5-cyano-1H-pyrrolo[2,3-b]pyridine-3-carbonyl)-2-fluoro-phenyl]-amide;
Butane-2-sulfonic acid [3-(5-cyano-1H-pyrrolo[2,3-b]pyridine-3-carbonyl)-2-fluoro-phenyl]-amide;
Cyclohexanesulfonic acid [3-(5-cyano-1H-pyrrolo[2,3-b]pyridine-3-carbonyl)-2-fluoro-phenyl]-amide;
Cyclopentanesulfonic acid [3-(5-cyano-1H-pyrrolo[2,3-b]pyridine-3-carbonyl)-2-fluoro-phenyl]-amide;
Cyclobutanesulfonic acid [3-(5-cyano-1H-pyrrolo[2,3-b]pyridine-3-carbonyl)-2-fluoro-phenyl]-amide;
Cyclopropanesulfonic acid {4-fluoro-3-[5-(1-methyl-1H-pyrazol-4-yl)-1H-pyrrolo[2,3-b]pyridine-3-carbonyl]-phenyl}-amide;
Cyclohexanesulfonic acid {4-fluoro-3-[5-(1-methyl-1H-pyrazol-4-yl)-1H-pyrrolo[2,3-b]pyridine-3-carbonyl]-phenyl}-amide;
Cyclopropanesulfonic acid [3-(5-chloro-1H-pyrrolo[2,3-b]pyridine-3-carbonyl)-4-fluoro-phenyl]-amide;
Cyclohexanesulfonic acid [4-fluoro-3-(5-methyl-1H-pyrrolo[2,3-b]pyridine-3-carbonyl)-phenyl]-amide;
Cyclohexanesulfonic acid {4-fluoro-3-[5-(3-methanesulfonyl-phenyl)-1H-pyrrolo[2,3-b]pyridine-3-carbonyl]-phenyl}-amide;
Cyclopentanesulfonic acid {4-fluoro-3-[5-(3-methanesulfonyl-phenyl)-1H-pyrrolo[2,3-b]pyridine-3-carbonyl]-phenyl}-amide;
Cyclohexanesulfonic acid {4-fluoro-3-[5-(3-methanesulfonylamino-phenyl)-1H-pyrrolo[2,3-b]pyridine-3-carbonyl]-phenyl}-amide;
Cyclopentanesulfonic acid {4-fluoro-3-[5-(3-methanesulfonylamino-phenyl)-1H-pyrrolo[2,3-b]pyridine-3-carbonyl]-phenyl}-amide;
Cyclopentanesulfonic acid [4-fluoro-3-(5-methyl-1H-pyrrolo[2,3-b]pyridine-3-carbonyl)-phenyl]-amide;
Piperidine-1-sulfonic acid [3-(5-chloro-1H-pyrrolo[2,3-b]pyridine-3-carbonyl)-4-fluoro-phenyl]-amide;
N,N-dimethylamino-sulfonic acid [3-(5-bromo-1H-pyrrolo[2,3-b]pyridine-3-carbonyl)-2-fluoro-phenyl]-amide;
Pyrrolidine-1-sulfonic acid [3-(5-bromo-1H-pyrrolo[2,3-b]pyridine-3-carbonyl)-2-fluoro-phenyl]-amide.

In another aspect, the present invention provides a method for preparing a compound of formulas (I) to (In). The method includes contacting a compound having formula II:

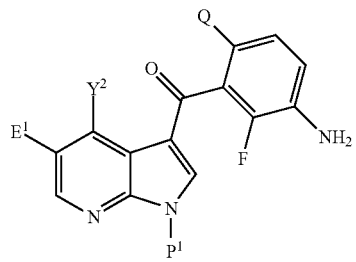
(II)

with an agent selected from $Y^1$-$G^1$ (III) or $A^1$-S(O)$_2$—Z (IV) under conditions sufficient to form a compound having formulas (V) or (VI):

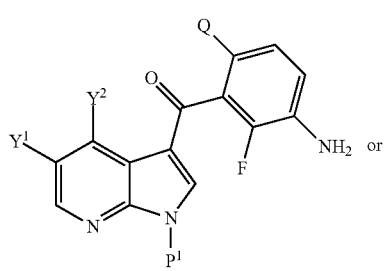
(V)

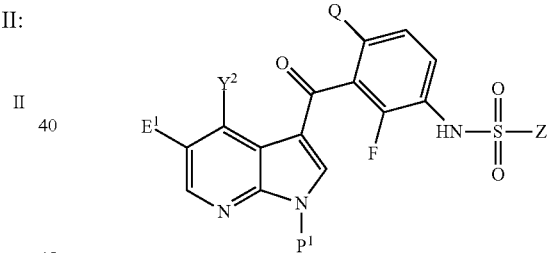
(VI)

reacting (i) a compound of formula (V) with a compound of formula (IV), or (ii) a compound of formula (VI) with a compound of formula (III) under conditions sufficient to form the compound of formula (I); and wherein $E^1$ is halogen, tosylate or mesylate; $G^1$ is —B(OR$^{25}$)$_2$ or —Sn(Bu)$_3$, wherein R$^{25}$ is —OH, alkyl or two —OR$^{25}$ substituents together with the boron atom to which they are attached to form an optionally substituted 5 or 6-membered ring; $A^1$ is a leaving group, which can be readily displaced by an arylamino group; and $P^1$ is H or an amino protecting group. In some instances, the substituents for the 5 or 6-membered ring are 1 to 4 members R$^e$ groups. In some embodiments, the reaction of compounds of formula (II) with In one embodiment, $E^1$ is Cl, Br or I. In another embodiment, $E^1$ is tosylate, mesylate or triflate. In one embodiment, $G^1$ is —B(OH)$_2$. In another embodiment, $G^1$ is 2-hydroxy-1,3,2-benzodioxaborole or 2-hydroxy-4,4,5,5-tetramethyl-1,3,2-benzodioxaboro. In another embodiment, $G^1$ is —Sn(Bu)$_3$. In one embodiment, $A^1$ is Cl or Br. In another embodiment, $A^1$ is tosylate or mesylate. In one embodiment, $P^1$ is H. The substituents $Y^1$, $Y^2$, Q and Z are as defined in any of formulas (I) to (In) and any of the embodiments disclosed herein.

In some embodiments, the method includes contacting a compound of formula (II) with an agent of formula (III): $Y^1$-$G^1$ to form a compound of formula (V), followed by reacting a compound of formula (V) with an agent of formula (IV): $A^1$-$S(O)_2$—Z to form a compound of formula (I). In other embodiments, the method includes contacting a compound of formula (II) with an agent of formula (IV): $A^1$-$S(O)_2$—Z to form a compound of formula (VI), followed by reacting a compound of formula (VI) with an agent of formula (III): $Y^1$-$G^1$ to form a compound of formula (I).

In yet other embodiments, the invention provides a method for preparing a compound of formulas (I) to (In). The method includes reacting a compound having formula II:

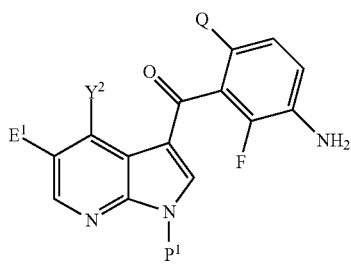

II with a compound of formula (IV): $A^1$-$S(O)_2$—Z under conditions sufficient to form a compound having formula (VI):

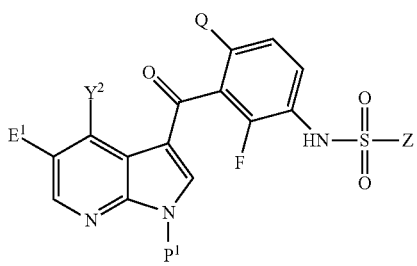

(VI)

contacting a compound of formula (VI) with a compound of the formula: $Y^1$-$E^2$ and a compound of the formula: $(OR^{31})_2$B—B$(OR^{31})_2$ in the presence of a palladium complex under conditions sufficient to form the compound of formula (I), wherein $R^{31}$ is —OH, alkyl or two —$OR^{31}$ substituents together with the boron atom to which they are attached to form a 5 or 6-membered ring; and wherein $E^1$ and $E^2$ are each independently halogen, tosylate or mesylate; $A^1$ is a leaving group; and $P^1$ is H or an amino protecting group. Both Pd(0) and Pd(II) complexes can be used. In some embodiments, $E^1$ is Cl, Br, I, tosylate or mesylate. In some embodiments, $E^2$ is Cl, Br, I, tosylate or mesylate. In certain instances, the palladium complexes include, but are not limited to, Pd(PPh$_3$)$_4$, bis(diphenylphosphino)ferrocene] dichloropalladium and the like. The substituents $Y^1$, $Y^2$, Q and Z are as defined in any of formulas (I) to (In) and any of the embodiments disclosed herein.

In another aspect, the invention provides a compound having formula (VIII):

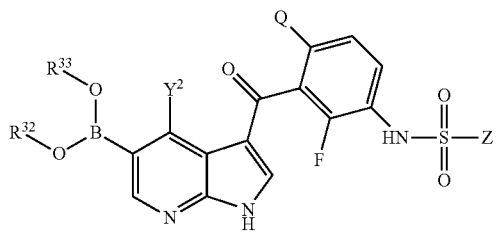

VIII wherein $R^{32}$ and $R^{33}$ are each independently H, optionally substituted alkyl, optionally substituted arylalkyl or optionally substituted aryl. In some embodiments, the aryl or alkyl portion of $R^{32}$ or $R^{33}$ is optionally substituted with from 1 to 4 $R^e$ substituents; or $R^{32}$ and $R^{33}$ together with the oxygen atoms to which they are attached form a 5- or 6-membered ring, wherein the 5- or 6-membered ring is optionally substituted with from 1 to 4 $R^e$ groups or fused with an optionally substituted 5- or 6-membered aromatic ring. The substituents $Y^2$, Q and Z in formula VIII are as defined in in any of formulas (I) to (In) and any of the embodiments as described herein.

In some embodiments, the compounds of formula VIII have sub formula VIIIa:

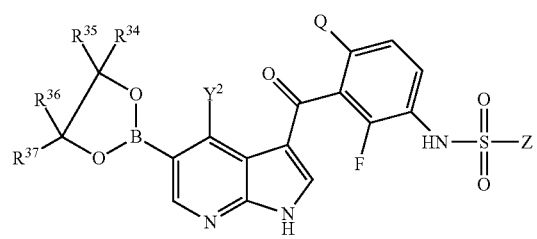

VIIIa $R^{34}$, $R^{35}$, $R^{36}$ and $R^{37}$ are each independently $R^e$ or $R^f$. In certain instances, $R^{34}$, $R^{35}$, $R^{36}$ and $R^{37}$ are each independently $C_{1-6}$ alkyl. In other instances, $R^{34}$, $R^{35}$, $R^{36}$ and $R^{37}$ are $CH_3$. The substituents $Y^2$, Q and Z in formula VIIIa are as defined in in any of formulas (I) to (In) and any of the embodiments as described herein.

In some embodiments, the compounds of formula VIII have sub formula VIIIb:

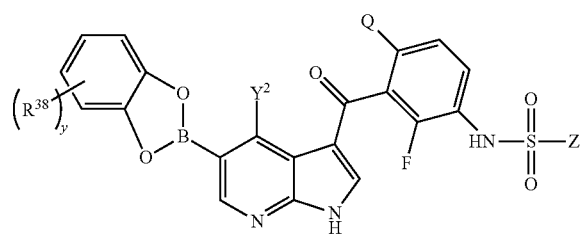

VIIIb

The subscript y is an integer of 1 to 4. Each $R^{38}$ is independently H, $R^e$ or $R^f$. The substituents $Y^2$, Q and Z in formula VIIIb are as defined in any of formulas (I) to (In) and any of the embodiments as described herein.

In some embodiments, the compounds of formula VIII have subformula VIIIc:

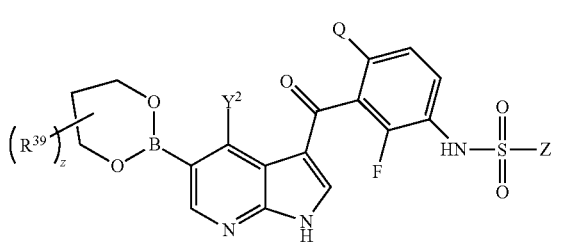

VIIIc

The subscript z is an integer of 1 to 4. Each $R^{39}$ is independently H, $R^e$ or $R^f$. The substituents $Y^2$, Q and Z in formula VIIIc are as defined in any of formulas (I) to (In) and any of the embodiments as described herein.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry: Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolism, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, CA, 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein and recited in any of the claims can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1, 6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19th ed., Mack Publishing Co., Easton, PA, Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

IV. Formulations and Administration

In another aspect, the present invention provides pharmaceutical compositions comprising/including a pharmaceutically acceptable carrier or excipient and a compound of the invention described herein or a pharmaceutically acceptable salt or solvate thereof. In an exemplary embodiment, the present invention provides a pharmaceutical formulation comprising/including a compound as described herein. In one embodiment, the compound has any of formulas I, and Ia to In.

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21st edition, Lippincott, Williams and Wilkins, Philadelphia, PA, 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrose, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the invention (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinil and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present invention provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

V. Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference as it relates to such kinase targets, as well as the following:

A-Raf: Target kinase A-Raf (i.e., v-raf murine sarcoma 3611 viral oncogene homolog 1) is a 67.6 kDa serine/threonine kinase encoded by chromosome Xp 11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

Many cancers associated with dysregulation of the RAS-RAF-ERK pathway, such as cancers having B-Raf V600, such as V600E mutations or NRAS mutations, may be treated with Raf kinase inhibitors, such as the Pan Raf kinase inhibitors as described herein. The ability of these compounds to inhibit multiple Raf kinase targets, including c-Raf-1, B-Raf, and B-Raf V600, such as V600E, provides additional benefits for inhibiting activating mutations in this pathway, with such cancers less likely to develop resistance to such inhibitors as they are targeting several points in the pathway. Pan Raf kinase inhibitors as described herein may be useful in treating a variety of cancers, including, but not limited to, melanoma, glioma, glioblastoma multiforme, pilocytic astrocytoma, carcinoma (e.g. gastrointestinal, liver, biliary tract, bile duct (cholangiocarcinoma), colorectal, lung, brain, bladder, gallbladder, breast, pancreatic, thyroid, kidney, ovarian, adrenocortical, prostate), gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. See McDermott et al., PNAS, 2007, 104(50): 19936-19941; and Jaiswal et al., PLoS One, 2009, 4(5):e5717.

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). c-Raf-1 inhibitors may also be useful for the treatment of acute myeloid leukemia and myelodysplastic syndromes (Crump, Curr Pharm Des 2002, 8(25):2243-8). c-Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

Raf inhibitors (A-Raf and/or B-Raf and/or c-Raf-1) may be useful in treating A-Raf-mediated, B-Raf-mediated or c-Raf-1-mediated diseases or conditions selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, brain, bladder, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, chronic myelomonocytic leukemia, childhood, acute lymphoblastic leukemia, plasma cell leukemia, multiple myeloma, tumor angiogenesis, gastrointestinal stromal tumors, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Erk2: Target kinase Erk2 (i.e., extracellular signal-regulated kinase 2) is a 41.4 kDa dual function serine/threonine-tyrosine kinase encoded by chromosome 22q11.2 (symbol: MAPK1). Erk2 is a member of the mitogen-activated protein (MAP) kinase family and is alternatively known as mitogen-activated protein kinase 1 (i.e., MAPK1). MAP kinases act as an integration point for multiple biochemical signals, and are involved in a wide variety of cellular processes such as proliferation, differentiation, transcription regulation and development.

The activation of Erk2 requires phosphorylation by upstream kinases. Upon activation, Erk2 translocates to the nucleus of the stimulated cells, where it phosphorylates nuclear targets, in addition to other targets including microtubule associated protein 2, myelin basic protein and ELK1. MacKenzie et al. state that the cAMP-specific phosphodiesterase family 4, subfamily D, isoform 3 (i.e., PDE4D3) is shown to have FQF (i.e., Phe-Gln-Phe) and KIM (i.e., Kinase Interaction Motif) docking sites for Erk2. These sites straddle the Ser(579) target residue for Erk2 phosphorylation of PDE4D3. Mutation of either or both of these docking sites prevent Erk2 from being co-immunoprecipitated with PDE4D3, ablate the ability of epidermal growth factor (EGF) to inhibit PDE4D3 through Erk2 action in transfected COS cells, and attenuate the ability of Erk2 to phosphorylate PDE4D3 in vitro. The two conserved NH(2)-terminal blocks of sequence, called upstream conserved regions 1 and 2 (i.e., UCR1 and UCR2), that characterize PDE4 long isoforms, are proposed to amplify the small, inherent inhibitory effect that Erk2 phosphorylation exerts on the PDE4D catalytic unit. In contrast to this, the lone intact UCR2 region found in PDE4D1 directs COOH-terminal Erk2 phosphorylation to cause the activation of this short isoform. From the analysis of PDE4D3 truncates, it is suggested that UCR1 and UCR2 provide a regulatory signal integration module that serves to orchestrate the functional consequences of Erk2 phosphorylation. The PDE4D gene thus encodes a series of isoenzymes that are either inhibited or activated by Erk2 phosphorylation and thereby offers the potential for ERK2 activation either to increase or decrease cAMP levels in cellular compartments (MacKenzie et al., J Biol Chem 2000, 275(22):16609-17).

According to OMIM, Pleschka et al. (Nature Cell Biol., 2001, 3: 301-305) proposed that Erk2 regulates a cellular factor involved in the viral nuclear export protein function. They suggested that local application of MEK inhibitors may have only minor toxic effects on the host while inhibiting viral replication without giving rise to drug-resistant virus variants (OMIM MIM Number: 176948: Oct. 27, 2005). Erk2 is involved in cytokine signaling and is a target for treating inflammation. Ramesh and Philipp state that lipoproteins are the key inflammatory molecule type of *Borrelia burgdorferi*, the spirochete that causes Lyme disease. They investigated whether specific inhibition of p38 and Erk1/2 MAPK would inhibit TNF-alpha and IL-6 production and thus astrocyte apoptosis, and proliferation, respectively. Lipoprotein-stimulated IL-6 production was unaffected by the MAPK inhibitors. In contrast, inhibition of both p38 and Erk1/2 significantly diminished TNF-alpha production, and totally abrogated production of this cytokine when both MAPK pathways were inhibited simultaneously. MAPK inhibition thus may be considered as a strategy to control inflammation and apoptosis in Lyme neuroborreliosis (Ramesh and Philipp, Neurosci Lett 2005, 384(1-2):112-6). The role of Erk2 in signaling of cell differentiation, proliferation and survival suggests that inhibition of Erk2 may be therapeutic for several types of cancer. Husain et al. studied the effect of NSAIDs on MAPK activity and phosphorylation in gastric cancer. They conclude that NS-398 (a selective COX-2 inhibitor) and indomethacin (a non-selective NSAID) significantly inhibit proliferation and growth of human gastric cancer cell line MKN28. This effect is mediated by NSAID-induced inhibition of MAPK (ERK2) kinase signaling pathway, essential for cell proliferation (Husain et al., Life Sci 2001, 69(25-6):3045-54). Erk2 inhibitors may be useful in treating cancer, including gastric cancer, and in treating inflammation, including control of inflammation and apoptosis in Lyme neuroborreliosis.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

In certain embodiments, compounds as disclosed herein are active in an assay measuring B-Raf protein kinase activity. In some embodiments, a compound as described herein has an $IC_{50}$ of less than 1,000 nM, less than 500 nM, less than 100 nM, less than 50 nM, less than 20 nM, less than 10 nM, less than 5 nM, or less than 1 nM as determined in a generally accepted B-Raf kinase activity assay. In some embodiments, a compound as described herein has an $IC_{50}$ of less than 1,000 nM, less than 500 nM, less than 100 nM, less than 50 nM, less than 20 nM, less than 10 nM, less than 5 nM, or less than 1 nM as determined in a generally accepted mutant B-Raf kinase (such as V600A, V600M, V600R, V600E, V600K or V600G) activity assay. In some embodiments the assay for measuring B-Raf kinase activity and/or mutant B-Raf kinase (such as V600A, V600M, V600R, V600E, V600K or V600G) activity includes an assay (e.g., biochemical or cell-bases assays) such as described in Example 9 or an assay well known in the art similar to those described in Example 9.

In some embodiments, compounds as described herein have little or no activity in an assay measuring activation of the ERK pathway (i.e., in stimulating the phosphorylation of ERK 1/2). In some embodiments, compounds as described herein have an $EC_{50}$ in an ERK activation assay that is greater than 1 µM; or greater than 2 µM; or greater than 3 µM; or greater than 4 µM; or greater than 5 µM; or greater than 8 µM; or greater than 10 µM. In certain embodiments, the assay for measuring activation of the ERK pathway includes an assay (e.g., biochemical or cell-bases assays) such as described in Example 9 or one or more assays well known in the art for measuring ERK activity similar to that described in Example 9.

In some embodiments, compounds as described herein are active in an assay measuring B-Raf protein kinase activity and/or an assay for measuring mutant B-Raf (such as V600A, V600M, V600R, V600E, V600K or V600G) protein kinase activity, and have little or no activity in an assay measuring activation of the ERK pathway. In some embodiments a compound as described herein has an $IC_{50}$ of less than 1,000 nM, less than 500 nM, less than 100 nM, less than 50 nM, less than 20 nM, less than 10 nM, less than 5 nM, or less than 1 nM as determined in a generally accepted B-Raf kinase activity assay (including a mutant B-Raf kinase activity assay) and an $EC_{50}$ in an ERK activation assay that is greater than 1 µM; or greater than 2 µM; or greater than 3 µM; or greater than 4 µM; or greater than 5 µM; or greater than 8 µM; or greater than 10 µM. In some embodiments, a compound as described herein has an $IC_{50}$ of less than 100 nM in a V600A, V600M, V600R, V600E, V600K or V600G mutant B-Raf activity assay and an $EC_{50}$ of greater than 10 in an ERK activation assay.

VI. Methods for Treating Conditions Mediated by Kinases

In another aspect, the present invention provides a method for treating a subject suffering from or at risk of a protein kinase mediated diseases or conditions. The method includes administering to the subject an effective amount of a compound of any of formulas I and Ia to In, or a compound as described herein, or a composition comprising any of formulas I and Ia to In and any of the compounds described herein or a pharmaceutically acceptable salt or a solvate or hydrate thereof. In certain embodiments, the method involves administering to the subject an effective amount of any one or more compound(s) as described herein in combination with one or more other therapies for the disease or condition.

In some embodiments, the diseases or conditions treatable with the compounds of the present invention include, but are not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In other embodiments, the diseases or conditions treatable with the compounds of the present invention include, but are not limited to, ischemic stroke, cerebrovascular ischemia, multi-infarct dementia, head injury, spinal cord injury, Alzheimer's disease, Parkinson's disease, amyotrophic lateral sclerosis, dementia, senile chorea, Huntington's disease, neoplastic disease, complications with neoplastic disease, chemotherapy-induced hypoxia, gastrointestinal stromal tumors, prostate tumors, mast cell tumors, canine mast cell tumors, acute myeloid leukemia, acute lymphocytic leukemia, chronic myeloid leukemia, chronic lymphocytic leukemia, multiple myeloma, melanoma, mastocytosis, glioma, glioblastoma, astrocytoma, neuroblastoma, sarcomas, sarcomas of neuroectodermal origin, leiomyosarcoma, lung carcinoma, breast carcinoma, pancreatic carcinoma, colon carcinoma, hepatocellular carcinoma, renal carcinoma, carcinoma of the female genital tract, squamous cell carcinoma, carcinoma in situ, lymphoma, histiocytic lymphoma, non-Hodgkin's lymphoma, MEN2 syndromes, neurofibromatosis, Schwann cell neoplasia, myelodysplastic syndrome, leukemia, tumor angiogenesis, thyroid cancer, liver cancer, bone cancer, skin cancer, brain cancer, cancer of the central nervous system, pancreatic cancer, lung cancer, small cell lung cancer, non small cell lung cancer, breast cancer, colon cancer, bladder cancer, prostate cancer, gastrointestinal tract cancer, cancer of the endometrium, fallopian tube cancer, testicular cancer, ovarian cancer, pain of neuropathic origin, pain of inflammatory origin, acute pain, chronic pain, migraine, cardiovascular disease, heart failure, cardiac hypertrophy, thrombosis, thrombotic microangiopathy syndromes, atherosclerosis, reperfusion injury, ischemia, cerebrovascular ischemia, liver ischemia, inflammation, polycystic kidney disease, age-related macular degeneration, rheumatoid arthritis, allergic rhinitis, inflammatory bowel disease, ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, dermal scarring, tissue scarring, vascular restenosis, fibrotic disorders, hypereosinophilia, CNS inflammation, pancreatitis, nephritis, atopic dermatitis, hepatitis, immunodeficiency diseases, severe combined immunodeficiency, organ transplant rejection, graft versus host disease, renal disease, prostatic disease, diabetic nephropathy, nephrosclerosis, glomerulonephritis, interstitial nephritis, Lupus nephritis, prostate hyperplasia, chronic renal failure, tubular necrosis, diabetes-associated renal complication, associated renal hypertrophy, type 1 diabetes, type 2 diabetes, metabolic syndrome, obesity, hepatic steatosis, insulin resistance, hyperglycemia, lipolysis obesity, infection, *Helicobacter pylori* infection, Influenza virus infection, fever, sepsis, pulmonary diseases, chronic obstructive pulmonary disease, acute respiratory distress syndrome, asthma, allergy, bronchitis, emphysema, pulmonary fibrosis, genetic developmental diseases, Noonan's syndrome, Crouzon syndrome, acrocephalo-syndactyly type I, Pfeiffer's syndrome, Jackson-Weiss syndrome, Costello syndrome, faciocutaneoskeletal syndrome, leopard syndrome, cardio-faciocutaneous syndrome, neural crest syndrome abnormalities causing cardiovascular, skeletal, intestinal, skin, hair or endocrine diseases, disorders of bone structure or mineralization, osteoporosis, increased risk of fracture, hypercalcemia, bone metastases, Grave's disease, Hirschsprung's disease, lymphedema, selective T-cell defect, X-linked agammaglobulinemia, diabetic retinopathy, alopecia, erectile dysfunction, and tuberous sclerosis In some embodiments, the disease is a cancer selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. In certain instances, the disease is a B-Raf V600, such as V600A, V600E, V600G, V600K, V600M or V600R mutant-mediated disease. In one embodiment, the disease is a V600E mutant mediated disease. In one embodiment, the disease is a cancer, preferably selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In one embodiment, the cancer is melanoma, colorectal cancer, thyroid cancer or lung cancer.

In some embodiments, the invention provides methods for treating any B-Raf protein kinase mediated disease or condition, including any B-Raf mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In some embodiments, the invention provides methods for treating any B-Raf V600 mutant protein kinase, such as V600A, V600E, V600G, V600K, V600M or V600R mutant protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In some embodiments, a compound as described herein is a Raf kinase inhibitor and has an $IC_{50}$ of less than 500 nM, less than 100 nM, less than 50 nM, less than 20 nM, less than 10 nM, less than 5 nM, or less than 1 nM as determined in a generally accepted Raf kinase activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to B-Raf, c-Raf-1, or B-Raf V600E mutant. In some embodiments, a compound as described herein will selectively inhibit one or more Raf kinases relative to one or more other Raf kinases.

In some embodiments, the invention provides a method for inhibiting a B-Raf V600 mutant protein kinase, such as V600A, V600E, V600G, V600K, V600M or V600R mutant protein kinase. The method includes contacting a compound of any of formulas I and Ia to In, or a compound as described herein, or a composition comprising any of formulas I and Ia to In and any of the compounds described herein or a pharmaceutically acceptable salt or a solvate thereof with a cell or a B-Raf V600 mutant protein kinase either in vitro or in vivo.

In certain embodiments, the invention provides use of a compound of any of formulas I and Ia to In, or a compound as described herein, or a composition comprising any of formulas I and Ia to In and any of the compounds described herein or a pharmaceutically acceptable salt or a solvate thereof in the manufacture of a medicament for the treatment of a disease or condition as described herein. In other embodiments, the invention provides a compound of any of formulas I and Ia to In, or a compound as described herein, or a composition comprising any of formulas I and Ia to In and any of the compounds described herein or a pharmaceutically acceptable salt or a solvate thereof for use in treating a disease or condition as described herein.

In some embodiments, the invention provides a method for suppressing UV induced cell apoptosis. The method includes contacting a cell with a compound of any of formulas I and Ia to In, or a compound as described herein, or a composition comprising any of formulas I and Ia to In and any of the compounds described herein or a pharmaceutically acceptable salt or a solvate thereof prior to subject the cell to UV exposure or radiation.

Combination Therapy

Protein kinase modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the invention provides a composition comprising a compound of any of formula (I) and formula Ia to formula In, or a compound described herein, or a pharmaceutically acceptable salt or solvate thereof, and one or more agents. In some embodiments, the one or more agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trophosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, megestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-♦, and interleukin-2; and other chemotherapeutics, including, but not limited to 3-AP (3-amino-2-carboxyaldehyde thiosemicarbazone), atrasentan, aminoglutethimide, anagrelide, asparaginase, bryostatin-1, cilengitide, elesclomol, eribulin mesylate (E7389), ixabepilone, lonidamine, masoprocol, mitoguazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib); MEK inhibitors (e.g., AS703026, AZD6244 (selumetinib), AZD8330, BIX02188, CI1040 (PD184352), D-87503, GSK1120212 (JTP-74057), PD0325901, PD318088, PD98059, PDEA119 (BAY 869766), TAK-733). Preferably, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-$\beta$, interleukin-2, or erlotinib. In some embodiments, a protein kinase modulator, particularly a compound of any of formula (I) to formula In, or a compound described herein, or a pharmaceutically acceptable salt or solvate thereof, as defined above, may be administered simultaneously, sequentially or separately in combination with one or more agents as described above.

In one embodiment, the invention provides methods for treating a disease or condition mediated by B-Raf kinase, including mutations thereof, by administering to the subject an effective amount of a composition including any one or more compound(s) as described herein in combination with one or more other suitable therapies for treating the disease.

In one embodiment, the invention provides methods for treating a disease or condition mediated by B-Raf V600 mutant kinases, such as V600A, V600E, V600G, V600K, V600M or V600R mutant kinase, by administering to the subject an effective amount of a composition including any one or more compound(s) as described herein in combination with one or more other suitable therapies for treating the disease. In one embodiment, the invention provides methods for treating a cancer mediated by B-Raf mutant kinases, such as V600A, V600E, V600G, V600M or V600R mutant by administering to the subject an effective amount of a composition including any one or more compound(s) as described herein. In one embodiment, the invention provides methods for treating a cancer mediated by B-Raf mutant kinases, such as V600A, V600E, V600G, V600K, V600M or V600R mutant by administering to the subject an effective amount of a composition including any one or more compound(s) as described herein in combination with one or more suitable anticancer therapies, such as one or more chemotherapeutic drugs. In one instance, the B-Raf mutant kinase is V600A. In another instance, the B-Raf mutant kinase is V600E. In yet another instance, the B-Raf mutant kinase is V600G. In another instance, the B-Raf mutant kinase is V600K. In another instance, the B-Raf mutant kinase is V600M. In another instance, the B-Raf mutant kinase is V600R.

In one embodiment, the invention provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, $\gamma$-ray, or electron, proton, neutron, or $\alpha$ particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

Kit

In another aspect, be invention provides kits that include a compound of any of formulas (I) to (In) or a compound as described herein or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit may include written instructions for use and/or other indication that the compound or composition is suitable or approved for administration to a mammal, e.g., a human, for a Raf protein kinase-mediated disease or condition; and the compound or composition may be packaged in unit dose or single dose form, e.g., single dose pills, capsules, or the like.

VII. EXAMPLES

The following examples are offered to illustrate, but not to limit the claimed invention.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest. In some examples, the mass spectrometry result indicated for a compound may have more than one value due to the isotope distribution of an atom in the molecule, such as a compound having a bromo or chloro substituent.

Certain molecules claimed in this patent can exist in different enantiomeric and diastereomeric forms and all such variants of these compounds are claimed.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Preparation of (3-Amino-2,6-difluoro-phenyl)(5-iodo-1H-pyrrolo[2,3-b]pyridin-3-yl)methanone (4)

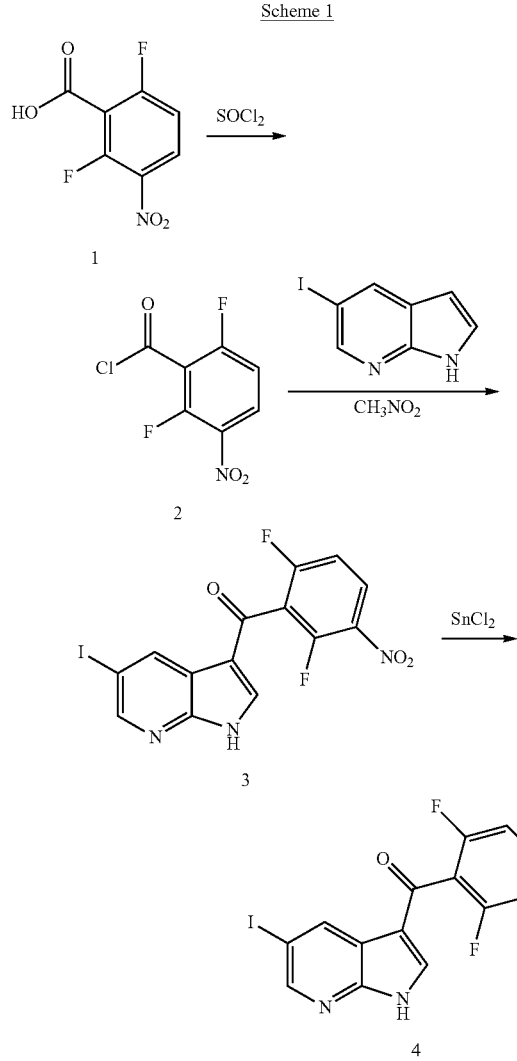

Synthesis of 2,6-Difluoro-3-nitrobenzoyl chloride (2): To 2,6-difluoro-3-nitrobenzoic acid (50 g, 246 mmol) was added thionyl chloride (185 mL, 2536 mmol). The reaction was heated at 80° C. overnight and allowed to cool to room temperature. The volatiles were removed under reduced pressure and then azeotroped from toluene several times to give an oil which was used directly in the next step.

Synthesis of (2,6-Difluoro-3-nitrophenyl)(5-iodo-1H-pyrrolo[2,3-b]pyridin-3-yl)methanone (3): 5-Iodo-1H-pyrrolo[2,3-b]pyridine (32.8 g, 134 mmol) and aluminum chloride (108 g, 806 mmol) in nitromethane (340 mL) were allowed to stir at room temperature for 1 hour. Then 2,6-difluoro-3-nitrobenzoyl chloride (44.7 g, 202 mmol) in nitromethane (340 mL) was added and the mixture was heated at 50° C. for 5 days. After cooling to 0° C., the reaction was quenched with methanol (250 mL) resulting in a ppt. The mixture was diluted with water (500 mL) and then filtered. The crude product which was triturated with ethyl acetate and filtered washing with additional ethyl acetate to give (2,6-difluoro-3-nitrophenyl)(5-iodo-1H-pyrrolo[2,3-b]pyridin-3-yl)methanone (42 g, 98 mmol, 72.8% yield) as a brown solid. $^1$H NMR spectrum is consistent with the structure of the compound.

Synthesis of (3-Amino-2,6-difluorophenyl)(5-iodo-1H-pyrrolo[2,3-b]pyridin-3-yl)methanone (4): To (2,6-difluoro-3-nitrophenyl)(5-iodo-1H-pyrrolo[2,3-b]pyridin-3-yl)methanone (44.6 g, 104 mmol) in ethyl acetate (1732 mL) and THF (1732 mL) was treated portionwise with tin(II) chloride dihydrate (82 g, 364 mmol) while heating 60° C. and held at this temperature overnight. After cooling to room temperature, the reaction mixture was quenched with half sat. aqueous sodium bicarbonate and filtered through Celite washing the cake with ethyl acetate. The layers were separated and the organic layer was washed with brine then concentrated under reduced pressure to give the crude product which was triturated with DCM and filtered to give (3-amino-2,6-difluorophenyl)(5-iodo-1H-pyrrolo[2,3-b]pyridin-3-yl)methanone (34 g, 85 mmol, 82% yield) as a tan solid. $^1$H NMR spectrum is consistent with the structure of the compound.

Example 2: N-[3-[5-(4-chlorophenyl)-1H-pyrrolo[2,3-b]pyridine-3-carbonyl]-2,4-difluoro-phenyl]pyrrolidine-1-sulfonamide (P-0021)

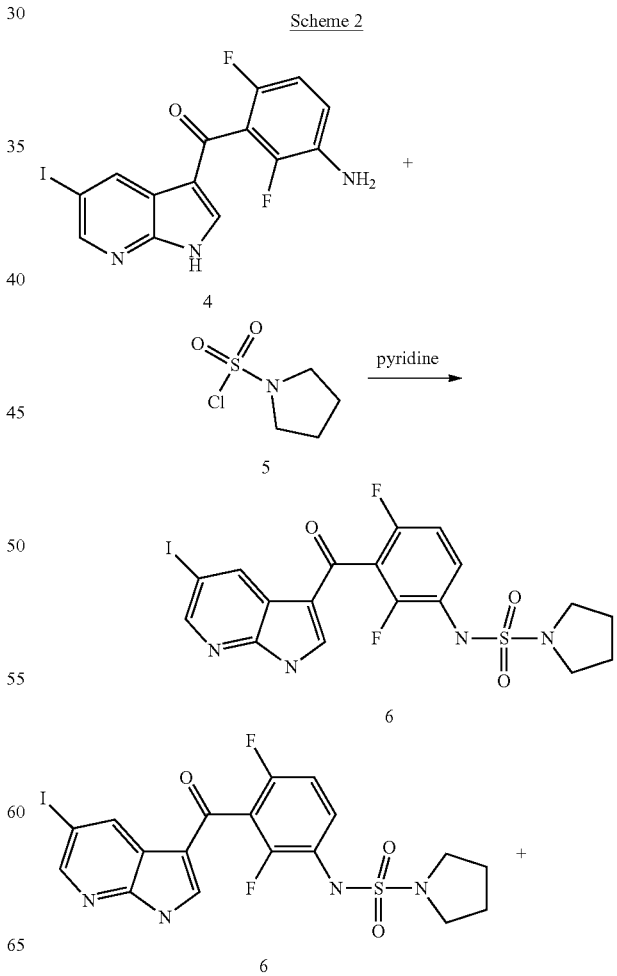

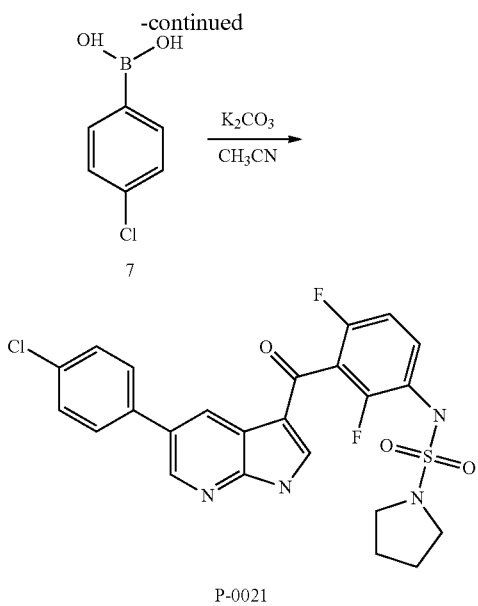

Synthesis of N-[2,4-difluoro-3-(5-iodo-1H-pyrrolo[2,3-b]pyridine-3-carbonyl)phenyl]pyrrolidine-1-sulfonamide (6): To (3-amino-2,6-difluoro-phenyl)-(5-iodo-1H-pyrrolo[2,3-b]pyridin-3-yl)methanone (4, 2.9 g, 7.27 mmol) in pyridine (11.2 mL), was added pyrrolidine-1-sulfonyl chloride (5, 1.68 mL, 14.53 mmol). The mixture was stirred at room temperature for 48 hours. The resulting mixture was poured into a saturated NH₄Cl aqueous solution and extracted with ethyl acetate. The organic layers were combined and washed with brine, dried over anhydrous sodium sulfate, filtered, and concentrated. The crude product was purified by flash chromatography using an 80 g-cartridge (eluted with ethyl acetate and DCM). The desired product was obtained as a solid (6, 2.06 g, 53.3% yield). MS(ESI) [M+H$^+$]$^+$=532.8. $^1$H NMR spectrum is consistent with the structure of the compound.

Synthesis of N-[3-[5-(4-chlorophenyl)-1H-pyrrolo[2,3-b]pyridine-3-carbonyl]-2,4-difluoro-phenyl]pyrrolidine-1-sulfonamide (P-0021): In a microwave vessel, N-[2,4-difluoro-3-(5-iodo-1H-pyrrolo[2,3-b]pyridine-3-carbonyl)phenyl]pyrrolidine-1-sulfonamide (6, 0.27 g, 0.51 mmol) and (4-chlorophenyl)boronic acid (7, 0.1 g, 0.61 mmol) and [1,1′-bis(diphenylphosphino)ferrocene]dichloropalladium (II) (27 mg) were mixed in 1 M of potassium carbonate in water and acetonitrile (1.31 mL). The mixture was heated at 130° C. under microwave for 15 minutes. The resulting mixture separated into an organic layer and aqueous layer. The aqueous layer was extracted with ethyl acetate and combined with the organic layer, washed with brine, dried over sodium sulfate, filtered, and concentrated. The crude product was purified by chromatography using a 40 g-cartridge (eluted with ethyl acetate and dichloromethane). The purified product was obtained as a solid (P-0021, 0.071 g, 27% yield). MS (ESI) [M+H$^+$]$^+$=517.0 and 519.0. $^1$H NMR spectrum is consistent with the structure of the compound.

The following compounds were prepared according to the protocols set forth in Examples 1, 2 and 4-9 and Schemes 1, 2 and 4-9.

TABLE 2

5-chloro-3-[3-[[ethyl(methyl)sulfamoyl]amino]-2,6-difluoro-benzoyl]-1H-pyrrolo[2,3-b]pyridine, (P-0012),
5-(4-chlorophenyl)-3-[3-[[ethyl(methyl)sulfamoyl]amino]-2,6-difluoro-benzoyl]-1H-pyrrolo[2,3-b]pyridine (P-0013),
3-[3-[[ethyl(methyl)sulfamoyl]amino]-2,6-difluoro-benzoyl]-5-(2-methoxypyrimidin-5-yl)-1H-pyrrolo[2,3-b]pyridine (P-0014),
N-[2,4-difluoro-3-(5-fluoro-4-iodo-1H-pyrrolo[2,3-b]pyridine-3-carbonyl)phenyl]pyrrolidine-1-sulfonamide (P-0015),
5-chloro-3-[3-[[ethyl(methyl)sulfamoyl]amino]-2-fluoro-benzoyl]-1H-pyrrolo[2,3-b]pyridine (P-0018),
5-(4-chlorophenyl)-3-[3-[[ethyl(methyl)sulfamoyl]amino]-2-fluoro-benzoyl]-1H-pyrrolo[2,3-b]pyridine (P-0019),
3-[3-[[ethyl(methyl)sulfamoyl]amino]-2-fluoro-benzoyl]-5-(2-methoxypyrimidin-5-yl)-1H-pyrrolo[2,3-b]pyridine (P-0020),
N-[3-[5-(4-chlorophenyl)-1H-pyrrolo[2,3-b]pyridine-3-carbonyl]-2,4-difluoro-phenyl]pyrrolidine-1-sulfonamide (P-0021),
N-[3-[5-[2-(dimethylamino)pyrimidin-5-yl]-1H-pyrrolo[2,3-b]pyridine-3-carbonyl]-2,4-difluoro-phenyl]pyrrolidine-1-sulfonamide (P-0022),
N-[2-fluoro-3-(5-methyl-1H-pyrrolo[2,3-b]pyridine-3-carbonyl)phenyl]pyrrolidine-1-sulfonamide (P-0023)
N-[2,4-difluoro-3-(5-iodo-1H-pyrrolo[2,3-b]pyridine-3-carbonyl)phenyl]pyrrolidine-1-sulfonamide (P-0024),
3-[3-[[cyclopropyl(methyl)sulfamoyl]amino]-2-fluoro-benzoyl]-5-(2-methoxypyrimidin-5-yl)-1H-pyrrolo[2,3-b]pyridine (P-0025),
[2-fluoro-3-(methylsulfamoylamino)phenyl]-[5-(2-methoxypyrimidin-5-yl)-1H-pyrrolo[2,3-b]pyridin-3-yl]methanone (P-0026),
5-(4-cyanophenyl)-3-[3-(dimethylsulfamoylamino)-2-fluoro-benzoyl]-1H-pyrrolo[2,3-b]pyridine (0027),
3-[3-(dimethylsulfamoylamino)-2-fluoro-benzoyl]-5-(3-pyridyl)-1H-pyrrolo[2,3-b]pyridine (P-0028),
3-[3-(dimethylsulfamoylamino)-2-fluoro-benzoyl]-5-(6-methyl-3-pyridyl)-1H-pyrrolo[2,3-b]pyridine (P-0029),
5-[6-(dimethylamino)-3-pyridyl]-3-[3-(dimethylsulfamoylamino)-2-fluoro-benzoyl]-1H-pyrrolo[2,3-b]pyridine (P-0030),
5-(4-cyanophenyl)-3-[3-[[ethyl(methyl)sulfamoyl]amino]-2-fluoro-benzoyl]-1H-pyrrolo[2,3-b]pyridine (P-0031),
3-[3-[[ethyl(methyl)sulfamoyl]amino]-2-fluoro-benzoyl]-5-(3-pyridyl)-1H-pyrrolo[2,3-b]pyridine (0032),
3-[3-[[ethyl(methyl)sulfamoyl]amino]-2-fluoro-benzoyl]-5-(6-methyl-3-pyridyl)-1H-pyrrolo[2,3-b]pyridine (0033),

TABLE 2-continued

3-[3-[[ethyl(methyl)sulfamoyl]amino]-2-fluoro-benzoyl]-5-(4-fluorophenyl)-1H-pyrrolo[2,3-b]pyridine (0034),
3-[3-(dimethylsulfamoylamino)-2-fluoro-benzoyl]-5-(4-fluorophenyl)-1H-pyrrolo[2,3-b]pyridine (P-0035),
3-[3-[[ethyl(methyl)sulfamoyl]amino]-2-fluoro-benzoyl]-5-phenyl-1H-pyrrolo[2,3-b]pyridine (P-0036),
3-[3-(dimethylsulfamoylamino)-2-fluoro-benzoyl]-5-phenyl-1H-pyrrolo[2,3-b]pyridine (P-0037),
5-bromo-3-[3-[[ethyl(methyl)sulfamoyl]amino]-2-fluoro-benzoyl]-1H-pyrrolo[2,3-b]pyridine (P-0038),
3-[2-fluoro-3-[[methyl(propyl)sulfamoyl]amino]benzoyl]-5-(2-methoxypyrimidin-5-yl)-1H-pyrrolo[2,3-b]pyridine (P-0040)
3-benzyloxy-N-[2-fluoro-3-[5-(2-methoxypyrimidin-5-yl)-1H-pyrrolo[2,3-b]pyridine-3-carbonyl]phenyl]pyrrolidine-1-sulfonamide (P-0041)
1-cyclopropyl-N-[2-fluoro-3-[5-(1-methylpyrazol-4-yl)-1H-pyrrolo[2,3-b]pyridine-3-carbonyl]phenyl]methanesulfonamide (P-0042)
N-[2-fluoro-3-[5-(3-pyridyl)-1H-pyrrolo[2,3-b]pyridine-3-carbonyl]phenyl]pyrrolidine-1-sulfonamide (P-0043)
N-[3-[5-(2,4-dimethoxypyrimidin-5-yl)-1H-pyrrolo[2,3-b]pyridine-3-carbonyl]-2-fluoro-phenyl]pyrrolidine-1-sulfonamide (P-0044)
N-[2-fluoro-3-[5-(6-methyl-3-pyridyl)-1H-pyrrolo[2,3-b]pyridine-3-carbonyl]phenyl]pyrrolidine-1-sulfonamide (P-0045)
N-[3-[5-[6-(dimethylamino)-3-pyridyl]-1H-pyrrolo[2,3-b]pyridine-3-carbonyl]-2-fluoro-phenyl]pyrrolidine-1-sulfonamide (P-0046)
N-[2-fluoro-3-[5-(2-isopropylpyrimidin-5-yl)-1H-pyrrolo[2,3-b]pyridine-3-carbonyl]phenyl]pyrrolidine-1-sulfonamide (P-0047)
N-[3-[5-(2-cyclopropylpyrimidin-5-yl)-1H-pyrrolo[2,3-b]pyridine-3-carbonyl]-2-fluoro-phenyl]pyrrolidine-1-sulfonamide (P-0048)
N-[3-[5-(4-cyano-3-methoxy-phenyl)-1H-pyrrolo[2,3-b]pyridine-3-carbonyl]-2-fluoro-phenyl]pyrrolidine-1-sulfonamide (P-0049)
N-[3-[5-[4-(1-cyanocyclopropyl)phenyl]-1H-pyrrolo[2,3-b]pyridine-3-carbonyl]-2-fluoro-phenyl]pyrrolidine-1-sulfonamide (P-0050)
3-[3-(dimethylsulfamoylamino)-2-fluoro-benzoyl]-5-(2-isopropylpyrimidin-5-yl)-1H-pyrrolo[2,3-b]pyridine (P-0051)
5-(2-cyclopropylpyrimidin-5-yl)-3-[3-(dimethylsulfamoylamino)-2-fluoro-benzoyl]-1H-pyrrolo[2,3-b]pyridine (P-0052)
3-[3-(dimethylsulfamoylamino)-2-fluoro-benzoyl]-5-[6-(trifluoromethyl)-3-pyridyl]-1H-pyrrolo[2,3-b]pyridine (P-0053)
5-(4-cyano-3-methoxy-phenyl)-3-[3-(dimethylsulfamoylamino)-2-fluoro-benzoyl]-1H-pyrrolo[2,3-b]pyridine (P-0054)
5-[4-(1-cyanocyclopropyl)phenyl]-3-[3-(dimethylsulfamoylamino)-2-fluoro-benzoyl]-1H-pyrrolo[2,3-b]pyridine (P-0055)
3-[3-[[ethyl(methyl)sulfamoyl]amino]-2-fluoro-benzoyl]-5-(2-methylpyrimidin-5-yl)-1H-pyrrolo[2,3-b]pyridine (P-0056)
3-[3-[[ethyl(methyl)sulfamoyl]amino]-2-fluoro-benzoyl]-5-(2-isopropylpyrimidin-5-yl)-1H-pyrrolo[2,3-b]pyridine (P-0057)
5-(2-cyclopropylpyrimidin-5-yl)-3-[3-[[ethyl(methyl)sulfamoyl]amino]-2-fluoro-benzoyl]-1H-pyrrolo[2,3-b]pyridine (P-0058)
3-[3-[[ethyl(methyl)sulfamoyl]amino]-2-fluoro-benzoyl]-5-[6-(trifluoromethyl)-3-pyridyl]-1H-pyrrolo[2,3-b]pyridine (P-0059)
5-(4-cyano-3-methoxy-phenyl)-3-[3-[[ethyl(methyl)sulfamoyl]amino]-2-fluoro-benzoyl]-1H-pyrrolo[2,3-b]pyridine (P-0060)
5-[4-(1-cyanocyclopropyl)phenyl]-3-[3-[[ethyl(methyl)sulfamoyl]amino]-2-fluoro-benzoyl]-1H-pyrrolo[2,3-b]pyridine (P-0061)
N-[2-fluoro-3-[5-(4-fluorophenyl)-1H-pyrrolo[2,3-b]pyridine-3-carbonyl]phenyl]pyrrolidine-1-sulfonamide (P-0062)
N-[2-fluoro-3-(5-phenyl-1H-pyrrolo[2,3-b]pyridine-3-carbonyl)phenyl]pyrrolidine-1-sulfonamide (P-0063)
5-[2-(cyclopropylamino)pyrimidin-5-yl]-3-[3-(dimethylsulfamoylamino)-2-fluoro-benzoyl]-1H-pyrrolo[2,3-b]pyridine (P-0064)
N-[2-fluoro-3-[5-(2-methoxypyrimidin-5-yl)-1H-pyrrolo[2,3-b]pyridine-3-carbonyl]phenyl]-2-methoxy-ethanesulfonamide (P-0065)
methyl 3-[[2-fluoro-3-[5-(2-methoxypyrimidin-5-yl)-1H-pyrrolo[2,3-b]pyridine-3-carbonyl]phenyl]sulfamoyl]propanoate (P-0066)
N-[2-fluoro-3-[5-(2-methoxypyrimidin-5-yl)-1H-pyrrolo[2,3-b]pyridine-3-carbonyl]phenyl]cyclopropanesulfonamide (P-0067)
[3-(ethylsulfamoylamino)-2-fluoro-phenyl]-[5-(2-methoxypyrimidin-5-yl)-1H-pyrrolo[2,3-b]pyridin-3-yl]methanone (P-0068)
[3-(ethylsulfamoylamino)-2-fluoro-phenyl]-(5-iodo-1H-pyrrolo[2,3-b]pyridin-3-yl)methanone (P-0069)
3-[2-fluoro-3-[[isobutyl(methyl)sulfamoyl]amino]benzoyl]-5-iodo-1H-pyrrolo[2,3-b]pyridine (P-0070)
[2-fluoro-3-(isopropylsulfamoylamino)phenyl]-(5-iodo-1H-pyrrolo[2,3-b]pyridin-3-yl)methanone (P-0071)
3-[2-fluoro-3-[[isobutyl(methyl)sulfamoyl]amino]benzoyl]-5-(2-methoxypyrimidin-5-yl)-1H-pyrrolo[2,3-b]pyridine (P-0072)
3-[2-fluoro-3-[[2-methoxyethyl(methyl)sulfamoyl]amino]benzoyl]-5-(2-methoxypyrimidin-5-yl)-1H-pyrrolo[2,3-b]pyridine (P-0073)

TABLE 2-continued

N-[2-fluoro-3-[5-(2-methoxypyrimidin-5-yl)-1H-pyrrolo[2,3-b]pyridine-3-carbonyl]phenyl]-2-methyl-pyrrolidine-1-sulfonamide (P-0074)
3-[2-fluoro-3-[[isopropyl(methyl)sulfamoyl]amino]benzoyl]-5-(2-methoxypyrimidin-5-yl)-1H-pyrrolo[2,3-b]pyridine (P-0075)
5-[6-(dimethylamino)-3-pyridyl]-3-[3-[[ethyl(methyl)sulfamoyl]amino]-2-fluoro-benzoyl]-1H-pyrrolo[2,3-b]pyridine (P-0076)
5-[2-(cyclopropylamino)pyrimidin-5-yl]-3-[3-[[ethyl(methyl)sulfamoyl]amino]-2-fluoro-benzoyl]-1H-pyrrolo[2,3-b]pyridine (P-0077)
5-(2-cyclopropylpyrimidin-5-yl)-3-[2,6-difluoro-3-[[methyl(propyl)sulfamoyl]amino]benzoyl]-1H-pyrrolo[2,3-b]pyridine (P-0078)
5-[4-(1-cyanocyclopropyl)phenyl]-3-[2,6-difluoro-3-[[methyl(propyl)sulfamoyl]amino]benzoyl]-1H-pyrrolo[2,3-b]pyridine (P-0079)
5-[4-(1-cyanocyclopropyl)phenyl]-3-[2-fluoro-3-[[2-methoxyethyl(methyl)sulfamoyl]amino]benzoyl]-1H-pyrrolo[2,3-b]pyridine (P-0080)
5-[2-(cyclopropylamino)pyrimidin-5-yl]-3-[2-fluoro-3-[[2-methoxyethyl(methyl)sulfamoyl]amino]benzoyl]-1H-pyrrolo[2,3-b]pyridine (P-0081)
5-[2-(cyclopropylamino)pyrimidin-5-yl]-3-[2-fluoro-3-[[methyl(propyl)sulfamoyl]amino]benzoyl]-1H-pyrrolo[2,3-b]pyridine (P-0082)
3-[3-[[cyclopropylmethyl(methyl)sulfamoyl]amino]-2-fluoro-benzoyl]-5-(2-methoxypyrimidin-5-yl)-1H-pyrrolo[2,3-b]pyridine (P-0083)
3-[3-[[cyclopropylmethyl(methyl)sulfamoyl]amino]-2-fluoro-benzoyl]-5-(2-cyclopropylpyrimidin-5-yl)-1H-pyrrolo[2,3-b]pyridine (P-0084)
5-(2-cyclopropylpyrimidin-5-yl)-3-[2-fluoro-3-[[2-methoxyethyl(methyl)sulfamoyl]amino]benzoyl]-1H-pyrrolo[2,3-b]pyridine (P-0085)
5-(2-cyclopropylpyrimidin-5-yl)-3-[2-fluoro-3-[[methyl(propyl)sulfamoyl]amino]benzoyl]-1H-pyrrolo[2,3-b]pyridine (P-0086)
5-(6-cyclopropyl-3-pyridyl)-3-[3-[[ethyl(methyl)sulfamoyl]amino]-2-fluoro-benzoyl]-1H-pyrrolo[2,3-b]pyridine (P-0087)
3,3-difluoro-N-[2-fluoro-3-[5-(2-methoxypyrimidin-5-yl)-1H-pyrrolo[2,3-b]pyridine-3-carbonyl]phenyl]azetidine-1-sulfonamide (P-0088)
4-[[(1S)-1-cyclopropylethyl]amino]-5-[3-[[ethyl(methyl)sulfamoyl]amino]-2-fluoro-benzoyl]-7H-pyrrolo[2,3-d]pyrimidine (P-0089)
N-[3-[5-(4-cyanophenyl)-1H-pyrrolo[2,3-b]pyridine-3-carbonyl]-2-fluoro-phenyl]pyrrolidine-1-sulfonamide (P-0090)
N-[3-[5-(2-cyanopyrimidin-5-yl)-1H-pyrrolo[2,3-b]pyridine-3-carbonyl]-2-fluoro-phenyl]pyrrolidine-1-sulfonamide (P-0091)
N-[2-fluoro-3-[5-(2-methylpyrimidin-5-yl)-1H-pyrrolo[2,3-b]pyridine-3-carbonyl]phenyl]pyrrolidine-1-sulfonamide (P-0092)
N-[3-[5-(5-cyano-3-pyridyl)-1H-pyrrolo[2,3-b]pyridine-3-carbonyl]-2-fluoro-phenyl]pyrrolidine-1-sulfonamide (P-0093)
N-[3-[5-(6-cyano-3-pyridyl)-1H-pyrrolo[2,3-b]pyridine-3-carbonyl]-2-fluoro-phenyl]pyrrolidine-1-sulfonamide (P-0094)
N-[2-fluoro-3-[5-[6-(trifluoromethyl)-3-pyridyl]-1H-pyrrolo[2,3-b]pyridine-3-carbonyl]phenyl]pyrrolidine-1-sulfonamide (P-0095)
5-(2-cyanopyrimidin-5-yl)-3-[3-(dimethylsulfamoylamino)-2-fluoro-benzoyl]-1H-pyrrolo[2,3-b]pyridine (P-0096)
3-[3-(dimethylsulfamoylamino)-2-fluoro-benzoyl]-5-(2-methylpyrimidin-5-yl)-1H-pyrrolo[2,3-b]pyridine (P-0097)
5-(5-cyano-3-pyridyl)-3-[3-(dimethylsulfamoylamino)-2-fluoro-benzoyl]-1H-pyrrolo[2,3-b]pyridine (P-0098)
5-(6-cyano-3-pyridyl)-3-[3-(dimethylsulfamoylamino)-2-fluoro-benzoyl]-1H-pyrrolo[2,3-b]pyridine (P-0099)
5-(2-cyanopyrimidin-5-yl)-3-[3-[[ethyl(methyl)sulfamoyl]amino]-2-fluoro-benzoyl]-1H-pyrrolo[2,3-b]pyridine (P-0100)
5-(5-cyano-3-pyridyl)-3-[3-[[ethyl(methyl)sulfamoyl]amino]-2-fluoro-benzoyl]-1H-pyrrolo[2,3-b]pyridine (P-0101)
5-(6-cyano-3-pyridyl)-3-[3-[[ethyl(methyl)sulfamoyl]amino]-2-fluoro-benzoyl]-1H-pyrrolo[2,3-b]pyridine (P-0102)
3-[3-(dimethylsulfamoylamino)-2-fluoro-benzoyl]-5-[4-(1-hydroxy-1-methyl-ethyl)phenyl]-1H-pyrrolo[2,3-b]pyridine (P-0103)
3-[3-[[ethyl(methyl)sulfamoyl]amino]-2-fluoro-benzoyl]-5-[4-(1-hydroxy-1-methyl-ethyl)phenyl]-1H-pyrrolo[2,3-b]pyridine (P-0104)
N-[2-fluoro-3-[5-[4-(1-hydroxy-1-methyl-ethyl)phenyl]-1H-pyrrolo[2,3-b]pyridine-3-carbonyl]phenyl]pyrrolidine-1-sulfonamide (P-0105)
5-[2-(dimethylamino)pyrimidin-5-yl]-3-[3-(dimethylsulfamoylamino)-2-fluoro-benzoyl]-1H-pyrrolo[2,3-b]pyridine (P-0106)
3-[3-(dimethylsulfamoylamino)-2-fluoro-benzoyl]-5-(2-pyrrolidin-1-ylpyrimidin-5-yl)-1H-pyrrolo[2,3-b]pyridine (P-0107)
3-[3-[[ethyl(methyl)sulfamoyl]amino]-2-fluoro-benzoyl]-5-(2-pyrrolidin-1-ylpyrimidin-5-yl)-1H-pyrrolo[2,3-b]pyridine (P-0108)
N-[2-fluoro-3-[5-(2-pyrrolidin-1-ylpyrimidin-5-yl)-1H-pyrrolo[2,3-b]pyridine-3-carbonyl]phenyl]pyrrolidine-1-sulfonamide (P-0109)
3-[3-(dimethylsulfamoylamino)-2-fluoro-benzoyl]-5-iodo-1H-pyrrolo[2,3-b]pyridine (P-0110)
3-[2-fluoro-3-[[methyl(propyl)sulfamoyl]amino]benzoyl]-5-(2-methylpyrimidin-5-yl)-1H-pyrrolo[2,3-b]pyridine (P-0111)
3-[3-[[cyclopropylmethyl(methyl)sulfamoyl]amino]-2-fluoro-benzoyl]-5-(2-methylpyrimidin-5-yl)-1H-pyrrolo[2,3-b]pyridine (P-0112)
5-(6-cyclopropyl-3-pyridyl)-3-[3-(dimethylsulfamoylamino)-2-fluoro-benzoyl]-1H-pyrrolo[2,3-b]pyridine (P-0113)

TABLE 2-continued 5-(6-cyclopropyl-3-pyridyl)-3-[2-fluoro-3-[[methyl(propyl)sulfamoyl]amino]benzoyl]-1H-pyrrolo[2,3-b]pyridine (P-0114)
3-[3-[[cyclopropylmethyl(methyl)sulfamoyl]amino]-2-fluoro-benzoyl]-5-(6-cyclopropyl-3-pyridyl)-1H-pyrrolo[2,3-b]pyridine (P-0115)
3-[2,6-difluoro-3-[[methyl(propyl)sulfamoyl]amino]benzoyl]-5-(2-methoxypyrimidin-5-yl)-1H-pyrrolo[2,3-b]pyridine (P-0116)
[2-fluoro-3-(propylsulfamoylamino)phenyl]-(5-iodo-1H-pyrrolo[2,3-b]pyridin-3-yl)methanone (P-0117)
[2-fluoro-3-(propylsulfamoylamino)phenyl]-(5-methyl-1H-pyrrolo[2,3-b]pyridin-3-yl)methanone (P-0223)
N-[2-fluoro-3-[5-(2-methoxypyrimidin-5-yl)-1H-pyrrolo[2,3-b]pyridine-3-carbonyl]phenyl]butane-2-sulfonamide (P-0224)
N-[2-fluoro-3-[5-(2-pyrrolidin-1-ylpyrimidin-5-yl)-1H-pyrrolo[2,3-b]pyridine-3-carbonyl]phenyl]butane-2-sulfonamide (P-0225)
N-[3-[5-[2-(cyclopropylamino)pyrimidin-5-yl]-1H-pyrrolo[2,3-b]pyridine-3-carbonyl]-2-fluoro-phenyl]butane-2-sulfonamide (P-0226)
N-[3-[5-[4-(1-cyanocyclopropyl)phenyl]-1H-pyrrolo[2,3-b]pyridine-3-carbonyl]-2-fluoro-phenyl]butane-2-sulfonamide (P-00227)
N-[3-[5-(2-cyclopropylpyrimidin-5-yl)-1H-pyrrolo[2,3-b]pyridine-3-carbonyl]-2-fluoro-phenyl]butane-2-sulfonamide (P-0228)
N-[2-fluoro-3-[5-(2-isopropylpyrimidin-5-yl)-1H-pyrrolo[2,3-b]pyridine-3-carbonyl]phenyl]butane-2-sulfonamide (P-0229)
N-[3-[5-[6-(dimethylamino)-3-pyridyl]-1H-pyrrolo[2,3-b]pyridine-3-carbonyl]-2-fluoro-phenyl]butane-2-sulfonamide (P-0230)
N-[2-fluoro-3-[5-(2-methylpyrimidin-5-yl)-1H-pyrrolo[2,3-b]pyridine-3-carbonyl]phenyl]butane-2-sulfonamide (P-0231)
N-[3-[5-[2-(cyclopropylamino)pyrimidin-5-yl]-1H-pyrrolo[2,3-b]pyridine-3-carbonyl]-2-fluoro-phenyl]pyrrolidine-1-sulfonamide (P-0232)
5-(2-cyclopropylpyrimidin-5-yl)-3-[2-fluoro-3-[[isopropyl(methyl)sulfamoyl]amino]benzoyl]-1H-pyrrolo[2,3-b]pyridine (P-0233)
N-[2-fluoro-3-[5-(2-morpholinopyrimidin-5-yl)-1H-pyrrolo[2,3-b]pyridine-3-carbonyl]phenyl]pyrrolidine-1-sulfonamide (P-0235)
N-[2-fluoro-3-[5-(2-morpholinopyrimidin-5-yl)-1H-pyrrolo[2,3-b]pyridine-3-carbonyl]phenyl]butane-2-sulfonamide (P-0236)
5-[4-(1-cyanocyclopropyl)phenyl]-3-[3-(dimethylsulfamoylamino)-2,6-difluoro-benzoyl]-1H-pyrrolo[2,3-b]pyridine (P-0237)
5-(2-cyclopropylpyrimidin-5-yl)-3-[3-(dimethylsulfamoylamino)-2,6-difluoro-benzoyl]-1H-pyrrolo[2,3-b]pyridine (P-0238)
5-[4-(1-cyanocyclopropyl)phenyl]-3-[3-[[ethyl(methyl)sulfamoyl]amino]-2,6-difluoro-benzoyl]-1H-pyrrolo[2,3-b]pyridine (P-0239)
5-(2-cyclopropylpyrimidin-5-yl)-3-[3-[[ethyl(methyl)sulfamoyl]amino]-2,6-difluoro-benzoyl]-1H-pyrrolo[2,3-b]pyridine (P-0240)
N-[3-[5-(2-cyclopropylpyrimidin-5-yl)-1H-pyrrolo[2,3-b]pyridine-3-carbonyl]-2,4-difluoro-phenyl]pyrrolidine-1-sulfonamide (P-0241)
[2-fluoro-3-(propylsulfamoylamino)phenyl]-[5-(1-methylpyrazol-4-yl)-1H-pyrrolo[2,3-b]pyridin-3-yl]methanone (P-0242)
1-[4-[3-[2-fluoro-3-(pyrrolidin-1-ylsulfonylamino)benzoyl]-1H-pyrrolo[2,3-b]pyridin-5-yl]phenyl]cyclopropanecarboxylic acid (P-0243)
3-[3-(dimethylsulfamoylamino)-2,6-difluoro-benzoyl]-5-(5-ethoxypyrazin-2-yl)-1H-pyrrolo[2,3-b]pyridine (P-0244)
5-[4-(1-cyano-1-methyl-ethyl)phenyl]-3-[3-(dimethylsulfamoylamino)-2-fluoro-benzoyl]-1H-pyrrolo[2,3-b]pyridine (P-0245)
N-[3-[5-(2-cyclopropylpyrimidin-5-yl)-1H-pyrrolo[2,3-b]pyridine-3-carbonyl]-2-fluoro-phenyl]-3,3-dimethyl-pyrrolidine-1-sulfonamide (P-0246)
N-[3-[5-(2-cyclopropylpyrimidin-5-yl)-1H-pyrrolo[2,3-b]pyridine-3-carbonyl]-2-fluoro-phenyl]-3-methyl-pyrrolidine-1-sulfonamide (P-0247);
N-[3-[5-[4-(1-cyanocyclopropyl)phenyl]-1H-pyrrolo[2,3-b]pyridine-3-carbonyl]-2,4-difluoro-phenyl]pyrrolidine-1-sulfonamide (P-0248)
3-[3-[[cyclopropyl(methyl)sulfamoyl]amino]-2-fluoro-benzoyl]-5-(2-cyclopropylpyrimidin-5-yl)-1H-pyrrolo[2,3-b]pyridine (P-0249)
[5-(2-cyclopropylpyrimidin-5-yl)-1H-pyrrolo[2,3-b]pyridin-3-yl]-[2-fluoro-3-(propylsulfamoylamino)phenyl]methanone (P-0251)
3-[3-[[cyclopropyl(methyl)sulfamoyl]amino]-2,6-difluoro-benzoyl]-5-(2-cyclopropylpyrimidin-5-yl)-1H-pyrrolo[2,3-b]pyridine (P-0252)
1-[4-[3-[2-fluoro-3-(pyrrolidin-1-ylsulfonylamino)benzoyl]-1H-pyrrolo[2,3-b]pyridin-5-yl]phenyl]cyclopropanecarboxamide (P-0253)
methyl 1-[4-[3-[2-fluoro-3-(pyrrolidin-1-ylsulfonylamino)benzoyl]-1H-pyrrolo[2,3-b]pyridin-5-yl]phenyl]cyclopropanecarboxylate (P-0254)
5-[4-(1-cyano-1-methyl-ethyl)phenyl]-3-[3-(dimethylsulfamoylamino)-2,6-difluoro-benzoyl]-1H-pyrrolo[2,3-b]pyridine (P-0255)
5-(2-ethoxypyrimidin-5-yl)-3-[3-[[ethyl(methyl)sulfamoyl]amino]-2,6-difluoro-benzoyl]-1H-pyrrolo[2,3-b]pyridine (P-0256)
ethyl 1-[[2-fluoro-3-[5-(2-methoxypyrimidin-5-yl)-1H-pyrrolo[2,3-b]pyridine-3-carbonyl]phenyl]sulfamoyl]pyrrolidine-2-carboxylate (P-0257)
4-[5-[3-[3-[[ethyl(methyl)sulfamoyl]amino]-2,6-difluoro-benzoyl]-1H-pyrrolo[2,3-b]pyridin-5-yl]pyrimidin-2-yl]morpholine (P-0258)
4-[3-[3-[[ethyl(methyl)sulfamoyl]amino]-2,6-difluoro-benzoyl]-1H-pyrrolo[2,3-b]pyridin-5-yl]phenyl]morpholine (P-0259)
N-[2,4-difluoro-3-[5-[2-(4-methylpiperazin-1-yl)pyrimidin-5-yl]-1H-pyrrolo[2,3-b]pyridine-3-carbonyl]phenyl]pyrrolidine-1-sulfonamide (P-0260)

TABLE 2-continued

N-[2,4-difluoro-3-[5-(2-piperazin-1-ylpyrimidin-5-yl)-1H-pyrrolo[2,3-b]pyridine-3-carbonyl]phenyl]pyrrolidine-1-sulfonamide (P-0261)
N-[2,4-difluoro-3-[5-[2-(4-hydroxy-1-piperidyl)pyrimidin-5-yl]-1H-pyrrolo[2,3-b]pyridine-3-carbonyl]phenyl]pyrrolidine-1-sulfonamide (P-0262)
3-[3-[[ethyl(methyl)sulfamoyl]amino]-2,6-difluoro-benzoyl]-5-[2-(4-methylpiperazin-1-yl)pyrimidin-5-yl]-1H-pyrrolo[2,3-b]pyridine (P-0263)
tert-butyl 4-[5-[3-[3-[[ethyl(methyl)sulfamoyl]amino]-2,6-difluoro-benzoyl]-1H-pyrrolo[2,3-b]pyridin-5-yl]pyrimidin-2-yl]piperazine-1-carboxylate (P-0264)
N-[2,4-difluoro-3-[5-[2-(1-hydroxy-1-methyl-ethyl)thiazol-4-yl]-1H-pyrrolo[2,3-b]pyridine-3-carbonyl]phenyl]pyrrolidine-1-sulfonamide (P-0265)
N-[2,4-difluoro-3-[5-(2-morpholinopyrimidin-5-yl)-1H-pyrrolo[2,3-b]pyridine-3-carbonyl]phenyl]pyrrolidine-1-sulfonamide (P-0266)
N-[1-[[3-[5-(2-cyclopropylpyrimidin-5-yl)-1H-pyrrolo[2,3-b]pyridine-3-carbonyl]-2-fluoro-phenyl]sulfamoyl]pyrrolidin-3-yl]-N-methyl-acetamide (P-0267)
3-[3-[[ethyl(methyl)sulfamoyl]amino]-2,6-difluoro-benzoyl]-5-(2-piperazin-1-ylpyrimidin-5-yl)-1H-pyrrolo[2,3-b]pyridine (P-0268)
N-[3-[5-[2-(azetidin-1-yl)pyrimidin-5-yl]-1H-pyrrolo[2,3-b]pyridine-3-carbonyl]-2,4-difluoro-phenyl]pyrrolidine-1-sulfonamide (P-0269)
N-[2,4-difluoro-3-[5-(2-methoxythiazol-5-yl)-1H-pyrrolo[2,3-b]pyridine-3-carbonyl]phenyl]pyrrolidine-1-sulfonamide (P-0270)
(3R)-N-[3-[5-(2-cyclopropylpyrimidin-5-yl)-1H-pyrrolo[2,3-b]pyridine-3-carbonyl]-2-fluoro-phenyl]-3-methyl-pyrrolidine-1-sulfonamide (P-0271)
N-[3-[5-(2-cyclopropylpyrimidin-5-yl)-1H-pyrrolo[2,3-b]pyridine-3-carbonyl]-2-fluoro-phenyl]-3-(methylamino)pyrrolidine-1-sulfonamide (P-0272)
N-[2,4-difluoro-3-[5-(4-pyridyl)-1H-pyrrolo[2,3-b]pyridine-3-carbonyl]phenyl]pyrrolidine-1-sulfonamide (P-0273)
N-[3-(5-cyclopropyl-1H-pyrrolo[2,3-b]pyridine-3-carbonyl)-2-fluoro-phenyl]pyrrolidine-1-sulfonamide (P-0274)
3-[3-[[ethyl(methyl)sulfamoyl]amino]-2,6-difluoro-benzoyl]-5-[2-(4-hydroxy-1-piperidyl)pyrimidin-5-yl]-1H-pyrrolo[2,3-b]pyridine (P-0275)
5-[3-(1-cyanocyclopropyl)phenyl]-3-[3-[[ethyl(methyl)sulfamoyl]amino]-2,6-difluoro-benzoyl]-1H-pyrrolo[2,3-b]pyridine (P-0276)
5-[2-(azetidin-1-yl)pyrimidin-5-yl]-3-[3-[[ethyl(methyl)sulfamoyl]amino]-2,6-difluoro-benzoyl]-1H-pyrrolo[2,3-b]pyridine (P-0277)
N-[3-[5-(2-aminopyrimidin-5-yl)-1H-pyrrolo[2,3-b]pyridine-3-carbonyl]-2,4-difluoro-phenyl]pyrrolidine-1-sulfonamide (P-0279)
N-[3-[5-(2-aminopyrimidin-4-yl)-1H-pyrrolo[2,3-b]pyridine-3-carbonyl]-2,4-difluoro-phenyl]pyrrolidine-1-sulfonamide (P-0280)
N-[2-fluoro-3-[5-(4-pyridyl)-1H-pyrrolo[2,3-b]pyridine-3-carbonyl]phenyl]pyrrolidine-1-sulfonamide (P-0281)
N-[2,4-difluoro-3-[5-(2-morpholinopyrimidin-4-yl)-1H-pyrrolo[2,3-b]pyridine-3-carbonyl]phenyl]pyrrolidine-1-sulfonamide (P-0282)
3-[3-[[ethyl(methyl)sulfamoyl]amino]-2,6-difluoro-benzoyl]-5-(2-fluoro-4-pyridyl)-1H-pyrrolo[2,3-b]pyridine (P-0283)
N-[2,4-difluoro-3-[5-(2-morpholino-4-pyridyl)-1H-pyrrolo[2,3-b]pyridine-3-carbonyl]phenyl]pyrrolidine-1-sulfonamide (P-0284)
N-[2,4-difluoro-3-[5-[2-(4-methylpiperazin-1-yl)-4-pyridyl]-1H-pyrrolo[2,3-b]pyridine-3-carbonyl]phenyl]pyrrolidine-1-sulfonamide (P-0285)
N-[3-[5-[2-(cyclobutoxy)-4-pyridyl]-1H-pyrrolo[2,3-b]pyridine-3-carbonyl]-2,4-difluoro-phenyl]pyrrolidine-1-sulfonamide (P-0286)
N-[2,4-difluoro-3-[5-(2-methoxy-4-pyridyl)-1H-pyrrolo[2,3-b]pyridine-3-carbonyl]phenyl]pyrrolidine-1-sulfonamide (P-0287)
N-[3-[5-(2-cyclopropylpyrimidin-5-yl)-1H-pyrrolo[2,3-b]pyridine-3-carbonyl]-2,4-difluoro-phenyl]-3,3-difluoro-pyrrolidine-1-sulfonamide (P-0288)
(3S)-N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0289)
methyl 2-[[3-[5-(2-cyclopropylpyrimidin-5-yl)-1H-pyrrolo[2,3-b]pyridine-3-carbonyl]-2-fluoro-phenyl]sulfamoyl]propanoate (P-0291)
5-[2-(dimethylamino)pyrimidin-5-yl]-3-[3-[[ethyl(methyl)sulfamoyl]amino]-2,6-difluoro-benzoyl]-1H-pyrrolo[2,3-b]pyridine (P-0292)
3-[3-[[ethyl(methyl)sulfamoyl]amino]-2,6-difluoro-benzoyl]-5-(2-pyrrolidin-1-ylpyrimidin-5-yl)-1H-pyrrolo[2,3-b]pyridine (P-0293)
N-[2,4-difluoro-3-[5-[6-(trifluoromethyl)pyrimidin-4-yl]-1H-pyrrolo[2,3-b]pyridine-3-carbonyl]phenyl]pyrrolidine-1-sulfonamide (P-0294)
N-[3-[5-(2-cyclopropyl-4-pyridyl)-1H-pyrrolo[2,3-b]pyridine-3-carbonyl]-2,4-difluoro-phenyl]pyrrolidine-1-sulfonamide (P-0295)
5-cyclobutyl-3-[3-[[ethyl(methyl)sulfamoyl]amino]-2-fluoro-benzoyl]-1H-pyrrolo[2,3-b]pyridine (P-0297)
5-cyclopropyl-3-[3-[[ethyl(methyl)sulfamoyl]amino]-2-fluoro-benzoyl]-1H-pyrrolo[2,3-b]pyridine (P-0298)
N-[3-[5-(6-aminopyrimidin-4-yl)-1H-pyrrolo[2,3-b]pyridine-3-carbonyl]-2-fluoro-phenyl]pyrrolidine-1-sulfonamide (P-0299)
5-(4-cyanophenyl)-3-[3-[[ethyl(methyl)sulfamoyl]amino]-2,6-difluoro-benzoyl]-1H-pyrrolo[2,3-b]pyridine (P-0300)
3-[3-[[ethyl(methyl)sulfamoyl]amino]-2,6-difluoro-benzoyl]-5-[4-(trifluoromethyl)phenyl]-1H-pyrrolo[2,3-b]pyridine (P-0301)
5-[3-(dimethylamino)phenyl]-3-[3-[[ethyl(methyl)sulfamoyl]amino]-2,6-difluoro-benzoyl]-1H-pyrrolo[2,3-b]pyridine (P-0302)
3-[3-[[ethyl(methyl)sulfamoyl]amino]-2,6-difluoro-benzoyl]-5-(4-pyrrolidin-1-ylphenyl)-1H-pyrrolo[2,3-b]pyridine (P-0303)

TABLE 2-continued

2-[4-[3-[3-[[ethyl(methyl)sulfamoyl]amino]-2,6-difluoro-benzoyl]-1H-pyrrolo[2,3-b]pyridin-5-yl]phenyl]-5-methyl-1,3,4-oxadiazole (P-0304)
2-[4-[3-[3-[[ethyl(methyl)sulfamoyl]amino]-2,6-difluoro-benzoyl]-1H-pyrrolo[2,3-b]pyridin-5-yl]phenyl]-5-(methylamino)-1,3,4-thiadiazole (P-0305)
3-[3-[[ethyl(methyl)sulfamoyl]amino]-2,6-difluoro-benzoyl]-5-[5-(1-hydroxy-1-methyl-ethyl)-3-pyridyl]-1H-pyrrolo[2,3-b]pyridine (P-0306)
3-[3-[[ethyl(methyl)sulfamoyl]amino]-2,6-difluoro-benzoyl]-5-[6-(1-hydroxy-1-methyl-ethyl)-3-pyridyl]-1H-pyrrolo[2,3-b]pyridine (P-0307)
5-[4-(diethylamino)phenyl]-3-[3-[[ethyl(methyl)sulfamoyl]amino]-2,6-difluoro-benzoyl]-1H-pyrrolo[2,3-b]pyridine (P-0308)
3-[3-[[ethyl(methyl)sulfamoyl]amino]-2,6-difluoro-benzoyl]-5-(2-oxoindolin-6-yl)-1H-pyrrolo[2,3-b]pyridine (P-0309)
3-[5-[3-[3-[[ethyl(methyl)sulfamoyl]amino]-2,6-difluoro-benzoyl]-1H-pyrrolo[2,3-b]pyridin-5-yl]-2-thienyl]-5-methyl-1,2,4-oxadiazole (P-0310)
2-amino-6-[3-[3-[[ethyl(methyl)sulfamoyl]amino]-2,6-difluoro-benzoyl]-1H-pyrrolo[2,3-b]pyridin-5-yl]quinazoline (P-0311)
N-cyclopropyl-5-[3-[3-[[ethyl(methyl)sulfamoyl]amino]-2,6-difluoro-benzoyl]-1H-pyrrolo[2,3-b]pyridin-5-yl]pyridine-2-carboxamide (P-0312)
2-(dimethylamino)-6-[3-[3-[[ethyl(methyl)sulfamoyl]amino]-2,6-difluoro-benzoyl]-1H-pyrrolo[2,3-b]pyridin-5-yl]quinazoline (P-0313)
3-[3-[[ethyl(methyl)sulfamoyl]amino]-2,6-difluoro-benzoyl]-5-[4-(1-hydroxycyclopropyl)phenyl]-1H-pyrrolo[2,3-b]pyridine (P-0314)
5-[3-[3-[[ethyl(methyl)sulfamoyl]amino]-2,6-difluoro-benzoyl]-1H-pyrrolo[2,3-b]pyridin-5-yl]thiazole (P-0315)
4-[3-[3-[[ethyl(methyl)sulfamoyl]amino]-2,6-difluoro-benzoyl]-1H-pyrrolo[2,3-b]pyridin-5-yl]-2-(1-hydroxy-1-methyl-ethyl)thiazole (P-0316)
3-[3-[[ethyl(methyl)sulfamoyl]amino]-2,6-difluoro-benzoyl]-5-(6-methoxypyridazin-3-yl)-1H-pyrrolo[2,3-b]pyridine (P-0317)
N-[2,4-difluoro-3-[5-(6-morpholinopyrimidin-4-yl)-1H-pyrrolo[2,3-b]pyridine-3-carbonyl]phenyl]pyrrolidine-1-sulfonamide (P-0318)
N-[2,4-difluoro-3-[5-[6-(4-methylpiperazin-1-yl)pyrimidin-4-yl]-1H-pyrrolo[2,3-b]pyridine-3-carbonyl]phenyl]pyrrolidine-1-sulfonamide (P-0319)
(3S)-N-[3-[5-(2-cyclopropylpyrimidin-5-yl)-1H-pyrrolo[2,3-b]pyridine-3-carbonyl]-2,4-difluoro-phenyl]-3-methyl-pyrrolidine-1-sulfonamide (P-0320)
N-[2-fluoro-3-[5-(6-morpholinopyrimidin-4-yl)-1H-pyrrolo[2,3-b]pyridine-3-carbonyl]phenyl]pyrrolidine-1-sulfonamide (P-0321)
N-[2-fluoro-3-[5-[6-(4-methylpiperazin-1-yl)pyrimidin-4-yl]-1H-pyrrolo[2,3-b]pyridine-3-carbonyl]phenyl]pyrrolidine-1-sulfonamide (P-0322)
N-[2-fluoro-3-[5-[6-(4-methylpiperazin-1-yl)-2-pyridyl]-1H-pyrrolo[2,3-b]pyridine-3-carbonyl]phenyl]pyrrolidine-1-sulfonamide (P-0324)
N-[2-fluoro-3-[5-(4-methoxypyrimidin-2-yl)-1H-pyrrolo[2,3-b]pyridine-3-carbonyl]phenyl]pyrrolidine-1-sulfonamide (P-0325)
N-[2-fluoro-3-[5-(4-methylpyrimidin-2-yl)-1H-pyrrolo[2,3-b]pyridine-3-carbonyl]phenyl]pyrrolidine-1-sulfonamide (P-0326)
(3R)-N-[3-[5-(2-cyclopropylpyrimidin-5-yl)-1H-pyrrolo[2,3-b]pyridine-3-carbonyl]-2-fluoro-phenyl]-3-fluoro-pyrrolidine-1-sulfonamide (P-0327)
[5-(2-cyclopropylpyrimidin-5-yl)-1H-pyrrolo[2,3-b]pyridin-3-yl]-[2,6-difluoro-3-(methylsulfamoylamino)phenyl]methanone (P-0334)
[5-(2-cyclopropylpyrimidin-5-yl)-1H-pyrrolo[2,3-b]pyridin-3-yl]-[3-(ethylsulfamoylamino)-2,6-difluoro-phenyl]methanone (P-0335)
5-(2-cyclopropylpyrimidin-5-yl)-3-[2,6-difluoro-3-(sulfamoylamino)benzoyl]-1H-pyrrolo[2,3-b]pyridine (P-0336)
N-[3-[5-(4-chlorophenyl)-1H-pyrrolo[2,3-b]pyridine-3-carbonyl]-2,4-difluoro-phenyl]butane-2-sulfonamide (P-0337)
(3R)-N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0338)
N-[3-[5-(2-cyclopropylpyrimidin-5-yl)-1H-pyrrolo[2,3-b]pyridine-3-carbonyl]-2,4-difluoro-phenyl]-3-fluoro-pyrrolidine-1-sulfonamide (P-0339)
5-(2-cyclopropylpyrimidin-5-yl)-3-[2,6-difluoro-3-[[methyl(2,2,2-trifluoroethyl)sulfamoyl]amino]benzoyl]-1H-pyrrolo[2,3-b]pyridine (P-0340)
N-[3-[5-(2-cyclopropylpyrimidin-5-yl)-1H-pyrrolo[2,3-b]pyridine-3-carbonyl]-2,4-difluoro-phenyl]butane-2-sulfonamide (P-0342)
5-[3-[3-[[ethyl(methyl)sulfamoyl]amino]-2,6-difluoro-benzoyl]-1H-pyrrolo[2,3-b]pyridin-5-yl]-2-methoxy-thiazole (P-0343)
3-[3-[[ethyl(methyl)sulfamoyl]amino]-2,6-difluoro-benzoyl]-5-(1H-indazol-6-yl)-1H-pyrrolo[2,3-b]pyridine (P-0344)
N-[2,4-difluoro-3-[5-(2-pyrrolidin-1-ylpyrimidin-5-yl)-1H-pyrrolo[2,3-b]pyridine-3-carbonyl]phenyl]pyrrolidine-1-sulfonamide (P-0345)
N-[3-(5-cyclobutyl-1H-pyrrolo[2,3-b]pyridine-3-carbonyl)-2-fluoro-phenyl]pyrrolidine-1-sulfonamide (P-0346)
N-[2-fluoro-3-[5-(2-methoxypyrimidin-5-yl)-1H-pyrrolo[2,3-b]pyridine-3-carbonyl]phenyl]cyclopropanesulfonamide (P-0347)
1-allyl-N-[3-[5-(5-cyano-1H-pyrrolo[2,3-b]pyridine-3-carbonyl)-2,4-difluoro-phenyl]cyclopropanesulfonamide (P-0348)
N-[2,4-difluoro-3-[5-(2-methoxypyrimidin-5-yl)-1H-pyrrolo[2,3-b]pyridine-3-carbonyl]phenyl]cyclopropanesulfonamide (P-0349)

TABLE 2-continued

N-[2,4-difluoro-3-[5-(5-methoxy-3-pyridyl)-1H-pyrrolo[2,3-b]pyridine-3-carbonyl]phenyl]cyclopropanesulfonamide (P-0350)
N-[3-(5-cyano-1H-pyrrolo[2,3-b]pyridine-3-carbonyl)-2,4-difluoro-phenyl]cyclopropanesulfonamide (P-0351)

The following table provides structures of certain compounds of the present invention and observed mass. $^1$H NMR spectra were consistent with the structures of the compounds.

| No. | Compounds | MS(ESI) [M + H$^+$]$^+$ observed |
|---|---|---|
| P-0012 | | 428.9 |
| P-0013 | | 504.9 |
| P-0014 | | 503.0 |
| P-0015 | | 551.1 |
| P-0018 | | 410.9 |

-continued

| No. | Compounds | MS(ESI) [M + H⁺]⁺ observed |
|---|---|---|
| P-0019 | | 489.0 |
| P-0020 | | 485.1 |
| P-0021 | | 517.0 and 519.0 |
| P-0022 | | 528.1 |
| P-0023 | | 402.9 |
| P-0024 | | 532.8 |

| No. | Compounds | MS(ESI) [M + H⁺]⁺ observed |
|---|---|---|
| P-0025 | | 497.0 |
| P-0026 | | 457.0 |
| P-0027 | | 463.5 |
| P-0028 | | 439.5 |
| P-0029 | | 454.5 |
| P-0030 | | 483.5 |
| P-0031 | | 478.5 |

-continued

| No. | Compounds | MS(ESI) [M + H$^+$]$^+$ observed |
|---|---|---|
| P-0032 | | 454.5 |
| P-0033 | | 468.2 |
| P-0034 | | 471.5 |
| P-0035 | | 457.5 |
| P-0036 | | 453.1 |
| P-0037 | | 439.2 |
| P-0040 | | 499.0 |

|  |  | MS(ESI) [M + H⁺]⁺ |
|---|---|---|
| No. | Compounds | observed |
| P-0041 | | 603.6 |
| P-0042 | | 454.0 |
| P-0043 | | 466.0 |
| P-0044 | | 427.5 |
| P-0045 | | 480.5 |
| P-0046 | | 509.6 |

-continued

| No. | Compounds | MS(ESI) [M + H⁺]⁺ observed |
|---|---|---|
| P-0047 | | 509.0 |
| P-0048 | | 507.0 |
| P-0049 | | 520.0 |
| P-0050 | | 530.0 |
| P-0051 | | 483.1 |
| P-0052 | | 481.0 |
| P-0053 | | 508.0 |

-continued

| No. | Compounds | MS(ESI) [M + H⁺]⁺ observed |
|---|---|---|
| P-0054 | | 494.0 |
| P-0055 | | 504.1 |
| P-0056 | | 469.0 |
| P-0057 | | 497.0 |
| P-0058 | | 495.0 |
| P-0059 | | 522.0 |

-continued

| No. | Compounds | MS(ESI) [M + H⁺]⁺ observed |
|---|---|---|
| P-0060 | | 508.0 |
| P-0061 | | 518.1 |
| P-0062 | | 483.0 |
| P-0063 | | 465.0 |
| P-0064 | | 496.0 |
| P-0065 | | 486.0 |
| P-0066 | | 514.0 |

-continued

| No. | Compounds | MS(ESI) [M + H⁺]⁺ observed |
|---|---|---|
| P-0067 | | 468.0 |
| P-0068 | | 471.0 |
| P-0069 | | 489.0 |
| P-0070 | | 499.0 |
| P-0071 | | 503.1 |
| P-0072 | | 513.5 |
| P-0073 | | 515.1 |

| No. | Compounds | MS(ESI) [M + H⁺]⁺ observed |
|---|---|---|
| P-0074 | 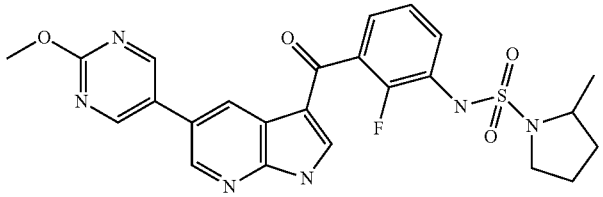 [SMILES: COc1ncc(-c2cnc3[nH]cc(C(=O)c4cccc(NS(=O)(=O)N5CCCC5C)c4F)c3c2)cn1] | 511.0 |
| P-0075 |  | 499.0 |
| P-0076 | 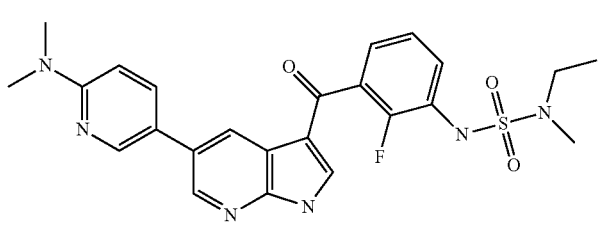 [SMILES: CCN(C)S(=O)(=O)Nc1cccc(C(=O)c2c[nH]c3ncc(-c4ccc(N(C)C)nc4)cc23)c1F] | 497.1 |
| P-0077 | 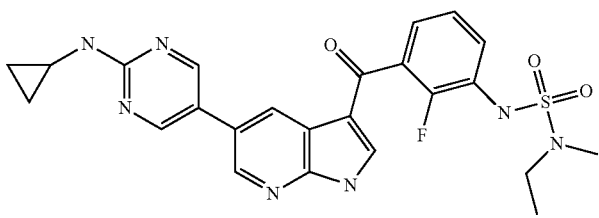 [SMILES: CCN(C)S(=O)(=O)Nc1cccc(C(=O)c2c[nH]c3ncc(-c4cnc(NC5CC5)nc4)cc23)c1F] | 510.5 |
| P-0078 | 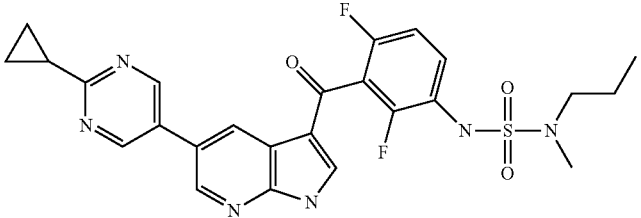 [SMILES: CCCN(C)S(=O)(=O)Nc1ccc(F)c(C(=O)c2c[nH]c3ncc(-c4cnc(C5CC5)nc4)cc23)c1F] | 527.1 |
| P-0079 | 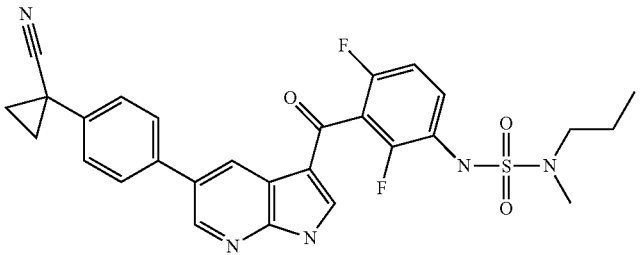 [SMILES: CCCN(C)S(=O)(=O)Nc1ccc(F)c(C(=O)c2c[nH]c3ncc(-c4ccc(C5(C#N)CC5)cc4)cc23)c1F] | 550.0 |

| No. | Compounds | MS(ESI) [M + H+]+ observed |
|---|---|---|
| P-0080 | 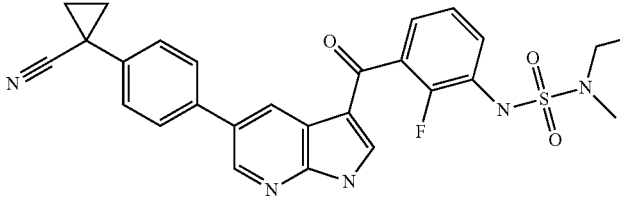 | 548.0 |
| P-0081 | 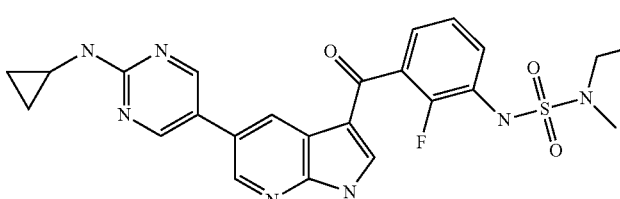 | 540.1 |
| P-0082 | 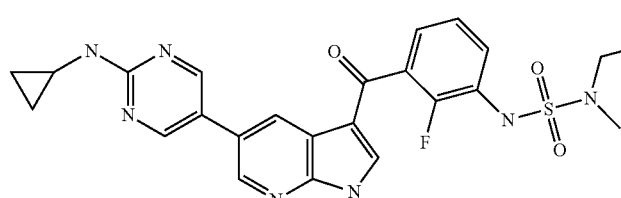 | 524.1 |
| P-0083 | 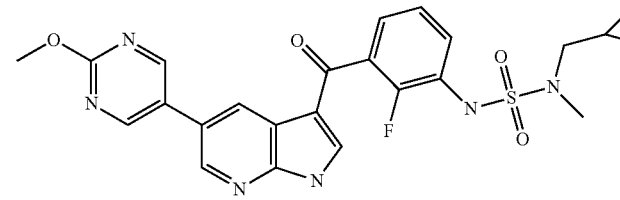 | 511.1 |
| P-0084 | 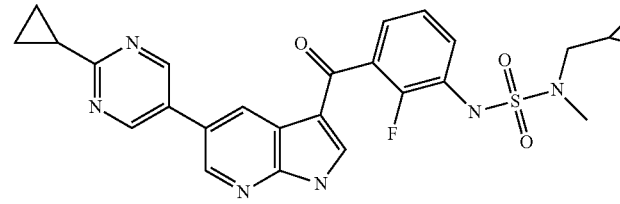 | 521.1 |
| P-0085 | 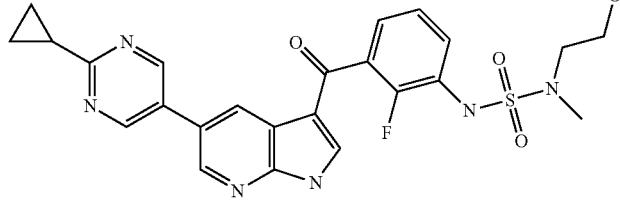 | 525.1 |
| P-0086 | 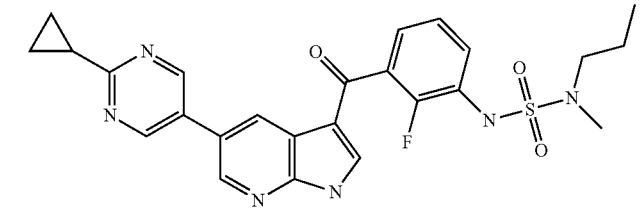 [SMILES: CCCN(C)S(=O)(=O)Nc1cccc(C(=O)c2c[nH]c3ncc(-c4cnc(C5CC5)nc4)cc23)c1F] | 509.1 |

| No. | Compounds | MS(ESI) [M + H⁺]⁺ observed |
|---|---|---|
| P-0087 | 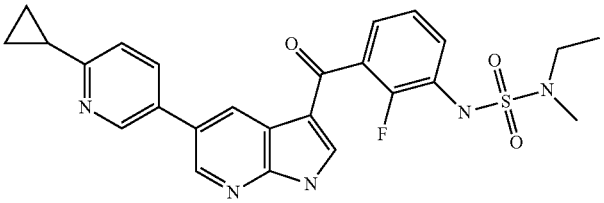 [SMILES: CCN(C)S(=O)(=O)Nc1cccc(C(=O)c2c[nH]c3ncc(-c4ccc(C5CC5)nc4)cc23)c1F] | 494.2 |
| P-0088 | 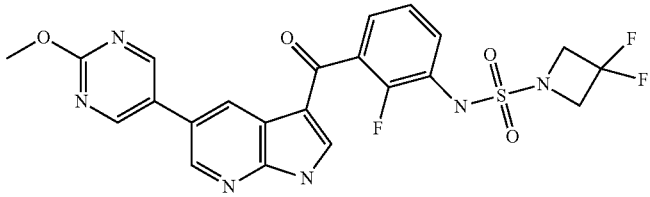 [SMILES: COc1ncc(-c2cnc3[nH]cc(C(=O)c4cccc(NS(=O)(=O)N5CC(F)(F)C5)c4F)c3c2)cn1] | 519.5 |
| P-0089 | 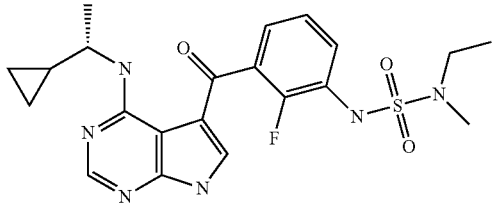 [SMILES: CCN(C)S(=O)(=O)Nc1cccc(C(=O)c2c[nH]c3ncnc(N[C@@H](C)C4CC4)c23)c1F] | 461.1 |
| P-0090 | 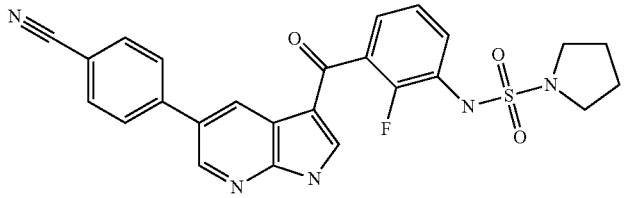 [SMILES: N#Cc1ccc(-c2cnc3[nH]cc(C(=O)c4cccc(NS(=O)(=O)N5CCCC5)c4F)c3c2)cc1] | 490.5 |
| P-0091 | 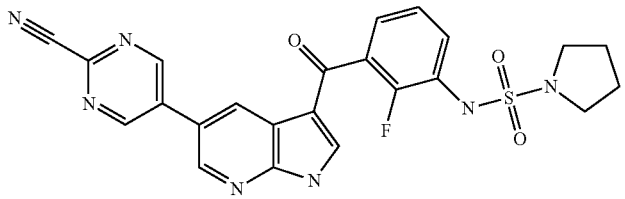 [SMILES: N#Cc1ncc(-c2cnc3[nH]cc(C(=O)c4cccc(NS(=O)(=O)N5CCCC5)c4F)c3c2)cn1] | 492.5 |
| P-0092 | 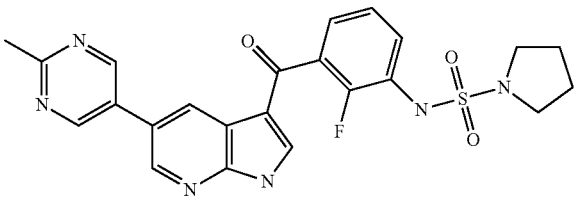 [SMILES: Cc1ncc(-c2cnc3[nH]cc(C(=O)c4cccc(NS(=O)(=O)N5CCCC5)c4F)c3c2)cn1] | 481.5 |
| P-0093 | 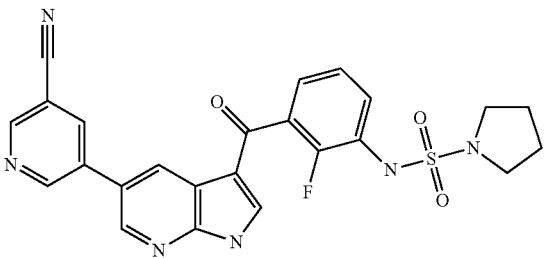 [SMILES: N#Cc1cncc(-c2cnc3[nH]cc(C(=O)c4cccc(NS(=O)(=O)N5CCCC5)c4F)c3c2)c1] | 491.5 |

-continued

| No. | Compounds | MS(ESI) [M + H+]+ observed |
|---|---|---|
| P-0094 | | 491.5 |
| P-0095 | | 534.5 |
| P-0096 | | 466.5 |
| P-0097 | | 455.5 |
| P-0098 | | 465.4 |
| P-0099 | | 465.5 |
| P-0100 | | 480.5 |

-continued

| No. | Compounds | MS(ESI) [M + H+]+ observed |
|---|---|---|
| P-0101 | | 479.5 |
| P-0102 | | 479.0 |
| P-0103 | | 497.5 |
| P-0104 | | 511.6 |
| P-0105 | | 523.6 |
| P-0106 | | 484.5 |

-continued

| No. | Compounds | MS(ESI) [M + H⁺]⁺ observed |
|---|---|---|
| P-0107 | | 510.6 |
| P-0108 | | 524.6 |
| P-0109 | | 536.6 |
| P-0110 | | 489.3 |
| P-0111 | | 483.5 |
| P-0112 | | 495.5 |
| P-0113 | | 480.1 |

-continued

| No. | Compounds | MS(ESI) [M + H⁺]⁺ observed |
|---|---|---|
| P-0114 | | 508.6 |
| P-0115 | | 520.6 |
| P-0116 | | 517.5 |
| P-0117 | | 503.0 |
| P-0223 | | 391.4 |
| P-0224 | | 484.5 |
| P-0225 | | 523.6 |

-continued

| No. | Compounds | MS(ESI) [M + H⁺]⁺ observed |
|---|---|---|
| P-0226 | | 509.6 |
| P-0227 | | 517.6 |
| P-0228 | | 4946 |
| P-0229 | | 496.6 |
| P-0230 | | 496.6 |
| P-0231 | | 468.6 |

| No. | Compounds | MS(ESI) [M + H+]+ observed |
|---|---|---|
| P-0232 | 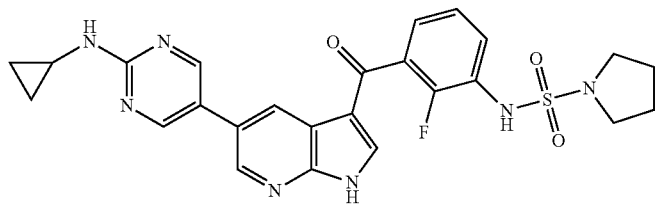 [SMILES: O=C(c1cccc(NS(=O)(=O)N2CCCC2)c1F)c1c[nH]c2ncc(-c3cnc(NC4CC4)nc3)cc12] | 522.6 |
| P-0233 | 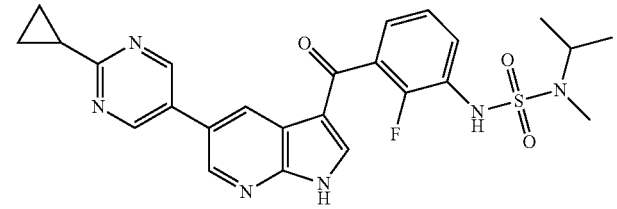 [SMILES: CC(C)N(C)S(=O)(=O)Nc1cccc(C(=O)c2c[nH]c3ncc(-c4cnc(C5CC5)nc4)cc23)c1F] | 509.6 |
| P-0235 | 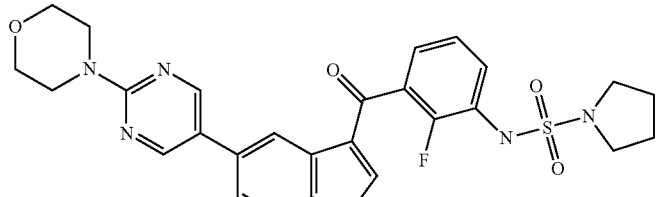 | 552.5 |
| P-0236 | 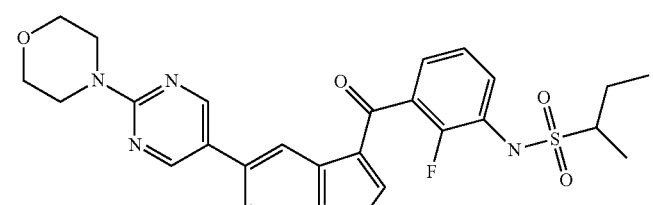 | 539.4 |
| P-0237 | 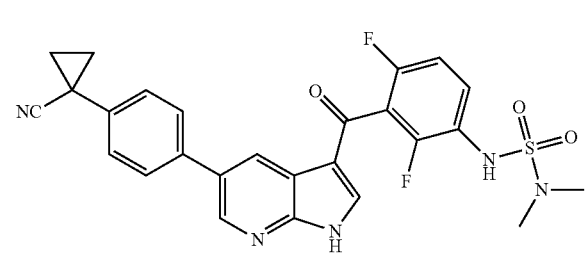 [SMILES: CN(C)S(=O)(=O)Nc1ccc(F)c(C(=O)c2c[nH]c3ncc(-c4ccc(C5(C#N)CC5)cc4)cc23)c1F] | 522.5 |
| P-0238 | 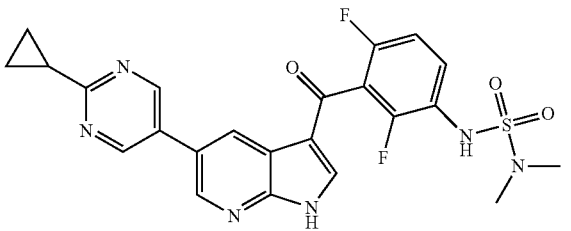 [SMILES: CN(C)S(=O)(=O)Nc1ccc(F)c(C(=O)c2c[nH]c3ncc(-c4cnc(C5CC5)nc4)cc23)c1F] | 499.5 |

| No. | Compounds | MS(ESI) [M + H⁺]⁺ observed |
|---|---|---|
| P-0239 | | 536.6 |
| P-0240 | | 513.5 |
| P-0241 | | 525.2 |
| P-0242 | | 457.5 |
| P-0243 | | 549.6 |
| P-0244 | | 503.5 |

-continued

| No. | Compounds | MS(ESI) [M + H+]+ observed |
|---|---|---|
| P-0245 | | 506.4 |
| P-0246 | | 535.6 |
| P-0247 | | 521.5 |
| P-0248 | | 548.5 |
| P-0249 | | 507.5 |
| P-0251 | | 495.5 |

| No. | Compounds | MS(ESI) [M + H+]+ observed |
|---|---|---|
| P-0252 | | 525.5 |
| P-0253 | | 548.6 |
| P-0254 | | 563.5 |
| P-0255 | | 524.5 |
| P-0256 | | 517.2 |
| P-0257 | | 569.6 |

| No. | Compounds | MS(ESI) [M + H+]+ observed |
|---|---|---|
| P-0258 | 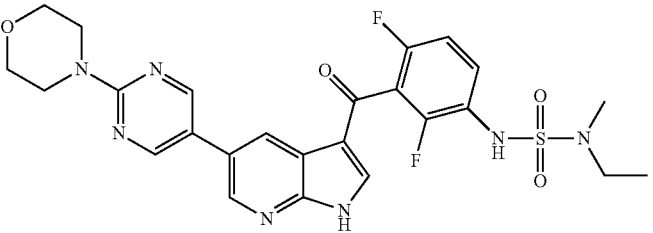 [SMILES: CCN(C)S(=O)(=O)Nc1ccc(F)c(C(=O)c2c[nH]c3ncc(-c4cnc(N5CCOCC5)nc4)cc23)c1F] | 558.5 |
| P-0259 | 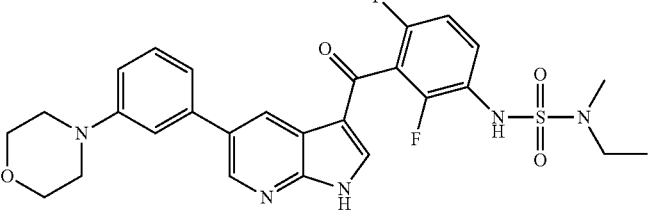 | 556.6 |
| P-0260 | 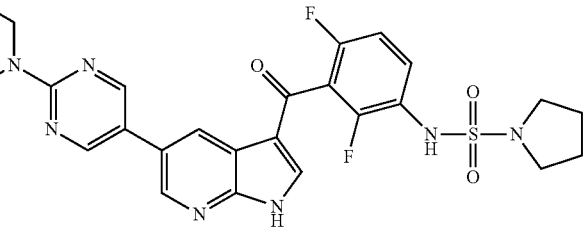 | 583.6 |
| P-0261 | 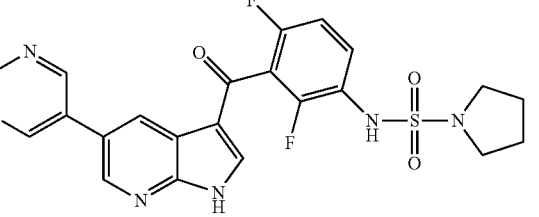 | 569.4 |
| P-0262 | 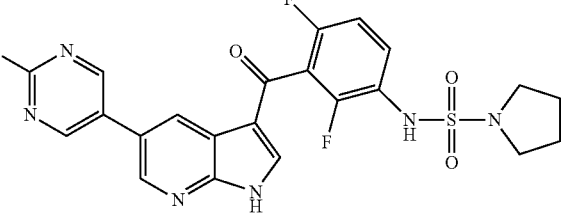 | 584.5 |
| P-0263 | 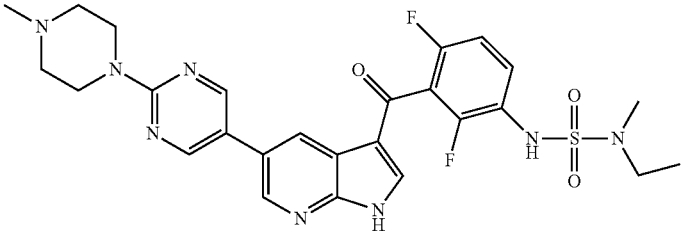 [SMILES: CCN(C)S(=O)(=O)Nc1ccc(F)c(C(=O)c2c[nH]c3ncc(-c4cnc(N5CCN(C)CC5)nc4)cc23)c1F] | 571.6 |

| No. | Compounds | MS(ESI) [M + H⁺]⁺ observed |
|---|---|---|
| P-0264 | 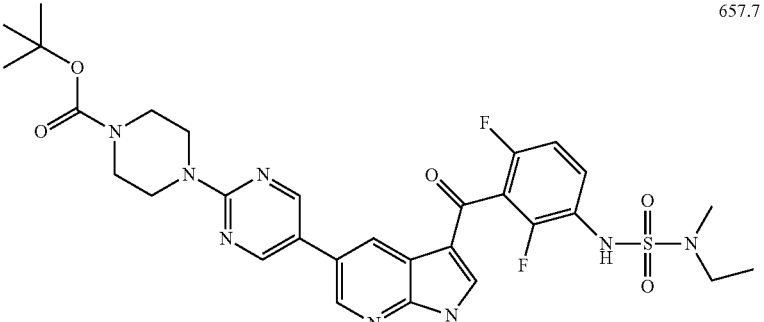 | 657.7 |
| P-0265 | 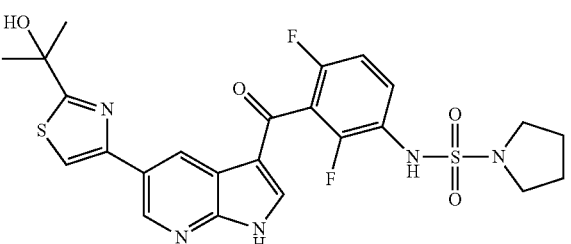 | 548.6 |
| P-0266 | 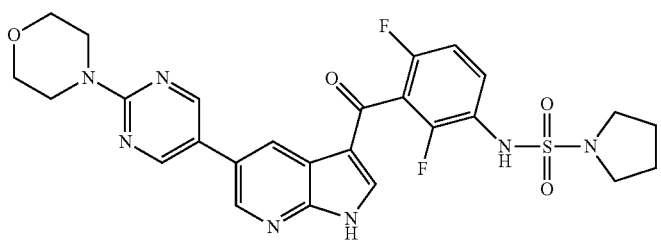 [SMILES: O=C(c1c(F)ccc(NS(=O)(=O)N2CCCC2)c1F)c1c[nH]c2ncc(-c3cnc(N4CCOCC4)nc3)cc12] | 570.5 |
| P-0267 | 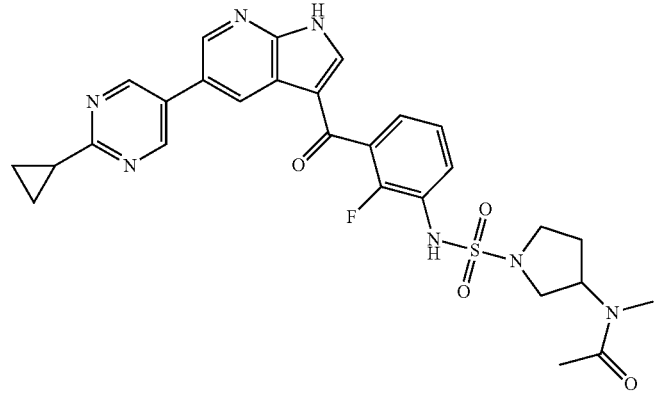 [SMILES: CC(=O)N(C)C1CCN(S(=O)(=O)Nc2cccc(C(=O)c3c[nH]c4ncc(-c5cnc(C6CC6)nc5)cc34)c2F)C1] | 578.6 |
| P-0268 | 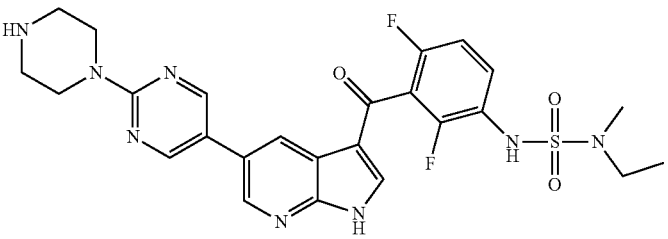 [SMILES: CCN(C)S(=O)(=O)Nc1ccc(F)c(C(=O)c2c[nH]c3ncc(-c4cnc(N5CCNCC5)nc4)cc23)c1F] | 557.5 |

-continued

| No. | Compounds | MS(ESI) [M + H$^+$]$^+$ observed |
|---|---|---|
| P-0269 | | 540.5 |
| P-0270 | | 520.6 |
| P-0271 | | 521.5 |
| P-0272 | | 536.6 |
| P-0273 | | 484.4 |
| P-0274 | | 429.4 |

-continued

| No. | Compounds | MS(ESI) [M + H⁺]⁺ observed |
|---|---|---|
| P-0275 | | 572.6 |
| P-0276 | | 536.5 |
| P-0277 | | 528.5 |
| P-0279 | | 500.3 |
| P-0280 | | 500.5 |
| P-0281 | | 466.5 |

| No. | Compounds | MS(ESI) [M + H+]+ observed |
|---|---|---|
| P-0282 | | 570.6 |
| P-0283 | | 490.4 |
| P-0284 | | 569.6 |
| P-0285 | | 582.5 |
| P-0286 | | 554.6 |
| P-0287 | | 514.5 |

| No. | Compounds | MS(ESI) [M + H⁺]⁺ observed |
|---|---|---|
| P-0288 | | 561.5 |
| P-0289 | | 543.4 |
| P-0291 | | 524.2 |
| P-0292 | | 516.2 |
| P-0293 | | 542.5 |
| P-0294 | | 553.5 |

| No. | Compounds | MS(ESI) [M + H⁺]⁺ observed |
|---|---|---|
| P-0295 | | 524.6 |
| P-0297 | | 431.5 |
| P-0298 | | 417.4 |
| P-0299 | | 482.5 |
| P-0300 | | 496.5 |
| P-0301 | | 539.4 |

| No. | Compounds | MS(ESI) [M + H⁺]⁺ observed |
|---|---|---|
| P-0302 | | 514.6 |
| P-0303 | | 540.5 |
| P-0304 | | 553.6 |
| P-0305 | | 584.6 |
| P-0306 | | 530.5 |
| P-0307 | | 530.2 |

| No. | Compounds | MS(ESI) [M + H⁺]⁺ observed |
|---|---|---|
| P-0308 | | 542.5 |
| P-0309 | | 526.5 |
| P-0310 | | 559.5 |
| P-0311 | | 538.5 |
| P-0312 | | 555.4 |
| P-0313 | | 566.6 |

| No. | Compounds | MS(ESI) [M + H⁺]⁺ observed |
|---|---|---|
| P-0314 | | 527.5 |
| P-0315 | | 478.5 |
| P-0316 | | 536.0 |
| P-0317 | | 503.5 |
| P-0318 | | 570.5 |
| P-0319 | | 583.6 |

-continued

| No. | Compounds | MS(ESI) [M + H+]+ observed |
|---|---|---|
| P-0320 | | 539.4 |
| P-0321 | | 552.5 |
| P-0322 | | 565.5 |
| P-0324 | | 564.8 |
| P-0325 | | 497.5 |
| P-0326 | | 481.4 |
| P-0327 | | 525.5 |

-continued

| No. | Compounds | MS(ESI) [M + H⁺]⁺ observed |
|---|---|---|
| P-0334 | | 485.4 |
| P-0335 | | 499.5 |
| P-0336 | | 471.4 |
| P-0337 | | 504.0 |
| P-0338 | | 542.9 |

-continued

| No. | Compounds | MS(ESI) [M + H+]+ observed |
|---|---|---|
| P-0339 | | 543.5 |
| P-0340 | | 567.5 |
| P-0342 | | 512.5 |
| P-0343 | | 507.5401 |
| P-0344 | | 511.5 |
| P-0345 | | 554.6 |

-continued

| No. | Compounds | MS(ESI) [M + H⁺]⁺ observed |
|---|---|---|
| P-0346 | | 443.5 |
| P-0347 | | 468.4 |
| P-0348 | | 443.4 |
| P-0349 | | 486.4 |
| P-0350 | | 485.5 |
| P-0351 | | 403.3 |

The following compounds are also prepared according to the protocols set forth in Examples 1, 2 and 4-9 and Schemes 1, 2 and 4-9. The data from the ¹H NMR and mass spectroscopies are consistent with the structures of the compounds.

TABLE 3

| Compound No. | Name (MS(ESI) [M + H⁺]⁺) | Structure |
|---|---|---|
| P-0118 | [2-fluoro-3-(phenylsulfamoylamino)phenyl]-[5-(2-methoxypyrimidin-5-yl)-1H-pyrrolo[2,3-b]pyridin-3-yl]methanone (519.1) | 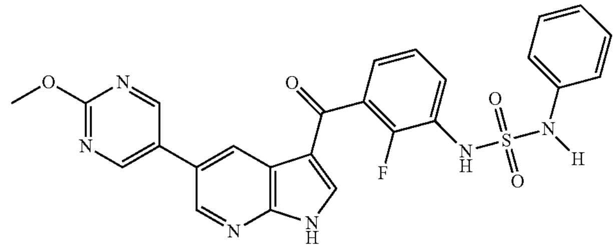 [SMILES: COc1ncc(-c2cnc3[nH]cc(C(=O)c4cccc(NS(=O)(=O)Nc5ccccc5)c4F)c3c2)cn1] |
| P-0119 | 3-[2-fluoro-3-[[methyl(phenyl)sulfamoyl]amino]benzoyl]-5-(2-methoxypyrimidin-5-yl)-1H-pyrrolo[2,3-b]pyridine (533.1) | 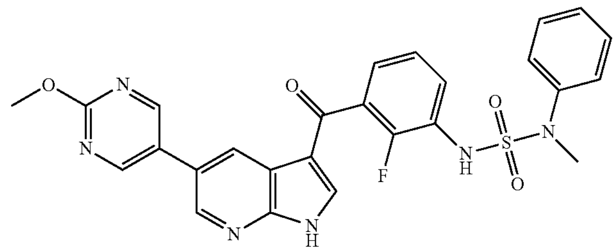 [SMILES: COc1ncc(-c2cnc3[nH]cc(C(=O)c4cccc(NS(=O)(=O)N(C)c5ccccc5)c4F)c3c2)cn1] |
| P-0120 | [2-fluoro-3-(3-pyridylsulfamoylamino)phenyl]-[5-(2-methoxypyrimidin-5-yl)-1H-pyrrolo[2,3-b]pyridin-3-yl]methanone (520.1) | 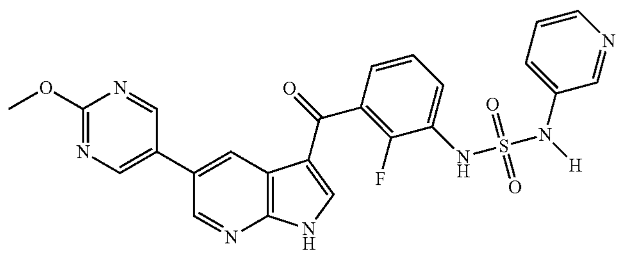 [SMILES: COc1ncc(-c2cnc3[nH]cc(C(=O)c4cccc(NS(=O)(=O)Nc5cccnc5)c4F)c3c2)cn1] |
| P-0121 | 3-[2-fluoro-3-[[methyl(3-pyridyl)sulfamoyl]amino]benzoyl]-5-(2-methoxypyrimidin-5-yl)-1H-pyrrolo[2,3-b]pyridine (534.1) | 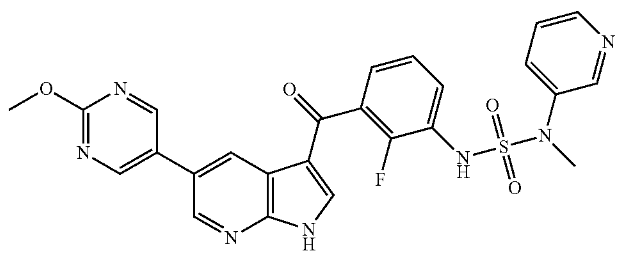 [SMILES: COc1ncc(-c2cnc3[nH]cc(C(=O)c4cccc(NS(=O)(=O)N(C)c5cccnc5)c4F)c3c2)cn1] |
| P-0122 | [2-fluoro-3-(thiazol-5-ylsulfamoylamino)phenyl]-[5-(2-methoxypyrimidin-5-yl)-1H-pyrrolo[2,3-b]pyridin-3-yl]methanone (526.1) | 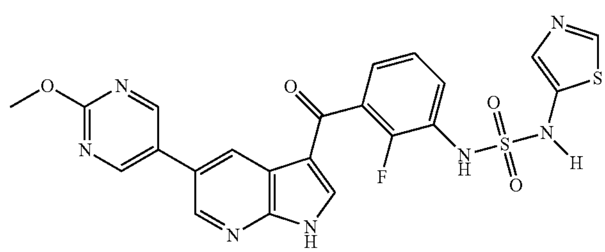 [SMILES: COc1ncc(-c2cnc3[nH]cc(C(=O)c4cccc(NS(=O)(=O)Nc5cncs5)c4F)c3c2)cn1] |
| P-0123 | 5-[[2-fluoro-3-[5-(2-methoxypyrimidin-5-yl)-1H-pyrrolo[2,3-b]pyridine-3-carbonyl]phenyl]sulfamoyl-methyl-amino]thiazole (540.1) | 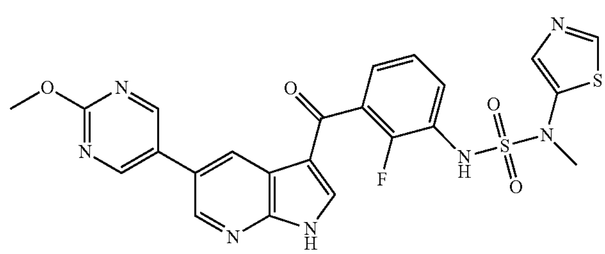 [SMILES: COc1ncc(-c2cnc3[nH]cc(C(=O)c4cccc(NS(=O)(=O)N(C)c5cncs5)c4F)c3c2)cn1] |

TABLE 3-continued

| Compound No. | Name (MS(ESI) [M + H⁺]⁺) | Structure |
|---|---|---|
| P-0124 | [3-(cyclopentylsulfamoylamino)-2-fluoro-phenyl]-[5-(2-methoxypyrimidin-5-yl)-1H-pyrrolo[2,3-b]pyridin-3-yl]methanone (511.1) | 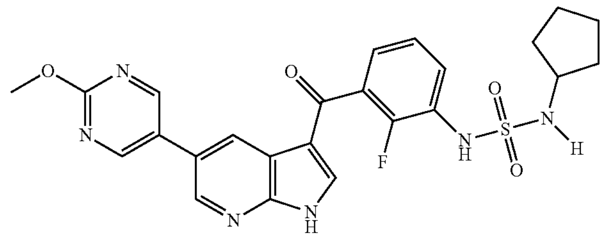 [SMILES: COc1ncc(-c2cnc3[nH]cc(C(=O)c4cccc(NS(=O)(=O)NC5CCCC5)c4F)c3c2)cn1] |
| P-0125 | 3-[3-[[cyclopentyl(methyl)sulfamoyl]amino]-2-fluoro-benzoyl]-5-(2-methoxypyrimidin-5-yl)-1H-pyrrolo[2,3-b]pyridine (525.2) | 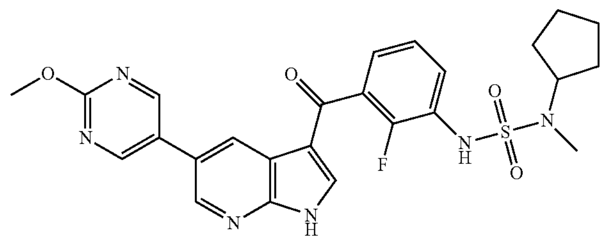 [SMILES: COc1ncc(-c2cnc3[nH]cc(C(=O)c4cccc(NS(=O)(=O)N(C)C5CCCC5)c4F)c3c2)cn1] |
| P-0126 | [3-(cyclopropylsulfamoylamino)-2-fluoro-phenyl]-[5-(2-methoxypyrimidin-5-yl)-1H-pyrrolo[2,3-b]pyridin-3-yl]methanone (483.1) | 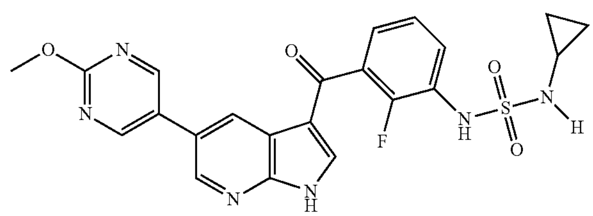 [SMILES: COc1ncc(-c2cnc3[nH]cc(C(=O)c4cccc(NS(=O)(=O)NC5CC5)c4F)c3c2)cn1] |
| P-0127 | [2-fluoro-3-(tetrahydropyran-4-ylsulfamoylamino)phenyl]-[5-(2-methoxypyrimidin-5-yl)-1H-pyrrolo[2,3-b]pyridin-3-yl]methanone (527.1) | 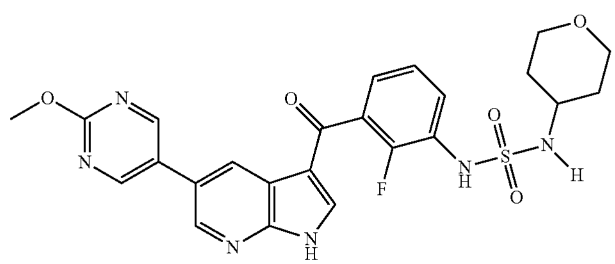 [SMILES: COc1ncc(-c2cnc3[nH]cc(C(=O)c4cccc(NS(=O)(=O)NC5CCOCC5)c4F)c3c2)cn1] |
| P-0128 | 3-[2-fluoro-3-[[methyl(tetrahydropyran-4-yl)sulfamoyl]amino]benzoyl]-5-(2-methoxypyrimidin-5-yl)-1H-pyrrolo[2,3-b]pyridine (541.2) | 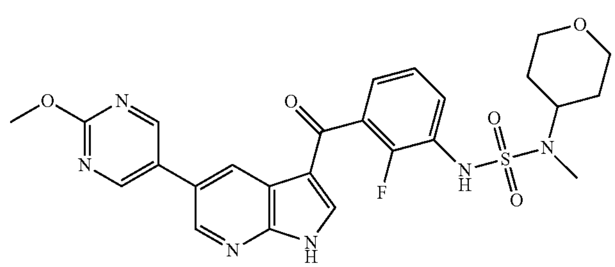 [SMILES: COc1ncc(-c2cnc3[nH]cc(C(=O)c4cccc(NS(=O)(=O)N(C)C5CCOCC5)c4F)c3c2)cn1] |
| P-0129 | 3-[2-fluoro-3-[[2-fluoroethyl(methyl)sulfamoyl]amino]benzoyl]-5-(2-methoxypyrimidin-5-yl)-1H-pyrrolo[2,3-b]pyridine (503.1) | 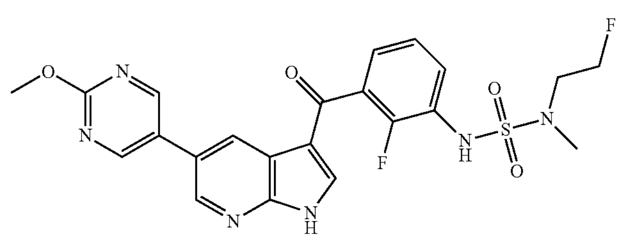 [SMILES: COc1ncc(-c2cnc3[nH]cc(C(=O)c4cccc(NS(=O)(=O)N(C)CCF)c4F)c3c2)cn1] |

TABLE 3-continued

| Compound No. | Name (MS(ESI) [M + H+]+) | Structure |
|---|---|---|
| P-0130 | 3-[2-fluoro-3-[[methyl(2,2,2-trifluoroethyl)sulfamoyl]amino]benzoyl]-5-(2-methoxypyrimidin-5-yl)-1H-pyrrolo[2,3-b]pyridine (539.1) | 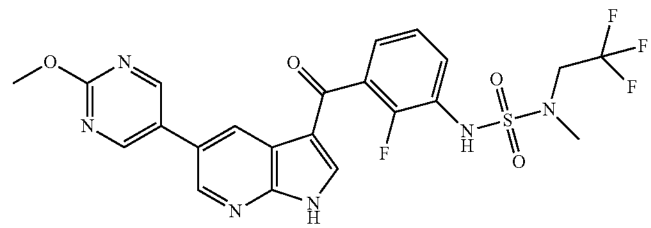 [SMILES: COc1ncc(-c2cnc3[nH]cc(C(=O)c4cccc(NS(=O)(=O)N(C)CC(F)(F)F)c4F)c3c2)cn1] |
| P-0131 | 3-[2-fluoro-3-[[3-fluoropropyl(methyl)sulfamoyl]amino]benzoyl]-5-(2-methoxypyrimidin-5-yl)-1H-pyrrolo[2,3-b]pyridine (517.1) | 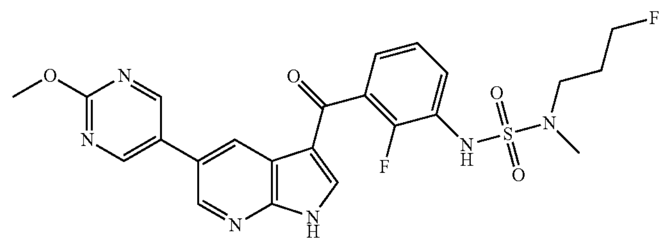 [SMILES: COc1ncc(-c2cnc3[nH]cc(C(=O)c4cccc(NS(=O)(=O)N(C)CCCF)c4F)c3c2)cn1] |
| P-0132 | 5-chloro-3-[2-fluoro-3-[[2-methoxyethyl(methyl)sulfamoyl]amino]benzoyl]-1H-pyrrolo[2,3-b]pyridine (441.1) | 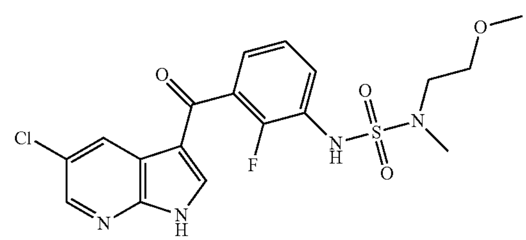 [SMILES: COCCN(C)S(=O)(=O)Nc1cccc(C(=O)c2c[nH]c3ncc(Cl)cc23)c1F] |
| P-0133 | 5-chloro-3-[2-fluoro-3-[[3-fluoropropyl(methyl)sulfamoyl]amino]benzoyl]-1H-pyrrolo[2,3-b]pyridine (443.1) | 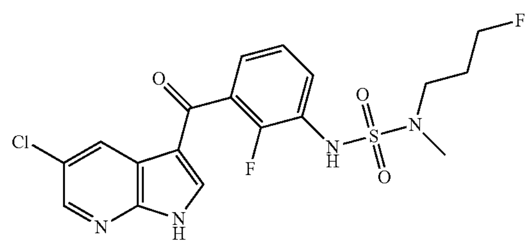 [SMILES: CN(CCCF)S(=O)(=O)Nc1cccc(C(=O)c2c[nH]c3ncc(Cl)cc23)c1F] |
| P-0134 | 3-[2-fluoro-3-[[3-fluoropropyl(methyl)sulfamoyl]amino]benzoyl]-5-(2-isopropylpyrimidin-5-yl)-1H-pyrrolo[2,3-b]pyridine (529.2) | 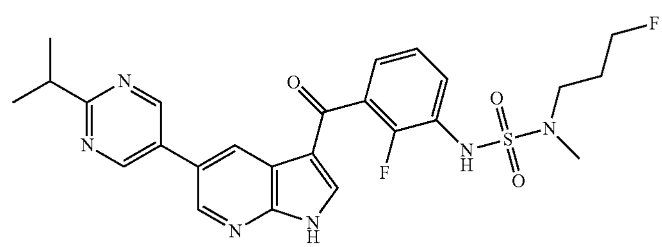 |
| P-0135 | 3-[2-fluoro-3-[[[1-(methoxymethyl)cyclopropyl]-methyl-sulfamoyl]amino]benzoyl]-5-(2-isopropylpyrimidin-5-yl)-1H-pyrrolo[2,3-b]pyridine (553.2) | 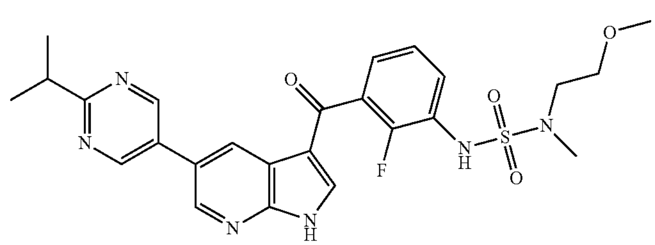 [SMILES: COCCN(C)S(=O)(=O)Nc1cccc(C(=O)c2c[nH]c3ncc(-c4cnc(C(C)C)nc4)cc23)c1F] |

TABLE 3-continued

| Compound No. | Name (MS(ESI) [M + H⁺]⁺) | Structure |
|---|---|---|
| P-0136 | 5-chloro-3-[2-fluoro-3-[[[1-(methoxymethyl)cyclopropyl]-methyl-sulfamoyl]amino]benzoyl]-1H-pyrrolo[2,3-b]pyridine (467.1) | 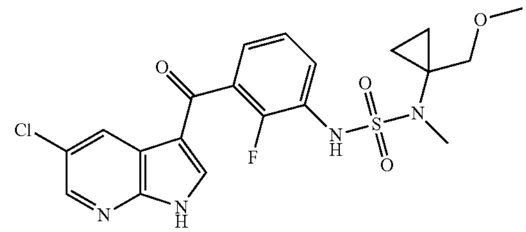 [SMILES: COCC1(N(C)S(=O)(=O)Nc2cccc(C(=O)c3c[nH]c4ncc(Cl)cc34)c2F)CC1] |
| P-0137 | 5-chloro-3-[3-[[2-cyclopropylethyl(methyl)sulfamoyl]amino]-2-fluoro-benzoyl]-1H-pyrrolo[2,3-b]pyridine (451.1) | 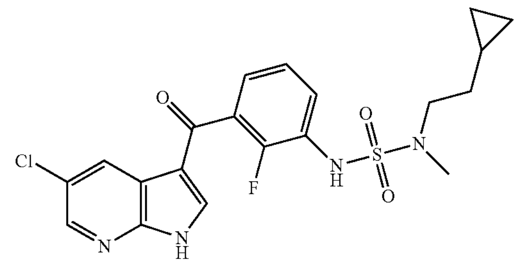 [SMILES: CN(CCC1CC1)S(=O)(=O)Nc1cccc(C(=O)c2c[nH]c3ncc(Cl)cc23)c1F] |
| P-0138 | 3-[3-[[2-cyclopropylethyl(methyl)sulfamoyl]amino]-2-fluoro-benzoyl]-5-(2-isopropylpyrimidin-5-yl)-1H-pyrrolo[2,3-b]pyridine (537.2) | 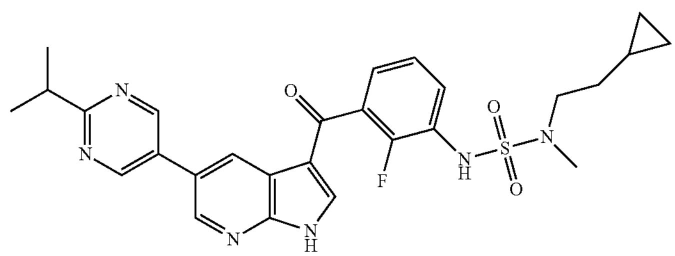 [SMILES: CC(C)c1ncc(-c2cnc3[nH]cc(C(=O)c4cccc(NS(=O)(=O)N(C)CCC5CC5)c4F)c3c2)cn1] |
| P-0139 | 5-chloro-3-[2-fluoro-3-[[[1-(hydroxymethyl)cyclopropyl]methyl-methyl-sulfamoyl]amino]benzoyl]-1H-pyrrolo[2,3-b]pyridine (467.1) | 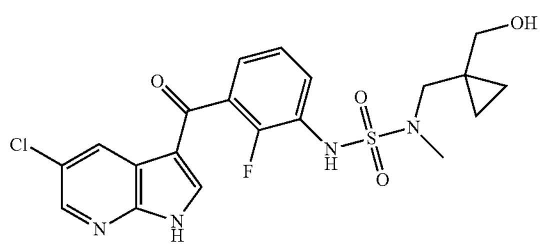 [SMILES: CN(CC1(CO)CC1)S(=O)(=O)Nc1cccc(C(=O)c2c[nH]c3ncc(Cl)cc23)c1F] |
| P-0140 | methyl 1-[[[3-(5-chloro-1H-pyrrolo[2,3-b]pyridine-3-carbonyl)-2-fluoro-phenyl]sulfamoyl-methyl-amino]methyl]cyclopropanecarboxylate (495.1) | 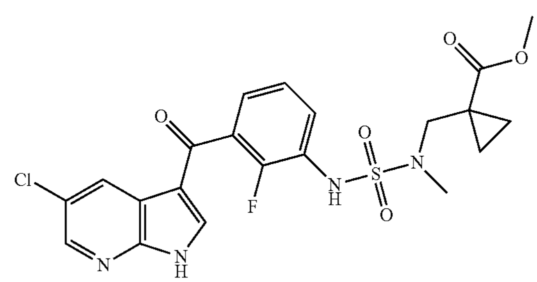 [SMILES: COC(=O)C1(CN(C)S(=O)(=O)Nc2cccc(C(=O)c3c[nH]c4ncc(Cl)cc34)c2F)CC1] |
| P-0141 | 5-chloro-3-[3-[[2-cyanoethyl(methyl)sulfamoyl]amino]-2-fluoro-benzoyl]-1H-pyrrolo[2,3-b]pyridine (436.1) | 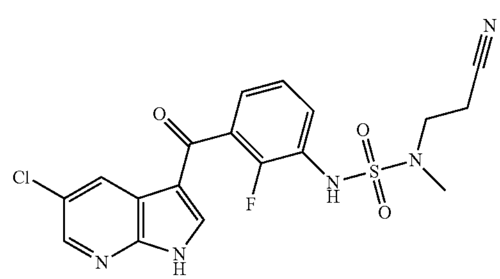 [SMILES: CN(CCC#N)S(=O)(=O)Nc1cccc(C(=O)c2c[nH]c3ncc(Cl)cc23)c1F] |

TABLE 3-continued

| Compound No. | Name (MS(ESI) [M + H⁺]⁺) | Structure |
|---|---|---|
| P-0142 | (5-chloro-1H-pyrrolo[2,3-b]pyridin-3-yl)-[2-fluoro-3-(3-methoxypropylsulfamoylamino)phenyl]methanone (441.1) | 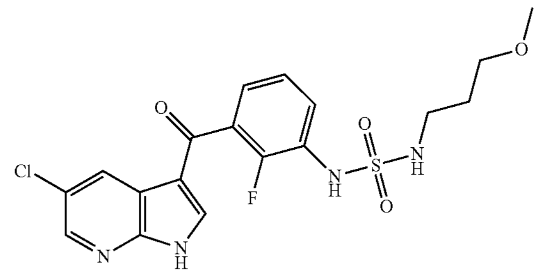 [SMILES: COCCCNS(=O)(=O)Nc1cccc(C(=O)c2c[nH]c3ncc(Cl)cc23)c1F] |
| P-0143 | N-[3-(5-chloro-1H-pyrrolo[2,3-b]pyridine-3-carbonyl)-2-fluoro-phenyl]-4-methyl-piperazine-1-sulfonamide (452.1) | 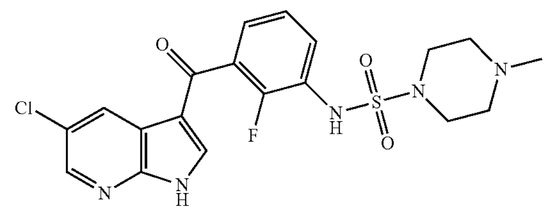 [SMILES: CN1CCN(S(=O)(=O)Nc2cccc(C(=O)c3c[nH]c4ncc(Cl)cc34)c2F)CC1] |
| P-0144 | 5-chloro-3-[2-fluoro-3-[[(2-hydroxy-2-methyl-propyl)-methyl-sulfamoyl]amino]benzoyl]-1H-pyrrolo[2,3-b]pyridine (455.1) | 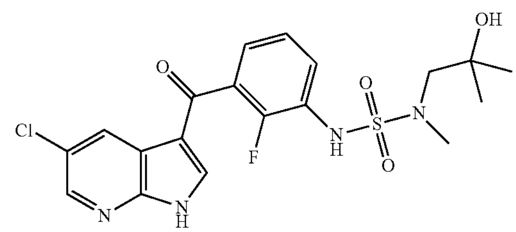 [SMILES: CN(CC(C)(C)O)S(=O)(=O)Nc1cccc(C(=O)c2c[nH]c3ncc(Cl)cc23)c1F] |
| P-0145 | 5-chloro-3-[2-fluoro-3-[[(2-hydroxy-1,1-dimethyl-ethyl)-methyl-sulfamoyl]amino]benzoyl]-1H-pyrrolo[2,3-b]pyridine (455.1) | 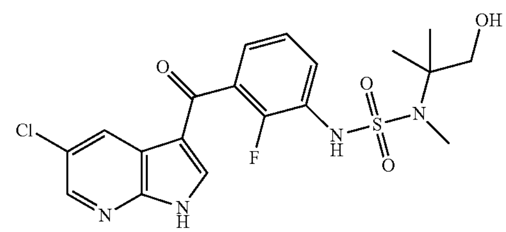 [SMILES: CN(C(C)(C)CO)S(=O)(=O)Nc1cccc(C(=O)c2c[nH]c3ncc(Cl)cc23)c1F] |
| P-0146 | N-[3-[5-(2-cyclopropylpyrimidin-5-yl)-1H-pyrrolo[2,3-b]pyridine-3-carbonyl]-2-fluoro-phenyl]azetidine-1-sulfonamide (493.1) | 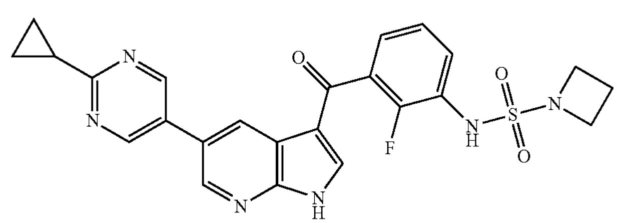 [SMILES: O=C(c1cccc(NS(=O)(=O)N2CCC2)c1F)c1c[nH]c2ncc(-c3cnc(C4CC4)nc3)cc12] |
| P-0147 | N-[3-[5-(2-cyclopropylpyrimidin-5-yl)-1H-pyrrolo[2,3-b]pyridine-3-carbonyl]-2-fluoro-phenyl]-3-fluoro-azetidine-1-sulfonamide (511.1) | 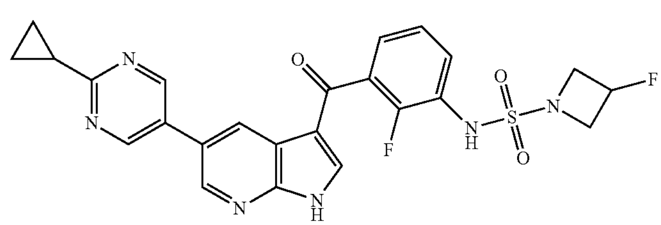 [SMILES: O=C(c1cccc(NS(=O)(=O)N2CC(F)C2)c1F)c1c[nH]c2ncc(-c3cnc(C4CC4)nc3)cc12] |

TABLE 3-continued

| Compound No. | Name (MS(ESI) [M + H+]+) | Structure |
|---|---|---|
| P-0148 | 5-(2-cyclopropylpyrimidin-5-yl)-3-[2-fluoro-3-[[methyl(oxetan-3-yl)sulfamoyl]amino]benzoyl]-1H-pyrrolo[2,3-b]pyridine (523.1) | 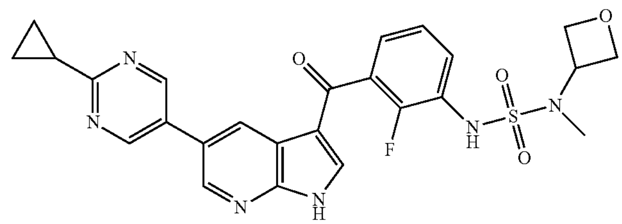 [SMILES: CN(C1COC1)S(=O)(=O)Nc1cccc(C(=O)c2c[nH]c3ncc(-c4cnc(C5CC5)nc4)cc23)c1F] |
| P-0149 | 3-[3-[[cyclobutyl(methyl)sulfamoyl]amino]-2-fluoro-benzoyl]-5-(2-cyclopropylpyrimidin-5-yl)-1H-pyrrolo[2,3-b]pyridine (521.2) | 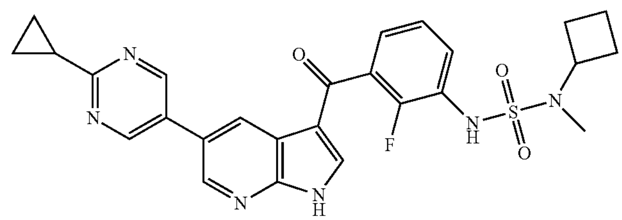 [SMILES: CN(C1CCC1)S(=O)(=O)Nc1cccc(C(=O)c2c[nH]c3ncc(-c4cnc(C5CC5)nc4)cc23)c1F] |
| P-0150 | 5-chloro-3-[2-fluoro-3-[[methyl(tetrahydrofuran-3-yl)sulfamoyl]amino]benzoyl]-1H-pyrrolo[2,3-b]pyridine (453.1) | 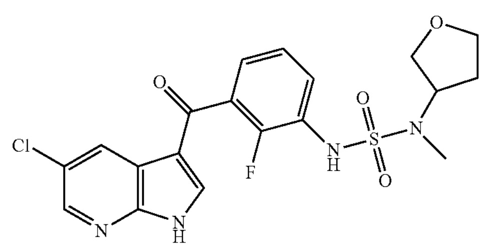 [SMILES: CN(C1CCOC1)S(=O)(=O)Nc1cccc(C(=O)c2c[nH]c3ncc(Cl)cc23)c1F] |
| P-0151 | N-[3-(5-chloro-1H-pyrrolo[2,3-b]pyridine-3-carbonyl)-2-fluoro-phenyl]-3-methoxy-pyrrolidine-1-sulfonamide (453.1) | 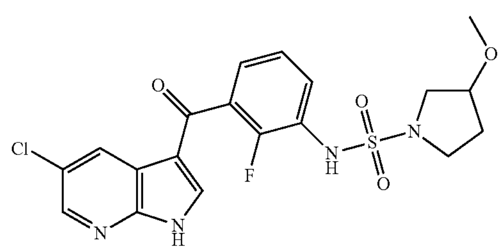 [SMILES: COC1CCN(S(=O)(=O)Nc2cccc(C(=O)c3c[nH]c4ncc(Cl)cc34)c2F)C1] |
| P-0152 | N-[3-(5-chloro-1H-pyrrolo[2,3-b]pyridine-3-carbonyl)-2-fluoro-phenyl]-3-(methylamino)pyrrolidine-1-sulfonamide (452.1) | 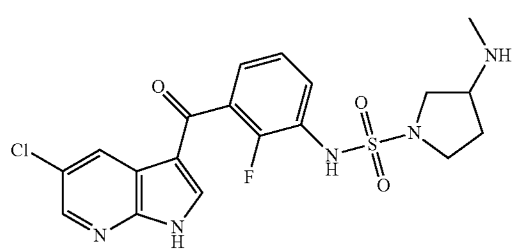 [SMILES: CNC1CCN(S(=O)(=O)Nc2cccc(C(=O)c3c[nH]c4ncc(Cl)cc34)c2F)C1] |
| P-0153 | N-[3-(5-chloro-1H-pyrrolo[2,3-b]pyridine-3-carbonyl)-2-fluoro-phenyl]-3-(dimethylamino)pyrrolidine-1-sulfonamide (466.1) | 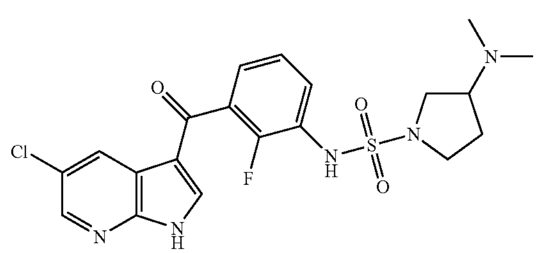 [SMILES: CN(C)C1CCN(S(=O)(=O)Nc2cccc(C(=O)c3c[nH]c4ncc(Cl)cc34)c2F)C1] |

TABLE 3-continued

| Compound No. | Name (MS(ESI) [M + H+]+) | Structure |
|---|---|---|
| P-0154 | N-[3-[5-[6-(1-cyanocyclopropyl)-3-pyridyl]-1H-pyrrolo[2,3-b]pyridine-3-carbonyl]-2-fluoro-phenyl]pyrrolidine-1-sulfonamide (531.2) | 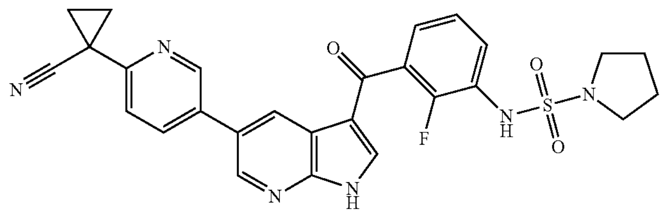 [SMILES: N#CC1(c2ccc(-c3cnc4[nH]cc(C(=O)c5cccc(NS(=O)(=O)N6CCCC6)c5F)c4c3)cn2)CC1] |
| P-0155 | 1-[5-[3-[2-fluoro-3-(pyrrolidin-1-ylsulfonylamino)benzoyl]-1H-pyrrolo[2,3-b]pyridin-5-yl]-2-pyridyl]cyclopropanecarboxamide (549.2) | 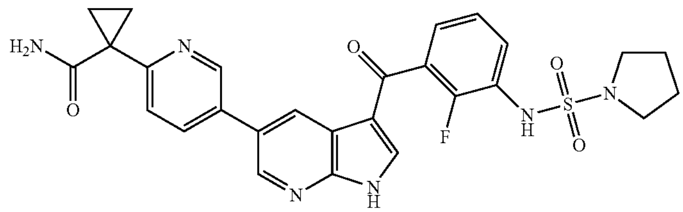 [SMILES: NC(=O)C1(c2ccc(-c3cnc4[nH]cc(C(=O)c5cccc(NS(=O)(=O)N6CCCC6)c5F)c4c3)cn2)CC1] |
| P-0156 | 1-[5-[3-[2-fluoro-3-(pyrrolidin-1-ylsulfonylamino)benzoyl]-1H-pyrrolo[2,3-b]pyridin-5-yl]-2-pyridyl]cyclopropanecarboxylic acid (550.2) | 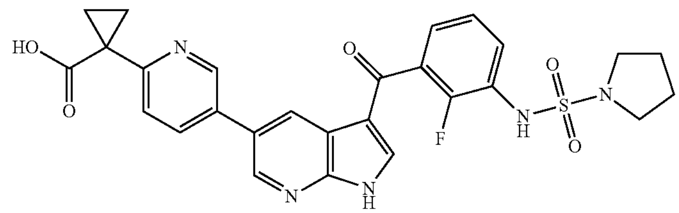 [SMILES: O=C(c1cccc(NS(=O)(=O)N2CCCC2)c1F)c1c[nH]c2ncc(-c3ccc(C4(C(=O)O)CC4)nc3)cc12] |
| P-0157 | 1-[4-[3-[2-fluoro-3-(pyrrolidin-1-ylsulfonylamino)benzoyl]-1H-pyrrolo[2,3-b]pyridin-5-yl]phenyl]cyclopropanecarboxamide (548.2) | 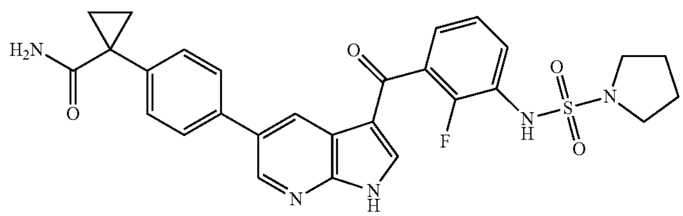 [SMILES: NC(=O)C1(c2ccc(-c3cnc4[nH]cc(C(=O)c5cccc(NS(=O)(=O)N6CCCC6)c5F)c4c3)cc2)CC1] |
| P-0158 | 1-[4-[3-[2-fluoro-3-(pyrrolidin-1-ylsulfonylamino)benzoyl]-1H-pyrrolo[2,3-b]pyridin-5-yl]phenyl]cyclopropanecarboxylic acid (548.2) | 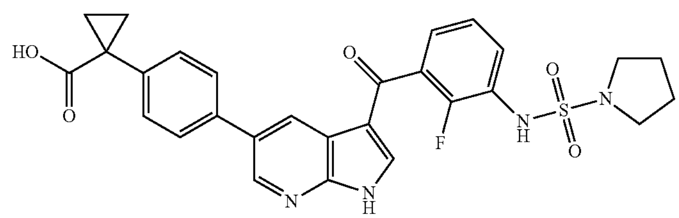 [SMILES: O=C(c1cccc(NS(=O)(=O)N2CCCC2)c1F)c1c[nH]c2ncc(-c3ccc(C4(C(=O)O)CC4)cc3)cc12] |
| P-0159 | 3-[3-(dimethylsulfamoylamino)-2-fluoro-benzoyl]-5-(5-methoxypyrazin-2-yl)-1H-pyrrolo[2,3-b]pyridine (471.1) | 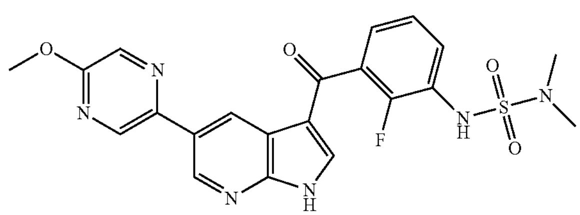 |
| P-0160 | 5-[5-(dimethylamino)pyrazin-2-yl]-3-[3-(dimethylsulfamoylamino)-2-fluoro-benzoyl]-1H-pyrrolo[2,3-b]pyridine (484.2) | 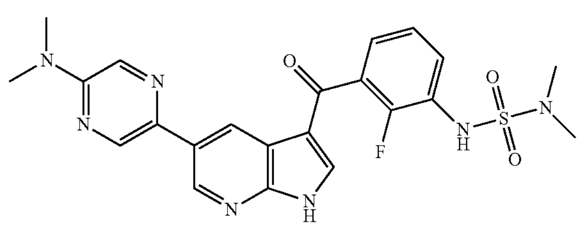 |

TABLE 3-continued

| Compound No. | Name (MS(ESI) [M + H⁺]⁺) | Structure |
|---|---|---|
| P-0161 | 3-[3-(dimethylsulfamoylamino)-2-fluoro-benzoyl]-5-(6-methoxypyridazin-3-yl)-1H-pyrrolo[2,3-b]pyridine (471.1) | 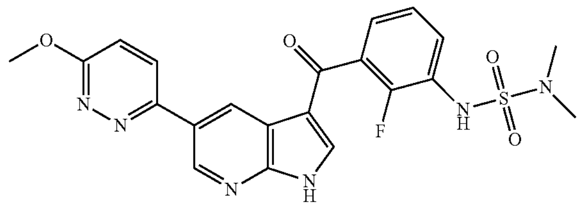 |
| P-0162 | 4-[5-[3-[3-[[ethyl(methyl)sulfamoyl]amino]-2-fluoro-benzoyl]-1H-pyrrolo[2,3-b]pyridin-5-yl]pyrimidin-2-yl]morpholine (540.2) | 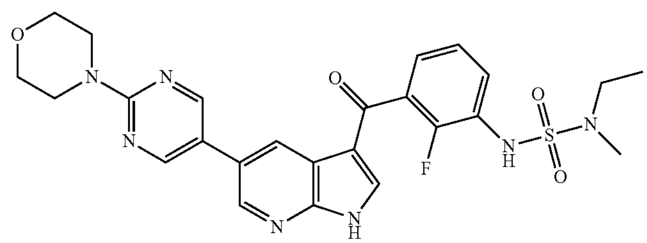 [SMILES: CCN(C)S(=O)(=O)Nc1cccc(C(=O)c2c[nH]c3ncc(-c4cnc(N5CCOCC5)nc4)cc23)c1F] |
| P-0163 | 5-chloro-3-[2-fluoro-3-[[(4-fluorophenyl)-methyl-sulfamoyl]amino]benzoyl]-1H-pyrrolo[2,3-b]pyridine (477.1) | 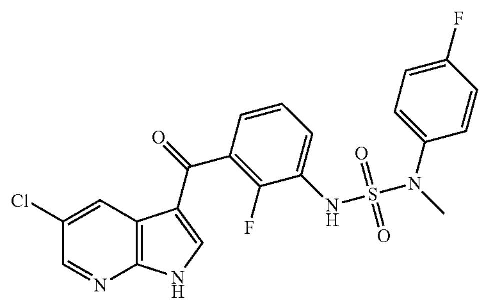 [SMILES: CN(c1ccc(F)cc1)S(=O)(=O)Nc1cccc(C(=O)c2c[nH]c3ncc(Cl)cc23)c1F] |
| P-0164 | 3-[3-[[ethyl(methyl)sulfamoyl]amino]-2-fluoro-benzoyl]-5-(1-methylpyrrol-3-yl)-1H-pyrrolo[2,3-b]pyridine (442.1) | 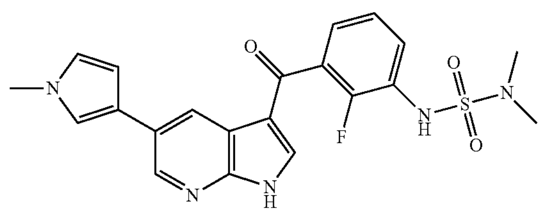 |
| P-0165 | 3-[2-fluoro-3-[[methyl(propyl)sulfamoyl]amino]benzoyl]-5-(1-methylpyrazol-4-yl)-1H-pyrrolo[2,3-b]pyridine (471.2) | 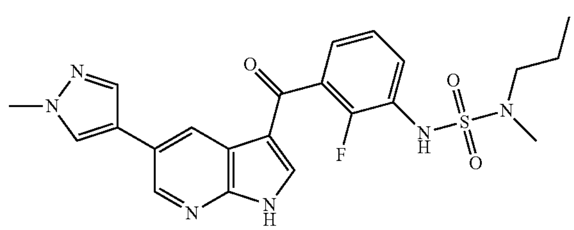 [SMILES: CCCN(C)S(=O)(=O)Nc1cccc(C(=O)c2c[nH]c3ncc(-c4cnn(C)c4)cc23)c1F] |
| P-0166 | 5-[3-[3-[[ethyl(methyl)sulfamoyl]amino]-2-fluoro-benzoyl]-1H-pyrrolo[2,3-b]pyridin-5-yl]thiazole (460.1) | 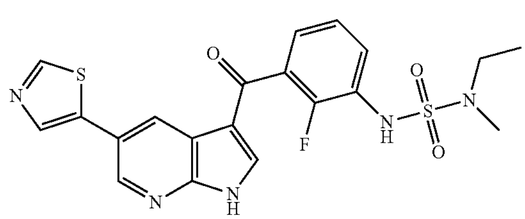 [SMILES: CCN(C)S(=O)(=O)Nc1cccc(C(=O)c2c[nH]c3ncc(-c4cncs4)cc23)c1F] |

TABLE 3-continued

| Compound No. | Name (MS(ESI) [M + H+]+) | Structure |
|---|---|---|
| P-0167 | 3-[3-[[ethyl(methyl)sulfamoyl]amino]-2-fluoro-benzoyl]-5-(1-methylimidazol-4-yl)-1H-pyrrolo[2,3-b]pyridine (457.1) | 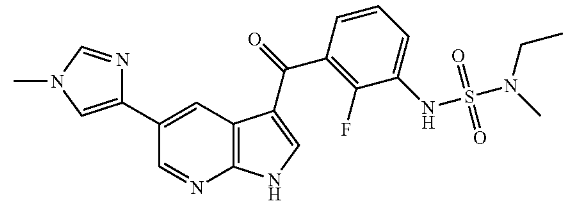 [SMILES: CCN(C)S(=O)(=O)Nc1cccc(C(=O)c2c[nH]c3ncc(-c4cn(C)cn4)cc23)c1F] |
| P-0168 | 4-[3-[3-[[ethyl(methyl)sulfamoyl]amino]-2-fluoro-benzoyl]-1H-pyrrolo[2,3-b]pyridin-5-yl]oxazole (444.1) | 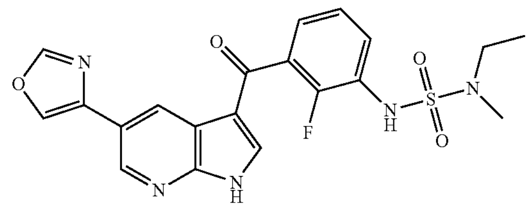 [SMILES: CCN(C)S(=O)(=O)Nc1cccc(C(=O)c2c[nH]c3ncc(-c4cocn4)cc23)c1F] |
| P-0169 | [2,6-difluoro-3-(phenylsulfamoylamino)phenyl]-[5-(2-methoxypyrimidin-5-yl)-1H-pyrrolo[2,3-b]pyridin-3-yl]methanone (537.1) | 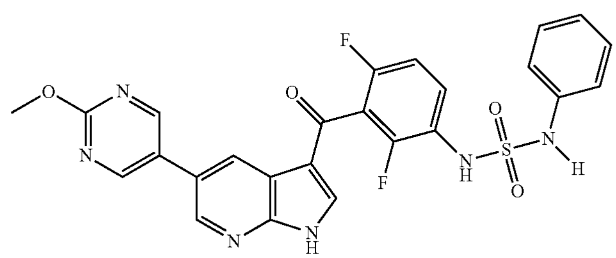 [SMILES: COc1ncc(-c2cnc3[nH]cc(C(=O)c4c(F)ccc(NS(=O)(=O)Nc5ccccc5)c4F)c3c2)cn1] |
| P-0170 | 3-[2,6-difluoro-3-[[methyl(phenyl)sulfamoyl]amino]benzoyl]-5-(2-methoxypyrimidin-5-yl)-1H-pyrrolo[2,3-b]pyridine (551.1) | 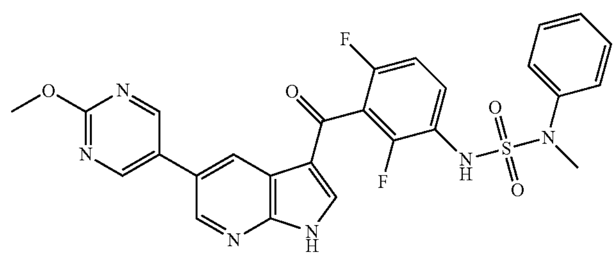 [SMILES: COc1ncc(-c2cnc3[nH]cc(C(=O)c4c(F)ccc(NS(=O)(=O)N(C)c5ccccc5)c4F)c3c2)cn1] |
| P-0171 | [2,6-difluoro-3-(3-pyridylsulfamoylamino)phenyl]-[5-(2-methoxypyrimidin-5-yl)-1H-pyrrolo[2,3-b]pyridin-3-yl]methanone (538.1) | 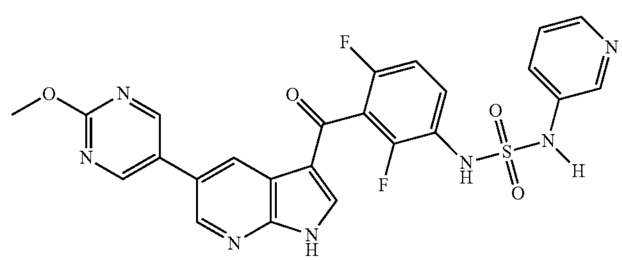 |
| P-0172 | 3-[2,6-difluoro-3-[[methyl(3-pyridyl)sulfamoyl]amino]benzoyl]-5-(2-methoxypyrimidin-5-yl)-1H-pyrrolo[2,3-b]pyridine (552.1) | 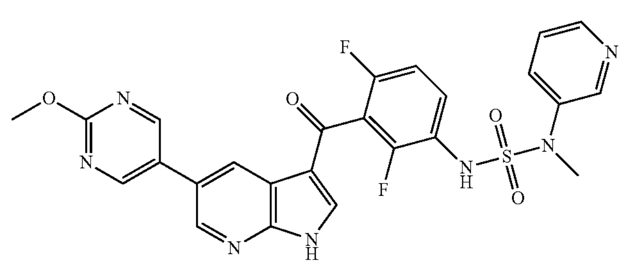 [SMILES: COc1ncc(-c2cnc3[nH]cc(C(=O)c4c(F)ccc(NS(=O)(=O)N(C)c5cccnc5)c4F)c3c2)cn1] |

TABLE 3-continued

| Compound No. | Name (MS(ESI) [M + H⁺]⁺) | Structure |
|---|---|---|
| P-0173 | [2,6-difluoro-3-(thiazol-5-ylsulfamoylamino)phenyl]-[5-(2-methoxypyrimidin-5-yl)-1H-pyrrolo[2,3-b]pyridin-3-yl]methanone (544.1) | 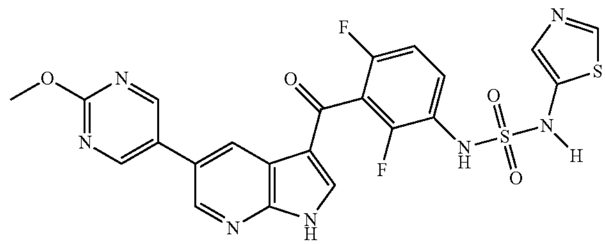 [SMILES: COc1ncc(-c2cnc3[nH]cc(C(=O)c4c(F)ccc(NS(=O)(=O)Nc5cncs5)c4F)c3c2)cn1] |
| P-0174 | 5-[[2,4-difluoro-3-[5-(2-methoxypyrimidin-5-yl)-1H-pyrrolo[2,3-b]pyridine-3-carbonyl]phenyl]sulfamoyl-methyl-amino]thiazole (558.1) | 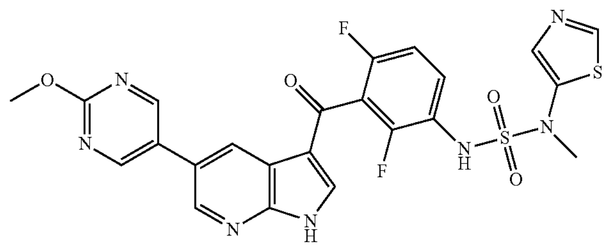 [SMILES: COc1ncc(-c2cnc3[nH]cc(C(=O)c4c(F)ccc(NS(=O)(=O)N(C)c5cncs5)c4F)c3c2)cn1] |
| P-0175 | [3-(cyclopentylsulfamoylamino)-2,6-difluoro-phenyl]-[5-(2-methoxypyrimidin-5-yl)-1H-pyrrolo[2,3-b]pyridin-3-yl]methanone (529.1) | 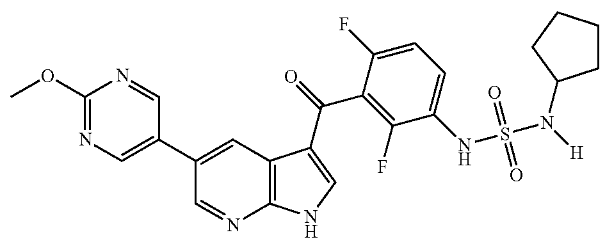 |
| P-0176 | 3-[3-[[cyclopentyl(methyl)sulfamoyl]amino]-2,6-difluoro-benzoyl]-5-(2-methoxypyrimidin-5-yl)-1H-pyrrolo[2,3-b]pyridine (543.2) | 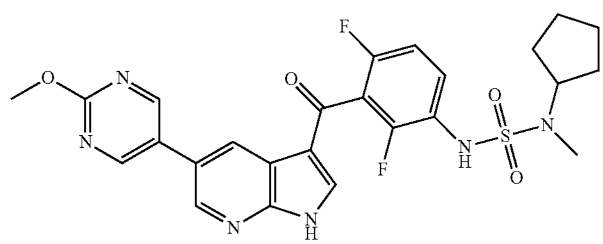 [SMILES: COc1ncc(-c2cnc3[nH]cc(C(=O)c4c(F)ccc(NS(=O)(=O)NC5CCCC5)c4F)c3c2)cn1] |
| P-0177 | [3-(cyclopropylsulfamoylamino)-2,6-difluoro-phenyl]-[5-(2-methoxypyrimidin-5-yl)-1H-pyrrolo[2,3-b]pyridin-3-yl]methanone (501.1) | 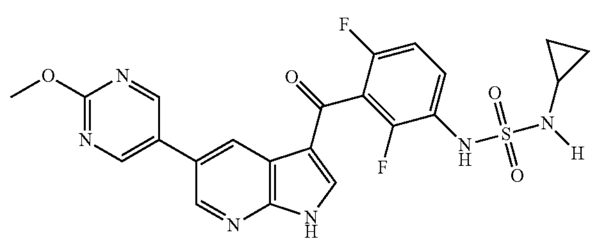 [SMILES: COc1ncc(-c2cnc3[nH]cc(C(=O)c4c(F)ccc(NS(=O)(=O)NC5CC5)c4F)c3c2)cn1] |
| P-0178 | [2,6-difluoro-3-(tetrahydropyran-4-ylsulfamoylamino)phenyl]-[5-(2-methoxypyrimidin-5-yl)-1H-pyrrolo[2,3-b]pyridin-3-yl]methanone (545.1) | 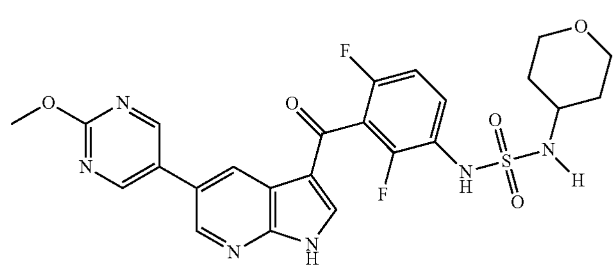 [SMILES: COc1ncc(-c2cnc3[nH]cc(C(=O)c4c(F)ccc(NS(=O)(=O)NC5CCOCC5)c4F)c3c2)cn1] |

TABLE 3-continued

| Compound No. | Name (MS(ESI) [M + H⁺]⁺) | Structure |
|---|---|---|
| P-0179 | 3-[2,6-difluoro-3-[[methyl(tetrahydropyran-4-yl)sulfamoyl]amino]benzoyl]-5-(2-methoxypyrimidin-5-yl)-1H-pyrrolo[2,3-b]pyridine (559.1) | 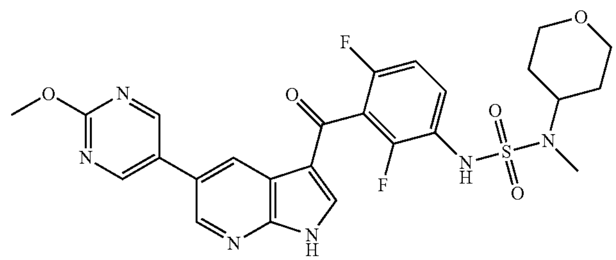 [SMILES: COc1ncc(-c2cnc3[nH]cc(C(=O)c4c(F)ccc(NS(=O)(=O)N(C)C5CCOCC5)c4F)c3c2)cn1] |
| P-0180 | 3-[2,6-difluoro-3-[[2-fluoroethyl(methyl)sulfamoyl]amino]benzoyl]-5-(2-methoxypyrimidin-5-yl)-1H-pyrrolo[2,3-b]pyridine (521.1) | 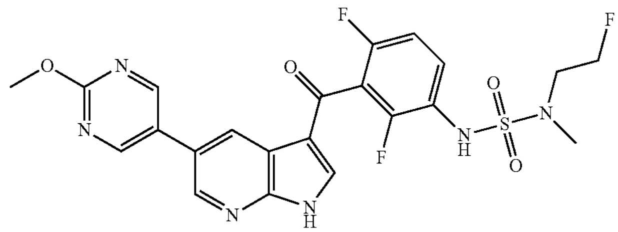 [SMILES: COc1ncc(-c2cnc3[nH]cc(C(=O)c4c(F)ccc(NS(=O)(=O)N(C)CCF)c4F)c3c2)cn1] |
| P-0181 | 3-[2,6-difluoro-3-[[methyl(2,2,2-trifluoroethyl)sulfamoyl]amino]benzoyl]-5-(2-methoxypyrimidin-5-yl)-1H-pyrrolo[2,3-b]pyridine (556.1) | 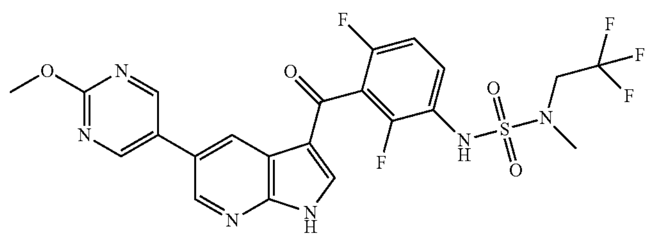 [SMILES: COc1ncc(-c2cnc3[nH]cc(C(=O)c4c(F)ccc(NS(=O)(=O)N(C)CC(F)(F)F)c4F)c3c2)cn1] |
| P-0182 | 3-[2,6-difluoro-3-[[3-fluoropropyl(methyl)sulfamoyl]amino]benzoyl]-5-(2-methoxypyrimidin-5-yl)-1H-pyrrolo[2,3-b]pyridine (534.1) | 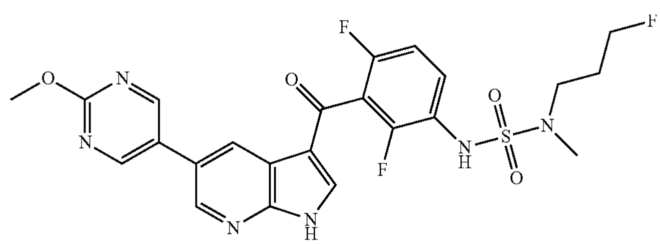 [SMILES: COc1ncc(-c2cnc3[nH]cc(C(=O)c4c(F)ccc(NS(=O)(=O)N(C)CCCF)c4F)c3c2)cn1] |
| P-0183 | 5-chloro-3-[2,6-difluoro-3-[[2-methoxyethyl(methyl)sulfamoyl]amino]benzoyl]-1H-pyrrolo[2,3-b]pyridine (458.1) | 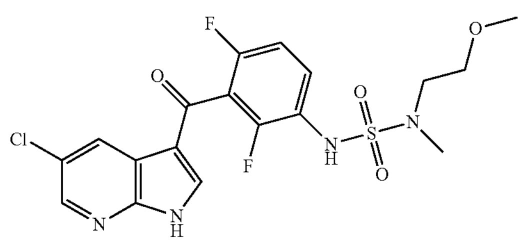 [SMILES: COCCN(C)S(=O)(=O)Nc1ccc(F)c(C(=O)c2c[nH]c3ncc(Cl)cc23)c1F] |
| P-0184 | 5-chloro-3-[2,6-difluoro-3-[[3-fluoropropyl(methyl)sulfamoyl]amino]benzoyl]-1H-pyrrolo[2,3-b]pyridine (561.1) | 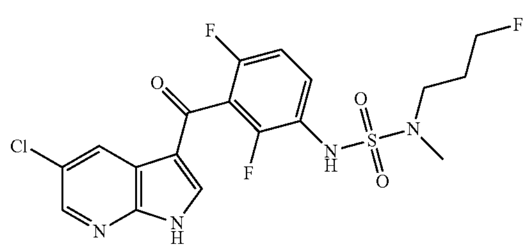 [SMILES: CN(CCCF)S(=O)(=O)Nc1ccc(F)c(C(=O)c2c[nH]c3ncc(Cl)cc23)c1F] |

TABLE 3-continued

| Compound No. | Name (MS(ESI) [M + H⁺]⁺) |
|---|---|
| P-0185 | 3-[2,6-difluoro-3-[[3-fluoropropyl(methyl)sulfamoyl]amino]benzoyl]-5-(2-isopropylpyrimidin-5-yl)-1H-pyrrolo[2,3-b]pyridine (547.2) |
| P-0186 | 3-[2,6-difluoro-3-[[[1-(methoxymethyl)cyclopropyl]-methyl-sulfamoyl]amino]benzoyl]-5-(2-isopropylpyrimidin-5-yl)-1H-pyrrolo[2,3-b]pyridine (571.2) |
| P-0187 | 5-chloro-3-[2,6-difluoro-3-[[[1-(methoxymethyl)cyclopropyl]-methyl-sulfamoyl]amino]benzoyl]-1H-pyrrolo[2,3-b]pyridine (485.1) |
| P-0188 | 5-chloro-3-[3-[[2-cyclopropylethyl(methyl)sulfamoyl]amino]-2,6-difluoro-benzoyl]-1H-pyrrolo[2,3-b]pyridine (469.1) |
| P-0189 | 3-[3-[[2-cyclopropylethyl(methyl)sulfamoyl]amino]-2,6-difluoro-benzoyl]-5-(2-isopropylpyrimidin-5-yl)-1H-pyrrolo[2,3-b]pyridine (555.2) |
| P-0190 | 5-chloro-3-[2,6-difluoro-3-[[[1-(hydroxymethyl)cyclopropyl]methyl-methyl-sulfamoyl]amino]benzoyl]-1H-pyrrolo[2,3-b]pyridine (485.1) |

TABLE 3-continued

| Compound No. | Name (MS(ESI) [M + H+]+) | Structure |
|---|---|---|
| P-0191 | methyl 1-[[[3-(5-chloro-1H-pyrrolo[2,3-b]pyridine-3-carbonyl)-2,4-difluoro-phenyl]sulfamoyl-methyl-amino]methyl]cyclopropanecarboxylate (513.1) | 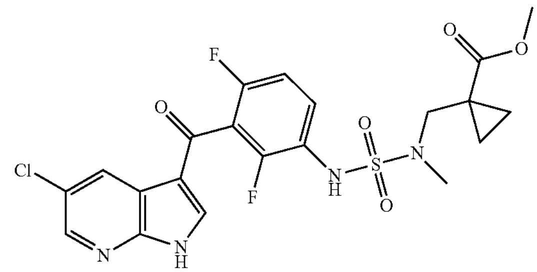 [SMILES: COC(=O)C1(CN(C)S(=O)(=O)Nc2ccc(F)c(C(=O)c3c[nH]c4ncc(Cl)cc34)c2F)CC1] |
| P-0192 | 5-chloro-3-[3-[[2-cyanoethyl(methyl)sulfamoyl]amino]-2,6-difluoro-benzoyl]-1H-pyrrolo[2,3-b]pyridine (454.0) | 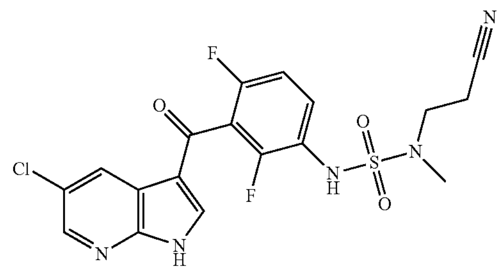 [SMILES: CN(CCC#N)S(=O)(=O)Nc1ccc(F)c(C(=O)c2c[nH]c3ncc(Cl)cc23)c1F] |
| P-0193 | (5-chloro-1H-pyrrolo[2,3-b]pyridin-3-yl)-[2,6-difluoro-3-(3-methoxypropylsulfamoylamino)phenyl] methanone (459.1) | 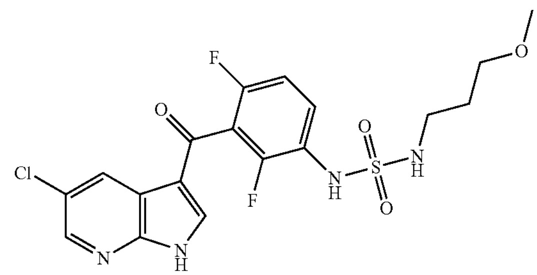 [SMILES: COCCCNS(=O)(=O)Nc1ccc(F)c(C(=O)c2c[nH]c3ncc(Cl)cc23)c1F] |
| P-0194 | N-[3-(5-chloro-1H-pyrrolo[2,3-b]pyridine-3-carbonyl)-2,4-difluoro-phenyl]-4-methyl-piperazine-1-sulfonamide (470.1) | 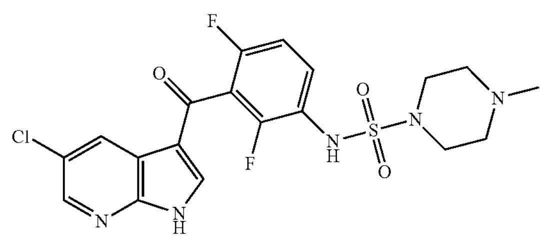 [SMILES: CN1CCN(S(=O)(=O)Nc2ccc(F)c(C(=O)c3c[nH]c4ncc(Cl)cc34)c2F)CC1] |
| P-0195 | 5-chloro-3-[2,6-difluoro-3-[[(2-hydroxy-2-methyl-propyl)-methyl-sulfamoyl]amino]benzoyl]-1H-pyrrolo[2,3-b]pyridine (473.1) | 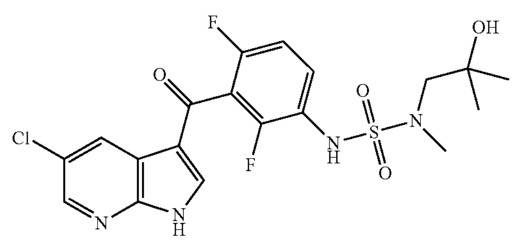 [SMILES: CN(CC(C)(C)O)S(=O)(=O)Nc1ccc(F)c(C(=O)c2c[nH]c3ncc(Cl)cc23)c1F] |
| P-0196 | 5-chloro-3-[2,6-difluoro-3-[[(2-hydroxy-1,1-dimethyl-ethyl)-methyl-sulfamoyl]amino]benzoyl]-1H-pyrrolo[2,3-b]pyridine (473.1) | 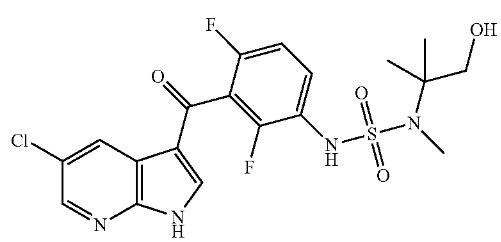 [SMILES: CN(C(C)(C)CO)S(=O)(=O)Nc1ccc(F)c(C(=O)c2c[nH]c3ncc(Cl)cc23)c1F] |

TABLE 3-continued

| Compound No. | Name (MS(ESI) [M + H⁺]⁺) | Structure |
|---|---|---|
| P-0197 | N-[3-[5-(2-cyclopropylpyrimidin-5-yl)-1H-pyrrolo[2,3-b]pyridine-3-carbonyl]-2,4-difluoro-phenyl]azetidine-1-sulfonamide (511.1) | 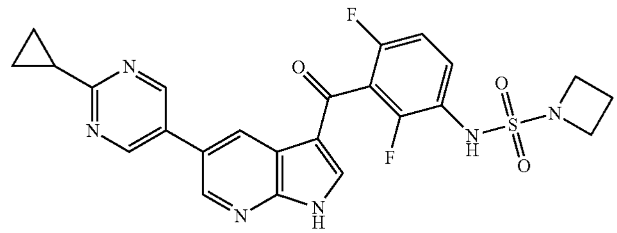 [SMILES: O=C(c1c(F)ccc(NS(=O)(=O)N2CCC2)c1F)c1c[nH]c2ncc(-c3cnc(C4CC4)nc3)cc12] |
| P-0198 | N-[3-[5-(2-cyclopropylpyrimidin-5-yl)-1H-pyrrolo[2,3-b]pyridine-3-carbonyl]-2,4-difluoro-phenyl]-3-fluoro-azetidine-1-sulfonamide (529.1) | 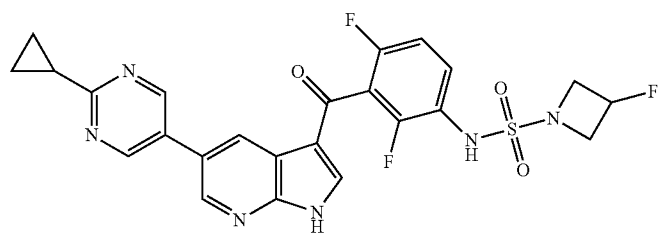 [SMILES: O=C(c1c(F)ccc(NS(=O)(=O)N2CC(F)C2)c1F)c1c[nH]c2ncc(-c3cnc(C4CC4)nc3)cc12] |
| P-0199 | 5-(2-cyclopropylpyrimidin-5-yl)-3-[2,6-difluoro-3-[[methyl(oxetan-3-yl)sulfamoyl]amino]benzoyl]-1H-pyrrolo[2,3-b]pyridine (541.1) | 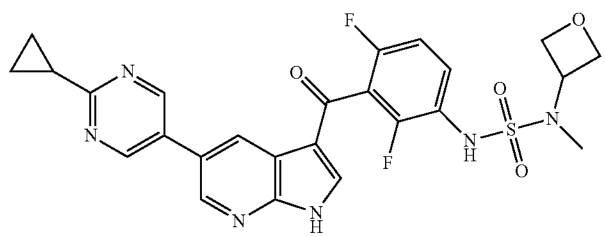 [SMILES: CN(C1COC1)S(=O)(=O)Nc1ccc(F)c(C(=O)c2c[nH]c3ncc(-c4cnc(C5CC5)nc4)cc23)c1F] |
| P-0200 | 3-[3-[[cyclobutyl(methyl)sulfamoyl]amino]-2,6-difluoro-benzoyl]-5-(2-cyclopropylpyrimidin-5-yl)-1H-pyrrolo[2,3-b]pyridine (539.2) | 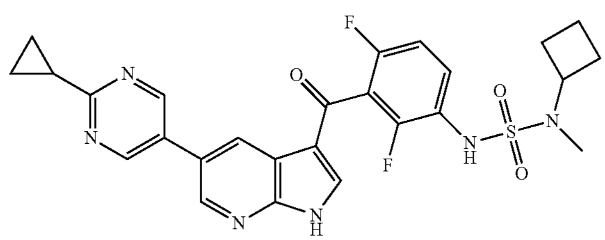 [SMILES: CN(C1CCC1)S(=O)(=O)Nc1ccc(F)c(C(=O)c2c[nH]c3ncc(-c4cnc(C5CC5)nc4)cc23)c1F] |
| P-0201 | 5-chloro-3-[2,6-difluoro-3-[[methyl(tetrahydrofuran-3-yl)sulfamoyl]amino]benzoyl]-1H-pyrrolo[2,3-b]pyridine (471.1) | 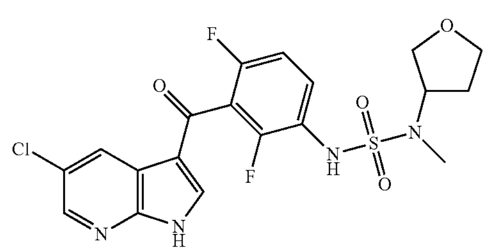 [SMILES: CN(C1CCOC1)S(=O)(=O)Nc1ccc(F)c(C(=O)c2c[nH]c3ncc(Cl)cc23)c1F] |
| P-0202 | N-[3-(5-chloro-1H-pyrrolo[2,3-b]pyridine-3-carbonyl)-2,4-difluoro-phenyl]-3-methoxy-pyrrolidine-1-sulfonamide (471.1) | 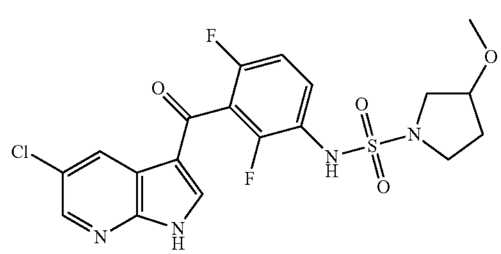 [SMILES: COC1CCN(S(=O)(=O)Nc2ccc(F)c(C(=O)c3c[nH]c4ncc(Cl)cc34)c2F)C1] |

TABLE 3-continued

| Compound No. | Name (MS(ESI) [M + H⁺]⁺) | Structure |
|---|---|---|
| P-0203 | N-[3-(5-chloro-1H-pyrrolo[2,3-b]pyridine-3-carbonyl)-2,4-difluoro-phenyl]-3-(methylamino)pyrrolidine-1-sulfonamide (470.1) | 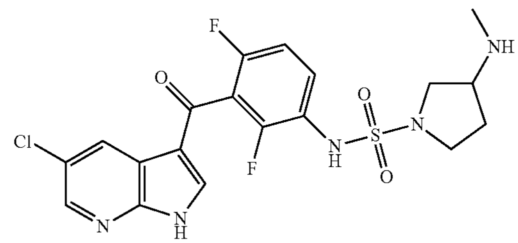 [SMILES: CNC1CCN(S(=O)(=O)Nc2ccc(F)c(C(=O)c3c[nH]c4ncc(Cl)cc34)c2F)C1] |
| P-0204 | N-[3-(5-chloro-1H-pyrrolo[2,3-b]pyridine-3-carbonyl)-2,4-difluoro-phenyl]-3-(dimethylamino)pyrrolidine-1-sulfonamide (484.1) | 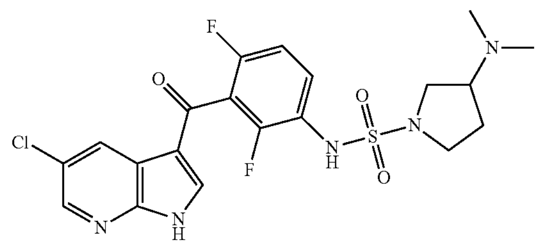 [SMILES: CN(C)C1CCN(S(=O)(=O)Nc2ccc(F)c(C(=O)c3c[nH]c4ncc(Cl)cc34)c2F)C1] |
| P-0205 | N-[3-[5-[6-(1-cyanocyclopropyl)-3-pyridyl]-1H-pyrrolo[2,3-b]pyridine-3-carbonyl]-2,4-difluoro-phenyl]pyrrolidine-1-sulfonamide (549.1) | 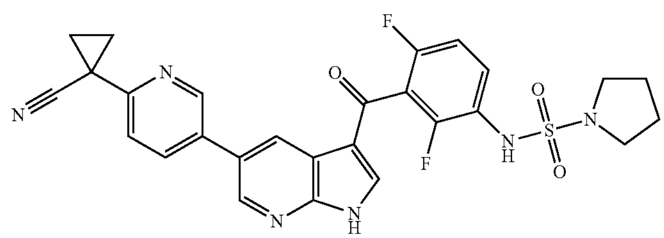 [SMILES: N#CC1(c2ccc(-c3cnc4[nH]cc(C(=O)c5c(F)ccc(NS(=O)(=O)N6CCCC6)c5F)c4c3)cn2)CC1] |
| P-0206 | 1-[5-[3-[2,6-difluoro-3-(pyrrolidin-1-ylsulfonylamino)benzoyl]-1H-pyrrolo[2,3-b]pyridin-5-yl]-2-pyridyl]cyclopropanecarboxamide (567.2) | 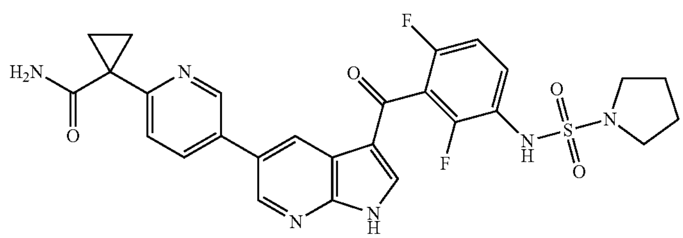 [SMILES: NC(=O)C1(c2ccc(-c3cnc4[nH]cc(C(=O)c5c(F)ccc(NS(=O)(=O)N6CCCC6)c5F)c4c3)cn2)CC1] |
| P-0207 | 1-[5-[3-[2,6-difluoro-3-(pyrrolidin-1-ylsulfonylamino)benzoyl]-1H-pyrrolo[2,3-b]pyridin-5-yl]-2-pyridyl]cyclopropanecarboxylic acid (568.1) | 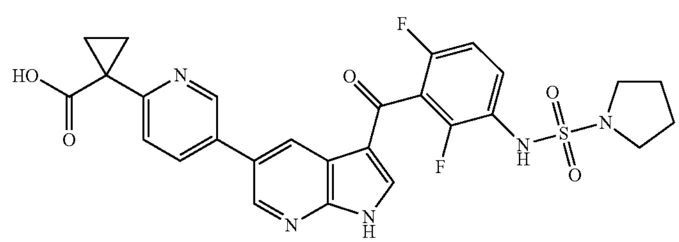 [SMILES: O=C(c1c(F)ccc(NS(=O)(=O)N2CCCC2)c1F)c1c[nH]c2ncc(-c3ccc(C4(C(=O)O)CC4)nc3)cc12] |
| P-0208 | 1-[4-[3-[2,6-difluoro-3-(pyrrolidin-1-ylsulfonylamino)benzoyl]-1H-pyrrolo[2,3-b]pyridin-5-yl]phenyl]cyclopropanecarboxamide (566.2) | 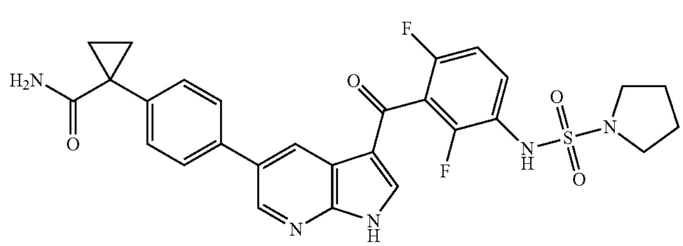 [SMILES: NC(=O)C1(c2ccc(-c3cnc4[nH]cc(C(=O)c5c(F)ccc(NS(=O)(=O)N6CCCC6)c5F)c4c3)cc2)CC1] |

TABLE 3-continued

| Compound No. | Name (MS(ESI) [M + H⁺]⁺) | Structure |
|---|---|---|
| P-0209 | 1-[4-[3-[2,6-difluoro-3-(pyrrolidin-1-ylsulfonylamino)benzoyl]-1H-pyrrolo[2,3-b]pyridin-5-yl]phenyl]cyclopropanecarboxylic acid (567.1) | 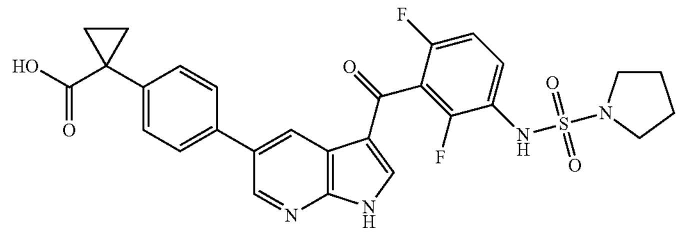 [SMILES: O=C(c1c(F)ccc(NS(=O)(=O)N2CCCC2)c1F)c1c[nH]c2ncc(-c3ccc(C4(C(=O)O)CC4)cc3)cc12] |
| P-0210 | 3-[3-(dimethylsulfamoylamino)-2,6-difluoro-benzoyl]-5-(5-methoxypyrazin-2-yl)-1H-pyrrolo[2,3-b]pyridine (489.1) | 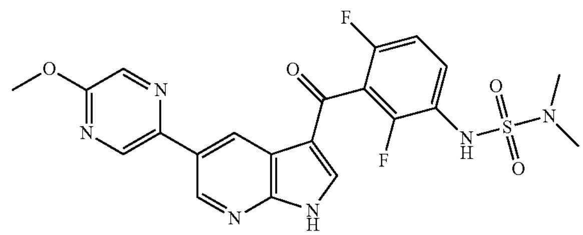 |
| P-0211 | 5-[5-(dimethylamino)pyrazin-2-yl]-3-[3-(dimethylsulfamoylainino)-2,6-difluoro-benzoyl]-1H-pyrrolo[2,3-b]pyridine (502.1) | 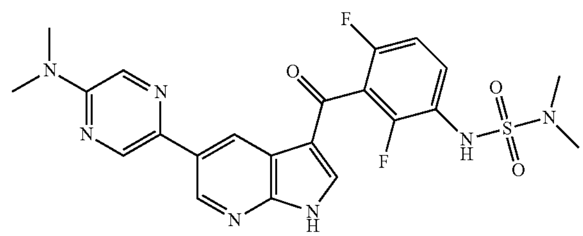 |
| P-0212 | 3-[3-(dimethylsulfamoylamino)-2,6-difluoro-benzoyl]-5-(6-methoxypyridazin-3-yl)-1H-pyrrolo[2,3-b]pyridine (489.1) | 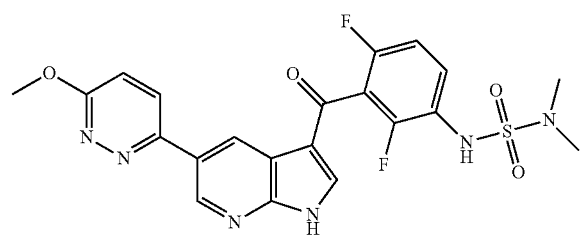 |
| P-0213 | 4-[5-[3-[3-[[ethyl(methyl)sulfamoyl]amino]-2,6-difluoro-benzoyl]-1H-pyrrolo[2,3-b]pyridin-5-yl]pyrimidin-2-yl]morpholine (558.2) | 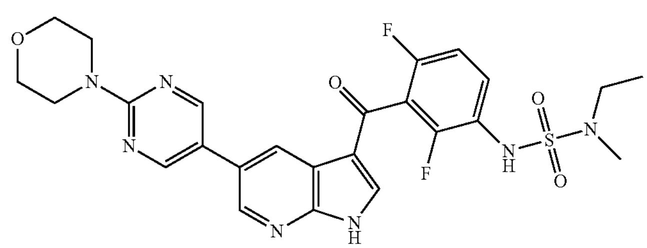 [SMILES: CCN(C)S(=O)(=O)Nc1ccc(F)c(C(=O)c2c[nH]c3ncc(-c4cnc(N5CCOCC5)nc4)cc23)c1F] |
| P-0214 | 5-chloro-3-[2,6-difluoro-3-[[(4-fluorophenyl)-methyl-sulfamoyl]amino]benzoyl]-1H-pyrrolo[2,3-b]pyridine (495.0) | 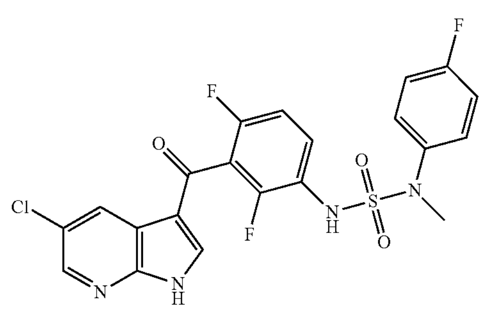 [SMILES: CN(c1ccc(F)cc1)S(=O)(=O)Nc1ccc(F)c(C(=O)c2c[nH]c3ncc(Cl)cc23)c1F] |

TABLE 3-continued

| Compound No. | Name (MS(ESI) [M + H⁺]⁺) | Structure |
|---|---|---|
| P-0215 | 3-[3-(dimethylsulfamoylamino)-2,6-difluoro-benzoyl]-5-(1-methylpyrrol-3-yl)-1H-pyrrolo[2,3-b]pyridine (460.1) | 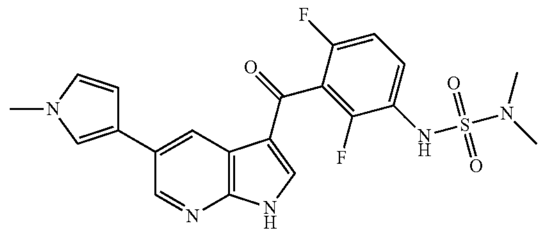 |
| P-0216 | 3-[2,6-difluoro-3-[[methyl(propyl)sulfamoyl]amino]benzoyl]-5-(1-methylpyrazol-4-yl)-1H-pyrrolo[2,3-b]pyridine (489.1) | 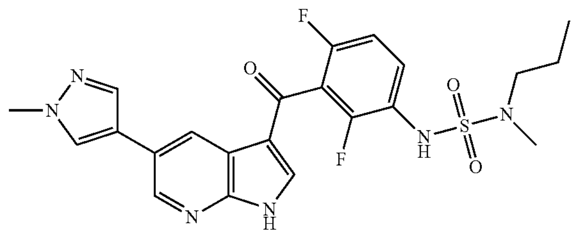 [SMILES: CCCN(C)S(=O)(=O)Nc1ccc(F)c(C(=O)c2c[nH]c3ncc(-c4cnn(C)c4)cc23)c1F] |
| P-0217 | 5-[3-[3-[[ethyl(methyl)sulfamoyl]amino]-2,6-difluoro-benzoyl]-1H-pyrrolo[2,3-b]pyridin-5-yl]thiazole (478.1) | 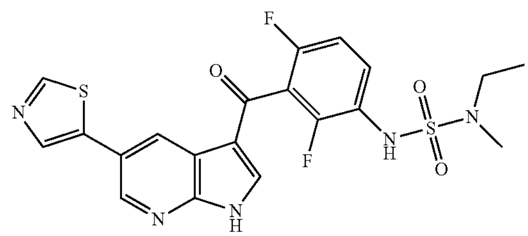 [SMILES: CCN(C)S(=O)(=O)Nc1ccc(F)c(C(=O)c2c[nH]c3ncc(-c4cncs4)cc23)c1F] |
| P-0218 | 3-[3-[[ethyl(methyl)sulfamoyl]amino]-2,6-difluoro-benzoyl]-5-(1-methylimidazol-4-yl)-1H-pyrrolo[2,3-b]pyridine (475.1) | 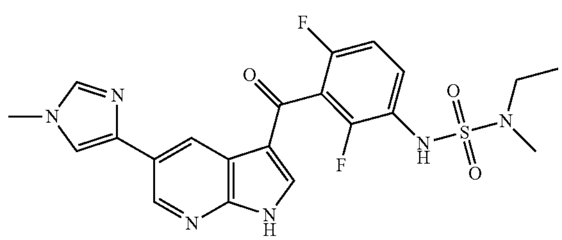 [SMILES: CCN(C)S(=O)(=O)Nc1ccc(F)c(C(=O)c2c[nH]c3ncc(-c4cn(C)cn4)cc23)c1F] |
| P-0219 | 4-[3-[3-[[ethyl(methyl)sulfamoyl]amino]-2,6-difluoro-benzoyl]-1H-pyrrolo[2,3-b]pyridin-5-yl]oxazole (462.1) | 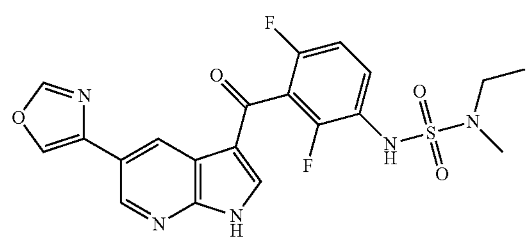 [SMILES: CCN(C)S(=O)(=O)Nc1ccc(F)c(C(=O)c2c[nH]c3ncc(-c4cocn4)cc23)c1F] |
| P-0220 | 6-[3-[3-(dimethylsulfamoylamino)-2,6-difluoro-benzoyl]-1H-pyrrolo[2,3-b]pyridin-5-yl]quinoline (508.1) | 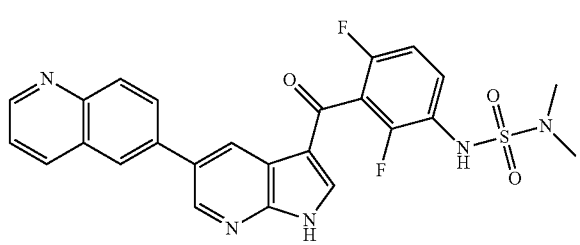 [SMILES: CN(C)S(=O)(=O)Nc1ccc(F)c(C(=O)c2c[nH]c3ncc(-c4ccc5ncccc5c4)cc23)c1F] |

TABLE 3-continued
| Compound No. | Name (MS(ESI) [M + H⁺]⁺) | Structure |
|---|---|---|
| P-0221 | 6-[3-[3-(dimethylsulfamoylamino)-2,6-difluoro-benzoyl]-1H-pyrrolo[2,3-b]pyridin-5-yl]quinazoline (509.1) | 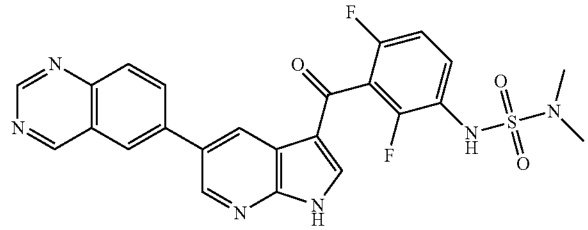 [SMILES: CN(C)S(=O)(=O)Nc1ccc(F)c(C(=O)c2c[nH]c3ncc(-c4ccc5ncncc5c4)cc23)c1F] |
| P-0222 | 6-[3-[3-(dimethylsulfamoylamino)-2,6-difluoro-benzoyl]-1H-pyrrolo[2,3-b]pyridin-5-yl]-1,3-benzothiazole (514.1) | 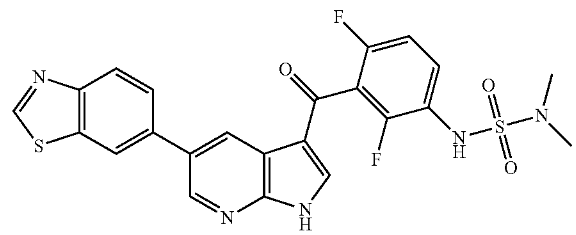 [SMILES: CN(C)S(=O)(=O)Nc1ccc(F)c(C(=O)c2c[nH]c3ncc(-c4ccc5ncsc5c4)cc23)c1F] |
Example 3: Preparation of 5-cyano-3-[3-[[ethyl(methyl)sulfamoyl]amino]-2,6-difluoro-benzoyl]-1H-pyrrolo[2,3-b]pyridine (P-0017)
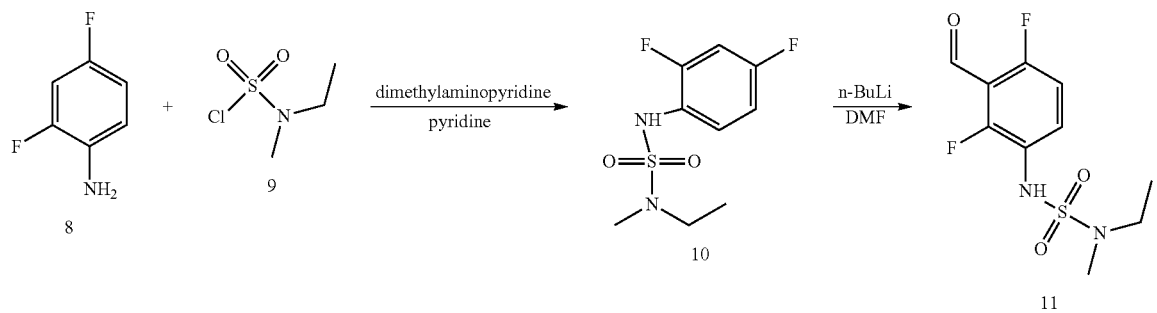
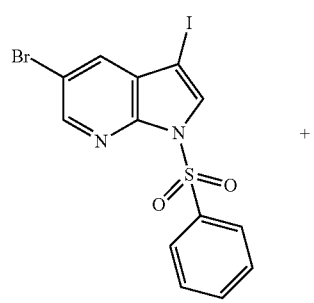

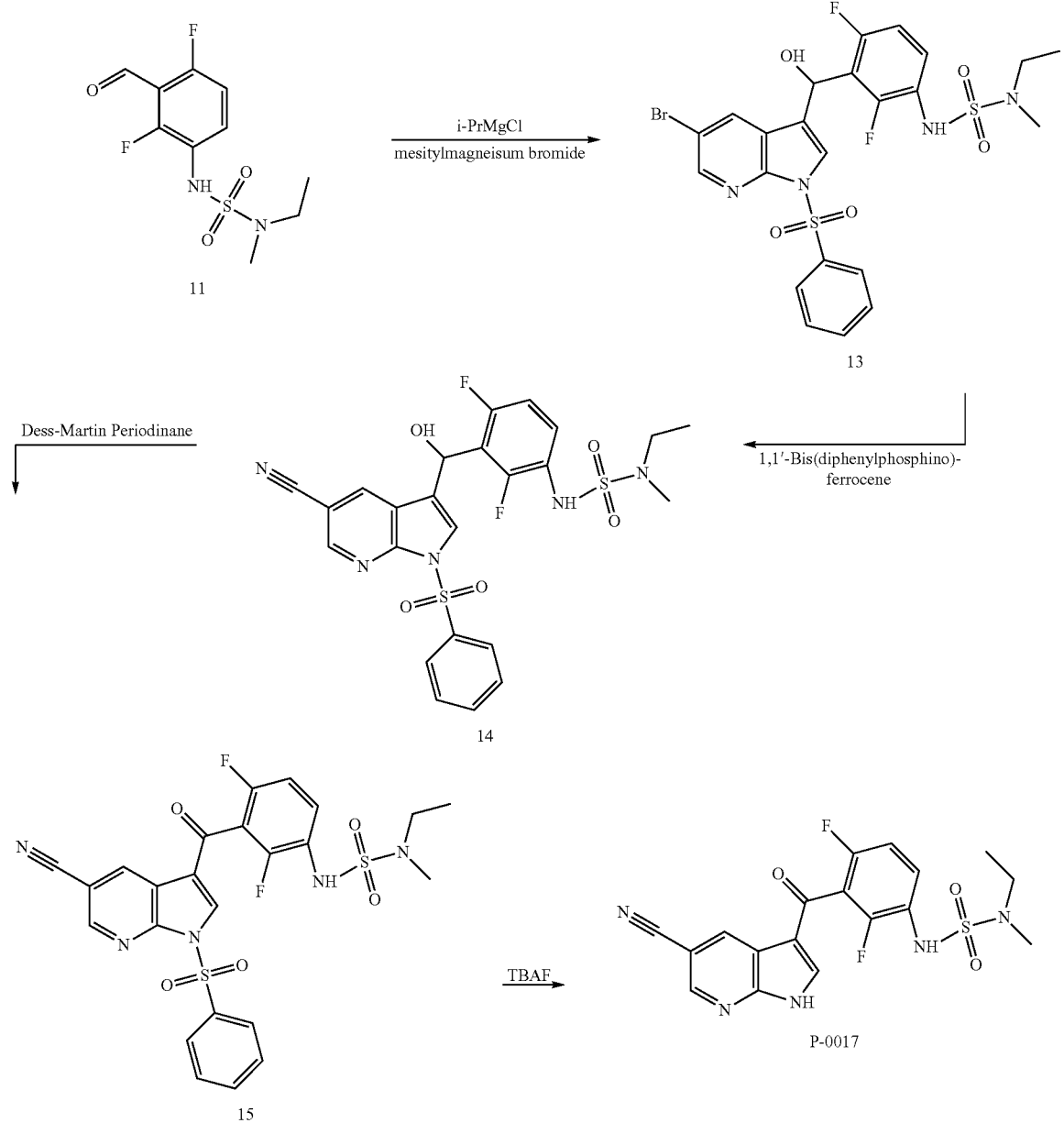

Synthesis of 1-[(ethyl(methyl)sulfamoyl)amino]-2,4-difluoro-benzene (10): To a solution of 2,4-Difluoroaniline (2.21 g, 17.13 mmol) in dichloroethane (10 mL) were added 4-Dimethylaminopyridine (0.1 g, 0.82 mmol), N-ethyl-N-methyl-sulfamoyl chloride (2.7 g, 17.13 mmol) and pyridine (2 g, 25.28 mmol). The mixture was stirred at room temperature overnight. The resulting mixture was poured into an aqueous potassium carbonate solution, and extracted with ethyl acetate (EtOAc). The organic layer was washed with brine, dried over sodium sulfate and filtered. The filtrate was concentrated and purified by silica gel column chromatography using 20% to 100% ethyl acetate in hexane as an eluent to give the desired product (10, 3.08 g, 71.8% yield). MS (ESI) [M+H$^+$]$^+$=250.8. $^1$H NMR spectrum is consistent with the structure of the compound.

Synthesis of 1-[(ethyl(methyl)sulfamoyl)amino]-2,4-difluoro-3-formyl-benzene (11): To a mixture of 1-[(ethyl (methyl)sulfamoyl)amino]-2,4-difluoro-benzene (10, 3.08 g, 12.31 mmol) in tetrahydrofuran (THF) (25.0 mL) under an atmosphere of nitrogen at −78° C. was added 2.5M n-butyl-lithium (n-BuLi) in THF (5 mL). The colorless reaction mixture was kept at −78° C. for one hour and 2.5M n-BuLi in THF (5.4 ml) was added to the reaction mixture. The reaction was kept at −78° C. for 1 hr and added N,N-Dimethylformamide (DMF) (1.8 mL, 23.25 mmol). The reaction mixture turned into solid. The solid reaction mixture was shaken for about 5 minutes to obtain a slurry. The reaction mixture was kept in a dry ice-acetone bath for 1 hr and was allowed to warm up to room temperature for 1 hour. The reaction mixture was poured into an aqueous ammonia chloride solution and extracted with ethyl acetate. The organic layer was washed with brine, dried over sodium sulfate, concentrated and purified with silica gel column chromatography using 30% to 100% ethyl acetate in hexane as an eluent to give the desired product (11, 1.10 g, 32.1% yield). MS (ESI) [M+H$^+$]$^+$=278.8. $^1$H NMR spectrum is consistent with the structure of the compound.

Synthesis of 1-(benzenesulfonyl)-5-bromo-3-iodo-pyrrolo[2,3-b]pyridine (12)

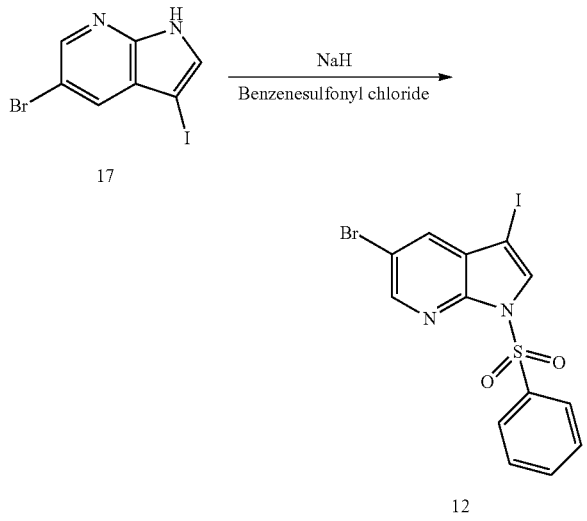

To a solution of 5-bromo-3-iodo-1H-pyrrolo[2,3-b]pyridine (2.7 g, 8.36 mmol) in DMF (30.0 mL) was added sodium hydride (60%, 0.37 g, 9.2 mmol) at room temperature. After 10 minutes, benzenesulfonyl chloride (1.13 ml, 8.78 mmol) was added to and the reaction mixture was stirred at room temperature for 3 hours. The reaction mixture was poured in to water and extracted with ethyl acetate. The organic layer was dried over anhydrous sodium sulfate and filtered. The filtrate was concentrated, filtered and washed with ethyl acetate to obtain the desired product 12 as a white solid (2.70 g). The mother liquid was purified with silica gel column chromatography using 20% to 100% ethyl acetate in hexane as an eluent to give addition product (0.90 g). The combined yield is 93.0%. MS (ESI) [M+H$^+$]$^+$=464.1. $^1$H NMR spectrum is consistent with the structure of the compound.

Synthesis of 1-(benzenesulfonyl)-5-bromo-3-[[3-[[ethyl(methyl)sulfamoyl]amino]-2,6-difluoro-phenyl]-hydroxy-methyl]pyrrolo[2,3-b]pyridine (13)

Step 1: To a solution of 1-[[ethyl(methyl)sulfamoyl]amino]-2,4-difluoro-3-formyl-benzene (11, 0.76 g, 2.73 mmol) in THF (5 mL), under nitrogen at −78° C., was added 1M mesitylmagnesium bromide in THF (2.8 ml). The reaction solution was stirred for 40 minutes.

Step 2: To 1-(benzenesulfonyl)-5-bromo-3-iodo-pyrrolo[2,3-b]pyridine (17, 1.76 g, 3.79 mmol) in THF (10 mL), under an atmosphere of nitrogen at −40° C., was added a solution of i-PrMgCl (2.0 M in THF, 1.9 mL). The reaction mixture was allowed to warm up to 5° C. in 1 hour. The reaction mixture was cooled to −40° C. and added the reaction solution from step 1. The resulting reaction mixture was allowed to warm to room temperature in 1 hr, poured into water and extracted with ethyl acetate. The organic layer was washed with brine, dried over sodium sulfate, concentrated and purified by silica gel column chromatography using 20% to 100% ethyl acetate in hexane as an eluent to give the desired product (13, 1.10 g, 65.4%). MS (ESI) [M+H$^+$]$^+$=614.7 and 616.7. $^1$H NMR spectrum is consistent with the structure of the compound.

Synthesis of 1-(benzenesulfonyl)-5-cyano-3-[[3-[[ethyl(methyl)sulfamoyl]amino]-2,6-difluoro-phenyl]-hydroxy-methyl]pyrrolo[2,3-b]pyridine (14): To 1-(benzenesulfonyl)-5-bromo-3-[[3-[[ethyl(methyl)sulfamoyl]amino]-2,6-difluoro-phenyl]-hydroxy-methyl]pyrrolo[2,3-b]pyridine (13, 500 mg, 0.81 mmol) were added zinc cyanide (0.05 ml, 0.77 mmol), zinc, tris(dibenzylideneacetone)dipalladium(0) (90 mg, 0.09 mmol), 1,1'-Bis(diphenylphosphino)ferrocene (90 mg, 0.16 mmol), and DMF (10 ml) under nitrogen. The reaction mixture was heated to 120° C. overnight. The resulting reaction mixture was poured into an aqueous potassium carbonate solution and extracted with ethyl acetate. The organic layer was washed with brine, dried over sodium sulfate and filtered. The filtrate was concentrated and purified with silica gel column chromatography using 20% to 100% ethyl acetate in hexane as an eluent to give the desired product (14, 0.20 g, 43.8% yield). MS (ESI) [M+H$^+$]$^+$=562.0. $^1$H NMR spectrum is consistent with the structure of the compound.

Synthesis of 1-(benzenesulfonyl)-5-cyano-3-[3-[[ethyl(methyl)sulfamoyl]amino]-2,6-difluoro-benzoyl]pyrrolo[2,3-b]pyridine (15): To 1-(benzenesulfonyl)-5-cyano-3-[[3-[[ethyl(methyl)sulfamoyl]amino]-2,6-difluoro-phenyl]-hydroxy-methyl]pyrrolo[2,3-b]pyridine (14, 0.2 g, 0.36 mmol) in methylene chloride (10 mL) was added Dess-Martin Periodinane (0.18 g, 0.43 mmol). The reaction mixture was stirred at room temperature for 20 minutes. The reaction mixture was concentrated, and purified by silica gel column chromatography using 25% to 100% ethyl acetate in hexane as an eluent to give the desired product (15, 170 mg, 85.3% yield). MS (ESI) [M+H$^+$]$^+$=560.5. $^1$H NMR spectrum is consistent with the structure of the compound.

Synthesis of 5-cyano-3-[3-[[ethyl(methyl)sulfamoyl]amino]-2,6-difluoro-benzoyl]-1H-pyrrolo[2,3-b]pyridine (P-0017): To 1-(benzenesulfonyl)-5-cyano-3-[3-[[ethyl(methyl)sulfamoyl]amino]-2,6-difluoro-benzoyl]pyrrolo[2,3-b]pyridine (15, 0.17 g, 0.3 mmol) in THF (10 mL) was added tetra-n-butylammonium fluoride (TBAF) (0.19 g, 0.61 mmol). The reaction mixture was stirred at room temperature overnight. The resulting reaction mixture was poured into an aqueous ammonia chloride solution and extracted with ethyl acetate. The organic layer was washed with brine, dried over sodium sulfate and filtered. The filtrate was concentrated and purified by silica gel column chromatography using 2% to 10% methanol in methylene chloride as an eluent to give the product (P-0017, 74.5 mg, 58.5% yield). MS (ESI) [M+H$^+$]$^+$=420.1. $^1$H NMR spectrum is consistent with the structure of the compound.

The following compounds were prepared according to the protocols set forth in Example 3 and Scheme 3.
5-chloro-3-[3-[[ethyl(methyl)sulfamoyl]amino]-2,6-difluoro-benzoyl]-1H-pyrrolo[2,3-b]pyridine (P-0012),
N-[2,4-difluoro-3-(5-fluoro-4-iodo-1H-pyrrolo[2,3-b]pyridine-3-carbonyl)phenyl]pyrrolidine-1-sulfonamide (P-0013),
5-chloro-3-[3-[[ethyl(methyl)sulfamoyl]amino]-2-fluoro-benzoyl]-1H-pyrrolo[2,3-b]pyridine (P-0018),
N-[2-fluoro-3-(5-methyl-1H-pyrrolo[2,3-b]pyridine-3-carbonyl)phenyl]pyrrolidine-1-sulfonamide (P-0023),
5-bromo-3-[3-[[ethyl(methyl)sulfamoyl]amino]-2-fluoro-benzoyl]-1H-pyrrolo[2,3-b]pyridine (P-0038),
5-cyano-3-[3-[[ethyl(methyl)sulfamoyl]amino]-2-fluoro-benzoyl]-1H-pyrrolo[2,3-b]pyridine (P-0039).

The following table provides structures of certain compounds of the present invention and observed mass. ¹H NMR spectra were consistent with the structures of the compounds.

| Compounds | MS(ESI) [M + H⁺]⁺ observed |
|---|---|
| P-0012 | 428.9 |
| P-0015 | 551.1 |
| P-0018 | 410.9 |
| P-0023 | 402.9 |
| P-0038 | 455.0 |
| P-0039 | 454.9 and 456.9 |

Example 4: Preparation of N-[3-[4-(cyclopropylmethylamino)-5-fluoro-1H-pyrrolo[2,3-b]pyridine-3-carbonyl]-2,4-difluoro-phenyl]pyrrolidine-1-sulfonamide (P-0016)

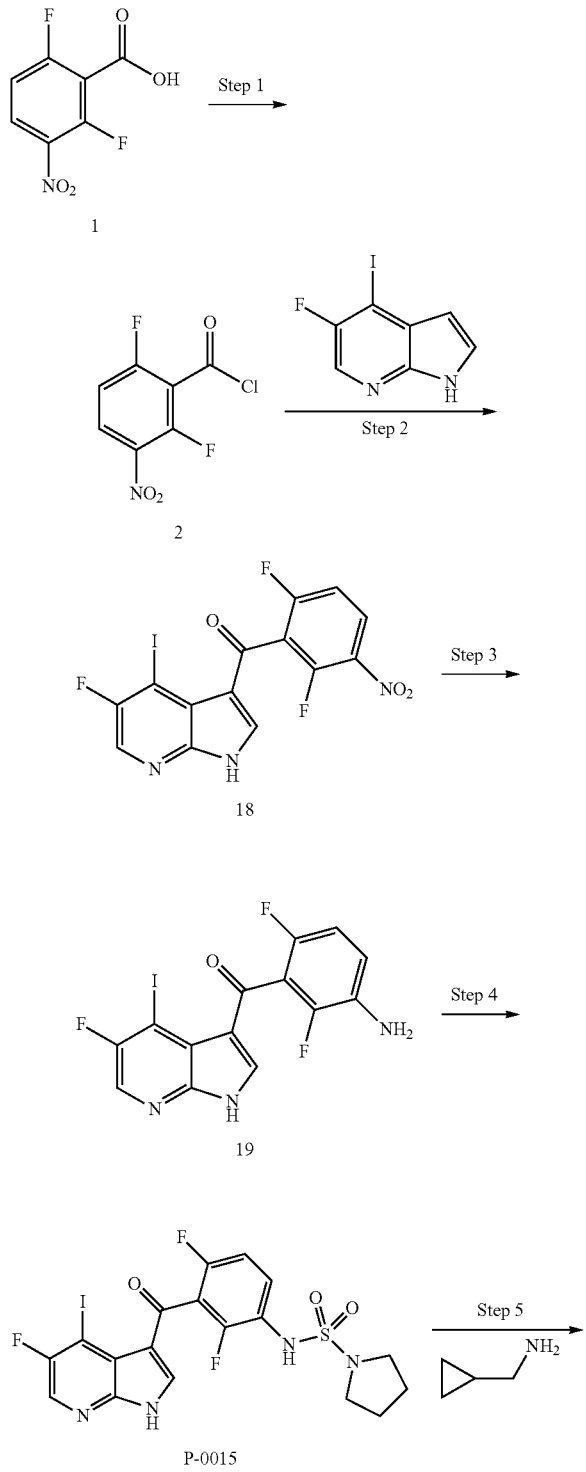

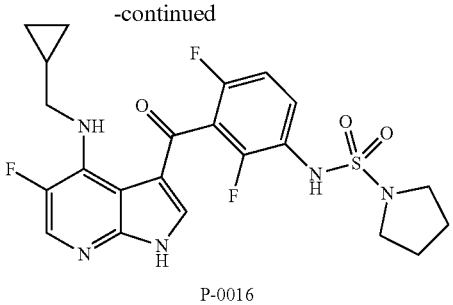

P-0016

Step 1-Synthesis of 2,6-difluoro-3-nitrobenzoyl chloride (2): In a round flask, 2,6-difluoro-3-nitrobenzoic acid (5.5 g, 0.03 mol) was added Thionyl chloride (20 mL, 0.27 mol) and N,N-Dimethylformamide (100 μl, 0.001 mol). The reaction mixture was placed in an oil bath at 80° C. for 4 hrs. All volatiles were removed and the residue was stripped from toluene twice and dried in high vacuo to give a yellow oily liquid (2, 5.95 g, 99%). It will be used as is.

Step 2—Synthesis of (2,6-difluoro-3-nitro-phenyl)-(5-fluoro-4-iodo-1H-pyrrolo[2,3-b]pyridin-3-yl)methanone (18): In a Vial, 5-fluoro-4-iodo-1H-pyrrolo[2,3-b]pyridine (450 mg, 1.72 mmol) was cooled in an ice-water bath and added Trifluoromethanesulfonic acid (1.52 ml, 17.17 mmol). The reaction was stirred in an ice-water bath for 5 minutes and followed by adding 2,6-difluoro-3-nitrobenzoyl chloride (2, 500 mg, 2.26 mmol). The resulting reaction mixture was stirred at an ice-water bath for 20 min and warmed up to room temperature. After 24 hrs at room temperature, the reaction mixture was quenched with 5 mL of methanol and stirred at r.t. for 1 hr. The mixture was poured to the saturated NaHCO$_3$ aqueous solution and extracted with EtOAc. The organic layer was washed with water and brine, dried with MgSO$_4$. The volatiles were removed under vacuo. The residue was suspended in acetonitrile and sonicated for 45 mins. The precipitate material was collected by filtration and washed with acetonitrile. The desired product (18, 532 mg, 69%) was a tan solid. MS (ESI) [M+H$^+$]$^+$=447.8.

Step 3—Preparation of (3-amino-2,6-difluoro-phenyl)-(5-fluoro-4-iodo-1H-pyrrolo[2,3-b]pyridin-3-yl)methanone (19): In a round flask, (2,6-difluoro-3-nitro-phenyl)-(5-fluoro-4-iodo-1H-pyrrolo[2,3-b]pyridin-3-yl)methanone (0.53 g, 0.001 mol) was added EtOH (50 ml) and TIN(II) CHLORIDE (788 mg, 4.16 mmol). The reaction mixture was heated at 50° C. for over weekend. The reaction mixture treated with 50 mL of water and 50 mL saturated sodium bicarbonate. Additional ethyl acetate (20 mL) was added and the milky suspension was treated with celite and mixed well before filtering. The filtrate was added by brine to give clear layers that were separated. The organic layer was washed with water and brine and dried with MgSO4. The volatiles were removed under vacuum. The desired product was isolated by silica gel column chromatography (EtOAc/Hexane, 0-80% gradient) as an off-white solid (19, 365 mg, 73%). MS (ESI) [M+H$^+$]$^+$=417.9.

Step 4—Preparation of N-[2,4-difluoro-3-(5-fluoro-4-iodo-1H-pyrrolo[2,3-b]pyridine-3-carbonyl)phenyl]pyrrolidine-1-sulfonamide (P-0015): In a round flask, (3-amino-2,6-difluoro-phenyl)-(5-fluoro-4-iodo-1H-pyrrolo[2,3-b]pyridin-3-yl)methanone (19, 180 mg, 0.43 mmol) was dissolved in 4 mL of THF and added PYRIDINE (106 μl, 1.29 mmol) and pyrrolidine-1-sulfonyl chloride (110 mg, 0.65 mmol). The solution was stirred at room temperature for about 90 hrs. The reaction mixture was added water and extracted with ethyl acetate. The organic layer was washed with water and brine and dried by MgSO4. The volatiles were removed under vacuum. The desired product was isolated by silica gel column chromatography (EtOAc/Hexane, 0-80% gradient) as a light yellow solid (P-0015, 99 mg, 41%). MS (ESI) [M+H$^+$]$^+$=551.1.

Step 5—Preparation of N-[3-[4-(cyclopropylmethylamino)-5-fluoro-1H-pyrrolo[2,3-b]pyridine-3-carbonyl]-2,4-difluoro-phenyl]pyrrolidine-1-sulfonamide (P-0016): To N-[2,4-difluoro-3-(5-fluoro-4-iodo-1H-pyrrolo[2,3-b]pyridine-3-carbonyl)phenyl]pyrrolidine-1-sulfonamide (95 mg, 0.17 mmol) in isopropyl alcohol (2 ml) was added cyclopropylmethanamine (0.5 mL, 49.11 mg, 0.69 mmol). The resulting solution was stirred at 90° C. overnight. The reaction mixture was concentrated in vacuo and purified by silica gel on the companion with 8 g-cartridge using EtOAc/Hexane (0-65% gradient) as an eluent. The resulting product was further purified by prep HPLC. The pure fractions were combined and were dried on a lyophilizer. The desired product was obtained as a tan solid (P-0016, 6.5 mg, 7.6% yield). MS (ESI) [M+H$^+$]$^+$=494.4. H$^1$ NMR(THF-d$_8$) spectrum is consistent with the structure of the compound.

Example 5: Synthesis of N-(2-Chloro-5-{3-[2,6-difluoro-3-(propane-1-sulfonylamino)-benzoyl]-1H-pyrrolo[2,3-b]pyridin-5-yl}-pyridin-3-yl)-benzenesulfonamide 25

N-(2-Chloro-5-{3-[2,6-difluoro-3-(propane-1-sulfonylamino)-benzoyl]-1H-pyrrolo[2,3-b]pyridin-5-yl}-pyridin-3-yl)-benzenesulfonamide 7 was prepared in six steps from 5-Bromo-1H-pyrrolo[2,3-b]pyridine 1 as shown in Scheme 1.

Scheme 5

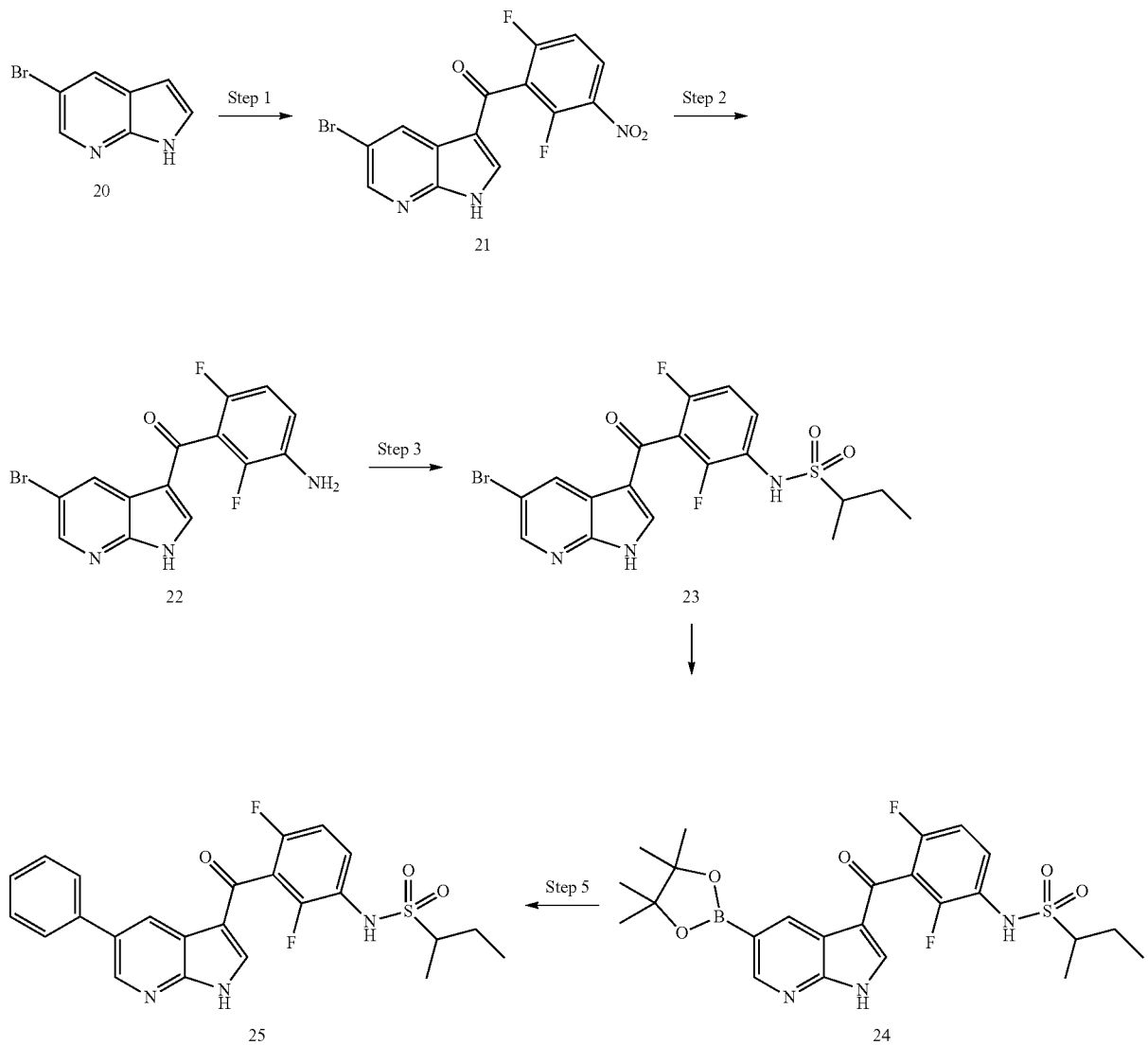

Step 1—Preparation of 2,6-Difluoro-3-nitro-phenyl)-(5-bromo-1H-pyrrolo[2,3-b]pyridin-3-yl)-methanone (21)

To 5-Bromo-1H-pyrrolo[2,3-b]pyridine (20, 0.5 g, 2 mmol) in nitromethane (11 mL) was added aluminum trichloride (1.64 g, 12 mmol). The mixture became clear instantly. The resulting solution was stirred at room temperature for 1 hour. To this mixture was then added 2,6-difluoro-3-nitro-benzoyl chloride (0.681 g, 3 mmol) in nitromethane. The reaction mixture was stirred at 45° C. overnight. The reaction was quenched with methanol. After a few minutes, some solids were crashed out. Solids were collected by filtration, and it was clean product (21, 0.58 g). Additional product was obtained from filtrate through chromatography (eluted with ethyl acetate and dichloromethane).

Preparation of 2,6-Difluoro-3-nitro-benzoyl chloride: To 2,6-Difluoro-3-nitro-benzoic acid (2 g, 1 mmol) was added thionyl chloride (0.9 mL, 12 mmol). The reaction mixture was stirred at 57° C. overnight. After removal of solvent, the residue was stripped once from toluene. This gave brown oil was checked by NMR which indicated complete conversion to the acid chloride (18 g, 99%). This material was used as is, without purification.

Step 2—Preparation of (3-Amino-2,6-difluoro-phenyl)-(5-bromo-1H-pyrrolo[2,3-b]pyridin-3-yl)-methanone (22)

To a suspension of 2,6-difluoro-3-nitro-phenyl)-(5-bromo-1H-pyrrolo[2,3-b]pyridin-3-yl)-methanone (0.123 g, 0.287 mmol) in ethyl acetate (5 mL) and tetrahydrofuran (5 mL) was added stannous chloride, dihydrate (0.223 g, 1 mmol). The reaction mixture was stirred at 60° C. for 24 hours. The reaction mixture was poured into a mixture of 25 mL of water and 25 mL of saturated sodium bicarbonate. This milky mixture was filtered through a bed of Celite, and the Celite bed was washed with some ethyl acetate. The two layers of the filtrate were separated. The organic layer were collected, washed with brine, and dried over anhydrous sodium sulfate. After removal of drying agent and solvent, the residue was purified by chromatography (eluted with ethyl acetate and dichloromethane) to provide solid product (22, 0.1 g, 87%).

Step 3—Preparation of isobutane-1-sulfonic acid [3-(5-bromo-1H-pyrrolo[2,3-b]pyridine-3-carbonyl)-2,4-difluoro-phenyl]-amide (23)

A mixture of (3-Amino-2,6-difluoro-phenyl)-(5-bromo-1H-pyrrolo[2,3-b]pyridin-3-yl)-methanone (47 mg, 0.13 mmol), isobutane-1-sulfonylchloride (62 mg, 0.4 mmol), and pyridine (0.5 mL, 6 mmol), in tetrahydrofuran (3 mL) was irradiated in microwave at 130° C. for 10 minutes. The mixture was diluted by ethyl acetate and then washed with water, brine, and dried over anhydrous sodium sulfate. After removal of drying agent and solvent, the residue was purified by chromatography (eluted with hexanes and ethyl acetate) to provide desired product (23, 24 mg, 36%).

Step 4—Preparation of isobutane-1-sulfonic acid {2,4-difluoro-3-[5-(4,4,5,5-tetramethyl-[1,3,2]dioxaborolan-2-yl)-1H-pyrrolo[2,3-b]pyridine-3-carbonyl]-phenyl}-amide (24)

To a suspension of compound 23, an appropriate amount of bis(pinacolato)diboron, and potassium acetate in anhydrous 1,4-dioxane or an appropriate solvent is added [1,1'-Bis(diphenylphosphino)ferrocene]dichloropalladium (II) (complex with dichloromethane 1:1). The suspension is heated in an oil bath for 2 to 24 hours. After cooling to room temperature, the mixture is diluted with ethyl acetate, filtered through a Celite pad, and concentrated. The residue is purification by chromatography to provide isobutane-1-sulfonic acid {2,4-difluoro-3-[5-(4,4,5,5-tetramethyl-[1,3,2]dioxaborolan-2-yl)-1H-pyrrolo[2,3-b]pyridine-3-carbonyl]-phenyl}-amide (24).

Step 5—Preparation of isobutane-1-sulfonic acid {3-[5-phenyl-]H-pyrrolo[2,3-b]pyridine-3-carbonyl]-2,4-difluoro-phenyl}-amide (25)

To a mixture of compound 24, phenyl bromide and an appropriate amount of cesium carbonate in anhydrous 1,4-dioxane or an appropriate solvent is added an appropriate amount of tetrakis(triphenylphosphine)palladium. The mixture is then heated in an oil bath for 2 to 48 hours. After cooling to room temperature, the mixture is diluted with ethyl acetate or an appropriate solvent, filtered through Celite, and concentrated. The residue is purified by chromatography to provide isobutane-1-sulfonic acid {3-[5-phenyl-1H-pyrrolo[2,3-b]pyridine-3-carbonyl]-2,4-difluoro-phenyl}-amide (25).

Example 6: Preparation of Compound 30

Compound 30 is prepared in four steps from 5-Bromo-1H-pyrrolo[2,3-b]pyridine 1 as shown in Scheme 2.

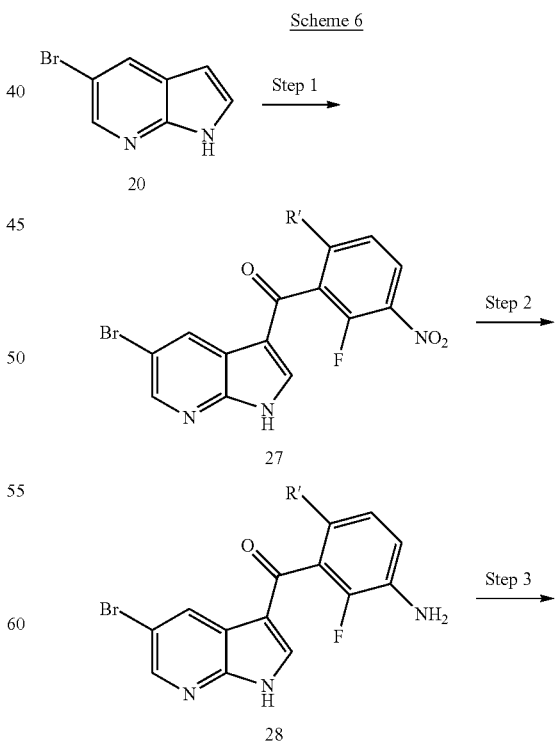

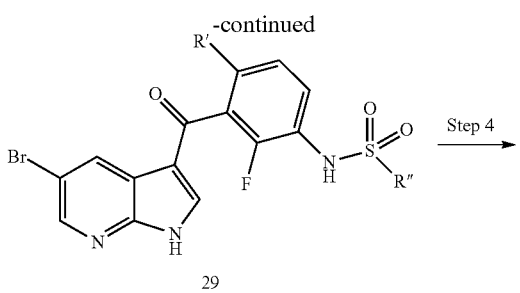

29

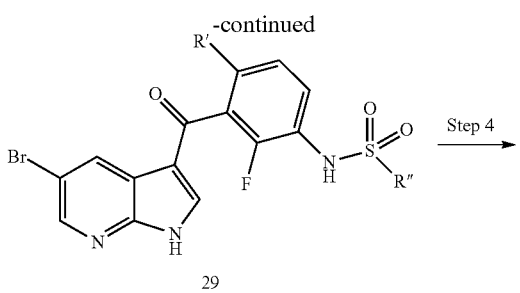

30

Step 1—Preparation of Compound 27

To 5-Bromo-1H-pyrrolo[2,3-b]pyridine (20) in nitromethane or an appropriate solvent is added an appropriate amount of aluminum trichloride. The resulting solution is stirred at room temperature for 1 to 24 hour (heated in an oil bath if necessary). To this mixture is then added appropriate amount of benzoyl chloride in nitromethane or an appropriate solvent. The reaction mixture is heated in an oil bath for 2 to 48 hours. The reaction is quenched with methanol or an appropriate solvent. Precipitate is collected by filtration, and it is purified by chromatography to provide compound 27.

Step 2—Preparation of Compound 28

To a suspension of compound 20 in an appropriate solvent is added an appropriate amount of stannous chloride. The reaction mixture is heated in an oil bath for 2 to 48 hours. The reaction mixture is poured into a mixture of water and saturated sodium bicarbonate. This milky mixture was filtered through a bed of Celite, and the Celite bed was washed with an appropriate solvent. The organic layers were collected, washed with brine, and dried over anhydrous sodium sulfate. After removal of drying agent and solvent, the residue is purified by chromatography to provide compound 28.

Step 3—Preparation of Compound 29

A mixture of compound 28, an appropriate sulfonyl chloride, and an appropriate amount of pyridine in an appropriate solvent is irradiated in microwave at over 50° C. for 10 to 60 minutes. The mixture is diluted by an appropriate solvent and then washed with water, brine, and dried over anhydrous sodium sulfate. After removal of drying agent and solvent, the residue is purified by chromatography to provide compound 29.

Step 4—Preparation of Compound 30

To a mixture of compound 29, an appropriate boronic acid or a boronic ester, and an appropriate amount of cesium carbonate in anhydrous 1,4-dioxane or an appropriate solvent is added an appropriate amount of tetrakis(triphenylphosphine)palladium. The mixture is then heated in an oil bath for 2 to 48 hours. After cooling to room temperature, the mixture is diluted with ethyl acetate or an appropriate solvent, filtered through Celite, and concentrated. The residue is purification by chromatography to provide compound 30. When boronic acid or a boronic ester is not commercially available, boronic acid or ester of compound 29 is prepared by following the procedure described at Example 1, step 4. Compound 30 is then prepared by following the abovementioned procedure from boronic acid or ester of compound 29 and an appropriate halide.

Example 7: Preparation of Compound 30

Compound 30 can also be prepared in three steps from 5-Bromo-1H-pyrrolo[2,3-b]pyridine 11 as shown in Scheme 3.

Scheme 7

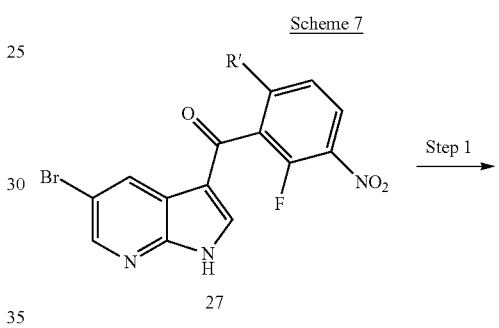

27

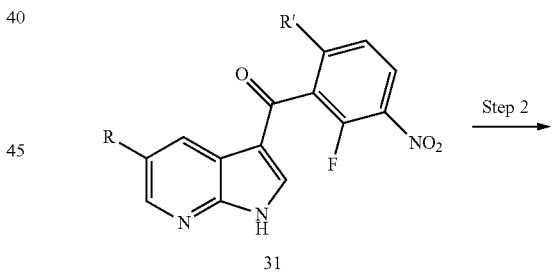

31

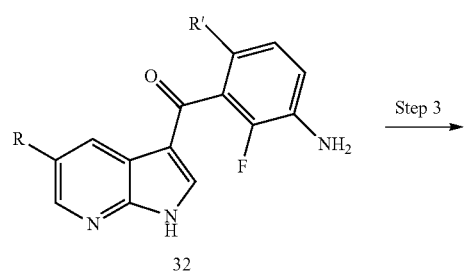

32

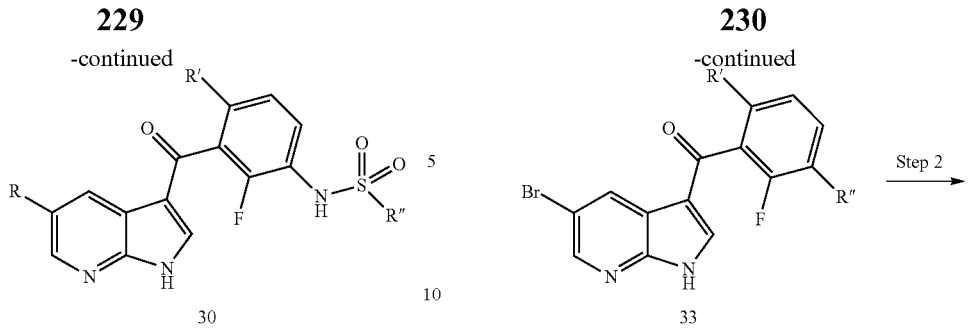

30

Step 1—Preparation of Compound 31

To a mixture of compound 27, an appropriate boronic acid or a boronic ester, and an appropriate amount of cesium carbonate in anhydrous 1,4-dioxane or an appropriate solvent is added an appropriate amount of tetrakis(triphenylphosphine)palladium. The mixture is then heated in an oil bath for 2 to 48 hours. After cooling to room temperature, the mixture is diluted with ethyl acetate or an appropriate solvent, filtered through Celite, and concentrated. The residue is purification by chromatography to provide compound 31. When boronic acid or a boronic ester is not commercially available, boronic acid or ester of compound 27 is prepared by following the procedure described at Example 1, step 4. Compound 31 is then prepared by following the abovementioned procedure from boronic acid or ester of compound 27 and an appropriate halide.

Step 2—Preparation of Compound 32

To a suspension of compound 31 in an appropriate solvent is added an appropriate amount of stannous chloride. The reaction mixture is heated in an oil bath for 2 to 48 hours. The reaction mixture is poured into a mixture of water and saturated sodium bicarbonate. This milky mixture was filtered through a bed of celite, and the celite bed was washed with an appropriate solvent. The organic layers were collected, washed with brine, and dried over anhydrous sodium sulfate. After removal of drying agent and solvent, the residue is purified by chromatography to provide compound 32.

Step 3—Preparation of Compound 30

A mixture of compound 32, an appropriate sulfonyl chloride, and an appropriate amount of pyridine in an appropriate solvent is irradiated in microwave at over 50° C. for 10 to 60 minutes. The mixture is diluted by an appropriate solvent and then washed with water, brine, and dried over anhydrous sodium sulfate. After removal of drying agent and solvent, the residue is purified by chromatography to provide compound 30.

Example 8: Preparation of Compound 34

Compound 34 is prepared in two steps from 5-Bromo-1H-pyrrolo[2,3-b]pyridine 1 as shown in Scheme 8.

Scheme 8.

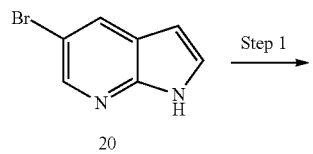

20

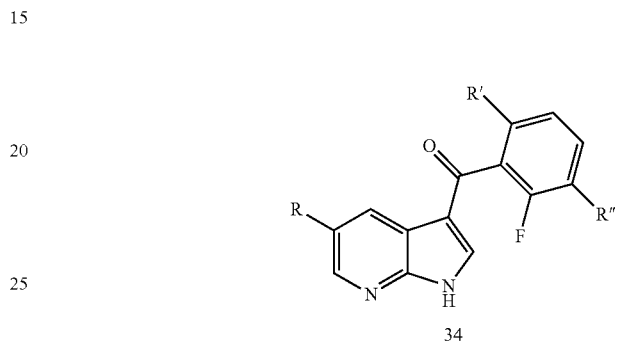

34

Step 1—Preparation of Compound 33

To 5-Bromo-1H-pyrrolo[2,3-b]pyridine (20) in nitromethane or an appropriate solvent is added appropriate amount of aluminum trichloride. The resulting solution is stirred at room temperature for 1 to 48 hour (heated in an oil bath if necessary). To this mixture is then added appropriate amount of benzoyl chloride in nitromethane or an appropriate solvent. The reaction mixture is heated in an oil bath for 2 to 48 hours. The reaction is quenched with an appropriate solvent. Precipitate is collected by filtration, and it is purified by chromatography to provide compound 33.

Step 2—Preparation of Compound 34

To a mixture of compound 33, an appropriate boronic acid or a boronic ester, and an appropriate amount of cesium carbonate in anhydrous 1,4-dioxane or an appropriate solvent is added an appropriate amount of tetrakis(triphenylphosphine)palladium. The mixture is then heated in an oil bath for 2 to 48 hours. After cooling to room temperature, the mixture is diluted with ethyl acetate or an appropriate solvent, filtered through Celite, and concentrated. The residue is purification by chromatography to provide compound 34.

When boronic acid or a boronic ester is not commercially available, boronic acid or ester of compound 33 is prepared by following the procedure described at Example 6, step 4. Compound 34 is then prepared by following the abovementioned procedure from boronic acid or ester of compound 33 and an appropriate halide.

Example 9: Preparation of 3-[3-(dimethylsulfamoylamino)-2,6-difluoro-benzoyl]-5-(5-ethoxypyrazin-2-yl)-1H-pyrrolo[2,3-b]pyridine (37)

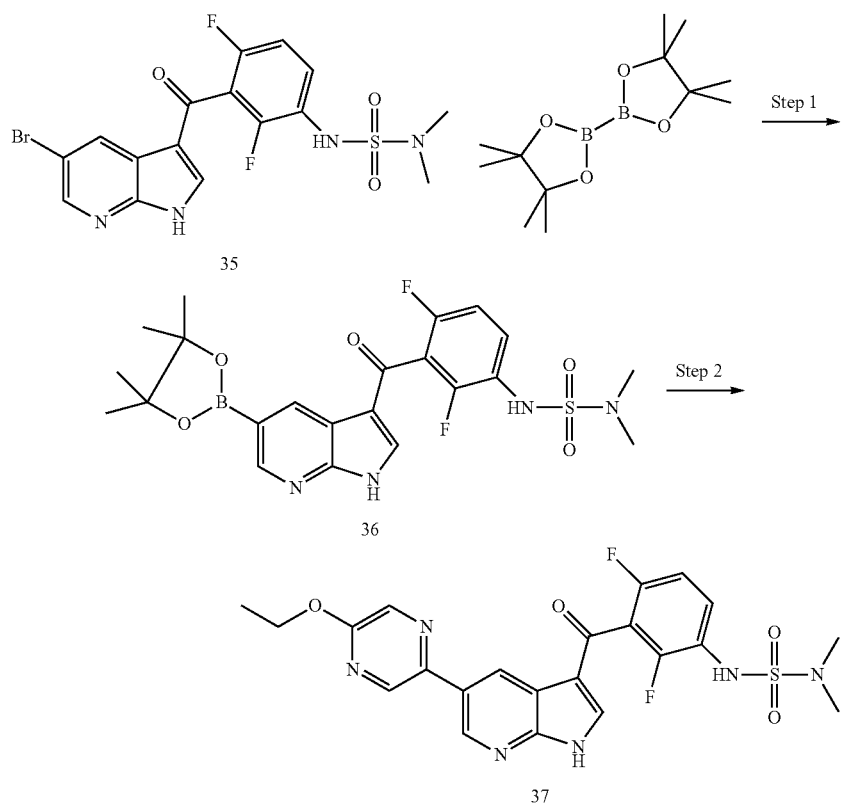

Step 1

Into a microwave vial 5-bromo-3-[3-(dimethylsulfamoylamino)-2,6-difluoro-benzoyl]-1H-pyrrolo[2,3-b]pyridine 35 (70% pure, 200 mg, 0.3 mmol) was placed with 4,4,5,5-tetramethyl-2-(4,4,5,5-tetramethyl-1,3,2-dioxaborolan-2-yl)-1,3,2-dioxaborolane (216.75 mg, 0.85 mmol) and potassium acetate (100 mg, 1.02 mmol) was added followed by 1,1'-bis(diphenylphosphino)ferrocene-palladium(II) dichloride dichloromethane complex (50 mg, 0.06 mmol). 1,4-dioxane (3 mL) was added and the mixture was irradiated in microwave reactor at 145° C. for 45 minutes. The formation of the intermediate 36 was confirmed by LCMS. MS ESI [M+H+]+=506.95 [M−H+]−=504.85.

Step 2

2-Bromo-5-ethoxypyrazine (200 mg, 0.99 mmol) in 1.5 mL of 1,4-dioxane was added into the reaction mixture, made in step 1, followed by the addition of 1,1'-bis(diphenylphosphino)ferrocene-palladium(II)dichloride dichloromethane complex (50 mg, 0.06 mmol) and 1M potassium carbonate in water (1.3 ml). The reaction was irradiated in microwave reactor at 135° C. for 10 minutes. After cooling the reaction was placed into brine and 1N HCl; the aqueous were extracted with ethyl acetate. The organic layers were combined and dried over anhydrous sodium sulfate. After removal of drying agent and solvent, the residue was purified by silica gel chromatography eluting with a gradient of ethyl acetate: hexanes (10-100%) to provide 3-[3-(dimethylsulfamoylamino)-2,6-difluoro-benzoyl]-5-(5-ethoxy-pyrazin-2-yl)-1H-pyrrolo[2,3-b]pyridine 37 (16 mg, 10.2%). ESI [M+H+]+=503.0 [M−H+]−=501.1.

Example 10: Compound Properties

While the inhibitory activity of the compounds on any Raf kinase is important to their activity in treating of disease, the compounds described herein show favorable properties that provide advantages as a pharmaceutical as well.

Assays for biochemical and cell based activity are known in the art, for example, as described in PCT publication WO 2007/002433, the disclosure of which is hereby incorporated by reference as it relates to such assays. For example, the biochemical activity $IC_{50}$ values are determined with respect to inhibition of B-Raf V600E kinase activity or p-Erk kinase activity, where inhibition of phosphorylation of a peptide substrate is measured as a function of compound concentration. Compounds to be tested are diluted in dimethyl sulfoxide to a concentration of 0.1 mM. These are serially diluted 15 μL into 30 μL of dimethyl sulfoxide seven times in 96 well plates for a total of 8 dilution points, and for each dilution point 1 μL is added to a well of an assay plate. Plates are prepared such that each well in a 384 well plate contains 1 µL of compound in 10 µL volume with 0.1 ng Raf enzyme (i.e. any of B-Raf, c-Raf-1 or B-Raf V600E, Upstate Biotechnology or prepared by methods known to one of skill in the art), 50 mM HEPES, pH 7.0, 50 mM NaCl, 2 mM $MgCl_2$, 1 mM $MnCl_2$, 0.01% Tween-20, 1 mM DTT, and 100 nM biotin-MEK1 as substrate. The reaction is started with addition of 10 µL of 200 µM ATP (i.e. final 100 µM ATP). After incubation of the kinase reaction for 45 minutes at room temperature, 5 µL/well of Stop Solution is added (25 mM Hepes pH 7.5, 100 mM EDTA, 0.01% BSA with donor beads (Streptavidin coated beads, Perkin Elmer), acceptor beads (Protein A coated, Perkin Elmer), and anti phosphor MEK1/2 antibody (CellSignal), each at final concentration 10 µg/mL). The plates are incubated for 3 hours at room temperature and read on Envision reader (Perkin Elmer). Phosphorylation of Mek1 results in binding of the anti-phosphor-MEK1/2 antibody and association of the donor and acceptor beads such that signal correlates with kinase activity. The signal vs. compound concentration is used to determine the $IC_{50}$.

Compounds are assessed in a variety of cell based assays. For example human cell lines with B-Raf V600E mutation (A375 melanoma, SKMEL3 melanoma, and COLO205 colon adenocarcinoma), as well as tumorigenic cell lines with wild-type B-RAF (SW620 colon adenocarcinoma) or with Ras mutations (SKMEL2 melanoma and IPC298 melanoma). Similar assays may be used to assess additional tumorigenic cell lines with Ras mutations, including, but not limited to, M202, M207, M243, M244, M296, S117, HCT116, HCT15, DLD1, MiaPaCa, A549, NCI-H23, NCI-H460, HOP62, MDA-MB231, Hs-578T, HL60, MOLT-4, and CCRF-CEM.

On day 1, cells are counted, then centrifuged in a conical tube for 5 minutes at 1000 rpm. The supernatant is removed and cells are re-suspended as follows:
  SW620 (ATCC catalog #CCL-27): resuspend in Leibovitz's L-15 medium, 2 mM L-glutamine, 10% fetal bovine serum to $6 \times 10^4$ cells/mL.
  A375 (ATCC catalog #CRL-1619): resuspend in Dulbecco's modified Eagle's medium, 4 mM L-glutamine, 4.5 g/L D-glucose, 10% fetal bovine serum to $6 \times 10^4$ cells/mL.
  COLO205 (ATCC catalog #CCL-222): resuspend in RPMI 1640, 2 mM L-glutamine, 1.5 g/L sodium bicarbonate, 4.5 g/L D-glucose, 10 mM HEPES, 1.0 mM sodium pyruvate, 10% fetal bovine serum to $6 \times 10^4$ cells/mL.
  SKMEL2 (ATCC catalog #HTB-68): resuspend in Minimum Eagle essential medium, 2 mM L-glutamine, 1.5 g/L sodium bicarbonate, 0.1 mM non-essential amino acids, 1.0 mM sodium pyruvate, 10% fetal bovine serum to $6 \times 10^4$ cells/mL.
  SKMEL3 (ATCC catalog #HTB-69): resuspend in McCoy's 5A medium, 1.5 mM L-glutamine, 15% fetal bovine serum to $6 \times 10^4$ cells/mL.
  IPC298 (DSMZ catalog #ACC 251): resuspend in RPMI 1640.2 mM L-glutamine, 10% fetal bovine serum to $6 \times 10^4$ cells/mL.

The cells are plated, 50 µL in each well of a 96-well dish (Corning 3610) and incubated at 37° C. in 5% $CO_2$ overnight, cells plated to a final concentration of cells as follows:
  SW620: 5,000 cells per well.
  A375: 2,000 cells per well.
  COLO205: 2,000 cells per well.
  SKMEL2: 2,000 cells per well.
  SKMEL3: 3,000 cells per well.
  IPC298: 2,000 cells per well.

On day 2, compound at a maximum concentration of 5 mM is serially diluted 1:3 (e.g. 10 µL with 30 µL dimethyl sulfoxide) for a total of 8 point titration with DMSO as a control. A 1 µL aliquot of each dilution point and control is added to 249 µL growth media and 50 µL is added to a well containing cells, providing 10 µM compound at the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added 25 µL to each well, shake for 2 minutes, and the cells are incubated at room temperature for 10 minutes, then luminescence is read on Safire reader. The measured luminescence correlates directly with cell number, such that the reading as a function of compound concentration is used to determine the $IC_{50}$ value.

B9 is a squamous cell carcinoma cell line expressing activated HRAS that was isolated from a DMBA/TPA-induced mouse model of skin carcinogenesis (Stoler, et al. *The Journal of Cell Biology*, 1993, 122(5), 1103-17). IPC-298 is a human melanoma cell line that expresses activated NRAS (Aubert, et al. International Journal of Cancer, 1993, 54(5), 484-92). To determine whether compounds induce phosphorylated ERK and MEK, cells are plated in a 96-well dish and treated with an 8-point titration of compound for one hour at 37° C. The media is then removed and the cells are incubated with lysis buffer containing protease and phosphatase inhibitors. Phosphorylated ERK and MEK in the resulting lysates is detected using AlphaScreen™ technology. To detect phosphorylated ERK, cell lysates are incubated with streptavidin-coated donor beads, anti-mouse IgG acceptor beads, a biotinylated anti-ERK1/2 rabbit antibody, and a mouse antibody that recognizes ERK1/2 only when it is phosphorylated on Thr202 and Tyr204. The biotinylated ERK1/2 antibody will bind to both the streptavidin-coated donor beads and to ERK1/2 (regardless of its phosphorylation state), and the phospho-ERK1/2 antibody will bind to the acceptor beads and to ERK1/2 that is phosphorylated at Thr202/Tyr204. Excitation of the beads with laser light at 680 nm produces singlet oxygen, which is rapidly quenched unless the beads are in close proximity. When ERK is phosphorylated, both antibodies can bind the same protein, bringing the donor and acceptor beads into close proximity, producing a signal that can be measured at 580 nm. MEK phosphorylation is detected using a similar approach, only with antibodies directed against total MEK1/2 and MEK1/2 that is phosphorylated at Ser217 and Ser221.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. In some instances, the compounds were not tested in all of the assays, or assay results were not valid, as indicated by NA in the tables below.

The following table provides data indicating the B-Raf V600E and IPC-298_P-ERK cell activation activity, A375_P-ERK and COLO205 cell growth inhibitory activity for exemplary compounds as described herein:

| Compound number | Biochemical activity (IC$_{50}$ µM) V600E | Cell activity (EC$_{50}$ µM) IPC-298_P-ERK | Cell activity (IC$_{50}$ µM) A375 | COLO205 |
|---|---|---|---|---|
| P-0012 | <0.1 | >10 | <1 | >1 |
| P-0013 | <0.1 | >10 | <1 | >1 |
| P-0014 | <0.1 | >8 | <1 | <1 |
| P-0015 | <0.1 | >10 | <1 | >1 |
| P-0016 | <0.1 | NA | <1 | <1 |
| P-0017 | <0.1 | >10 | <1 | >1 |
| P-0018 | <0.1 | >10 | <1 | >1 |
| P-0019 | <0.1 | >10 | <1 | >1 |
| P-0020 | <0.1 | >10 | <1 | <1 |
| P-0021 | <0.1 | >10 | <1 | <1 |
| P-0022 | <0.1 | >10 | <1 | <1 |
| P-0023 | <0.1 | >10 | <1 | >1 |
| P-0024 | <0.1 | >10 | <1 | >1 |
| P-0025 | <0.1 | >10 | <1 | <1 |
| P-0026 | >0.1 | >10 | >1 | |
| P-0027 | <0.1 | NA | <1 | <1 |
| P-0028 | <0.1 | >10 | <1 | <1 |
| P-0029 | <0.1 | >10 | <1 | <1 |
| P-0030 | <0.1 | >10 | <1 | <1 |
| P-0031 | <0.1 | >10 | <1 | <1 |
| P-0032 | <0.1 | >10 | <1 | <1 |
| P-0033 | <0.1 | >10 | <1 | <1 |
| P-0034 | <0.1 | >10 | <1 | >1 |
| P-0035 | <0.1 | >10 | <1 | >1 |
| P-0036 | <0.1 | >10 | <1 | >1 |
| P-0037 | <0.1 | >10 | <1 | >1 |
| P-0038 | <0.1 | >10 | <1 | >1 |
| P-0039 | <0.1 | >10 | <1 | >1 |
| P-0040 | <0.1 | >10 | <1 | <1 |
| P-0041 | >0.1 | >10 | >1 | |
| P-0042 | <0.1 | >10 | <1 | <1 |
| P-0043 | <0.1 | >10 | <1 | <1 |
| P-0044 | <0.1 | >10 | <1 | <1 |
| P-0045 | <0.1 | >10 | <1 | <1 |
| P-0046 | <0.1 | >10 | <1 | <1 |
| P-0047 | <0.1 | >10 | <1 | <1 |
| P-0048 | <0.1 | >10 | | <1 |
| P-0049 | <0.1 | >4 | <1 | <1 |
| P-0050 | <0.1 | >10 | <1 | <1 |
| P-0051 | <0.1 | >10 | <1 | <1 |
| P-0052 | <0.1 | >10 | <1 | <1 |
| P-0053 | <0.1 | >10 | <1 | <1 |
| P-0054 | <0.1 | >1 | <1 | >1 |
| P-0055 | <0.1 | >10 | <1 | <1 |
| P-0056 | <0.1 | >10 | <1 | <1 |
| P-0057 | <0.1 | >10 | <1 | <1 |
| P-0058 | <0.1 | >10 | <1 | <1 |
| P-0059 | <0.1 | >10 | <1 | <1 |
| P-0060 | <0.1 | >2 | <1 | <1 |
| P-0061 | <0.1 | >10 | <1 | <1 |
| P-0062 | <0.1 | >10 | <1 | <1 |
| P-0063 | <0.1 | >10 | <1 | <1 |
| P-0064 | <0.1 | >10 | <1 | <1 |
| P-0065 | <0.1 | | <1 | >1 |
| P-0066 | <0.1 | | <1 | <1 |
| P-0067 | <0.1 | | <1 | >1 |
| P-0068 | <0.1 | | | |
| P-0069 | <0.1 | | | |
| P-0070 | >0.1 | | <1 | >1 |
| P-0071 | >0.1 | | <1 | >1 |
| P-0072 | >0.1 | | <1 | >1 |
| P-0073 | >0.1 | | <1 | >1 |
| P-0074 | >0.1 | | <1 | >1 |
| P-0075 | >0.1 | | <1 | >1 |
| P-0076 | <0.1 | | <1 | <1 |
| P-0077 | <0.1 | | <1 | <1 |
| P-0078 | <0.1 | | <1 | <1 |
| P-0079 | <0.1 | | <1 | <1 |
| P-0080 | <0.1 | | <1 | >1 |
| P-0081 | <0.1 | | <1 | <1 |
| P-0082 | <0.1 | | <1 | <1 |
| P-0083 | <0.1 | | <1 | <1 |
| P-0084 | <0.1 | | <1 | <1 |
| P-0085 | <0.1 | | <1 | >1 |
| P-0086 | <0.1 | | <1 | <1 |
| P-0087 | <0.1 | | <1 | <1 |
| P-0088 | <0.1 | | <1 | <1 |
| P-0089 | <0.1 | | <1 | >1 |
| P-0090 | <0.1 | | <1 | <1 |
| P-0091 | <0.1 | | <1 | <1 |
| P-0092 | <0.1 | | <1 | <1 |
| P-0093 | <0.1 | | <1 | <1 |
| P-0094 | <0.1 | | <1 | <1 |
| P-0095 | <0.1 | | <1 | <1 |
| P-0096 | <0.1 | | <1 | <1 |
| P-0097 | <0.1 | | <1 | <1 |
| P-0098 | <0.1 | | <1 | <1 |
| P-0099 | <0.1 | | <1 | >1 |
| P-0100 | <0.1 | | <1 | >1 |
| P-0101 | <0.1 | | <1 | >1 |
| P-0102 | <0.1 | | <1 | >1 |
| P-0103 | <0.1 | | <1 | <1 |
| P-0104 | <0.1 | | <1 | <1 |
| P-0105 | <0.1 | | <1 | <1 |
| P-0106 | <0.1 | | <1 | <1 |
| P-0107 | <0.1 | | <1 | <1 |
| P-0108 | <0.1 | | <1 | >1 |
| P-0109 | <0.1 | | <1 | <1 |
| P-0235 | <0.1 | | <1 | <1 |
| P-0236 | <0.1 | | <1 | <1 |
| P-0237 | <0.1 | | <1 | <1 |
| P-0238 | <0.1 | | <1 | <1 |
| P-0239 | <0.1 | | <1 | <1 |
| P-0240 | <0.1 | | <1 | <1 |
| P-0241 | <0.1 | | <1 | <1 |
| P-0242 | <0.1 | | >1 | >1 |
| P-0243 | <0.1 | | >1 | >1 |
| P-0244 | <0.1 | | >1 | >1 |
| P-0245 | <0.1 | | <1 | <1 |
| P-0246 | <0.1 | | >1 | >1 |
| P-0247 | <0.1 | | <1 | <1 |
| P-0248 | <0.1 | | <1 | <1 |
| P-0249 | <0.1 | | <1 | <1 |
| P-0251 | <0.1 | | >1 | >1 |
| P-0252 | <0.1 | | <1 | <1 |
| P-0253 | <0.1 | | >1 | >1 |
| P-0254 | <0.1 | | <1 | <1 |
| P-0255 | <0.1 | | <1 | <1 |
| P-0256 | <0.1 | | <1 | |
| P-0257 | >0.1 | | | >1 |
| P-0258 | <0.1 | | <1 | <1 |
| P-0259 | <0.1 | | <1 | <1 |
| P-0260 | <0.1 | | <1 | <1 |
| P-0261 | <0.1 | | <1 | <1 |
| P-0262 | <0.1 | | <1 | <1 |
| P-0263 | <0.1 | | <1 | <1 |
| P-0264 | <0.1 | | <1 | <1 |
| P-0265 | <0.1 | >2 | <1 | <1 |
| P-0266 | <0.1 | | <1 | <1 |
| P-0267 | >0.1 | | | |
| P-0268 | <0.1 | | <1 | <1 |
| P-0269 | <0.1 | | <1 | <1 |
| P-0270 | <0.1 | | <1 | <1 |
| P-0271 | <0.1 | | <1 | <1 |
| P-0272 | >0.1 | | | |
| P-0273 | | | <1 | <1 |
| P-0274 | <0.1 | | <1 | >1 |
| P-0275 | <0.1 | | <1 | <1 |
| P-0276 | <0.1 | | <1 | >1 |
| P-0277 | >0.1 | | <1 | <1 |
| P-0279 | <0.1 | | >1 | <1 |
| P-0280 | | | <1 | <1 |
| P-0281 | <0.1 | | <1 | <1 |
| P-0282 | <0.1 | | <1 | <1 |

-continued

| Compound number | Biochemical activity (IC$_{50}$ μM) V600E | Cell activity (EC$_{50}$ μM) IPC-298_P-ERK | Cell activity (IC$_{50}$ μM) A375 | Cell activity (IC$_{50}$ μM) COLO205 |
|---|---|---|---|---|
| P-0283 | <0.1 | | >1 | <1 |
| P-0284 | | | <1 | <1 |
| P-0285 | <0.1 | | <1 | <1 |
| P-0286 | <0.1 | | >1 | <1 |
| P-0287 | | >4 | <1 | <1 |
| P-0288 | <0.1 | >2 | <1 | <1 |
| P-0289 | <0.1 | | <1 | <1 |
| P-0291 | >0.1 | | | |
| P-0292 | | | <1 | <1 |
| P-0293 | <0.1 | | <1 | <1 |
| P-0294 | <0.1 | | >1 | >1 |
| P-0295 | <0.1 | >2 | <1 | <1 |
| P-0297 | <0.1 | | >1 | >1 |
| P-0298 | <0.1 | | >1 | >1 |
| P-0299 | <0.1 | | >1 | >1 |
| P-0300 | <0.1 | >4 | <1 | >1 |
| P-0301 | <0.1 | | <1 | >1 |
| P-0302 | <0.1 | | <1 | <1 |
| P-0303 | <0.1 | | >1 | >1 |
| P-0304 | <0.1 | | <1 | <1 |
| P-0305 | <0.1 | | <1 | <1 |
| P-0306 | <0.1 | | >1 | <1 |
| P-0307 | <0.1 | | <1 | <1 |
| P-0308 | <0.1 | | <1 | <1 |
| P-0309 | <0.1 | | <1 | <1 |
| P-0310 | <0.1 | | <1 | <1 |
| P-0311 | <0.1 | | <1 | <1 |
| P-0312 | <0.1 | | <1 | <1 |
| P-0313 | <0.1 | | <1 | <1 |
| P-0314 | <0.1 | | <1 | <1 |
| P-0315 | <0.1 | | <1 | <1 |
| P-0316 | <0.1 | | <1 | <1 |
| P-0317 | <0.1 | | <1 | <1 |
| P-0318 | <0.1 | | <1 | <1 |
| P-0319 | <0.1 | | <1 | <1 |
| P-0320 | >0.1 | | | |
| P-0321 | <0.1 | | <1 | <1 |
| P-0322 | <0.1 | | <1 | <1 |
| P-0324 | <0.1 | | <1 | <1 |
| P-0325 | <0.1 | | <1 | >1 |
| P-0326 | <0.1 | | >1 | >1 |
| P-0327 | <0.1 | | <1 | <1 |
| P-0334 | <0.1 | >2 | >1 | >1 |
| P-0335 | <0.1 | | <1 | <1 |
| P-0336 | >0.1 | >4 | | |
| P-0337 | <0.1 | | >1 | >1 |
| P-0338 | <0.1 | | <1 | <1 |
| P-0339 | <0.1 | | <1 | <1 |
| P-0340 | <0.1 | | <1 | <1 |
| P-0223 | >0.1 | | | |
| P-0224 | <0.1 | | <1 | <1 |
| P-0225 | <0.1 | | <1 | <1 |
| P-0226 | <0.1 | | <1 | <1 |
| P-0227 | <0.1 | | <1 | <1 |
| P-0228 | <0.1 | | <1 | <1 |
| P-0229 | <0.1 | | <1 | <1 |
| P-0230 | <0.1 | | <1 | <1 |
| P-0231 | <0.1 | | <1 | <1 |
| P-0232 | <0.1 | | <1 | <1 |
| P-0233 | <0.1 | | >1 | >1 |
| P-0117 | >0.1 | | >1 | >1 |
| P-0116 | <0.1 | | <1 | <1 |
| P-0115 | <0.1 | | <1 | <1 |
| P-0114 | <0.1 | | <1 | <1 |
| P-0113 | <0.1 | | <1 | <1 |
| P-0112 | <0.1 | | <1 | <1 |
| P-0111 | <0.1 | | <1 | <1 |
| P-0110 | <0.1 | | <1 | <1 |

The table below provides the IPC-298_P-ERK cell activation activity, A375_P-ERK and COLO205 cell growth inhibitory activity data for a few exemplary compounds known in the art.

| Compound | Cell activity (EC$_{50}$ μM) IPC-298_P-ERK | Cell activity (IC$_{50}$ μM) A375 | Cell activity (IC$_{50}$ μM) COLO205 |
|---|---|---|---|
| N-[3-(5-chloro-1H-pyrrolo[2,3-b]pyridine-3-carbonyl)-2,4-difluoro-phenyl]propane-1-sulfonamide | <0.5 | <0.8 | <1 |
| N-[2,4-difluoro-3-[5-(2-methoxy-pyrimidin-5-yl)-1H-pyrrolo[2,3-b]pyridine-3-carbonyl]phenyl]-2-fluoro-benzenesulfonamide | <0.5 | <0.5 | <1 |
| N-[2,4-difluoro-3-[5-(2-methoxy-pyrimidin-5-yl)-1H-pyrrolo[2,3-b]pyridine-3-carbonyl]phenyl]-2,5-difluoro-benzenesulfonamide | <1 | <0.5 | <1 |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol @:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, Cmax and half-life relative to previously described compounds.

All patents, patent applications and other references cited in the specification are indicative of the level of skill of those skilled in the art to which the invention pertains, and are incorporated by reference in their entireties, including any tables and FIGURES, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

While this invention has been disclosed with reference to specific embodiments, it is apparent that other embodiments and variations of this invention may be devised by others skilled in the art without departing from the true spirit and scope of the invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

What is claimed is:

1. A method for treating a subject with a B-Raf mediated disease or condition, said method comprising administering to said subject an effective amount of a compound of formula:

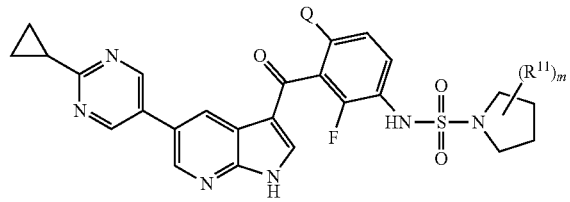

or a pharmaceutically acceptable salt or stereoisomer thereof, wherein:

each $R^{11}$ is independently halogen;

Q is H or F; and m is 0, 1, or 2;

wherein the B-Raf mediated disease or condition is glioma.

2. The method of claim 1, wherein $R^{11}$ is fluoro.
3. The method of claim 1, wherein Q is H.
4. The method of claim 1, wherein Q is fluoro.
5. The method of claim 1, wherein m is 0.
6. The method of claim 1, wherein m is 1.
7. The method of claim 1, wherein the compound is:

(P-0338)

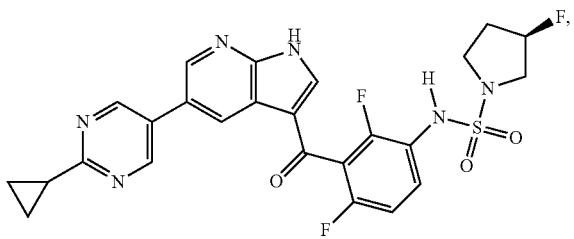

or a pharmaceutically acceptable salt thereof.

* * * * *